US010370431B2

(12) United States Patent
Tan et al.

(10) Patent No.: US 10,370,431 B2
(45) Date of Patent: Aug. 6, 2019

(54) OPTIMIZED FACTOR VIII GENE

(71) Applicant: Bioverativ Therapeutics Inc., Waltham, MA (US)

(72) Inventors: Siyuan Tan, Lexington, MA (US); Robert T. Peters, Needham, MA (US)

(73) Assignee: Bioverativ Therapeutics Inc., Waltham, MA (US)

( * ) Notice: Subject to any disclaimer, the term of this patent is extended or adjusted under 35 U.S.C. 154(b) by 623 days.

(21) Appl. No.: 14/767,425

(22) PCT Filed: Feb. 14, 2014

(86) PCT No.: PCT/US2014/016441
§ 371 (c)(1),
(2) Date: Aug. 12, 2015

(87) PCT Pub. No.: WO2014/127215
PCT Pub. Date: Aug. 21, 2014

(65) Prior Publication Data
US 2015/0361158 A1 Dec. 17, 2015

Related U.S. Application Data

(60) Provisional application No. 61/765,626, filed on Feb. 15, 2013.

(51) Int. Cl.
*C07K 14/755* (2006.01)
*C12N 9/64* (2006.01)

(52) U.S. Cl.
CPC .......... *C07K 14/755* (2013.01); *C12N 9/6424* (2013.01); *C07K 2319/30* (2013.01); *C07K 2319/31* (2013.01)

(58) Field of Classification Search
None
See application file for complete search history.

(56) References Cited

U.S. PATENT DOCUMENTS

| | | |
|---|---|---|
| 4,683,195 A | 7/1987 | Mullis et al. |
| 4,683,202 A | 7/1987 | Mullis |
| 4,704,362 A | 11/1987 | Itakura et al. |
| 4,800,159 A | 1/1989 | Mullis et al. |
| 4,868,112 A | 9/1989 | Toole, Jr. |
| 4,965,188 A | 10/1990 | Mullis et al. |
| 5,112,950 A | 5/1992 | Meulien et al. |
| 5,171,844 A | 12/1992 | Van Ooyen et al. |
| 5,304,489 A | 4/1994 | Rosen |
| 5,543,502 A | 8/1996 | Nordfang et al. |
| 5,595,886 A | 1/1997 | Chapman et al. |
| 5,610,278 A | 3/1997 | Nordfang et al. |
| 5,648,260 A | 7/1997 | Winter et al. |
| 5,658,570 A | 8/1997 | Newman et al. |
| 5,712,122 A | 1/1998 | Boime et al. |
| 5,736,137 A | 4/1998 | Anderson et al. |
| 5,739,277 A | 4/1998 | Presta et al. |
| 5,741,957 A | 4/1998 | Deboer et al. |
| 5,789,203 A | 8/1998 | Chapman et al. |
| 5,834,250 A | 11/1998 | Wells et al. |
| 5,849,992 A | 12/1998 | Meade et al. |
| 5,869,046 A | 2/1999 | Presta et al. |
| 5,972,885 A | 10/1999 | Spira et al. |
| 6,030,613 A | 2/2000 | Blumberg et al. |
| 6,048,720 A | 4/2000 | Dalborg et al. |
| 6,060,447 A | 5/2000 | Chapman et al. |
| 6,086,875 A | 7/2000 | Blumberg et al. |
| 6,096,871 A | 8/2000 | Presta et al. |
| 6,121,022 A | 9/2000 | Presta et al. |
| 6,159,730 A | 12/2000 | Reff |
| 6,193,980 B1 | 2/2001 | Efstathiou et al. |
| 6,194,551 B1 | 2/2001 | Idusogie et al. |
| 6,228,620 B1 | 5/2001 | Chapman et al. |
| 6,242,195 B1 | 6/2001 | Idusogie et al. |
| 6,251,632 B1 | 6/2001 | Lillicrap et al. |
| 6,277,375 B1 | 8/2001 | Ward |
| 6,316,226 B1 | 11/2001 | Van Ooyen et al. |
| 6,346,513 B1 | 2/2002 | Van Ooyen et al. |
| 6,413,777 B1 | 7/2002 | Reff et al. |
| 6,458,563 B1 | 10/2002 | Lollar |
| 6,485,726 B1 | 11/2002 | Blumberg et al. |
| 6,528,624 B1 | 3/2003 | Idusogie et al. |
| 6,538,124 B1 | 3/2003 | Idusogie et al. |
| 6,696,245 B2 | 2/2004 | Winter et al. |
| 6,737,056 B1 | 5/2004 | Presta |
| 6,821,505 B2 | 11/2004 | Ward |
| 6,924,365 B1 | 8/2005 | Miller et al. |
| 6,998,253 B1 | 2/2006 | Presta et al. |
| 7,041,635 B2 | 5/2006 | Kim et al. |
| 7,083,784 B2 | 8/2006 | Dall'Acqua et al. |
| 7,317,091 B2 | 1/2008 | Lazar et al. |
| 7,404,956 B2 | 7/2008 | Peters et al. |
| 8,326,547 B2 * | 12/2012 | Liu .......................... G06F 19/22 702/19 |
| 9,050,318 B2 * | 6/2015 | Dumont ................. A61K 38/37 |
| 2003/0069395 A1 | 4/2003 | Sato et al. |
| 2003/0235536 A1 | 12/2003 | Blumberg |
| 2004/0147436 A1 | 7/2004 | Kim et al. |
| 2007/0231329 A1 | 10/2007 | Lazar et al. |
| 2007/0237765 A1 | 10/2007 | Lazar et al. |
| 2007/0237766 A1 | 10/2007 | Lazar et al. |
| 2007/0237767 A1 | 10/2007 | Lazar et al. |

(Continued)

FOREIGN PATENT DOCUMENTS

EP 0295597 A2 12/1988
RU 2 500 816 C1 12/2013

(Continued)

OTHER PUBLICATIONS

Codon Optimization—Increase Protein Expression, downlaoded Mar. 26, 2018 from GenScript, OptimumGene—Codon Optimization, 4 pages.*

(Continued)

*Primary Examiner* — Michael Szperka
(74) *Attorney, Agent, or Firm* — Lathrop Gage LLP; James H. Velema, Esq.

(57) ABSTRACT

The present invention provides codon optimized Factor VIII sequences, vectors and host cells comprising codon optimized Factor VIII sequences, polypeptides encoded by codon optimized Factor VIII sequences, and methods of producing such polypeptides.

16 Claims, 7 Drawing Sheets

Specification includes a Sequence Listing.

(56) References Cited

U.S. PATENT DOCUMENTS

| | | |
|---|---|---|
| 2007/0243188 A1 | 10/2007 | Lazar et al. |
| 2007/0248603 A1 | 10/2007 | Lazar et al. |
| 2007/0286859 A1 | 12/2007 | Lazar et al. |
| 2008/0004206 A1 | 1/2008 | Rosen et al. |
| 2008/0057056 A1 | 3/2008 | Lazar et al. |
| 2008/0076174 A1 | 3/2008 | Selden et al. |
| 2008/0153751 A1 | 6/2008 | Rosen et al. |
| 2008/0161243 A1 | 7/2008 | Rosen et al. |
| 2008/0194481 A1 | 8/2008 | Rosen et al. |
| 2008/0260738 A1 | 10/2008 | Moore et al. |
| 2008/0261877 A1 | 10/2008 | Ballance et al. |
| 2009/0017533 A1 | 1/2009 | Selden et al. |
| 2009/0042283 A1 | 2/2009 | Selden et al. |
| 2009/0087411 A1 | 4/2009 | Fares et al. |
| 2010/0239554 A1 | 9/2010 | Schellenberger et al. |
| 2010/0284971 A1 | 11/2010 | Samulski |
| 2010/0292130 A1 | 11/2010 | Skerra et al. |
| 2010/0323956 A1 | 12/2010 | Schellenberger et al. |
| 2011/0046060 A1 | 2/2011 | Schellenberger et al. |
| 2011/0046061 A1 | 2/2011 | Schellenberger et al. |
| 2011/0077199 A1 | 3/2011 | Schellenberger et al. |
| 2011/0172146 A1 | 7/2011 | Schellenberger et al. |
| 2013/0024960 A1* | 1/2013 | Nathwani ............ C07K 14/755 800/16 |
| 2014/0010861 A1 | 1/2014 | Bancel et al. |

FOREIGN PATENT DOCUMENTS

| | | | |
|---|---|---|---|
| WO | WO-8704187 A1 | 7/1987 | |
| WO | WO-8800831 A1 | 2/1988 | |
| WO | WO-8807089 A1 | 9/1988 | |
| WO | WO-9109122 A1 | 6/1991 | |
| WO | WO-9614339 A1 | 5/1996 | |
| WO | WO-9805787 A1 | 2/1998 | |
| WO | WO-9823289 A1 | 6/1998 | |
| WO | WO-9951642 A1 | 10/1999 | |
| WO | WO-9958572 A1 | 11/1999 | |
| WO | WO-0009560 A2 | 2/2000 | |
| WO | WO-0032767 A1 | 6/2000 | |
| WO | WO-0042072 A2 | 7/2000 | |
| WO | WO-0244215 A2 | 6/2002 | |
| WO | WO-02060919 A2 | 8/2002 | |
| WO | WO-02063025 A2 * | 8/2002 | ............ C12N 9/647 |
| WO | WO-03074569 A2 | 9/2003 | |
| WO | WO-03077834 A2 | 9/2003 | |
| WO | WO-2004016750 A2 | 2/2004 | |
| WO | WO-2004029207 A2 | 4/2004 | |
| WO | WO-2004035752 A2 | 4/2004 | |
| WO | WO-2004063351 A2 | 7/2004 | |
| WO | WO-2004074455 A2 | 9/2004 | |
| WO | WO-2004099249 A2 | 11/2004 | |
| WO | WO-2005040217 A2 | 5/2005 | |
| WO | WO-2005070963 A1 | 8/2005 | |
| WO | WO-2005077981 A2 | 8/2005 | |
| WO | WO-2005092925 A2 | 10/2005 | |
| WO | WO-2005123780 A2 | 12/2005 | |
| WO | WO-2006019447 A1 | 2/2006 | |
| WO | WO-2006047350 A2 | 5/2006 | |
| WO | WO-2006085967 A2 | 8/2006 | |
| WO | WO-2007021494 A2 | 2/2007 | |
| WO | WO-2007149852 A2 | 12/2007 | |
| WO | WO-2008012543 A1 | 1/2008 | |
| WO | WO-2008033413 A2 | 3/2008 | |
| WO | WO-2008143954 A2 | 11/2008 | |
| WO | WO-2008155134 A1 | 12/2008 | |
| WO | WO-2009058322 A1 | 5/2009 | |
| WO | WO-2010091122 A1 | 8/2010 | |
| WO | WO-2010115866 A1 | 10/2010 | |
| WO | WO 2010115866 A1 * | 10/2010 | ........... C07K 14/755 |
| WO | WO-2010140148 A1 | 12/2010 | |
| WO | WO-2010144502 A2 | 12/2010 | |
| WO | WO-2010144508 A1 | 12/2010 | |
| WO | WO-2011005968 A1 | 1/2011 | |
| WO | WO-2011028228 A1 | 3/2011 | |
| WO | WO-2011028229 A1 | 3/2011 | |
| WO | WO-2011028344 A2 | 3/2011 | |
| WO | WO-2011069164 A2 * | 6/2011 | ............ A61K 38/37 |
| WO | WO-2012006635 A1 | 1/2012 | |
| WO | WO-2013009627 A2 | 1/2013 | |
| WO | WO-2013093760 A2 * | 6/2013 | ............ A61K 38/36 |
| WO | WO-2016004113 A1 | 1/2016 | |

OTHER PUBLICATIONS

Altschul, S.F., et al., "Basic Local Alignment Search Tool," Journal of Molecular Biology 215(3):403-410, Elsevier, England (1990).

Armour, K.L., et al., "Recombinant Human IgG Molecules Lacking Fc Gamma Receptor I Binding and Monocyte Triggering Activities,"European Journal of Immunology 29(8):2613-2624, Wiley-VCH, Germany (1999).

Baldassarre, H., et al., "Production of Transgenic Goats by Pronuclear Microinjection of In Vitro Produced Zygotes Derived From Oocytes Recovered by Laparoscopy," Theriogenology 59(3-4):831-839, Elsevier, United States (2003).

Benhar, I. And Pastan, I., "Cloning, Expression and Characterization of the Fv Fragments of the Anti-Carbohydrate mAbs B1 and B5 as Single-Chain Immunotoxins," Protein Engineering Design and Selection 7(11):1509-1515, Oxford University Press, England (1994).

Brinster, R.L., et al., "Expression of a Microinjected Immunoglobulin Gene in the Spleen of Transgenic Mice," Nature 306(5941):332-326, Nature Publishing Group, England (1983).

Brinster, R.L., et al., "Factors Affecting the Efficiency of Introducing Foreign DNA into Mice by Microinjecting Eggs," Proceedings of the National Academy of Sciences USA 82(13):4438-4442, National Academy of Sciences, United States (1985).

Burgess-Brown, N.A., et al., "Codon Optimization Can Improve Expression of Human Genes in *Escherichia coli*: a Multi-gene Study," Protein Expression and Purification 59(1):94-102, Academic Press, United States (2008).

Burmeister, W.P., et al., "Crystal Structure of the Complex of Rat Neonatal Fc Receptor with Fc," Nature 372(6504):379-383, Nature Publishing Group, England (1994).

Cameron, C., et al., "The Canine Factor VIII cDNA and 5' Flanking Sequence," Thrombosis and Haemostasis 79(2):317-322, Schattauer, Germany (1998).

Capon, D.J., et al., "Designing CD4 Immunoadhesins for AIDS Therapy," Nature 337(6207):525-531, Nature Publishing Group, England (1989).

Chabner, B.A., et al., "Antineoplastic Agents," in Goodman & Gilman's The Pharmacological Basis of Therapeutics, 9th ed., Hardman, G.H., et al., eds.,pp. 1233-1287, McGraw-Hill, United States (1996).

"Codon Usage Database" accessed at http://www.kazusa.or.jp/codon/ on Apr. 23, 2013, 1 page.

Dennis, M.S., et al., "Albumin Binding as a General Strategy for Improving the Pharmacokinetics of Proteins," The Journal of Biological Chemistry 277(38):35035-35043, American Society for Biochemistry and Molecular Biology, United States (2002).

Eaton, D.L., et al., "Construction and Characterization of an Active Factor VIII Variant Lacking the Central One-Third of the Molecule," Biochemistry 25(26):8343-8347, American Chemical Society, United States (1986).

Ellman, J., et al., "Biosynthetic Method for Introducing Unnatural Amino Acids Site-Specifically into Proteins," Methods in Enzymology 202:301-336, Elsevier, United States (1991).

Fallaux, F.J., et al., "The Human Clotting Factor VIII cDNA Contains an Autonomously Replicating Sequence Consensus-and Matrix Attachment Region-like Sequence That Binds a Nuclear Factor, Represses Heterologous Gene Expression, and Mediates the Transcriptional Effects of Sodium Butyrate," Molecular and Cellular Biology 16(8):4264-4272, American Society for Microbiology, United States (1996).

Friend, P.J., et al., "Phase I Study of an Engineered Aglycosylated Humanized CD3 Antibody in Renal Transplant Rejection," Transplantation 68(11):1632-1637, Lippincott Williams & Wilkins, Inc., United States (1999).

(56) References Cited

OTHER PUBLICATIONS

GenBank, "*Homo sapiens* Transferrin (TF), mRNA," Accession No. NM001063.3 published on May 25, 2014, accessed at http://www.ncbi.nlm.nih.gov/nuccore/NM_001063, accessed on Sep. 24, 2014, 5 pages.
GenBank, "*Homo sapiens* Transferrin (TF), mRNA," Accession No. XM002793 published on May 13, 2002, accessed at https://www.ncbi.nlm.nih.gov/nuccore/XM_002793.7?report=genbank, accessed on Sep. 24, 2014, 2 pages.
GenBank, "*Homo sapiens* Transferrin (TF), mRNA," Accession No. XM039847 published on Jul. 16, 2001, accessed at http://www.ncbi.nlm.nih.gov/nuccore/XM_039847.1?report=genbank, accessed on Sep. 24, 2014, 2 pages.
GenBank, "*Homo sapiens* Transferrin (TF), mRNA," Accession No. XM039845 published Jul. 16, 2001, accessed at https://www.ncbi.nlm.nih.gov/nuccore/XM_039845.1?report=genbank, accessed on Sep. 24, 2014, 2 pages.
Genbank, "*Homo sapiens* von Willebrand factor (VWF), mRNA," Accession No. NM_000552.3, Accessed at http://www.ncbi.nlm.nih.gov/nuccore/NM_000552.
GenBank, "Human Transferrin mRNA, Complete cds," Accession No. M12530.1, published on Jan. 14, 1995, accessed at http://www.ncbi.nlm.nih.gov/nuccore/M1253014, accessed on Jan. 15, 2015, 2 pages.
GenBank, "Transferrin [human, liver, mRNA, 2347 nt]," Accession No. S95936.1, published on May 7, 1993, accessed at http://www.ncbi.nlm.nih.gov/nuccore/S95936, accessed on Sep. 24, 2014, 2 pages.
Genbank, "transferrin precursor [*Homo sapiens*]" Accession AAA61140.1, accessed at http://www.ncbi.nlm.nih.gov/protein/AAA61140, accessed on Mar. 29, 2016, 3 pages.
Genbank, "Von Willebrand Factor Preproprotein [*Homo sapiens*]," Accession No. NP000543 .2, Accessed at http://www.ncbi.nlm.nih.gov/protein/NP_000543.
Graf, M., et al., "Concerted Action of Multiple Cis-acting Sequences is Required for Rev Dependence of Late Human Immunodeficiency Virus Type 1 Gene Expression," Journal of Virology 74(22):10822-10826, American Society for Microbiology, United States (2000).
Ho, S.N., et al., "Site-Directed Mutagenesis by Overlap Extension Using the Polymerase Chain Reaction," Gene 77(1):51-59, Elsevier Science Publishers B.V., Netherlands (1989).
Hoeben, R.C., et al., "Expression of Functional Factor VIII in Primary Human Skin Fibroblasts after Retrovirus-mediated Gene Transfer," The Journal of Biological Chemistry 265(13):7318-7323, The American Society for Biochemistry and Molecular Biology, United States (1990).
Hoeben, R.C., et al., "Expression of the Blood-clotting Factor-VIII cDNA is Repressed by a Transcriptional Silencer Located in Its Coding Region," Blood 85(9):2447-2454, American Society of Hematology, United States (1995).
Holt, L.J., et al., "Anti-Serum Albumin Domain Antibodies for Extending the Half-Lives of Short Lived Drugs," Protein Engineering, Design and Selection 21(5):283-288, Oxford University Press, England (2008).
Horton, R.M., et al., "Gene Splicing by Overlap Extension," Methods in Enzymology 217:270-279, Academic Press, United States (1993).
International Search Report and Written Opinion for International Application No. PCT/US2014/016441, ISA/US, Alexandria, Virginia, United States, dated May 23, 2014, 7 pages.
International Search Report for International Application No. PCT/US2015/038678, ISA/US, Alexandria, Virginia, dated Dec. 8, 2015, 5 pages.
Israel, E.J., et al., "Expression of the neonatal Fc receptor, FcRn, on human intestinal epithelial cells," Immunology 92(1):69-74, Blackwell Sciences, England (1997).
Kobayashi, N., et al., "FcRn-Mediated Transcytosis of Immunoglobulin G in Human Renal Proximal Tubular Epithelial Cells," American Journal of Physiology 282(2):F358-F365, American Physiological Society, United States (2002).
Koeberl, D.D., et al., "Sequences within the Coding Regions of Clotting Factor VIII and CFTR Block Transcriptional Elongation," Human Gene Therapy 6(4):469-479, M.A. Liebert, United States (1995).
Konig, T. and Skerra, A., "Use of an Albumin-Binding Domain for the Selective Immobilisation of Recombinant Capture Antibody Fragments on ELISA Plates," Journal of Immunological Methods 218(1-2):73-83, Elsevier Science B.V., Netherlands (1998).
Kraulis, P.J., et al., "The Serum Albumin-Binding Domain of Streptococcal Protein G is a Three-Helical Bundle: a Heteronuclear NMR study," FEBS Letters 378(2):190-194, Elsevier Science B.V,Netherlands (1996).
Kudla, G., et al., "High Guanine and Cytosine Content Increases mRNA Levels in Mammalian Cells," PLoS Biology 4(6):e180, Public Library of Science, United States (2006).
Langner, K-D., et al., "Synthesis of Biologically Active Deletion Mutants of Human Factor VIII:C," Behring Institute Mitteilungen 82:16-25, Behringwerke AG, Germany (1988).
Larrick, J.W., et al., "Rapid Cloning of Rearranged Immunoglobulin Genes from Human Hybridoma Cells using Mixed Primers and the Polymerase Chain Reaction," Biochemical and Biophysical Research Communications 160(3):1250-1256, Academic Press, United States (1989).
Lenting, P.J., et al., "Clearance Mechanisms of Von Willebrand Factor and Factor VIII," Journal of Thrombosis and Haemostasis 5(7):1353-1360, International Society on Thrombosis and Haemostasis, England (2007).
Lenting, P.J., et al., "The Life Cycle of Coagulation Factor VIII in View of its Structure and Function," Blood, 92(11):3983-3996, American Society of Hematology, United States (1998).
Linhult, M., et al., "Mutational Analysis of the Interaction Between Albumin-Binding Domain from Streptococcal Protein G and Human Serum Albumin," Protein Science 11(2):206-213, Cold Spring Harbor Laboratory Press, United States (2002).
Lynch, C.M., et al., "Sequences in the Coding Region of Clotting Factor VIII Act as Dominant Inhibitors of RNA Accumulation and Protein Production," Human Gene Therapy 4(3):259-272, M.A. Liebert, United States (1993).
Malassagne, B., et al., "Hypodermin A, A New Inhibitor of Human Complement for the Prevention of Xenogeneic Hyperacute Rejection," Xenotransplantation 10(3):267-277, John Wiley & Sons, United States (2003).
Manco-Johnson, M.J., et al., "Prophylaxis Versus Episodic Treatment to Prevent Joint Disease in Boys with Severe Hemophilia," The New England Journal of Medicine 357(6):535-544, Massachusetts Medical Society, United States (2007).
Mannucci, P.M. and Tuddenham, E.G.D., "The Hemophilias—from Royal Genes to Gene Therapy," New England Journal of Medicine 344(23):1773-1779, Massachusetts Medical Society, United States (2001).
McKnight, G.S., et al., "Expression of the Chicken Transferrin Gene in Transgenic Mice," Cell 34(2):335-341, Cell Press, United States (1983).
Meulien, P., et al., "A New Recombinant Procoagulant Protein Derived from the cDNA Encoding Human Factor VIII," Protein Engineering 2(4):301-306, IRL Press Ltd., England (1988).
Morfini, M., "Pharmacokinetics of Factor VIII and Factor IX," Haemophilia 9(Suppl. 1):94-100, Blackwell Publishing Ltd., England (2003).
Mount, J.D., et al., "Sustained Phenotypic Correction of Hemophilia B dogs with a Factor IX Null Mutation by Liver-Directed Gene Therapy," Blood 99(8):2670-2676, The American Society of Hematology, United States (2002).
Muller, D. and Kontermann, R.E., "Recombinant Bispecific Antibodies for Cellular Cancer Immunotherapy," Current Opinion in Molecular Therapeutics 9(4):319-326, The Thomson Corporation, United States (2007).
Nakamura, Y., et al., "Codon usage tabulated from international DNA sequence databases: status for the year 2000," Nucleic Acids Research 28(1):292, Oxford University Press, United Kingdom (2000).

(56) References Cited

OTHER PUBLICATIONS

Narita, M., et al., "The Low-Density Lipoprotein Receptor-Related Protein (LRP) Mediates Clearance of Coagulation Factor Xa In Vivo," Blood 91(2):555-560, The American Society of Hematology, United States (1998).

Neumann, E., et al., "Gene Transfer into Mouse Lyoma Cells by Electroporation in High Electric Fields," The EMBO Journal 1(7):841-845, IRL Press Limited, England (1982).

Noren, C.J., et al., "A General Method for Site-Specific Incorporation of Unnatural Amino Acids into Proteins," Science 244(4901):182-188, Association for the Advancement of Science, United States (1989).

Peyvandi, F., et al., "Genetic Diagnosis of Gaemophilia and Other Inherited Bleeding Disorders," Haemophilia 12(Suppl 3):82-89, Blackwell Publishing Ltd., England (2006).

Ridgway, A. A. G., et al., "Introduction of Vector into Host Cells," in Mammalian Expression Vectors, Chapter 24.2, Rodriguez and Denhardt, Eds.,pp. 470-472, Butterworths, Boston, Mass. (1988).

Ritchie, K.A., et al., "Allelic Exclusion and Control of Endogenous Immunoglobulin Gene Rearrangement in Kappa Transgenic Mice," Nature 312(5994):517-520, Nature Publishing Group, England (1984).

Robl, J.M., et al., "Artificial Chromosome Vectors and Expression of Complex Proteins in Transgenic Animals," Theriogenology 59(1):107-113, Elsevier, United States (2003).

Rodriguez-Merchan, E.C. "Management of Musculoskeletal Complications of Hemophilia," Seminars in Thrombosis and Hemostasis 29(1):87-96, Thieme, United States (2003).

Roovers, R.C., et al., "Efficient Inhibition of EGFR Signaling and of Tumour Growth by Antagonistic Anti-EGFR Nanobodies," Cancer Immunology, Immunotherapy 56(3):303-317, Springer Verlag, Germany (2007).

Routledge, E.G., et al., "The Effect of Aglycosylation on the Immunogenicity of a Humanized Therapeutic CD3 Monoclonal Antibody," Transplantation 60(8):847-853, Williams & Wilkins, United States (1995).

Ruberti, F., et al., "The Use of the RACE Method to Clone Hybridoma cDNA When V Region Primers Fail," Journal of Immunological Methods 173(1):33-39, Elsevier, United States (1994).

Ruther, U. and Muller-Hill, B., "Easy Identification of cDNA Clones," The EMBO Journal 2(10):1791-1794, IRL Press Ltd, England (1983).

Sarver, N., et al., "Stable Expression of Recombinant Factor VIII Molecules Using a Bovine Papillomavirus Vector," DNA 6(6):553-564, Mary Ann Liebert, Inc., United States (1987).

Sharp, P.M. and Li, W.H., "The Codon Adaptation Index—a Measure of Directional Synonymous Codon Usage Bias, and Its Potential Applications," Nucleic Acids Research 15(3):1281-1295, Oxford University Press, England (1987).

Shields, R.L., et al., "High Resolution Mapping of the Binding Site on Human IgG1 for Fc gamma RI, Fc gamma RII, Fc gamma RIII, and FcRn and Design of IgG1 Variants with Improved Binding to the Fc gamma R," The Journal of Biological Chemistry 276(9):6591-6604, American Society for the Biochemistry and Molecular Biology, United States (2001).

Story, C.M., et al., "A Major Histocompatibility Complex Class I-like Fc Receptor Cloned from Human Placenta: Possible Role in Transfer of Immunoglobulin G from Mother to Fetus," The Journal of Experimental Medicine 180(6):2377-2381, The Rockefeller University Press, United States (1994).

Toole, J.J., et al., "A Large Region (≈95 kDa) of Human Factor VIII is Dispensable for in vitro Procoagulant Activity," Proceedings of the National Academy of Sciences USA 83(16):5939-5942, National Academy of Sciences, United States (1986).

Trussel, S., et al., "New Strategy for the Extension of the Serum Half-Life of Antibody Fragments," Bioconjugate Chemistry 20(12):2286-2292, American Chemical Society, United States (2009).

Wagner, T.E., et al., "Microinjection of a Rabbit Beta-Globin Gene into Zygotes and Its Subsequent Expression in Adult Mice and Their Offspring," Proceedings of the National Academy of Sciences USA 78(10):6376-6380, National Academy of Sciences, United States (1981).

Ward, E.S. and Ghetie, V., "The Effector Functions of Immunoglobulins: Implications for Therapy," Therapeutic Immunology 2(2):77-94, Blackwell Science Ltd., England (1995).

White, G.C. II, et al., "A Multicenter Study of Recombinant Factor VIII (Recombinate(TM)) in Previously Treated Patients with Hemophilia A," Thrombosis and Haemostasis 77(4):660-667, F.K. Schattauer Verlagsgesellschaft mbH, Germany (1997).

Wigler, M., et al., "Biochemical Transfer of Single-Copy Eucaryotic Genes Using Total Cellular DNA as Donor," Cell 14(3):725-731, Cell Press, United States (1978).

Ward, N.J., et al., "Codon optimization of human factor VIII cDNAs leads to high-level expression," Blood 117(3):798-807, American Association of Hematology, United States (2011).

\* cited by examiner

Figure 2

```
CGTACGGCCGCCACCATGCAGATTGAGCTGTCTACTTGCTTTTTCCTGTGCCTGCTGAGGTTTTGCTTTTCCGCTACACG
AAGGTATTATCTGGGGGCTGTGGAACTGTCTTGGGATTACATGCAGAGTGACCTGGGAGAGCTGCCAGTGGACGCAAGGT
TTCCCCCTAGAGTCCCTAAGTCATTCCCCTTCAACACTAGCGTGGTCTACAAGAAAACACTGTTCGTGGAGTTTACTGAT
CACCTGTTCAACATCGCAAAGCCTAGGCCACCCTGGATGGGACTGCTGGGGCCAACAATCCAGGCCGAGGTGTACGACAC
CGTGGTCATTACACTTAAGAACATGGCCTCACACCCGTGAGCCTGCATGCTGTGGGCGTCAGCTACTGGAAGGCTTCCG
AAGGAGCAGAGTATGACGATCAGACTTCCCAGAGAGAAAAGAGGACGATAAGGTGTTTCCTGGCGGATCTCATACCTAC
GTGTGGCAGGTCCTGAAAGAGAATGGCCCTATGGCCTCCGACCCTCTGTGCCTGACCTACTCTTATCTGAGTCACGTGGA
CCTGGTCAAGGATCTGAACAGCGGCCTGATCGGAGCCCTGCTGGTGTGCAGGGAAGGAAGCCTGGCTAAGGAGAAAACCC
AGACACTGCATAAGTTCATTCTGCTGTTCGCCGTGTTTGACGAAGGGAAATCATGGCACAGCGAGACAAAGAATAGTCTG
ATGCAGGACAGGGATGCCGCTTCAGCCAGAGCTTGGCCCAAAATGCACACTGTGAACGGCTACGTCAATCGCTCACTGCC
TGGGCTGATCGGCTGCCACCGAAAGAGCGTGTATTGGCATGTCATCGGGATGGGCACCACACCTGAAGTGCACTCCATTT
TCCTGGAGGGACATACCTTTCTGGTCCGCAACCACCGACAGGCTTCCCTGGAGATCTCTCCAATTACCTTCCTGACAGCA
CAGACTCTGCTGATGGACCTGGGGCAGTTCCTGCTGTTTTGCCACATCAGCTCCCACCAGCATGATGGCATGGAGGCTTA
CGTGAAAGTGGACTCTTGTCCCGAGGAACCTCAGCTGCGGATGAAGAACAATGAGGAAGCAGAAGACTATGACGATGACC
TGACCGACTCCGAGATGGATGTGGTCCGATTCGATGACGATAACAGCCCCTCCTTTATCCAGATTAGATCTGTGGCCAAG
AAACACCCTAAGACATGGGTCCATTACATCGCAGCCGAGGAAGAGGACTGGGATTATGCACCACTGGTGCTGGCACCAGA
CGATCGCTCCTACAAATCTCAGTATCTGAACAATGGGCCACAGAGGATTGGCAGAAAGTACAAGAAAGTGCGGTTCATGG
CATATACCGATGAGACCTTCAAGACTCGCGAAGCCATCCAGCACGAGAGCGGCATCCTGGGACCACTGCTGTACGGAGAA
GTGGGAGACACCCTGCTGATCATTTTCAAGAACCAGGCCAGCCGGCCTTACAATATCTATCCACATGGGATTACAGATGT
GCGCCCTCTGTACAGCAGGAGACTGCCAAAGGGCGTCAAACACCTGAAGGACTTCCCAATCCTGCCCGGAGAAATCTTCA
AGTACAAGTGGACTGTCACCGTCGAGGATGGCCCCACTAAGAGCGACCCTCGGTGCCTGACCCGCTACTATTCTAGTTTC
GTGAATATGGAAAGAGATCTGGCAAGCGGACTGATCGGACCACTGCTGATTTGTTACAAAGAGAGCGTGGATCAGAGAGG
CAACCAGATCATGTCCGACAAGCGGAATGTGATTCTGTTCAGTGTCTTTGACGAAAACAGGTCATGGTACCTGACCGAGA
ACATCCAGAGATTCCTGCCCTAATCCAGCTGGGGTGCAGCTGGAAGATCCTGAGTTTCAGGCATCTAACATCATGCATAGT
ATTAATGGCTACGTGTTCGACAGTTTGCAGCTGAGCGTGTGCCTGCACGAGGTCGCTTACTGGTATATCCTGAGCATTGG
GGCACAGACAGATTTCCTGAGCGTGTTCTTTTCCGGCTACACTTTTAAGCATAAAATGGTCTATGAGGACACACTGACTC
TGTTCCCCTTCAGCGGCGAAACCGTGTTTATGAGCATGGAGAATCCCGGACTGTGGATTCTGGGGTGCCACAACAGCGAT
TTCAGAAATCGCGGAATGACTGCCCTGCTGAAAGTGTCAAGCTGTGACAAGAACACCGGGGACTACTATGAAGATTCATA
CGAGGACATCAGCGCATATCTGCTGTCCAAAAACAATGCCATTGAACCCCGGTCTTTTAGTCAGAATCCTCCAGTGCTGA
AGCGGCACCAGCGCGAGATCACCCGCACTACCCTGCAGAGTGATCAGGAAGAGATCGACTACGACGATACAATTTCTGTG
GAAATGAAGAAAGAGGACTTCGATATCTATGACGAAGATGAGAACCAGAGTCCTCGATCATTCCAGAAGAAAACCAGGCA
TTACTTTATTGCCGCAGTGGAGCGGCTGTGGGATTATGGCATGTCCTCTAGTCCTCACGTGCTGCGAAATAGGGCCCAGT
CAGGAAGCGTCCCACAGTTCAAGAAAGTGGTCTTCCAGGAGTTTACAGACGGGTCCTTTACTCAGCCACTGTACAGGGGC
GAACTGAACGAGCACCTGGGACTGCTGGGGCCCTATATCAGAGCAGAAGTGGAGGATAACATTATGGTCACCTTCAGAAA
TCAGGCCTCTCGGCCTTACAGTTTTTATTCAAGCCTGATCTCTTACGAAGAGGACCAGCGACAGGGAGCTGAACCACGAA
AAAACTTCGTGAAGCCTAATGAGACCAAAACATACTTTTGGAAGGTGCAGCACCATATGGCCCCAACAAAAGACGAGTTC
GATTGCAAGGCATGGGCCTATTTTTCTGACGTGGATCTGGAGAAGGACGTGCACAGTGGCCTGATTGGCCCACTGCTGGT
GTGCCATACTAACACCCTGAATCCAGCCCACGCCGGCAGGTCACTGTCCAGGAGTTCGCTCTGTTCTTTACCATCTTTG
ATGAGACAAAGAGCTGGTACTTCACCGAAAACATGGAGCGAAATTGCAGGGCTCCATGTAACATTCAGATGGAAGACCCC
ACATTCAAGGAGAACTACCGCTTTCATGCTATCAATGGATACATCATGGATACTCTGCCCGGGCTGGTCATGGCACAGGA
CCAGAGAATCCGGTGGTATCTGCTGAGCATGGGCAGCAACGAGAATATCCACTCAATTCATTTCAGCGGGCACGTGTTTA
CTGTCAGGAAGAAAGAAGAGTACAAGATGGCCCTGTACAACCTGTATCCCGGCGTGTTCGAAACCGTCGAGATGCTGCCT
AGCAAGGCCGGAATCTGGAGAGTGGAATGCCTGATTGGAGAGCACCTGCATGCTGGGATGTCTACCCTGTTTCTGGTGTA
CAGTAATAAGTGTCAGACACCCCTGGGAATGGCATCCGGGCATATCAGGGATTTCCAGATTACCGCATCTGGACAGTACG
GACAGTGGGCACCTAAGCTGGCTAGACTGCACTATTCCGGATCTATCAACGCTTGGTCCACAAAAGAGCCTTTCTCTTGG
ATTAAGGTGGACCTGCTGGCCCCAATGATCATTCATGGCATCAAAACTCAGGGAGCTCGGCAGAAGTTCTCCTCTCTGTA
CATCTCACAGTTTATCATCATGTACAGCCTGGATGGGAAGAAATGGCAGACATACCGCGGCAATAGCACAGGAACTCTGA
TGGTGTTCTTTGGCAACGTGGACAGCAGCGGAATCAAGCACAACATTTTCAATCCCCCTATCATTGCTAGATACATCCGG
CTGCACCCAACCCATTATTCTATTCGAAGTACACTGAGGATGGAACTGATGGGATGCGATCTGAACAGTTGTTCAATGCC
CCTGGGGATGGAGTCCAAGGCAATCTCTGACGCCCAGATTACCGCTAGCTCCTACTTCACTAATATGTTTGCTACCTGGA
GCCCTTCCAAAGCAAGACTGCACCTGCAAGGCCGCAGCAACGCATGGCGACCACAGGTGAACAATCCCAAGGAGTGGTTG
CAGGTCGATTTTCAGAAAACTATGAAGGTGACCGGGGTCACAACTCAGGGCGTGAAAAGTCTGCTGACCTCAATGTACGT
CAAGGAGTTCCTGATCTCTAGTTCACAGGACGGACATCAGTGGACACTGTTCTTTCAGAACGGGAAGGTGAAAGTCTTCC
AGGGCAATCAGGATTCCTTTACACCTGTGGTCAACAGTCTAGACCCTCCACTGCTGACCAGATACCTGAGAATCCACCCT
CAGTCCTGGGTGCACCAGATTGCCCTGAGAATGGAAGTGCTGGGATGCGAGGCCCAGGATCTGTACTGATAACTCGAGTC
GACC
```

SEQ ID NO:1

Figure 3

```
GGCGCGCCCGTACGGCCGCCACCATGCAGATCGAGCTGTCTACCTGCTTCTTCCTGTGCCTGCTGCGGTTCTGCTTC
AGCGCCACCCGGCGGTACTACCTGGGCGCCGTGGAACTGAGCTGGACTACATGCAGAGCGACCTGGGGGAGCTGCC
CGTGGACGCCAGATTCCCCCAAGAGTGCCCAAGAGCTTCCCCTTCAACACCTCCGTGGTGTACAAGAAAACCCTGT
TCGTCGAGTTCACCGACCACCTGTTCAATATCGCCAAGCCCAGACCCCCTGGATGGGCCTGCTGGGCCCTACAATC
CAGGCCGAGGTGTACGACACCGTGGTCATCACCCTTAAGAACATGGCCAGCCACCCCGTGTCCCTGCACGCCGTGGG
CGTGTCCTACTGGAAGGCCTCTGAGGGCGCTGAGTACGACGACCAGACCAGCCAGCGCGAGAAGAGGACGACAAAG
TCTTTCCTGGCGGCAGCCATACCTACGTGTGGCAGGTCCTGAAAGAAAACGGCCCTATGGCCTCCGACCCCCTGTGC
CTGACCTACAGCTACCTGAGCCACGTGGACCTGGTCAAGGACCTGAACAGCGGCCCTGATTGGCGCCCTGCTCGTGTG
TAGAGAGGGCAGCCTCGCCAAAGAGAAAACCCAGACCCTGCACAAGTTCATCCTGCTGTTCGCCGTGTTCGACGAGG
GCAAGAGCTGGCACAGCGAGACAAAGAACAGCCTGATGCAGGACCGGGACGCCGCCTCTGCCAGAGCCTGGCCTAAG
ATGCACACCGTGAACGGCTACGTGAACAGAAGCCTGCCCGGACTGATCGGCTGCCACCGGAAGTCCGTGTACTGGCA
CGTGATCGGCATGGGCACCACCCCCGAGGTGCACAGCATCTTTCTGGAAGGCCACACCTTCCTCGTGCGGAACCACA
GACAGGCCAGCCTGGAAATCAGCCCTATCACCTTCCTGACCGCCCAGACACTGCTGATGGACCTGGGCCAGTTCCTG
CTGTTTTGCCACATCAGCAGCCACCAGCACGACGGCATGGAAGCCTACGTGAAGGTGGACAGCTGCCCCGAGGAACC
CCAGCTGCGCGATGAAGAACAACGAGGAAGCCGAGGACTACGACGACGACCTGACCGACAGCGAGATGGACGTCGTGC
GCTTCGACGACGACAACAGCCCCAGCTTCATCCCAGATCAGAAGCGTGGCCAAGAAGCACCCCAAGACCTGGGTGCAC
TATATCGCCGCCGAGGAAGAGGACTGGGACTACGCCCCTCTGGTGCTGGCCCCCGACGACAGAAGCTACAAGAGCCA
GTACCTGAACAATGGCCCCCAGCGGATCGGCCGGAAGTACAAGAAAGTGCGGTTCATGGCCTACACCGACGAGACAT
TCAAGACCAGAGAGGCCATCCAGCACGAGAGCGGCATCCTGGGCCCCCTGCTGTATGGCGAAGTGGGCGACACCCTG
CTGATCATCTTCAAGAACCAGGCCAGCCGGCCCTACAACATCTACCCCCACGGCATCACCGACGTGCGGCCCCTGTA
CAGCAGACGGCTGCCCAAGGGCGTGAAGCACCTGAAGGACTTCCCCATCCTGCCCGGCGAGATCTTCAAGTACAAGT
GGACCGTGACCGTGGAAGATGGCCCCACCAAGAGCGACCCCAGATGCCTGACCCGGTACTACAGCAGCTTCGTGAAC
ATGGAACGGGACCTGGCCTCCGGGCTGATCGGCCCTCTGCTGATCTGCTACAAAGAAAGCGTGGACCAGCGGGCAA
CCAGATCATGAGCGACAAGCGGAACGTGATCCTGTTCAGCGTGTTCGATGAGAATCGGTCCTGGTACCTGACCGAGA
ATATCCAGCGGTTCCTGCCCAACCCTGCCGGCGTGCAGCTGGAAGATCCCGAGTTCCAGGCCAGCAACATCATGCAC
TCCATCAATGGCTACGTGTTCGACAGCCTCCAGCTGAGCGTGTGCCTGCACGAGGTGGCCTACTGGTACATCCTGAG
CATCGGCGCCCAGACCGACTTCCTGAGCGTGTTCTTCAGCGGCTACACCTTCAAGCACAAGATGGTGTACGAGGATA
CCCTGACCCTGTTCCCCTTCTCCGGCGAAACCGTGTTCATGAGCATGGAAAACCCCGGCCCTGTGGATTCTGGGCTGC
CACAACAGCGACTTCAGAAACCGGGGCATGACCGCCCTGCTGAAGGTGTCCAGCTGCGACAAGAACACCGGCGACTA
CTACGAGGACAGCTATGAGGACATCAGCGCCTACCTGCTGAGCAAGAACAACGCCATCGAGCCCAGATCCTTCAGCC
AGAACCCCCCGTGCTGAAGCGGCACCAGAGAGAGATCACCCGGACCACCCTGCAGTCCGACCAGGAAGAGATTGAT
TACGACGACACCATCAGCGTCGAGATGAAGAAAGAGGATTTCGACATCTACGACGAGGACGAGAACCAGAGCCCCCG
GTCCTTCCAGAAGAAAACCCGGCACTACTTCATTGCCGCCGTGGAAAGACTGTGGGACTACGGCATGAGCAGCAGCC
CCCACGTGCTGCGGAACAGAGCCCAGAGCGGCAGCGTGCCCCAGTTCAAGAAAGTGGTGTTCCAGGAGTTCACCGAC
GGCAGCTTCACCCAGCCCCTGTATCGGGGCGAGCTGAACGAGCACCTGGGACTGCTGGGACCTTACATTAGAGCCGA
GGTGGAAGATAACATCATGGTCACCTTCAGAAACCAGGCCTCCAGACCCTACAGCTTCTACAGCAGCCTGATCAGCT
ACGAAGAGGACCAGCGGCAGGGCGCCGAACCCCGGAAGAACTTCGTGAAGCCCAACGAGACTAAGACCTACTTCTGG
AAGGTGCAGCACCACATGGCCCCCACAAAGGACGAGTTCGACTGCAAGGCCTGGGCCTACTTCTCCGATGTGGACCT
GGAAAAGGACGTGCACTCTGGCCTGATTGGACCTCTGCTCGTCTGCCACACCAACACCCTGAACCCCGCCCACGGCC
GGCAGGTCACAGTGCAGGAATTTGCCCTGTTCTTCACCATCTTCGATGAGACAAAGAGCTGGTACTTCACCGAGAAC
ATGGAAAGAAACTGTAGAGCCCCCTGCAACATCCAGATGGAAGATCCTACCTTCAAAGAGAACATATCGGTTCCACGC
CATCAACGGCTACATCATGGACACACCCTGCCCGGCCTGGTCATGGCCCAGGATCAGAGAATCCGGTGGTATCTGCTGA
GCATGGGCAGCAACGAGAACATCCACAGCATCCACTTCAGCGGCCACGTGTTCACAGTGCGGAAGAAAGAAGAGTAC
AAGATGGCCCTGTACAACCTGTACCCCGGCGTGTTCGAGACAGTGGAAATGCTGCCCAGCAAGGCCGGCATCTGGCG
GGTGGAATGTCTGATCGGCGAGCATCTGCACGCCGAATGAGCACCCTGTTTCTGGTGTACAGCAACAAGTGCCAGA
CCCCTCTGGGCATGGCCAGCGGCCACATCCGGGACTTCCAGATCACCGCCTCCGGCCAGTACGGCCAGTGGGCCCCT
AAGCTGGCCCGGCTCCACTACTCCGGATCTATCAACGCCTGGTCCACCAAAGAGCCCTTCAGCTGGATCAAGGTGGA
CCTGCTGGCCCCTATGATCATCCACGGAATCAAGACCCAGGGCGCCAGACAGAAGTTCAGCAGCCTGTACATCAGCC
AGTTCATCATCATGTACAGCCTGGACGGCAAGAAGTGGCAGACCTACCGGGGCAACAGCACCGGCACCCTGATGGTG
TTCTTCGGCAACGTGGACAGCAGCGGCATCAAGCACAACATCTTCAACCCCCCCATCATTGCCCGGTACATCCGGCT
GCACCCCACCCACTACAGCATCCGGTCCACCCTGCGGATGGAACTGATGGGCTGCGACCTGAACTCTTGCAGCATGC
CCCTGGGGATGGAAAGCAAGGCCATCAGCGACGCCCAGATCACAGCCAGCAGCTACTTCACCAACATGTTCGCCACC
TGGTCCCCAAGCAAAGCCCGCCTGCATCTCCAAGGCAGAAGCAATGCCTGGCGGCCTCAGGTCAACAACCCCAAAGA
ATGGCTCCAGGTGGACTTTCAGAAAACCATGAAGGTCACAGGCGTGACCACCCAGGGCGTGAAAAGCCTGCTGACCT
CTATGTACGTGAAAGAGTTCCTGATCAGCAGCAGCCAGGACGGGCACCAGTGGACCCTGTTCTTTCAGAACGGCAAA
GTGAAAGTGTTCCAGGGCAACCAGGACTCCTTTACCCCCGTGGTCAACTCTCTAGACCCTCACTGCTGACCAGATA
CCTGAGAATCCACCCTCAGTCCTGGGTGCACCAGATTGCCCTGAGAATGGAAGTGCTGGGATGCGAGGCCCAGGATC
TGTACTGATAACTCGAGTCGACTTAATTAA
```

SEQ ID NO:2

Figure 4
4A: BDD FVIII Before Codon Optimization
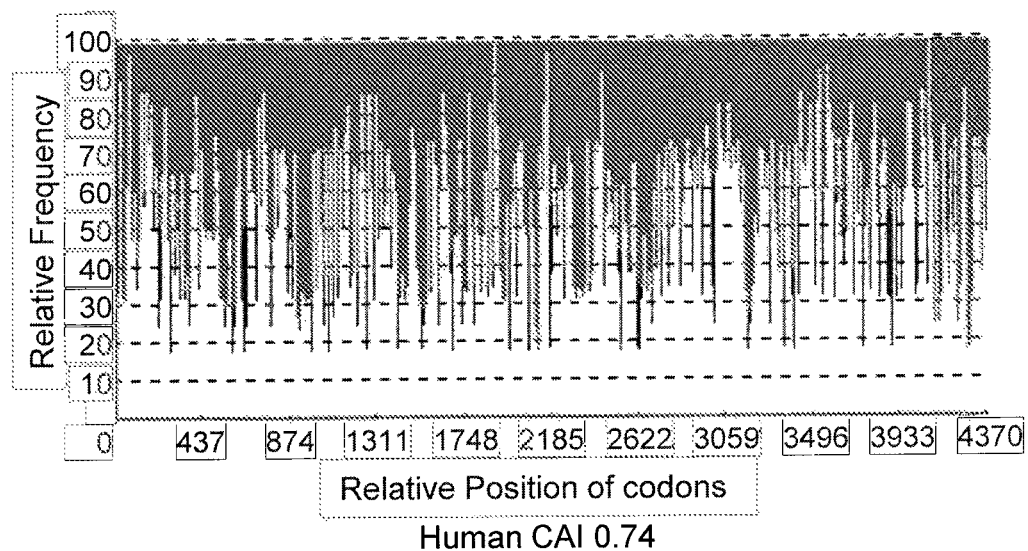
Human CAI 0.74
4B: BDD FVIII After Codon Optimization with GENESCRIPT OPTIMUMGENE™
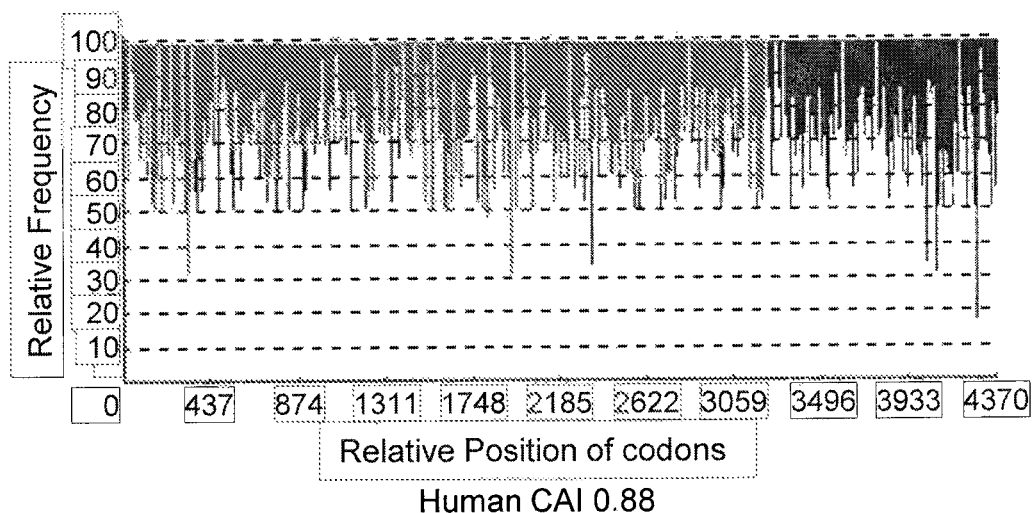
Human CAI 0.88

Figure 5
5A: BDD FVIII Frequency of Optimal Codons Before Codon Optimization
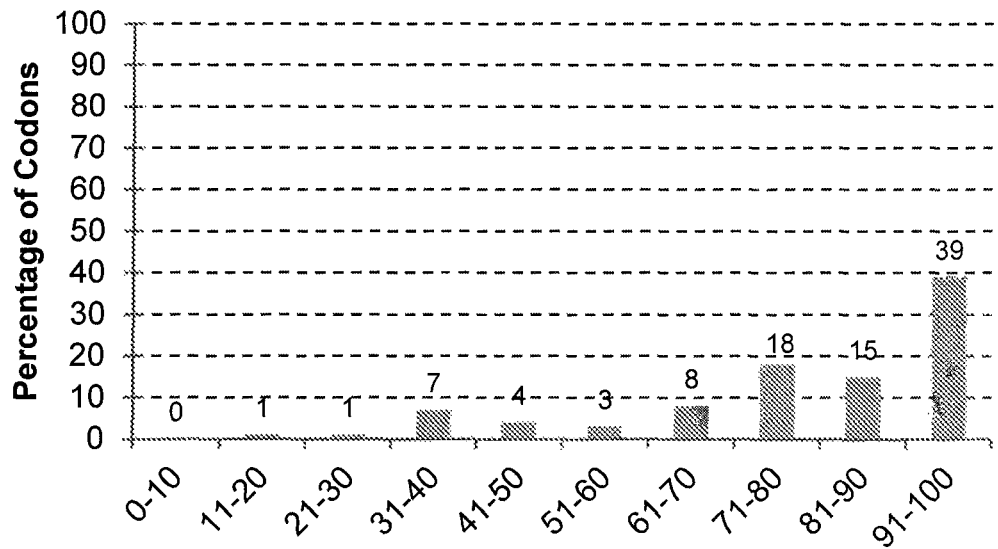
5B: BDD FVIII Frequency of Optimal Codons After Codon Optimization with GENSCRIPT OPTIMUMGENE™
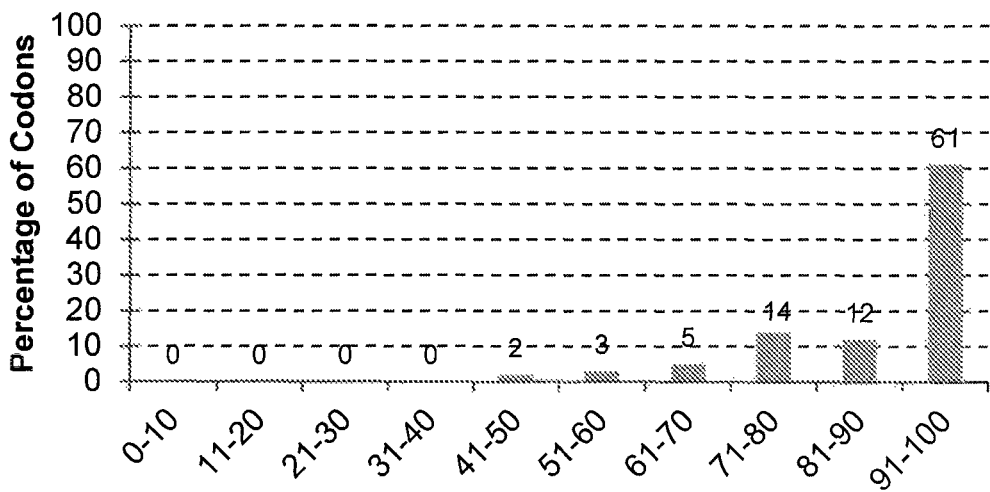

Figure 6
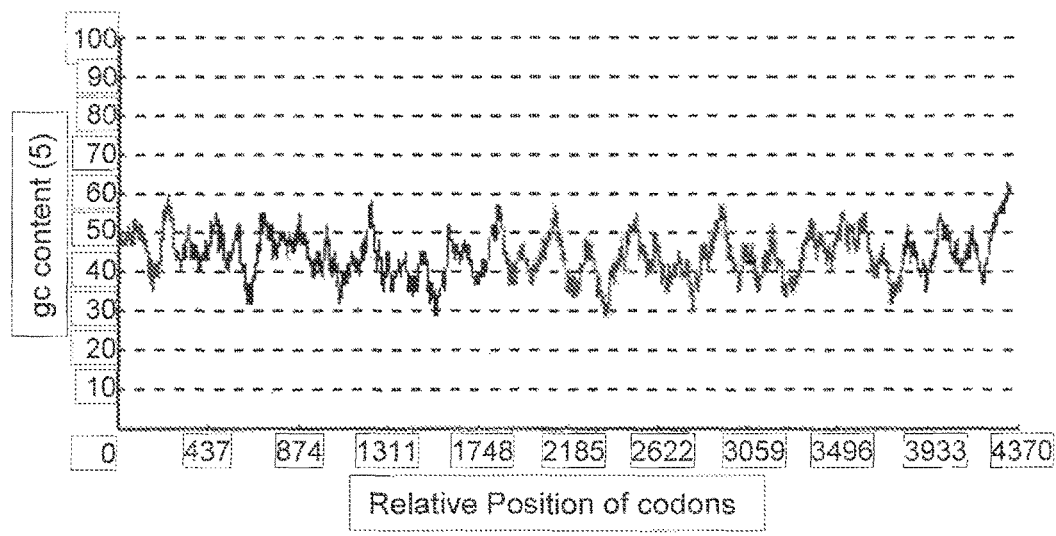
6A: BDD FVIII G/C Content Before Codon Optimization
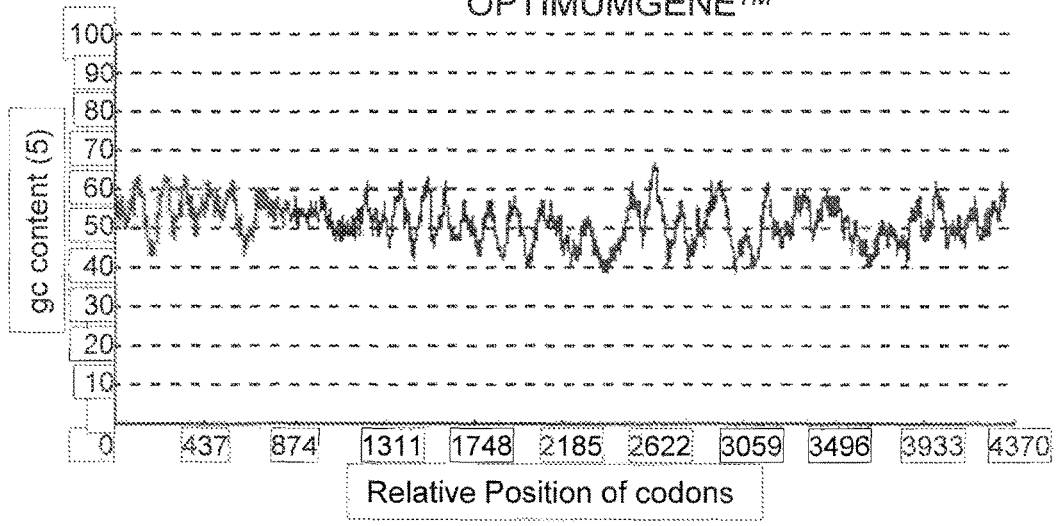
6B: BDD FVIII G/C Content After Codon Optimization with GENSCRIPT OPTIMUMGENE™

OPTIMIZED FACTOR VIII GENE

BACKGROUND OF THE INVENTION

The blood coagulation pathway, in part, involves the formation of an enzymatic complex of Factor VIIIa (FVIIIa) and Factor IXa (FIXa) (Xase complex) on the surface of platelets. FIXa is a serine protease with relatively weak catalytic activity without its cofactor FVIIIa. The Xase complex cleaves Factor X (FX) into Factor Xa (FXa), which in turn interacts with Factor Va (FVa) to cleave prothrombin and generate thrombin. Hemophilia A is a bleeding disorder caused by mutations and/or deletions in the FVIII (FVIII) gene resulting in a deficiency of FVIII activity (Peyvandi et al. 2006). In some cases, patients have reduced levels of FVIII due to the presence of FVIII inhibitors, such as anti-FVIII antibodies.

Hemophilia A is characterized by spontaneous hemorrhage and excessive bleeding. Over time, the repeated bleeding into muscles and joints, which often begins in early childhood, results in hemophilic arthropathy and irreversible joint damage. This damage is progressive and can lead to severely limited mobility of joints, muscle atrophy and chronic pain (Rodriguez-Merchan, E. C., *Semin. Thromb. Hemost.* 29:87-96 (2003), which is herein incorporated by reference in its entirety).

The disease can be treated by replacement therapy targeting restoration of FVIII activity to 1 to 5% of normal levels to prevent spontaneous bleeding (see, e.g., Mannucci, P. M., et al., *N. Engl. J. Med.* 344:1773-9 (2001), herein incorporated by reference in its entirety). There are plasma-derived and recombinant FVIII products available to treat bleeding episodes on-demand or to prevent bleeding episodes from occurring by treating prophylactically. Based on the half-life of these products (10-12 hr) (White G. C., et al., *Thromb. Haemost.* 77:660-7 (1997); Morfini, M., *Haemophilia* 9 (suppl 1):94-99; discussion 100 (2003)), treatment regimens require frequent intravenous administration, commonly two to three times weekly for prophylaxis and one to three times daily for on-demand treatment (Manco-Johnson, M. J., et al., *N. Engl. J. Med.* 357:535-544 (2007)), each of which is incorporated herein by reference in its entirety. Such frequent administration is inconvenient and costly.

A major impediment in providing a low-cost recombinant FVIII protein to patients is the high cost of commercial production. FVIII protein expresses poorly in heterologous expression systems, two to three orders of magnitude lower than similarly sized proteins. (Lynch et al., *Hum. Gene. Ther.;* 4:259-72 (1993). The poor expression of FVIII is due in part to the presence of cis-acting elements in the FVIII coding sequence that inhibit FVIII expression, such as transcriptional silencer elements (Hoeben et al., *Blood* 85:2447-2454 (1995)), matrix attachment-like sequences (MARs) (Fallux et al., *Mol. Cell. Biol.* 16:4264-4272 (1996)), and transcriptional elongation inhibitory elements (Koeberl et al., *Hum. Gene. Ther.;* 6:469-479 (1995)).

Advances in our understanding of the biology of FVIII expression has led to the development of more potent FVIII variants. For instance, biochemical studies demonstrated that the FVIII B-domain was dispensable for FVIII cofactor activity. Deletion of the B-domain resulted in a 17-fold increase in mRNA levels over full-length wild-type FVIII and a 30% increase in secreted protein. (Toole et al., *Proc Natl Acad Sci USA* 83:5939-42 (1986)). This led to the development of B domain-deleted (BDD) FVIII protein concentrate, which is now widely used in the clinic. Recent studies, however, indicate that full length and BDD hFVIII misfold in the ER lumen, resulting in activation of the unfolded protein response (UPR) and apoptosis of murine hepatocytes.

Thus, there exists a need in the art for FVIII sequences that express efficiently in heterologous systems.

SUMMARY OF THE INVENTION

The present invention provides an isolated nucleic acid molecule comprising a nucleotide sequence at least 85% identical to SEQ ID NO:1, wherein the nucleotide sequence encodes a polypeptide with Factor VIII activity. In one embodiment, the invention provides an isolated nucleic acid molecule comprising a nucleotide sequence at least 90% identical to SEQ ID NO:1. In another embodiment, the invention provides an isolated nucleic acid molecule comprising a nucleotide sequence at least 95%, at least 96%, at least 97%, at least 98%, at least 99%, or at least 100% identical to SEQ ID NO:1. In other embodiments, the invention provides an isolated nucleic acid molecule comprising SEQ ID NO:1.

The present invention also provides an isolated nucleic acid molecule comprising a nucleotide sequence at least 95%, at least 96%, at least 97%, at least 98%, at least 99%, or at least 100% identical to SEQ ID NO:2, wherein the nucleotide sequence encodes a polypeptide with Factor VIII activity. In one embodiment, the invention provides an isolated nucleic acid molecule comprising SEQ ID NO:2.

In some embodiments, the isolated nucleic acid molecule of the invention has a human codon adaptation index that is increased relative to SEQ ID NO:3. In other embodiments, the isolated nucleic acid molecule of the invention has a human codon adaptation index that is at least about 0.75, at least about 0.76, at least about 0.77, at least about 0.78 at least about 0.79, or at least about 0.80. In still other embodiments, the isolated nucleic acid molecule of the invention has a human codon adaptation index that is at least about 0.80, at least about 0.81, at least about 0.82, at least about 0.83 at least about 0.84, at least about 0.85, at least about 0.86, at least about 0.87, or at least about 0.88.

In certain embodiments, the isolated nucleic acid molecule of the invention contains a higher percentage of G/C nucleotides compared to the percentage of G/C nucleotides in SEQ ID NO:3. In other embodiments, the isolated nucleic acid molecule of the invention contains a percentage of G/C nucleotides that is at least about 45%, at least about 46%, at least about 47%, at least about 48%, at least about 49%, or at least about 50%.

In still other embodiments, the isolated nucleic acid molecule of the invention contains fewer MARS/ARS sequences (SEQ ID NOs:5 and 6) relative to SEQ ID NO:3. In yet other embodiments, the isolated nucleic acid molecule of the invention contains at most one MARS/ARS sequence. In some embodiments, the isolated nucleic acid molecule of the invention does not contain a MARS/ARS sequence.

In some embodiments, the isolated nucleic acid molecule of the invention does not contain the splice site GGTGAT (SEQ ID NO:7).

In certain embodiments the isolated nucleic acid molecule of the invention contains fewer destabilizing sequences (SEQ ID NOs:8 and 9) relative to SEQ ID NO:3. In other embodiments, the isolated nucleic acid molecule of the invention contains at most 4 destabilizing sequences. In still other embodiments, the isolated nucleic acid molecule of the invention contains at most 2 destabilizing sequences. In yet other embodiments, the isolated nucleic acid molecule of the invention does not contain a destabilizing sequence.

In other embodiments, the isolated nucleic acid molecule of the invention does not contain a poly-T sequence (SEQ ID NO:10). In yet other embodiments, the isolated nucleic acid molecule of the invention does not contain a poly-A sequence (SEQ ID NO:11).

In one embodiment, the isolated nucleic acid molecule of the invention further comprises a heterologous nucleotide sequence. For example, the heterologous nucleotide sequence can encode a heterologous amino acid sequence that is a half-life extender. In some embodiments, the heterologous amino acid sequence is an immunoglobulin constant region or a portion thereof, transferrin, albumin, albumin-binding polypeptide, an XTEN sequence, Fc, the C-terminal peptide (CTP) of the β subunit of human chorionic gonadotropin, or a PAS sequence. In other embodiments, the heterologous amino acid sequence is an Fc region or an FcRn binding partner. In still other embodiments, the heterologous amino acid sequence is linked to the N-terminus or the C-terminus of the amino acid sequence encoded by the nucleotide sequence or inserted between two amino acids in the amino acid sequence encoded by the nucleotide sequence.

In a particular embodiment, the isolated nucleic acid molecule of the invention encodes a monomer-dimer hybrid molecule comprising Factor VIII.

In another embodiment, the isolated nucleic acid molecule of the invention is operatively linked to at least one transcription control sequence.

The present invention also provides a vector comprising the nucleic acid molecule of the invention.

The present invention also provides a host cell comprising the nucleic acid molecule of the invention. In some embodiments, the host cell is selected from the group consisting of a CHO cell, a HEK293 cell, a BHK21 cell, a PER.C6 cell, a NS0 cell, and a CAP cell.

The present invention also provides a polypeptide encoded by the nucleic acid molecule of the invention or the vector of the invention or produced by the host cell of the invention.

The present invention also provides a method of producing a polypeptide with Factor VIII activity, comprising: culturing the host cell of the invention under conditions whereby a polypeptide with Factor VIII activity is produced; and, recovering the polypeptide with Factor VIII activity. In other embodiments of the method of producing a polypeptide with Factor VIII activity, the expression of the polypeptide with Factor VIII activity is increased relative to a host cell cultured under the same conditions comprising a reference nucleotide sequence comprising SEQ ID NO: 3. In other embodiments of the method, the host cell is a CHO cell. In other embodiments of the method, the host cell is a HEK293 cell.

The present invention also provides a method of increasing expression of a polypeptide with Factor VIII activity in a subject comprising administering the isolated nucleic acid molecule of the invention or the vector of the invention to a subject in need thereof, wherein the expression of the polypeptide with Factor VIII activity is increased relative to a reference nucleic acid molecule comprising SEQ ID NO 3 or the vector comprising the reference nucleic acid molecule.

The present invention also provides a method of increasing expression of a polypeptide with Factor VIII activity comprising culturing the host cell of the invention under conditions whereby a polypeptide with Factor VIII activity is expressed by the nucleic acid molecule, wherein the expression of the polypeptide with Factor VIII activity is increased relative to a host cell cultured under the same conditions comprising a reference nucleic acid sequence comprising SEQ ID NO 3.

The present invention also provides a method of improving yield of a polypeptide with Factor VIII activity comprising culturing the host cell of the invention under conditions whereby a polypeptide with Factor VIII activity is produced by the nucleic acid molecule, wherein the yield of the polypeptide with Factor VIII activity is increased relative to a host cell cultured under the same conditions comprising a reference nucleic acid sequence comprising SEQ ID NO: 3.

The present invention also provides a method of treating a bleeding disorder comprising: administering to a subject in need thereof a nucleic acid molecule of the invention, a vector of the invention, or a polypeptide of the invention. In some embodiments of the method of treating a bleeding disorder, the bleeding disorder is characterized by a deficiency in Factor VIII. In some embodiments, the bleeding disorder is hemophilia. In some embodiments, the bleeding disorder is hemophilia A.

In some embodiments of the method of treating a bleeding disorder, plasma Factor VIII activity at 24 hours post administration is increased relative to a subject administered a reference nucleic acid molecule comprising SEQ ID NO: 3, a vector comprising the reference nucleic acid molecule, or a polypeptide encoded by the reference nucleic acid molecule.

BRIEF DESCRIPTION OF THE DRAWINGS

FIG. 2 is the nucleotide sequence of BDD Factor VIII (SEQ ID NO:1), codon optimized by a first codon optimization method, described in Example 1.

FIG. 3 is the nucleotide sequence of BDD Factor VIII (SEQ ID NO:2), codon optimized by a second codon optimization method, described in Example 2.

FIGS. 4 A-B show the codon usage bias adjustment in the optimized BDD FVIII sequence (SEQ ID NO:1). FIG. 4A shows the relative frequency of codons in the BDD FVIII sequence before codon optimization. The human codon adaptation index (CAI) of the starting BDD FVIII sequence is 0.74. FIG. 4B shows the relative frequency of codons in the optimized BDD FVIII sequence (SEQ ID NO:1). The human CAI of the resulting optimized sequence is 0.88. The X-axis indicates the relative position of the codons along the length of the BDD FVIII nucleotide sequence. The Y-axis indicates the relative frequency of the codon at each position within the human genome.

FIGS. 5 A-B show the frequency of optimal human codons in the optimized BDD FVIII sequence (SEQ ID NO:1). FIG. 5A shows the frequency of optimal codons in the BDD FVIII sequence before codon optimization. FIG. 5B shows the frequency of optimal codons in the BDD FVIII sequence after codon, optimization (SEQ ID NO:1). The X-axis indicates codon frequency in the human genome. The Y-axis indicates the percentage of codons in the BDD FVIII sequence that fall into each category delineated on the X-axis.

FIGS. 6 A-B shows the G/C content of the optimized BDD FVIII sequence (SEQ ID NO:1). FIG. 6A shows the G/C content of the BDD FVIII sequence before codon optimization. The G/C content of the starting BDD FVIII sequence is 46.16%. FIG. 6B shows the G/C content of the BDD FVIII sequence after codon optimization (SEQ ID NO:1). The G/C content of the optimized BDD FVIII sequence is 51.56%. The X-axis indicates the relative position of the codons along the length of the BDD FVIII nucleotide sequence. The Y-axis indicates the percent G/C content.

DETAILED DESCRIPTION OF THE INVENTION

Figure 1:
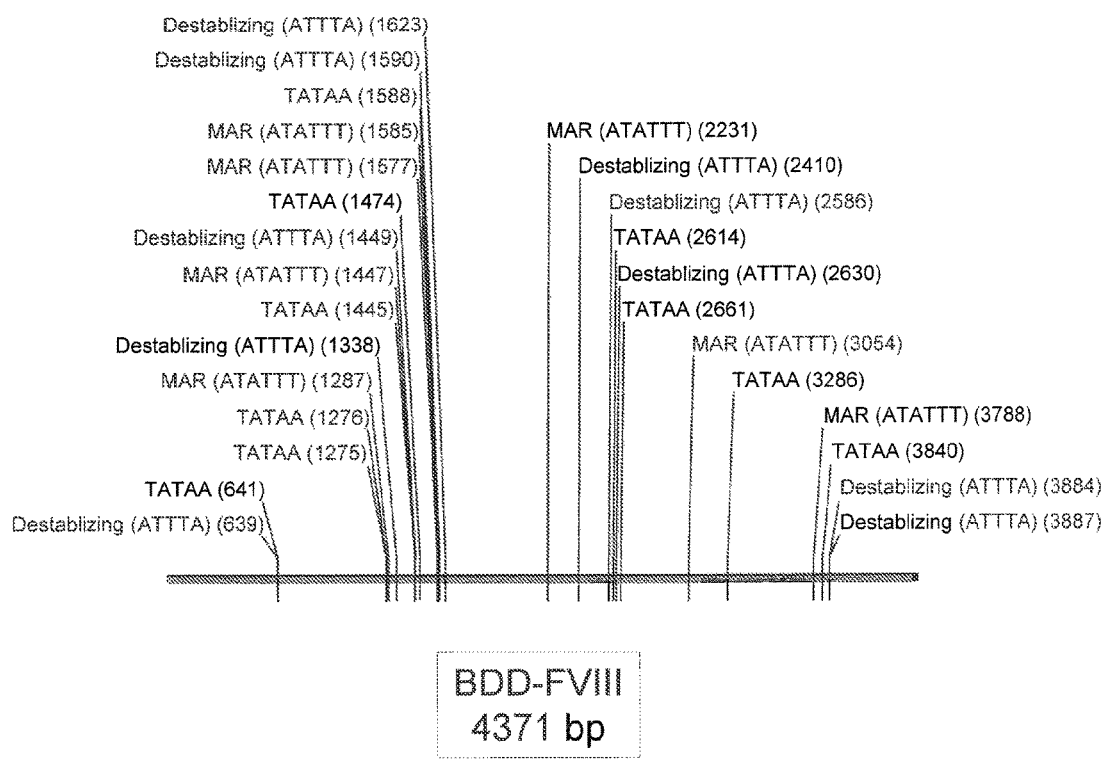
FIG. 1 is a schematic diagram showing the location of various sites in the BDD Factor VIII coding sequence. These sites were removed during the codon optimization process.

Exemplary constructs of the invention are illustrated in the accompanying Figures and sequence listing. In order to provide a clear understanding of the specification and claims, the following definitions are provided below.

I. DEFINITIONS

It is to be noted that the term "a" or "an" entity refers to one or more of that entity: for example, "a nucleotide sequence" is understood to represent one or more nucleotide sequences. As such, the terms "a" (or "an"), "one or more," and at least one can be used interchangeably herein.

The term "about" is used herein to mean approximately, roughly, around, or in the regions of. When the term "about" is used in conjunction with a numerical range, it modifies that range by extending the boundaries above and below the numerical values set forth. In general, the term "about" is used herein to modify a numerical value above and below the stated value by a variance of 10 percent, up or down (higher or lower).

The term "isolated" for the purposes of the present invention designates a biological material (cell, nucleic acid or protein) that has been removed from its original environment (the environment in which it is naturally present). For example, a polynucleotide present in the natural state in a plant or an animal is not isolated, however the same polynucleotide separated from the adjacent nucleic acids in which it is naturally present, is considered "isolated."

"Nucleic acid," "nucleic acid molecule," "oligonucleotide," and "polynucleotide" are used interchangeably and refer to the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules"), or any phosphoester analogs thereof, such as phosphorothioates and thioesters, in either single stranded form, or a double-stranded helix. Double stranded DNA-DNA, DNA-RNA and RNA-RNA helices are possible. The term nucleic acid molecule, and in particular DNA or RNA molecule, refers only to the primary and secondary structure of the molecule, and does not limit it to any particular tertiary forms. Thus, this term includes double-stranded DNA found, inter alia, in linear or circular DNA molecules (e.g., restriction fragments), plasmids, supercoiled DNA and chromosomes. In discussing the structure of particular double-stranded DNA molecules, sequences can be described herein according to the normal convention of giving only the sequence in the 5' to 3' direction along the non-transcribed strand of DNA (i.e., the strand having a sequence homologous to the mRNA). A "recombinant DNA molecule" is a DNA molecule that has undergone a molecular biological manipulation. DNA includes, but is not limited to, cDNA, genomic DNA, plasmid DNA, synthetic DNA, and semi-synthetic DNA. A "nucleic acid composition" of the invention comprises one or more nucleic acids as described herein.

As used herein, a "coding region" or "coding sequence" is a portion of polynucleotide which consists of codons translatable into amino acids. Although a "stop codon" (TAG, TGA, or TAA) is typically not translated into an amino acid, it can be considered to be part of a coding region, but any flanking sequences, for example promoters, ribosome binding sites, transcriptional terminators, introns, and the like, are not part of a coding region. The boundaries of a coding region are typically determined by a start codon at the 5' terminus, encoding the amino terminus of the resultant polypeptide, and a translation stop codon at the 3' terminus, encoding the carboxyl terminus of the resulting polypeptide. Two or more coding regions can be present in a single polynucleotide construct, e.g., on a single vector, or in separate polynucleotide constructs, e.g., on separate (different) vectors. It follows, then that a single vector can contain just a single coding region, or comprise two or more coding regions.

Certain proteins secreted by mammalian cells are associated with a secretory signal peptide which is cleaved from the mature protein once export of the growing protein chain across the rough endoplasmic reticulum has been initiated. Those of ordinary skill in the art are aware that signal peptides are generally fused to the N-terminus of the polypeptide, and are cleaved from the complete or "full-length" polypeptide to produce a secreted or "mature" form of the polypeptide. In certain embodiments, a native signal peptide or a functional derivative of that sequence that retains the ability to direct the secretion of the polypeptide that is operably associated with it. Alternatively, a heterologous mammalian signal peptide, e.g., a human tissue plasminogen activator (TPA) or mouse β-glucuronidase signal peptide, or a functional derivative thereof, can be used.

The term "downstream" refers to a nucleotide sequence that is located 3' to a reference nucleotide sequence. In certain embodiments, downstream nucleotide sequences relate to sequences that follow the starting point of transcription. For example, the translation initiation codon of a gene is located downstream of the start site of transcription.

The term "upstream" refers to a nucleotide sequence that is located 5' to a reference nucleotide sequence. In certain embodiments, upstream nucleotide sequences relate to sequences that are located on the 5' side of a coding region or starting point of transcription. For example, most promoters are located upstream of the start site of transcription.

As used herein, the term "regulatory region" refers to nucleotide sequences located upstream (5' non-coding sequences), within, or downstream (3' non-coding sequences) of a coding region, and which influence the transcription, RNA processing, stability, or translation of the associated coding region. Regulatory regions can include promoters, translation leader sequences, introns, polyadenylation recognition sequences, RNA processing sites, effector binding sites and stem-loop structures. If a coding region is intended for expression in a eukaryotic cell, a polyadenylation signal and transcription termination sequence will usually be located 3' to the coding sequence.

A polynucleotide which encodes a gene product, e.g., a polypeptide, can include a promoter and/or other transcription or translation control elements operably associated with one or more coding regions. In an operable association a coding region for a gene product, e.g., a polypeptide, is associated with one or more regulatory regions in such a way as to place expression of the gene product under the influence or control of the regulatory region(s). For example, a coding region and a promoter are "operably associated" if induction of promoter function results in the transcription of mRNA encoding the gene product encoded by the coding region, and if the nature of the linkage between the promoter and the coding region does not interfere with the ability of the promoter to direct the expression of the gene product or interfere with the ability of the DNA template to be transcribed. Other transcription control elements, besides a promoter, for example enhancers, operators, repressors, and transcription termination signals, can also be operably associated with a coding region to direct gene product expression.

"Transcriptional control sequences" refer to DNA regulatory sequences, such as promoters, enhancers, terminators, and the like, that provide for the expression of a coding sequence in a host cell. A variety of transcription control regions are known to those skilled in the art. These include, without limitation, transcription control regions which function in vertebrate cells, such as, but not limited to, promoter and enhancer segments from cytomegaloviruses (the immediate early promoter, in conjunction with intron-A), simian virus 40 (the early promoter), and retroviruses (such as Rous sarcoma virus). Other transcription control regions include those derived from vertebrate genes such as actin, heat shock protein, bovine growth hormone and rabbit β-globin, as well as other sequences capable of controlling gene expression in eukaryotic cells. Additional suitable transcription control regions include tissue-specific promoters and enhancers as well as lymphokine-inducible promoters (e.g., promoters inducible by interferons or interleukins).

Similarly, a variety of translation control elements are known to those of ordinary skill in the art. These include, but are not limited to ribosome binding sites, translation initiation and termination codons, and elements derived from picornaviruses (particularly an internal ribosome entry site, or IRES, also referred to as a CITE sequence).

The term "expression" as used herein refers to a process by which a polynucleotide produces a gene product, for example, an RNA or a polypeptide. It includes without limitation transcription of the polynucleotide into messenger RNA (mRNA), transfer RNA (tRNA), small hairpin RNA (shRNA), small interfering RNA (siRNA) or any other RNA product, and the translation of an mRNA into a polypeptide. Expression produces a "gene product." As used herein, a gene product can be either a nucleic acid, e.g., a messenger RNA produced by transcription of a gene, or a polypeptide which is translated from a transcript. Gene products described herein further include nucleic acids with post transcriptional modifications, e.g., polyadenylation or splicing, or polypeptides with post translational modifications, e.g., methylation, glycosylation, the addition of lipids, association with other protein subunits, or proteolytic cleavage. The term "yield," as used herein, refers to the amount of a polypeptide produced by the expression of a gene.

A "vector" refers to any vehicle for the cloning of and/or transfer of a nucleic acid into a host cell. A vector can be a replicon to which another nucleic acid segment can be attached so as to bring about the replication of the attached segment. A "replicon" refers to any genetic element (e.g., plasmid, phage, cosmid, chromosome, virus) that functions as an autonomous unit of replication in vivo, i.e., capable of replication under its own control. The term "vector" includes both viral and nonviral vehicles for introducing the nucleic acid into a cell in vitro, ex vivo or in vivo. A large number of vectors are known and used in the art including, for example, plasmids, modified eukaryotic viruses, or modified bacterial viruses. Insertion, of a polynucleotide into a suitable vector can be accomplished by ligating the appropriate polynucleotide fragments into a chosen vector that has complementary cohesive termini.

Vectors can be engineered to encode selectable markers or reporters that provide for the selection or identification of cells that have incorporated the vector. Expression of selectable markers or reporters allows identification and/or selection of host cells that incorporate and express other coding regions contained on the vector. Examples of selectable marker genes known and used in the art include: genes providing resistance to ampicillin, streptomycin, gentamycin, kanamycin, hygromycin, bialaphos herbicide, sulfonamide, and the like; and genes that are used as phenotypic markers, i.e., anthocyanin regulatory genes, isopentanyl transferase gene, and the like. Examples of reporters known and used in the art include: luciferase (Luc), green fluorescent protein (GFP), chloramphenicol acetyltransferase (CAT), -galactosidase (LacZ), -glucuronidase (Gus), and the like. Selectable markers can also be considered to be reporters.

The term "selectable marker" refers to an identifying factor, usually an antibiotic or chemical resistance gene, that is able to be selected for based upon the marker gene's effect, i.e., resistance to an antibiotic, resistance to a herbicide, colorimetric markers, enzymes, fluorescent markers, and the like, wherein the effect is used to track the inheritance of a nucleic acid of interest and/or to identify a cell or organism that has inherited the nucleic acid of interest. Examples of selectable marker genes known and used in the art include: genes providing resistance to ampicillin, streptomycin, gentamycin, kanamycin, hygromycin, bialaphos herbicide, sulfonamide, and the like; and genes that are used as phenotypic markers, i.e., anthocyanin regulatory genes, isopentanyl transferase gene, and the like.

The term "reporter gene" refers to a nucleic acid encoding an identifying factor that is able to be identified based upon the reporter gene's effect, wherein the effect is used to track the inheritance of a nucleic acid of interest, to identify a cell or organism that has inherited the nucleic acid of interest, and/or to measure gene expression induction or transcription. Examples of reporter genes known and used in the art include: luciferase (Luc), green fluorescent protein (GFP), chloramphenicol acetyltransferase (CAT), β-galactosidase (LacZ), β-glucuronidase (Gus), and the like. Selectable marker genes can also be considered reporter genes.

"Promoter" and "promoter sequence" are used interchangeably and refer to a DNA sequence capable of controlling the expression of a coding sequence or functional RNA. In general, a coding sequence is located 3' to a promoter sequence. Promoters can be derived in their entirety from a native gene, or be composed of different elements derived from different promoters found in nature, or even comprise synthetic DNA segments. It is understood by those skilled in the art that different, promoters can direct the expression of a gene in different tissues or cell types, or at different stages of development, or in response to different environmental or physiological conditions. Promoters that cause a gene to be expressed in most cell types at most times are commonly referred to as "constitutive promoters." Promoters that cause a gene to be expressed in a specific cell type are commonly referred to as "cell-specific promoters" or "tissue-specific promoters." Promoters that cause a gene to be expressed at a specific stage of development or cell differentiation are commonly referred to as "developmentally-specific promoters" or "cell differentiation-specific promoters." Promoters that are induced and cause a gene to be expressed following exposure or treatment of the cell with an agent, biological molecule, chemical, ligand, light, or the like that induces the promoter are commonly referred to as "inducible promoters" or "regulatable promoters." It is further recognized that since in most cases the exact boundaries of regulatory sequences have not been completely defined, DNA fragments of different lengths can have identical promoter activity.

The promoter sequence is typically bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined for example, by mapping with nuclease S1), as well as protein binding domains (consensus sequences) responsible for the binding of RNA polymerase.

The terms "restriction endonuclease" and "restriction enzyme" are used interchangeably and refer to an enzyme that binds and cuts within a specific nucleotide sequence within double stranded DNA.

The term "plasmid" refers to an extra-chromosomal element often carrying a gene that is not part of the central metabolism of the cell, and usually in the form of circular double-stranded DNA molecules. Such elements can be autonomously replicating sequences, genome integrating sequences, phage or nucleotide sequences, linear, circular, or supercoiled, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell.

Eukaryotic viral vectors that can be used include, but are not limited to, adenovirus vectors, retrovirus vectors, adeno-associated virus vectors, poxvirus, e.g., vaccinia virus vectors, baculovirus vectors, or herpesvirus vectors. Non-viral vectors include plasmids, liposomes, electrically charged lipids (cytofectins), DNA-protein complexes, and biopolymers.

A "cloning vector" refers to a "replicon," which is a unit length of a nucleic acid that replicates sequentially and which comprises an origin of replication, such as a plasmid, phage or cosmid, to which another nucleic acid segment can be attached so as to bring about the replication of the attached segment. Certain cloning vectors are capable of replication in one cell type, e.g., bacteria and expression in another, e.g., eukaryotic cells. Cloning vectors typically comprise one or more sequences that can be used for selection of cells comprising the vector and/or one or more multiple cloning sites for insertion of nucleic acid sequences of interest.

The term "expression vector" refers to a vehicle designed to enable the expression of an inserted nucleic acid sequence following insertion into a host cell. The inserted nucleic acid sequence is placed in operable association with regulatory regions as described above.

Vectors are introduced into host cells by methods well known in the art, e.g., transfection, electroporation, microinjection, transduction, cell fusion, DEAE dextran, calcium phosphate precipitation, lipofection (lysosome fusion), use of a gene gun, or a DNA vector transporter.

"Culture," "to culture" and "culturing," as used herein, means to incubate cells under in vitro conditions that allow for cell growth or division or to maintain cells in a living state. "Cultured cells," as used herein, means cells that are propagated in vitro.

As used herein, the term "polypeptide" is intended to encompass a singular "polypeptide" as well as plural "polypeptides," and refers to a molecule composed of monomers (amino acids) linearly linked by amide bonds (also known as peptide bonds). The term "polypeptide" refers to any chain or chains of two or more amino acids, and does not refer to a specific length of the product. Thus, peptides, dipeptides, tripeptides, oligopeptides, "protein," "amino acid chain," or any other term used to refer to a chain or chains of two or more amino acids, are included within the definition of "polypeptide," and the term "polypeptide" can be used instead of, or interchangeably with any of these terms. The term "polypeptide" is also intended to refer to the products of post-expression modifications of the polypeptide, including without limitation glycosylation, acetylation, phosphorylation, amidation, derivatization by known protecting/blocking groups, proteolytic cleavage, or modification by non-naturally occurring amino acids. A polypeptide can be derived from a natural biological source or produced recombinant technology, but is not necessarily translated from a designated nucleic acid sequence. It can be generated in any manner, including by chemical synthesis.

The term "amino acid" includes alanine (Ala or A); arginine (Arg or R); asparagine (Asn or N); aspartic acid (Asp or D); cysteine (Cys or C); glutamine (Gln or Q); glutamic acid (Glu or E); glycine (Gly or G); histidine (His or H); isoleucine (Ile or I): leucine (Leu or L); lysine (Lys or K); methionine (Met or M); phenylalanine (Phe or F); proline (Pro or P); serine (Ser or S); threonine (Thr or T); tryptophan (Trp or W); tyrosine (Tyr or Y); and valine (Val or V). Non-traditional amino acids are also within the scope of the invention and include norleucine, ornithine, norvaline, homoserine, and other amino acid residue analogues such as those described in Ellman et al. Meth. Enzym. 202:301-336 (1991). To generate such non-naturally occurring amino acid residues, the procedures of Noren et al. Science 244:182 (1989) and Ellman et al., supra, can be used. Briefly, these procedures involve chemically activating a suppressor tRNA with a non-naturally occurring amino acid residue followed by in vitro transcription and translation of the RNA. Introduction of the non-traditional amino acid can also be achieved using peptide chemistries known in the art. As used herein, the term "polar amino acid" includes amino acids that have net zero charge, but have non-zero partial charges in different portions of their side chains (e.g. M, F, W, S, Y, N, Q, C). These amino acids can participate in hydrophobic interactions and electrostatic interactions. As used herein, the term "charged amino acid" includes amino acids that can have non-zero net charge on their side chains (e.g. R, K, H, E, D). These amino acids can participate in hydrophobic interactions and electrostatic interactions.

An "isolated" polypeptide or a fragment, variant, or derivative thereof refers to a polypeptide that is not in its natural milieu. No particular level of purification is required. For example, an isolated polypeptide can simply be removed from its native or natural environment. Recombinantly produced polypeptides and proteins expressed in host cells are considered isolated for the purpose of the invention, as are native or recombinant polypeptides which have been separated, fractionated, or partially or substantially purified by any suitable technique.

Also included in the present invention are fragments or variants of polypeptides, and any combination thereof. The term "fragment" or "variant" when referring to polypeptide binding domains or binding molecules of the present invention include any polypeptides which retain at least some of the properties (e.g., FcRn binding affinity for an FcRn binding domain or Fc variant, coagulation activity for an FVIII variant, or FVIII binding activity for the VWF fragment) of the reference polypeptide. Fragments of polypeptides include proteolytic fragments, as well as deletion fragments, in addition to specific antibody fragments discussed elsewhere herein, but do not include the naturally occurring full-length polypeptide (or mature polypeptide). Variants of polypeptide binding domains or, binding molecules of the present invention include fragments as described above, and also polypeptides with altered amino acid sequences due to amino acid substitutions, deletions, or insertions. Variants can be naturally or non-naturally occurring. Non-naturally occurring variants can be produced using art-known mutagenesis techniques. Variant polypeptides can comprise conservative or non-conservative amino acid substitutions, deletions or additions.

A "conservative amino acid substitution" is one in which the amino acid residue is replaced with an amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, if an amino acid in a polypeptide is replaced with another amino acid from the same side chain family, the substitution is considered to be conservative. In another embodiment, a string of amino acids can be conservatively replaced with a structurally similar string that differs in order and/or composition of side chain family members.

The term "percent identity" as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case can be, as determined by the match between strings of such sequences. "Identity" can be readily calculated by known methods, including but not limited to those described in: *Computational Molecular Biology* (Lesk, A. M., ed.) Oxford University Press, New York (1988); *Biocomputing: Informatics and Genome Projects* (Smith, D. W., ed.) Academic Press, New York (1993); *Computer Analysis of Sequence Data, Part I* (Griffin, A. M., and Griffin, H. G., eds.) Humana Press, New Jersey (1994); *Sequence Analysis in Molecular Biology* (von Heinje, G., ed.) Academic Press (1987); and *Sequence Analysis Primer* (Gribskov, M. and Devereux, J., eds.) Stockton Press, New York (1991). Preferred methods to determine identity are designed to give the best match between the sequences tested. Methods to determine identity are codified in publicly available computer programs. Sequence alignments and percent identity calculations can be performed using sequence analysis software such as the Megalign program of the LASERGENE bioinformatics computing suite (DNASTAR Inc., Madison, Wis.), the GCG suite of programs (Wisconsin Package Version 9.0, Genetics Computer Group (GCG), Madison, Wis.), BLASTP, BLASTN, BLASTX (Altschul et al., *J. Mol. Biol.* 215:403 (1990)), and DNASTAR (DNASTAR, Inc. 1228 S. Park St. Madison, Wis. 53715 USA). Within the context of this application it will be understood that where sequence analysis software is used for analysis, that the results of the analysis will be based on the "default values" of the program referenced, unless otherwise specified. As used herein "default values" will mean any set of values or parameters which originally load with the software when first initialized. For the purposes of determining percent identity between an optimized BDD FVIII sequence of the invention and a reference sequence, only nucleotides in the reference sequence corresponding to nucleotides in the optimized BDD FVIII sequence of the invention are used to calculate percent identity. For example when comparing a full length FVIII nucleotide sequence containing the B domain to an optimized B domain deleted (BDD) FVIII nucleotide sequence of the invention, the portion of the alignment including the A1, A2, A3, C1, and C2 domain will be used to calculate percent identity. The nucleotides in the portion of the full length FVIII sequence encoding the B domain (which will result in a large "gap" in the alignment) will not be counted as a mismatch.

As used herein, "nucleotides corresponding to nucleotides in the optimized BDD FVIII sequence of the invention" are identified by alignment of the optimized BDD FVIII sequence of the invention to maximize the identity to the reference FVIII sequence. The number used to identify an equivalent amino acid in a reference FVIII sequence is based on the number used to identify the corresponding amino acid in the optimized BDD FVIII sequence of the invention.

A "fusion" or "chimeric" protein comprises a first amino acid, sequence linked to a second amino acid sequence with which it is not naturally linked in nature. The amino acid sequences which normally exist in separate proteins, can be brought together in the fusion polypeptide, or the amino acid sequences which normally exist in the same protein can be placed in a new arrangement in the fusion polypeptide, e.g., fusion of a Factor VIII domain of the invention with an Ig Fc domain. A fusion protein, is created, for example, by chemical synthesis, or by creating and translating a polynucleotide in which the peptide regions are encoded in the desired relationship. A chimeric protein can further comprises a second amino acid sequence associated with the first amino acid sequence by a covalent, non-peptide bond or a non-covalent bond.

As used herein, the term "half-life" refers to a biological half-life of a particular polypeptide in vivo. Half-life can be represented by the time required for half the quantity administered to a subject to be cleared from the circulation and/or other tissues in the animal. When a clearance curve of a given polypeptide is constructed as a function of time, the curve is usually biphasic with, a rapid α-phase and longer β-phase. The α-phase typically represents an equilibration of the administered Fc polypeptide between the intra- and extra-vascular space and is, in part, determined by the size of the polypeptide. The β-phase typically represents the catabolism of the polypeptide in the intravascular space. In some embodiments, FVIII and chimeric proteins comprising FVIII are monophasic, and thus do not have an alpha phase, but just the single beta phase. Therefore, in certain embodiments, the term half-life as used herein refers to the half-life of the polypeptide in the β-phase.

The term "linked" as used herein refers to a first amino acid sequence or nucleotide sequence covalently or non-covalently joined to a second amino acid sequence or nucleotide sequence, respectively. The first amino acid or nucleotide sequence can be directly joined or juxtaposed to the second amino acid or nucleotide sequence or alternatively an intervening, sequence can covalently join the first sequence to the second sequence. The term "linked" means not only a fusion of a first amino acid sequence to a second amino acid sequence at the C-terminus or the N-terminus, but also includes insertion of the whole first amino acid sequence (or the second amino acid sequence) into any two amino acids in the second amino acid sequence (or the first amino acid sequence, respectively). In one embodiment, the first amino acid sequence can be linked to a second amino acid sequence by a peptide bond or a linker. The first nucleotide sequence can be linked to a second nucleotide sequence by a phosphodiester bond or a linker. The linker can be a peptide or a polypeptide (for polypeptide chains) or a nucleotide or a nucleotide chain (for nucleotide chains) or any chemical moiety (for both polypeptide and polynucleotide chains). The term "linked" is also indicated by a hyphen (-).

As used herein the term "associated with" refers to a covalent or non-covalent bond formed between a first amino acid chain and a second amino acid chain. In one embodiment, the term "associated with" means a covalent, non-peptide bond or a non-covalent bond. This association can be indicated by a colon, i.e., (:). In another embodiment, it means a covalent bond except a peptide bond. For example, the amino acid cysteine comprises a thiol group that can form a disulfide bond or bridge with a thiol group on a second cysteine residue. In most naturally occurring IgG molecules, the CH1 and CL regions are associated by a disulfide bond and the two heavy chains are associated by two disulfide bonds at positions corresponding to 239 and 242 using the Kabat numbering system (position 226 or 229, EU numbering system). Examples of covalent bonds include, but are not limited to, a peptide bond, a metal bond, a hydrogen bond, a disulfide bond, a sigma bond, a pi bond, a delta bond, a glycosidic bond, an agnostic bond, a bent bond, a dipolar bond, a Pi backbond, a double bond, a triple bond, a quadruple bond, a quintuple bond, a sextuple bond, conjugation, hyperconjugation, aromaticity, hapticity, or antibonding. Non-limiting examples of non-covalent bond include an ionic bond (e.g., cation-pi bond or salt bond), a metal bond, an hydrogen bond (e.g., dihydrogen bond, dihydrogen complex, low-barrier hydrogen bond, or symmetric hydrogen bond), van der Walls force, London dispersion force, a mechanical bond, a halogen bond, aurophilicity, intercalation, stacking, entropic force, or chemical polarity.

The term "monomer-dimer hybrid" used herein refers to a chimeric protein comprising a first polypeptide chain and a second polypeptide chain, which are associated with each other by a disulfide bond, wherein the first chain comprises a clotting factor, e.g., Factor VIII, and a first Fc region and the second chain comprises, consists essentially of, or consists of a second Fc region without the clotting factor. The monomer-dimer hybrid construct thus is a hybrid comprising a monomer aspect having only one clotting factor and a dimer aspect having two Fc regions.

Hemostasis, as used herein, means the stopping or slowing of bleeding or hemorrhage; or the stopping or slowing of blood flow through a blood vessel or body part.

Hemostatic disorder, as used herein, means a genetically inherited or acquired condition characterized by a tendency to hemorrhage, either spontaneously or as a result of trauma, due to an impaired ability or inability to form a fibrin clot. Examples of such disorders include the hemophilias. The three main forms are hemophilia A (factor VIII deficiency), hemophilia B (factor IX deficiency or "Christmas disease") and hemophilia C (factor XI deficiency, mild bleeding tendency). Other hemostatic disorders include, e.g., von Willebrand disease, Factor XI deficiency (PTA deficiency), Factor XII deficiency, deficiencies or structural abnormalities in fibrinogen, prothrombin, Factor V, Factor VII, Factor X or factor XIII, Bernard-Soulier syndrome, which is a defect or deficiency in GPIb. GPIb, the receptor for vWF, can be defective and lead to lack of primary clot formation (primary hemostasis) and increased bleeding tendency), and thrombasthenia of Glanzman and Naegeli (Glanzmann thrombasthenia). In liver failure (acute and chronic forms), there is insufficient production of coagulation factors by the liver; this can increase bleeding risk.

The isolated nucleic acid molecules or polypeptides of the invention can be used prophylactically. As used herein the term "prophylactic treatment" refers to the administration of a molecule prior to a bleeding episode. In one embodiment, the subject in need of a general hemostatic agent is undergoing, or is about to undergo, surgery. The chimeric protein of the invention can be administered prior to or after surgery as a prophylactic. Tree chimeric protein of the invention can be administered during or after surgery to control an acute bleeding episode. The surgery can include, but is not limited to, liver transplantation, liver resection, dental procedures, or stem cell transplantation.

The isolated nucleic acid molecules and polypeptides of the invention are also used for on-demand treatment. The term "on-demand treatment" refers to the administration of an isolated nucleic acid molecule or polypeptide in response to symptoms of a bleeding episode or before an activity that can cause bleeding. In one aspect, the on-demand treatment can be given to a subject when bleeding starts, such as after an injury, or when bleeding is expected, such as before surgery. In another aspect, the on-demand treatment can be given prior to activities that increase the risk of bleeding, such as contact sports.

As used herein the term "acute bleeding" refers to a bleeding episode regardless of the underlying cause. For example, a subject can have trauma, uremia, a hereditary bleeding disorder (e.g., factor VII deficiency) a platelet disorder, or resistance owing to the development of antibodies to clotting factors.

Treat, treatment, treating, as used herein refers to, e.g., the reduction in severity of a disease or condition; the reduction in the duration of a disease course; the amelioration of one or more symptoms associated with a disease or condition; the provision of beneficial effects to a subject with a disease or condition, without necessarily curing the disease or condition, or the prophylaxis of one or more symptoms associated with a disease or condition. In one embodiment, the term "treating" or "treatment" means maintaining a FVIII trough level at least about 1 IU/dL, 2 IU/dL, 3 IU/dL, 4 IU/dL, 5 IU/dL, 6 IU/dL, 7 IU/dL, 8 IU/dL, 9 IU/dL, 10 IU/dL, 11 IU/dL, 12 IU/dL, 13 IU/dL, 14 IU/dL, 15 IU/dL, 16 IU/dL, 17 IU/dL, 18 IU/dL, 19 IU/dL, or 20 IU/dL in a subject by administering an isolated nucleic acid molecule or polypeptide of the invention. In another embodiment, treating or treatment means maintaining a FVIII trough level between about 1 and about 20 IU/dL, about 2 and about 20 IU/dL, about 3 and about 20 IU/dL, about 4 and about 20 IU/dL, about 5 and about 20 IU/dL, about 6 and about 20 IU/dL, about 7 and about 20 IU/dL, about 8 and about 20 IU/dL, about 9 and about 20 IU/dL, or about 10 and about 20 IU/dL. Treatment or treating of a disease or condition can also include maintaining FVIII activity in a subject at a level comparable to at least about 1%, 2%, 3%, 4%, 5%, 6%, 7%, 8%, 9%, 10%, 11%, 12%, 13%, 14%, 15%, 16%, 17%, 18%, 19%, or 20% of the FVIII activity in a non-hemophiliac subject. The minimum trough level required for treatment can be measured by one or more known methods and can be adjusted (increased or decreased) for each person.

"Administering," as used herein, means to give a pharmaceutically acceptable Factor VIII polypeptide of the invention to a subject via a pharmaceutically acceptable route. Routes of administration can be intravenous, e.g., intravenous injection and intravenous infusion. Additional routes of administration include, e.g., subcutaneous, intramuscular, oral, nasal, and pulmonary administration. Chimeric polypeptides and hybrid proteins can be administered as part of a pharmaceutical composition comprising at least one excipient.

As used herein, the phrase "subject in need thereof" includes subjects, such as mammalian subjects, that would benefit from administration of a nucleic acid molecule, or a polypeptide of the invention, e.g., to improve hemostasis. In one embodiment, the subjects include, but are not limited to, individuals with hemophilia. In another embodiment, the subjects include, but are not limited to, the individuals who have developed a FVIII inhibitor and thus are in need of a bypass therapy. The subject can be an adult or a minor (e.g., under 12 years old).

As used herein, the term "clotting factor," refers to molecules, or analogs thereof, naturally occurring or recombinantly produced which prevent or decrease the duration of a bleeding episode in a subject. In other words, it means molecules having pro-clotting activity, i.e., are responsible for the conversion of fibrinogen into a mesh of insoluble fibrin causing the blood to coagulate or clot. An "activatable clotting factor" is a clotting factor in an inactive form (e.g., in its zymogen form) that is capable of being converted to an active form.

Clotting activity, as used herein, means the ability to participate in a cascade of biochemical reactions that culminates in the formation of a fibrin clot and/or reduces the severity, duration or frequency of hemorrhage or bleeding episode.

As used herein the terms "heterologous" or "exogenous" refer to such molecules that are not normally found in a given context, e.g., in a cell or in a polypeptide. For example, an exogenous or heterologous molecule can be introduced into a cell and are only present after manipulation of the cell, e.g., by transfection or other forms of genetic engineering or a heterologous amino acid sequence can be present in a protein in which it is not naturally found.

As used herein, the term "heterologous nucleotide sequence" refers to a nucleotide sequence that does not naturally occur with a given polynucleotide sequence. In one embodiment, the heterologous nucleotide sequence encodes a polypeptide capable of extending the half-life of FVIII. In another embodiment, the heterologous nucleotide sequence encodes a polypeptide that increases the hydrodynamic radius of FVIII. In other embodiments, the heterologous nucleotide sequence encodes a polypeptide that improves one or more pharmacokinetic properties of FVIII without significantly affecting its biological activity or function (e.g., its procoagulant activity). In some embodiments, FVIII is linked or connected to the polypeptide encoded by the heterologous nucleotide sequence by a linker. Non-limiting examples of polypeptide moieties encoded by heterologous nucleotide sequences include an immunoglobulin constant region or a portion thereof, albumin or a fragment thereof, an albumin-binding moiety, a transferrin, the PAS polypeptides of U.S. Pat Application No. 20100292130, a HAP sequence, transferrin or a fragment thereof, the C-terminal peptide (CTP) of the β subunit of human chorionic gonadotropin, albumin-binding small molecule, an XTEN sequence, FcRn binding moieties (e.g., complete Fc regions or portions thereof which bind to FcRn), single chain Fc regions (ScFc regions, e.g., as described in US 2008/0260738, WO 2008/012543, or WO 2008/1439545), polyglycine linkers, polyserine linkers, peptides and short polypeptides of 6-40 amino acids of two types of amino acids selected from glycine (G), alanine (A), serine (S), threonine (T), glutamate (E) and proline (P) with varying degrees of secondary structure from less than 50% to greater than 50%, amongst others, or two or more combinations thereof. In some embodiments, the polypeptide encoded by the heterologous nucleotide sequence is linked to a non-polypeptide moiety. Non-limiting examples of the non-polypeptide moieties include polyethylene glycol (PEG), albumin-binding small molecules, polysialic acid, hydroxyethyl starch (HES), a derivative thereof, or any combinations thereof.

As used herein, the term "Fc region" is defined as the portion of a polypeptide which corresponds to the Fc region of native Ig, i.e., as formed by the dimeric association of the respective Fc domains of its two heavy chains. A native Fc region forms a homodimer with another Fc region. In contrast, the term "genetically-fused Fc region" or "single-chain Fc region" (scFc region), as used herein, refers to a synthetic dimeric Fc region comprised of Fc domains genetically linked within a single polypeptide chain (i.e., encoded in a single contiguous genetic sequence).

In one embodiment, the "Fc region" refers to the portion of a single Ig heavy chain beginning in the hinge region just upstream of the papain cleavage site (i.e. residue 216 in IgG, taking the first residue of heavy chain constant region to be 114) and ending at the C-terminus of the antibody. Accordingly, a complete Fc domain comprises at least a hinge domain, a CH2 domain, and a CH3 domain.

The Fc region of an Ig constant region, depending on the Ig isotype can include the CH2, CH3, and CH4 domains, as well as the hinge region. Chimeric proteins comprising an Fc region of an Ig bestow several desirable properties on a chimeric protein including increased stability, increased serum half-life (see Capon et al., 1989, *Nature* 337:525) as well as binding to Fc receptors such as the neonatal Fc receptor (FcRn) (U.S. Pat. Nos. 6,086,875, 6,485,726, 6,030,613; WO 03/077834; US2003-0235536A1), which are incorporated herein by reference in their entireties.

A "reference nucleotide sequence," when used herein as a comparison to a nucleotide sequence of the invention, is a polynucleotide sequence essentially identical to the nucleotide sequence of the invention except that the portions corresponding to FVIII sequence are not optimized. For example, the reference nucleotide sequence for a nucleic acid molecule consisting of the codon optimized BDD FVIII of SEQ ID NO:1 and a heterologous nucleotide sequence that encodes a single chain Fc region linked to SEQ ID NO:1 at its 3' end is a nucleic acid molecule consisting of the original (or "parent") BDD FVIII of SEQ ID NO:3 and the identical heterologous nucleotide sequence that encodes a single chain Fc region linked to SEQ ID NO:3 at its 3' end.

A "codon adaptation index," as used herein, refers to a measure of codon usage bias. A codon adaptation index (CAI) measures the deviation of a given protein coding gene sequence with respect to a reference set of genes (Sharp P M and Li W H, *Nucleic Acids Res.* 15(3):1281-95 (1987)). CAI is calculated by determining the geometric mean of the weight associated to each codon over the length of the gene sequence (measured in codons):

$$CAI = \exp\left(1/L\sum_{l=1}^{L}\ln(w_i(l))\right),\quad \text{(I)}$$

For each amino acid, the weight of each of its codons, in CAI, is computed as the ratio between the observed frequency of the codon (fi) and the frequency of the synonymous codon (fj) for that amino acid:

Formula 2:

$$w_i = \frac{f_i}{\max(f_j)}\quad ij \in [\text{synonymous codons for amino acid}] \quad \text{(II)}$$

As used herein, the term "optimized," with regard to nucleotide sequences, refers to a polynucleotide sequence that encodes a polypeptide, wherein the polynucleotide sequence has been mutated to enhance a property of that polynucleotide sequence. In some embodiments, the optimization is done to increase transcription levels, increase translation levels, increase steady-state mRNA levels, increase or decrease the binding of regulatory proteins such as general transcription factors, increase or decrease splicing, or increase the yield of the polypeptide produced by the polynucleotide sequence. Examples of changes that can be made to a polynucleotide sequence to optimize it include codon optimization, G/C content optimization, removal of repeat sequences, removal of AT rich elements, removal of cryptic splice sites, removal of cis-acting elements that repress transcription or translation, adding or removing poly-T or poly-A sequences, adding sequences around the transcription start site that enhance transcription, such as Kozak consensus sequences, removal of sequences that could form stem loop structures, removal of destabilizing sequences, and two or more combinations thereof.

The present invention is directed to optimized Factor VIII sequences, vectors and host cells comprising optimized Factor VIII sequences, polypeptides encoded by optimized Factor VIII sequences, and methods of producing such polypeptides. The present invention is also directed to methods of treating bleeding disorders such as hemophilia comprising administering to the subject an optimized Factor VIII nucleic acid sequence or the polypeptide encoded thereby. The present invention meets an important need in the art by providing optimized Factor VIII sequences that demonstrate increased expression in host cells, improved yield of Factor VIII protein in methods to produce recombinant Factor VIII, and potentially result in greater therapeutic efficacy when used in gene therapy methods.

In some embodiments, the present invention provides an isolated nucleic acid molecule comprising a nucleotide sequence that encodes a polypeptide with Factor VIII (FVIII) activity, wherein the nucleotide sequence is at least 85% identical to SEQ ID NO: 1. In other embodiments, the nucleotide sequence is at least 86%, at least 87%, at least 88%, at least 89%, at least 90%, at least 91%, at least 92%, at least 93%, at least 94%, at least 95%, at least 96%, at least 97%, at least 98%, or at least 99% identical to SEQ ID NO:1 and encodes a polypeptide with FVIII activity. In still other embodiments, the nucleotide sequence comprises SEQ ID NO:1.

In some embodiments, the present invention provides an isolated nucleic acid molecule comprising a nucleotide sequence that encodes a polypeptide with FVIII activity, wherein the nucleotide sequence is at least 95% identical to SEQ ID NO:2. In other embodiments, the nucleotide sequence is at least 96%, at least 97%, at least 98%, or at least 99% identical to SEQ ID NO:2 and encodes a polypeptide with FVIII activity. In still other embodiments, the nucleotide sequence comprises SEQ ID NO:2.

SEQ ID NOs:1 and 2 are optimized versions of SEQ ID NO:3, the starting or "parental" FVIII nucleotide sequence. SEQ ID NO:3 encodes a B domain-deleted human FVIII. While SEQ ID NOs:1 and 2 are derived from a specific B domain-deleted form of FVIII (SEQ ID NO:3), it is to be understood that the present invention is also directed to optimized versions of nucleic acids encoding other versions of FVIII. For example, other version of FVIII can include full length FVIII, other B-domain deletions of FVIII (described below), or other fragments of FVIII that retain FVIII activity.

"A polypeptide with FVIII activity" as used herein means a functional FVIII polypeptide in its normal role in coagulation, unless otherwise specified. The term a polypeptide with FVIII activity includes a functional fragment, variant, analog, or derivative thereof that retains the function of full-length wild-type Factor VIII in the coagulation pathway. "A polypeptide with FVIII activity" is used interchangeably with FVIII protein, FVIII polypeptide, or FVIII. Examples of FVIII functions include, but are not limited to, an ability to activate coagulation, an ability to act as a cofactor for factor IX, or an ability to form a tenase complex with factor IX in the presence of $Ca^{2+}$ and phospholipids, which then converts Factor X to the activated form Xa. In one embodiment, a polypeptide having FVIII activity comprises two polypeptide chains, the first chain having the FVIII heavy chain and the second chain having the FVIII light chain. In another embodiment, the polypeptide having FVIII activity is single chain FVIII. Single chain FVIII can contain one or more mutation or substitutions at amino acid residue 1645 and/or 1648 corresponding to mature FVIII sequence. See International Application No. PCT/US2012/045784, incorporated herein by reference in its entirety. The FVIII protein can be the human, porcine, canine, rat, or murine FVIII protein. In addition, comparisons between FVIII from humans and other species have identified conserved residues that are likely to be required for function (Cameron et al., Thromb. Haemost. 79:317-22 (1998); U.S. Pat. No. 6,251, 632).

The "B domain" of FVIII, as used herein, is the same as the B domain known in the art that is defined by internal amino acid sequence identity and sites of proteolytic cleavage by thrombin, e.g., residues Ser741-Arg1648 of full length human FVIII. The other human FVIII domains are defined by the following amino acid residues: A1, residues Ala1-Arg372; A2, residues Ser373-Arg740; A3, residues Ser1690-Ile2032; C1, residues Arg2033-Asn2172; C2, residues Ser2173-Tyr2332. The A3-C1-C2 sequence includes residues Ser1690-Tyr2332. The remaining sequence, residues Glu1649-Arg1689, is usually referred to as the FVIII light chain activation peptide. The locations of the boundaries for all of the domains, including the B domains, for porcine, mouse and canine FVIII are also known in the art. An example of a BDD FVIII is REFACTO® recombinant BDD FVIII (Wyeth Pharmaceuticals, Inc.).

A "B domain deleted FVIII" can have the full or partial deletions disclosed in U.S. Pat. Nos. 6,316,226, 6,346,513, 7,041,635, 5,789,203, 6,060,447, 5,595,886, 6,228,620, 5,972,885, 6,048,720, 5,543,502, 5,610,278, 5,171,844, 5,112,950, 4,868,112, and 6,458,563, each of which is incorporated herein by reference in its entirety. In some embodiments, a B domain deleted FVIII sequence of the present invention comprises any one of the deletions disclosed at col. 4, line 4 to col. 5, line 28 and examples 1-5 of U.S. Pat. No. 6,316,226 (also in U.S. Pat. No. 6,346,513). In some embodiments, a B domain deleted FVIII of the present invention has a deletion disclosed at col. 2, lines 26-51 and examples 5-8 of U.S. Pat. No. 5,789,203 (also U.S. Pat. Nos. 6,060,447, 5,595,886, and 6,228,620). In some embodiments, a B domain deleted FVIII has a deletion described in col. 1, lines 25 to col. 2, line 40 of U.S. Pat. No. 5,972,885; col. 6, lines 1-22 and example 1 of U.S. Pat. No. 6,048,720; col. 2, lines 17-46 of U.S. Pat. No. 5,543,502; col. 4, line 22 to col. 5, line 36 of U.S. Pat. No. 5,171,844; col. 2, lines 55-68, FIG. 2, and example 1 of U.S. Pat. No. 5,112,950; col. 2, line 2 to col. 19, line 21 and table 2 of U.S. Pat. No. 4,868,112; col. 2, line 1 to col. 3, line 19, col. 3, line 40 to col. 4, line 67, col. 7, line 43 to col. 8, line 26, and col. 11, line 5 to col. 13, line 39 of U.S. Pat. No. 7,041,635; or col. 4, lines 25-53, of U.S. Pat. No. 6,458,563. In some embodiments, a B domain deleted FVIII has a deletion of most of the B domain, but still contains amino-terminal sequences of the B domain that are essential for in vivo proteolytic processing of the primary translation product into two polypeptide chain, as disclosed in WO 91/09122, which is incorporated herein by reference in its entirety. In some embodiments, a B domain deleted FVIII is constructed with a deletion of amino acids 747-1638, i.e., virtually a complete deletion of the B domain. Hoeben R. C., et al. *J. Biol. Chem.* 265 (13): 7318-7323 (1990), incorporated herein by reference in its entirety. A B domain deleted FVIII can also contain a deletion of amino acids 771-1666 or amino acids 868-1562 of FVIII. Meulien P., et al. *Protein Eng.* 2(4): 301-6 (1988), incorporated herein by reference in its entirety. Additional B domain deletions that are part of the invention include, e.g.: deletion of amino acids 982 through 1562 or 760 through 1639 (Toole et al., Proc. Natl. Acad. Sci. U.S.A. (1986) 83, 5939-5942)), 797 through 1562 (Eaton, et al. Biochemistry (1986) 25:8343-8347)), 741 through 1646 (Kaufman (PCT published application No. WO 87/04187)), 747-1560 (Sarver, et al., DNA (1987) 6:553-564)), 741 through 1648 (Pasek (PCT application No. 88/00831)), 816 through 1598 or 741 through 1689 (Lagner (Behring Inst. Mitt. (1988) No 82:16-25, EP 295597)), each of which is incorporated herein by reference in its entirety. Each of the foregoing deletions can be made in any FVIII sequence.

A number of functional FVIII molecules, including B-domain deletions, are disclosed in the following U.S. Pat. Nos. 6,316,226 and 6,346,513, both assigned to Baxter; U.S. Pat. No. 7,041,635 assigned to In2Gen; U.S. Pat. Nos. 5,789,203, 6,060,447, 5,595,886, and 6,228,620 assigned to Chiron; U.S. Pat. Nos. 5,972,885 and 6,048,720 assigned to Biovitrum, U.S. Pat. Nos. 5,543,502 and 5,610,278 assigned to Novo Nordisk; U.S. Pat. No. 5,171,844 assigned to Immuno Ag; U.S. Pat. No. 5,112,950 assigned to Transgene S. A.; U.S. Pat. No. 4,868,112 assigned to Genetics Institute, each of which is incorporated herein by reference in its entirety.

Codon Optimization

In one embodiment, the present invention provides an isolated nucleic acid molecule comprising a nucleotide sequence that encodes a polypeptide with FVIII activity, wherein the nucleic acid sequence has been codon optimized. In another embodiment, the starting nucleic acid sequence that encodes a polypeptide with FVIII activity and that is subject to codon optimization is SEQ ID NO:3. In some embodiments, the sequence that encodes a polypeptide with FVIII activity is codon optimized for human expression. In other embodiments, the sequence that encodes a polypeptide with FVIII activity is codon optimized for murine expression. SEQ ID NOs:1 and 2 are codon optimized versions of SEQ ID NO:3, optimized for human expression.

The term "codon-optimized" as it refers to genes or coding regions of nucleic acid molecules for transformation of various hosts, refers to the alteration of codons in the gene or coding regions of the nucleic acid molecules to reflect the typical codon usage of the host organism without altering the polypeptide encoded by the DNA. Such optimization includes replacing at least one, or more than one, or a significant number, of codons with one or more codons that are more frequently used in the genes of that organism.

Deviations in the nucleotide sequence that comprises the codons encoding the amino acids of, any polypeptide chain allow for variations in the sequence coding for the gene. Since each codon consists of three nucleotides, and the nucleotides comprising DNA are restricted to four specific bases, there are 64 possible combinations of nucleotides, 61 of which encode amino acids (the remaining three codons encode signals ending translation). The "genetic code" which shows which codons encode which amino acids is reproduced herein as Table 1. As a result, many amino acids are designated by more than one codon. For example, the amino acids alanine and proline are coded for by four triplets, serine and arginine by six, whereas tryptophan and methionine are coded by just one triplet. This degeneracy allows for DNA base composition to vary over a wide range without altering the amino acid sequence, of the proteins encoded by the DNA.

TABLE 1

The Standard Genetic Code

| | T | C | A | G |
|---|---|---|---|---|
| T | TTT Phe (F) | TCT Ser (S) | TAT Tyr (Y) | TGT Cys (C) |
| | TTC Phe (F) | TCC Ser (S) | TAC Tyr (Y) | TGC |
| | TTA Leu (L) | TCA Ser (S) | TAA Stop | TGA Stop |
| | TTG Leu (L) | TCG Ser (S) | TAG Stop | TGG Trp (W) |
| C | CTT Leu (L) | CCT Pro (P) | CAT His (H) | CGT Arg (R) |
| | CTC Leu (L) | CCC Pro (P) | CAC His (H) | CGC Arg (R) |
| | CTA Leu (L) | CCA Pro (P) | CAA Gln (Q) | CGA Arg (R) |
| | CTG Leu (L) | CCG Pro (P) | CAG Gln (Q) | CGG Arg (R) |
| A | ATT Ile (I) | ACT Thr (T) | AAT Asn (N) | AGT Ser (S) |
| | ATC Ile (I) | ACC Thr (T) | AAC Asn (N) | AGC Ser (S) |
| | ATA Ile (I) | ACA Thr (T) | AAA Lys (K) | AGA Arg (R) |
| | ATG Met (M) | ACG Thr (T) | AAG Lys (K) | AGG Arg (R) |
| G | GTT Val (V) | GCT Ala (A) | GAT Asp (D) | GGT Gly (G) |
| | GTC Val (V) | GCC Ala (A) | GAC Asp (D) | GGC Gly (G) |
| | GTA Val (V) | GCA Ala (A) | GAA Glu (E) | GGA Gly (G) |
| | GTG Val (V) | GCG Ala (A) | GAG Glu (E) | GGG Gly (G) |

Many organisms display a bias for use of particular codons to code for insertion of a particular amino acid in a growing peptide chain. Codon preference, or codon bias, differences in codon usage between organisms, is afforded by degeneracy of the genetic code, and is well documented among many organisms. Codon bias often correlates with the efficiency of translation of messenger RNA (mRNA), which is in turn believed to be dependent on, inter alia, the properties of the codons being, translated and the availability of particular transfer RNA (tRNA) molecules. The predominance of selected tRNAs in a cell is generally a reflection of the codons used most frequently in peptide synthesis. Accordingly, genes can be tailored for optimal gene expression in a given organism based on codon optimization.

Given the large number of gene sequences available for a wide variety of animal, plant and microbial species, the relative frequencies of codon usage have been calculated. Codon usage tables are available, for example, at the "Codon Usage Database" available at www.kazusa.or.jp/codon/ (visited Jun. 18, 2012). See Nakamura, Y., et al. Nucl. Acids Res. 28:292 (2000).

Randomly assigning codons at an optimized frequency to encode a given polypeptide sequence can be done manually by calculating codon frequencies for each amino acid, and then assigning the codons to the polypeptide sequence randomly. Additionally, various algorithms and computer software programs can be used to calculate an optimal sequence.

In one embodiment, the present invention provides an isolated nucleic acid molecule comprising a nucleotide sequence that encodes a polypeptide with FVIII activity, wherein the nucleotide sequence is at least 85% identical to SEQ ID NO:1, and wherein the human codon adaptation index is increased relative to SEQ ID NO:3. For example, the nucleotide sequence that encodes a polypeptide with FVIII activity and that is at least 85% identical to SEQ ID NO:1 can have a human codon adaptation index that is at least about 0.75, at least about 0.76, at least about 0.77, at least about 0.78, at least about 0.79, at, least about 0.80, at least about 0.81, at least about 0.82, at least about 0.83, at least about 0.84, at least about 0.85, at least about 0.86, at least about 0.87, at least about 0.88, at least about 0.89, or at least about 0.90.

In another embodiment, the present invention provides an isolated nucleic acid molecule comprising a nucleotide sequence that encodes a polypeptide with Factor VIII (FVIII) activity, wherein the nucleotide sequence is at least 95% identical to SEQ ID NO:2, and wherein the human codon adaptation index is increased relative to SEQ ID NO:3. For example, the nucleotide sequence that encodes a polypeptide with FVIII activity and that is at least 85% identical to SEQ ID NO:2 can have a human codon adaptation index that is at least about 0.75, at least about 0.76, at least about 0.77, at least about 0.78, at least about 0.79, at least about 0.80, at least about 0.81 at least about 0.82, at least about 0.83, at least about 0.84, at least about 0.85, at least about 0.86, at least about 0.87, at least about 0.88, at least about 0.89, or at least about 0.90.

In other embodiments, the present invention provides an isolated nucleic acid molecule comprising a nucleotide sequence that encodes a polypeptide with Factor VIII activity, wherein the nucleotide sequence is at least 85% identical to SEQ ID NO:1 and has one or more of the following characteristics: (1) the nucleotide sequence contains a higher percentage of G/C nucleotides compared to SEQ ID NO:3, (2) the nucleotide sequence contains fewer MARS/ARS sequences compared to SEQ ID NO:3, (3) the nucleotide sequence does not contain the splice site GGTGAT, (4) the nucleotide sequence contains fewer destabilizing elements, (5) the nucleotide sequence does not contain a poly-T sequence, (6) the nucleotide sequence does not contain a poly-A sequence, (7) the nucleotide sequence has a codon adaptation index that is increased relative to SEQ ID NO:3, or a combination of two or more such characteristics. In a particular embodiment, the nucleotide sequence contains all of the characteristics (1) to (6).

In other embodiments, the present invention provides an isolated nucleic acid molecule comprising a nucleotide sequence that encodes a polypeptide with Factor VIII activity, wherein the nucleotide sequence is at least 95% identical to SEQ ID NO:2 and has one or more of the following characteristics: (1) the nucleotide sequence contains a higher percentage of G/C nucleotides compared to SEQ ID NO:3, (2) the nucleotide sequence contains fewer MARS/ARS sequences, (3) the nucleotide sequence does not contain the splice site GGTGAT, (4) the nucleotide sequence contains fewer destabilizing elements, (5) the nucleotide sequence does not contain a poly-T sequence, (6) the nucleotide sequence does not contain a poly-A, sequence, (7) the nucleotide sequence has a codon adaptation index that is increased relative to SEQ ID NO:3, or a combination of two or more such characteristics. In a particular embodiment, the nucleotide sequence contains all of the character (1) to (6).

G/C Content Optimization

In some embodiments, the present invention provides an isolated nucleic acid molecule comprising a nucleotide sequence that encodes a polypeptide with FVIII activity, wherein the nucleotide sequence is at least 85% identical to SEQ ID NO:1, and wherein the nucleotide sequence contains a higher percentage of G/C nucleotides compared to the percentage of G/C nucleotides in SEQ ID NO:3. In other embodiments, the nucleotide sequence that encodes a polypeptide with FVIII activity and that is at least 85% identical to SEQ ID NO:1 has a G/C content that is at least about 45%, at least about 46%, at least about 47%, at least about 48%, at least about 49%, at least about 50%, at least about 51%, at least about 52%, at least about 53%, at least about 54%, or at least about 55%.

In some embodiments, the present invention provides an isolated nucleic acid molecule comprising a nucleotide sequence that encodes a polypeptide with FVIII activity, wherein the nucleotide sequence is at least 95% identical to SEQ ID NO:2, and wherein the nucleotide sequence contains a higher percentage of G/C nucleotides compared to the percentage of G/C nucleotides in SEQ ID NO:3. In other embodiments, the nucleotide sequence that encodes a polypeptide with FVIII activity and that is at least 95% identical to SEQ ID NO:2 has a G/C content that is at least about 45%, at least about 46%, at least about 47%, at least about 48%, at least about 49%, at least about 50%, at least about 51%, at least about 52%, at least about 53%, at least about 54%, or at least about 55%.

"G/C content" (or guanine-cytosine content), or "percentage of G/C nucleotides," refers to the percentage of nitrogenous bases in a DNA molecule that are either guanine or cytosine. G/C content can be calculated using the following formula:

$$\frac{G+C}{A+T+G+C} \times 100 \tag{III}$$

Human genes are highly, heterogeneous in their G/C content, with some genes having a G/C content as low as 20%, and other genes having a G/C content as high as 95%. In general, G/C rich genes are more highly expressed. In fact, it has been demonstrated that increasing the G/C content of a gene can lead to increased expression of the gene, due mostly to an increase in transcription and higher steady state mRNA levels. See Kudla et al., PLoS Biol., 4(6): e180 (2006).

Matrix Attachment Region-Like Sequences

In some embodiments, the present invention provides an isolated nucleic acid molecule comprising a nucleotide sequence that encodes a polypeptide with FVIII activity, wherein the nucleotide sequence is at least 85% identical to SEQ ID NO:1, and wherein the nucleotide sequence contains fewer MARS/ARS sequences relative to SEQ ID NO:3. In other embodiments, the nucleotide sequence that encodes a polypeptide with FVIII activity and that is at least 85% identical to SEQ ID NO:1 contains at most 6, at most 5, at most 4, at most 3, or at most 2 MARS/ARS sequences. In other embodiments, the nucleotide sequence that encodes a polypeptide with FVIII activity and that is at least 85% identical to SEQ ID NO:1 contains at most 1 MARS/ARS sequence. In yet other embodiments, the nucleotide sequence that encodes a polypeptide with FVIII activity and that is at least 85% identical to SEQ ID NO:1 does not contain a MARS/ARS sequence.

In some embodiments, the present invention provides an isolated nucleic acid molecule comprising a nucleotide sequence that encodes a polypeptide with FVIII activity, wherein the nucleotide sequence is at least 95% identical to SEQ ID NO:2, and wherein the nucleotide sequence contains fewer MARS/ARS sequences relative to SEQ ID NO:3. In, other embodiments, the nucleotide sequence that encodes a polypeptide with FVIII activity and that is at least 95% identical to SEQ ID NO:2 contains at most 6, at most 5, at most 4, at most 3, or at most 2 MARS/ARS sequences. In other embodiments, the nucleotide sequence that encodes a polypeptide with FVIII activity and that is at least 95% identical to SEQ ID NO:2 contains at most 1 MARS/ARS sequence. In yet other embodiments, the nucleotide sequence that encodes a polypeptide with FVIII activity and that is at least 95% identical to SEQ ID NO:2 does not contain a MARS/ARS sequence.

AT-rich elements in the human FVIII nucleotide sequence that share sequence similarity with *Saccharomyces cerevisiae* autonomously replicating sequences (ARSs) and nuclear-matrix attachment regions (MARs) have been identified. (Fallux et al., *Mol. Cell. Biol.* 16:4264-4272 (1996). One of these elements has been demonstrated to bind nuclear factors in vitro and to repress the expression of a chloramphenicol acetyltransferase (CAT) reporter gene. Id. It has been hypothesized that these sequences can contribute to the transcriptional repression of the human FVIII gene. Thus, in one embodiment, all MAR/ARS sequences are abolished in the FVIII gene of the present invention. There are four MAR/ARS ATATTT sequences (SEQ ID NO:5) and three MAR/ARS AAATAT sequences (SEQ ID NO:6) in the parental FVIII sequence (SEQ ID NO:3). All of these sites were mutated to destroy the MAR/ARS sequences in the optimized FVIII sequences (SEQ ID NO:1 and SEQ ID NO:2). The location, of each of these elements, and the sequence of the corresponding nucleotides in the optimized sequences are shown in Table 2, below.

TABLE 2

Summary of Changes to Repressive Elements

| Location of Element | Starting BDD FVIII Sequence (SEQ ID NO: 3) | Optimized BDD FVIII Sequence (SEQ ID NO: 1) | Optimized BDD FVIII Sequence (SEQ ID NO: 2) |
|---|---|---|---|
| Destabilizing Sequences | | | |
| 639 | ATTTA | GTTCA | GTTCA |
| 1338 | ATTTA | GTTCA | GTTCA |
| 1449 | ATTTA | TTTCA | CTTCA |
| 1590 | TAAAT | CAAGT | CAAGT |
| 1623 | TAAAT | TAAGA | CAAGA |
| 2410 | ATTTA | ATCTA | ATCTA |
| 2586 | ATTTA | GTTTA | GTTCA |
| 2630 | TAAAT | TGAAC | TGAAC |
| 3884 | ATTTA | ATCTG | ACCTG |
| 3887 | TAAAT | TGAAC | TGAAC |
| Potential Promoter Binding Sites | | | |
| 641 | TTATA | TCATT | TCATC |
| 1275 | TATAA | TACAA | TACAA |
| 1276 | TTATA | CTACA | CTACA |
| 1445 | TTATA | TCATT | TCATC |
| 1474 | TATAA | TACAA | TACAA |
| 1588 | TATAA | TACAA | TACAA |
| 2614 | TTATA | CTGTA | CTGTA |
| 2661 | TATAA | TATCA | CATTA |
| 3286 | TATAA | TACAA | TACAA |
| 3840 | TTATA | TTATT | CTACA |

TABLE 2 -continued

Summary of Changes to Repressive Elements

| Location of Element | Starting BDD FVIII Sequence (SEQ ID NO: 3) | Optimized BDD FVIII Sequence (SEQ ID NO: 1) | Optimized BDD FVIII Sequence (SEQ ID NO: 2) |
|---|---|---|---|
| Matrix Attachment-Like Sequences (MARS/ARS) | | | |
| 1287 | ATATTT | GTATCT | GTACCT |
| 1447 | ATATTT | ATTTTC | ATCTTC |
| 1577 | AAATAT | AAATCT | AGATCT |
| 1585 | AAATAT | AAGTAC | AAGTAC |
| 2231 | ATATTT | ACATCA | ACATCA |
| 3054 | AAATAT | AAACAT | GAACAT |
| 3788 | ATATTT | ACATTT | ACATCT |
| AU Rich Sequence Elements (AREs) | | | |
| 2468 | ATTTTATT | ACTTTATT | ACTTCATT |
| 3790 | ATTTTTAA | ATTTTCAA | ATCTTCAA |
| Poly A/Poly T Sequences | | | |
| 3273 | AAAAAAA | GAAGAAA | GAAGAAA |
| 4195 | TTTTTT | TTCTTT | TTCTTT |
| Splice Sites | | | |
| 2203 | GGTGAT | GGGGAC | GGCGAC |

Destabilizing Sequences

In some embodiments, the present invention provides an isolated nucleic acid molecule comprising a nucleotide sequence that encodes a polypeptide with FVIII activity, wherein the nucleotide sequence is at least 85% identical to SEQ ID NO:1, and wherein the nucleotide sequence contains fewer destabilizing elements relative to SEQ ID NO:3. In other embodiments, the nucleotide sequence that encodes a polypeptide with FVIII activity and that is at least 85% identical to SEQ ID NO:1 contains at most 9, at most 8, at most 7, at most 6, or at most 5 destabilizing elements. In other embodiments, the nucleotide sequence that encodes a polypeptide with FVIII activity and that is at least 85% identical to SEQ ID NO:1 contains at most 4, at most 3, at most 2, or at most 1 destabilizing elements. In yet other embodiments, the nucleotide sequence that encodes a polypeptide with FVIII activity and that is at least 85% identical to SEQ ID NO:1 does not contain a destabilizing element.

In some embodiments, the present invention provides an isolated nucleic acid molecule comprising a nucleotide sequence that encodes a polypeptide with FVIII activity, wherein the nucleotide sequence is at least 95% identical to SEQ ID NO:2, and wherein the nucleotide sequence contains fewer destabilizing elements relative to SEQ ID NO:3. In other embodiments, the nucleotide sequence that encodes a polypeptide with FVIII activity and that is at least 95% identical to SEQ ID NO:2 contains at most 9, at most 8, at most 7, at most 6, or at most 5 destabilizing elements. In other embodiments, the nucleotide sequence that encodes a polypeptide with FVIII activity and that is at least 95% identical to SEQ ID NO:2 contains at most 4, at most 3, at most 2, or at most 1 destabilizing elements. In yet other embodiments, the nucleotide sequence that encodes a polypeptide with FVIII activity and that is at least 95% identical to SEQ ID NO:2 does not contain a destabilizing element.

There are ten destabilizing elements in the parental FVIII sequence (SEQ ID NO:3); six ATTTA sequences (SEQ ID NO:8) and four TAAAT sequences (SEQ ID NO:9). In one embodiment, sequences of these sites were mutated to destroy the destabilizing elements in optimized FVIII SEQ ID NO:1 and SEQ ID NO:2. The location of each of these elements, and the sequence of the corresponding nucleotides in the optimized sequences are shown in Table 2.

Potential Promoter Binding Sites

In some embodiments, the present invention provides an isolated nucleic acid molecule comprising a nucleotide sequence that encodes a polypeptide with FVIII activity, wherein the nucleotide sequence is at least 85%, at least 90%, at least 95%, at least 96%, at least 97%, at least 98%, at least 99%, or 100% identical to SEQ ID NO:1, and wherein the nucleotide sequence contains fewer potential promoter binding sites relative to SEQ ID NO:3. In other embodiments, the nucleotide sequence that encodes a polypeptide with FVIII activity and that is at least 85%, at least 90%, at least 95%, at least 96%, at least 97%, at least 98%, at least 99%, or 100% identical to SEQ ID NO:1 contains at most 9, at most 8, at most 7, at most 6, or at most 5 potential promoter binding sites. In other embodiments, the nucleotide sequence that encodes a polypeptide with FVIII activity and that is at least 85%, at least 90%, at least 95%, at least 96%, at least 97%, at least 98%, at least 99%, or 100% identical to SEQ ID NO:1 contains at most 4, at most 3, at most 2, or at most 1 potential promoter binding sites. In yet other embodiments, the nucleotide sequence that encodes a polypeptide with FVIII activity and that is at least 85%, at least 90%, at least 95%, at least 96%, at least 97%, at least 98%, at least 99%, or 100% identical to SEQ ID NO:1 does not contain a potential promoter binding site.

In some embodiments, the present invention provides an isolated nucleic acid molecule comprising a nucleotide sequence that encodes a polypeptide with FVIII activity, wherein the nucleotide sequence is at least 95%, at least 96%, at least 97%, at least 98%, at least 99%, or 100% identical to SEQ ID NO:2, and wherein the nucleotide sequence contains fewer potential promoter binding sites relative to SEQ ID NO:3. In other embodiments, the nucleotide sequence that encodes a polypeptide with FVIII activity and that is at least 95%, at least 96%, at least 97%, at least 98%, at least 99%, or 100% identical to SEQ ID NO:2 contains at most 9, at most 8, at most 7, at most 6, or at most 5 potential promoter binding sites. In other embodiments, the nucleotide sequence that encodes a polypeptide with FVIII activity and that is at least 95%, at least 96%, at least 97%, at least 98%, at least 99%, or 100% identical to SEQ ID NO:2 contains at most 4, at most 3, at most 2, or at most 1 potential promoter binding sites. In yet other embodiments, the nucleotide sequence that encodes a polypeptide with FVIII activity and that is at least 95%, at least 96%, at least 97%, at least 98%, at least 99%, or 100% identical to SEQ ID NO:2 does not contain a potential promoter binding, site.

TATA boxes are regulatory sequences often found in the promoter regions of eukaryotes. They serve as the binding site of TATA binding protein (TBP), a general transcription factor. TATA boxes usually comprise the sequence TATAAA (SEQ ID NO:12) or a close variant. TATA boxes within a coding sequence, however, can inhibit the translation of fall-length protein. There are ten potential promoter binding sequences in the wild type BDD FVIII sequence (SEQ ID NO:3); five TATAA sequences (SEQ ID NO:12) and five TTATA sequences (SEQ ID NO:13). In one embodiment, all promoter binding sites are abolished in the FVIII genes of the present invention. The location of each potential promoter binding site and the sequence of the corresponding nucleotides in the optimized sequences are shown in Table 2.

Other Cis Acting Negative Regulatory Elements

In addition to the MAR/ARS sequences, destabilizing elements, and potential promoter sites described above, several additional potentially inhibitory sequences can be identified in the wild type BDD FVIII sequence (SEQ ID NO:3). Two AU rich sequence elements (AREs) can be identified (SEQ ID NOs:14 and 15), along with a poly-A site (SEQ ID NO:11), a poly-T site (SEQ ID NO:10), and a splice site (SEQ ID NO:7) in the wild type BDD FVIII sequence. One or more of these elements can be removed from the optimized FVIII sequences. The location of each of these sites and the sequence of the corresponding nucleotides in the optimized sequences are shown in Table 2.

In certain embodiments, the present invention provides an isolated nucleic acid molecule comprising, a nucleotide sequence that encodes a polypeptide with FVIII activity, wherein the nucleotide sequence is at least 85%, at least 90%, at least 95%, at least 96%, at least 97%, at least 98%, at least 99%, or 100% identical to SEQ ID NO:1, wherein the nucleotide sequence does not contain one or more cis-acting negative regulatory elements, for example, a splice site, a poly-T sequence, a poly-A sequence, an ARE sequence, or any combinations thereof.

In certain embodiments, the present invention provides an isolated nucleic acid molecule comprising a nucleotide sequence that encodes a polypeptide with FVIII activity, wherein the nucleotide sequence is at least 95%, at least 96%, at least 97%, at least 98%, at least 99%, or 100% identical to SEQ ID NO:2, wherein the nucleotide sequence does not contain one or more cis-acting negative regulatory elements, for example, a splice site, a poly-T sequence, a poly-A sequence, an ARE sequence, or any combinations thereof.

In some embodiments, the present invention provides an isolated nucleic acid molecule comprising a nucleotide sequence that encodes a polypeptide with FVIII activity, wherein the nucleotide sequence is at least 85%, at least 90%, at least 95%, at least 96%, at least 97%, at least 98%, at least 99%, or 100% identical to SEQ ID NO:1, and wherein the nucleotide sequence does not contain the splice site GGTGAT (SEQ ID NO:7). In some embodiments, the present invention provides an isolated nucleic acid molecule comprising a nucleotide sequence that encodes a polypeptide with FVIII activity, wherein the nucleotide sequence is at least 85%, at least 90%, at least 95%, at least 96%, at least 97%, at least 98%, at least 99%, or 100% identical to SEQ ID NO:1, and wherein the nucleotide sequence does not contain a poly-T sequence (SEQ ID NO:10). In some embodiments, the present invention provides an isolated nucleic acid molecule comprising a nucleotide sequence that encodes a polypeptide with FVIII activity, wherein the nucleotide sequence is at least 85%, at least 90%, at least 95%, at least 96%, at, least 97%, at least 98%, at least 99%, or 100% identical to SEQ ID NO:1, and wherein the nucleotide sequence does not contain a poly-A sequence (SEQ ID NO:11). In some embodiments, the present invention provides an isolated nucleic acid molecule comprising a nucleotide sequence that encodes a polypeptide with FVIII activity, wherein the nucleotide sequence is at least 85%, at least 90%, at least 95%, at least 96%, at least 97%, at least 98%, at least 99%, or 100% identical to SEQ ID NO:1, and wherein the nucleotide sequence does not contain an ARE element (SEQ ID NO:14 or SEQ ID NO:15).

In some embodiments, the present invention provides an isolated nucleic acid molecule comprising a nucleotide sequence that encodes a polypeptide with FVIII activity, wherein the nucleotide sequence is at least 95%, at least 96%, at least 97%, at least 98%, at least 99%, or 100% identical to SEQ ID NO:2, and wherein the nucleotide sequence does not contain the splice site GGTGAT (SEQ ID NO:7). In some embodiments, the present invention provides an isolated nucleic acid molecule comprising a nucleotide sequence that encodes a polypeptide with FVIII activity, wherein the nucleotide sequence is at least 95%, at least 96%, at least 97%, at least 98%, at least 99%, or 100% identical to SEQ ID NO:2, and wherein the nucleotide sequence does not contain a poly-T sequence (SEQ ID NO:10). In some embodiments, the present invention provides an isolated nucleic acid molecule comprising a nucleotide sequence that encodes a polypeptide with FVIII activity, wherein the nucleotide sequence is at least 95%, at least 96%, at least 97%, at least 98%, at least 99%, or 100% identical to SEQ ID NO:2, and wherein the nucleotide sequence does not contain a poly-A sequence (SEQ ID NO:11). In some embodiments, the present invention provides an isolated nucleic acid molecule comprising a nucleotide sequence that encodes a polypeptide with FVIII activity, wherein the nucleotide, sequence is at least 95%, at least 96%, at least 97%, at least 98%, at least 99%, or 100% identical to SEQ ID NO:2, and wherein the nucleotide sequence does not contain an ARE element (SEQ ID NO:14 or SEQ ID NO:15).

In other embodiments, an optimized FVIII sequence of the invention does not comprise one or more of antiviral motifs, stem-loop structures, and repeat sequences.

In still other embodiments, the nucleotides surrounding the transcription start site are changed to a kozak consensus sequence (GCCGCCACCATGC, wherein the underlined nucleotides are the start codon; SEQ ID NO:16). In other embodiments, restriction sites can be added or removed to facilitate the cloning process.

Heterologous Nucleotide Sequences

In some embodiments, the isolated nucleic acid molecules of the invention further comprise a heterologous nucleotide sequence. In some embodiments, the isolated nucleic acid molecules of the invention further comprise at least one heterologous nucleotide sequence. The heterologous nucleotide sequence can be linked with the optimized BDD-FVIII nucleotide sequences of the invention at the 5' end, at the 3' end, or inserted into the middle of the optimized BDD-FVIII nucleotide sequence. Thus, in some embodiments, the heterologous amino acid sequence encoded by the heterologous nucleotide sequence is linked to the N-terminus or the C-terminus of the FVIII amino acid sequence encoded by the nucleotide sequence or inserted between two amino acids in the FVIII amino acid sequence. In other embodiments, the isolated nucleic acid molecules of the invention further comprise two, three, four, five, six, seven, or eight heterologous nucleotide sequences. In some embodiments, all the heterologous nucleotide sequences are identical. In some embodiments, at least one heterologous nucleotide sequence is different from the other heterologous nucleotide sequences. In some embodiments, the invention can comprise two, three, four, five, six, or more than seven heterologous nucleotide sequences in tandem.

In some embodiments, the heterologous nucleotide sequence encodes an amino acid sequence. In some embodiments, the amino acid sequence encoded by the heterologous nucleotide sequence is a heterologous moiety that can increase the half-life (a "half-life extender") of a FVIII molecule.

In some embodiments, the heterologous moiety is a peptide or a polypeptide with either unstructured or structured characteristics that are associated with the prolongation of in vivo half-life when incorporated in a protein of the invention. Non-limiting examples include albumin, albumin fragments, Fc fragments of immunoglobulins, the C-terminal peptide (CTP) of the β subunit of human chorionic gonadotropin, a HAP sequence, an XTEN sequence, a transferrin or a fragment thereof, a PAS polypeptide, polyglycine linkers, polyserine linkers, albumin-binding moieties, or any fragments, derivatives, variants, or combinations of these polypeptides. In some aspects, a heterologous moiety includes von Willebrand factor or a fragment thereof. In other related aspects a heterologous moiety can include an attachment site (e.g., a cysteine amino acid) for a non-polypeptide moiety such as polyethylene glycol (PEG), hydroxyethyl starch (HES), polysialic acid, or any derivatives, variants, or combinations of these elements. In some aspects, a heterologous moiety comprises a cysteine amino acid that functions as an attachment site for a non-polypeptide moiety such as polyethylene glycol (PEG), hydroxyethyl starch (HES), polysialic acid, or any derivatives, variants, or combinations of these elements.

In one specific embodiment, a first heterologous nucleotide sequence encodes a first heterologous moiety that is a half-life extending molecule which is known in the art, and a second heterologous nucleotide sequence encodes a second heterologous moiety that can also be a half-life extending molecule which is known in the art. In certain embodiments, the first heterologous moiety (e.g., a first Fc moiety) and the second heterologous moiety (e.g., a second Fc moiety) are associated with each other to form a dimer. In one embodiment, the second heterologous moiety is a second Fc moiety, wherein the second Fc moiety is linked to or associated with the first heterologous moiety, e.g., the first Fc moiety. For example, the second heterologous moiety (e.g., the second Fc moiety) can be linked to the first heterologous moiety (e.g., the first Fc moiety) by a linker or associated with the first heterologous moiety by a covalent or non-covalent bond.

In some embodiments, the heterologous moiety is a polypeptide comprising, consisting essentially of, or consisting of at least about 10, at least about 100, at least about 200, at least about 300, at least about 400, at least about 500, at least about 600, at least about 700, at least about 800, at least about 900, at least about 1000, at least about 1100, at least about 1200, at least about 1300, at least about 1400, at least about 1500, at least about 1600, at least about 1700, at least about 1800, at least about 1900, at least about 2000, at least about 2500, at least about 3000, or at least about 4000 amino acids. In other embodiments, the heterologous moiety is a polypeptide comprising, consisting essentially of, or consisting of about 100 to about 200 amino acids, about 200 to about 300 amino acids, about 300 to about 400 amino acids, about 400 to about 500 amino acids, about 500 to about 600 amino acids, about 600 to about 700 amino acids, about 700 to about 800 amino acids, about 800 to about 900 amino acids, or about 900 to about 1000 amino acids.

In certain embodiments, a heterologous moiety improves one or more pharmacokinetic properties of the FVIII protein without significantly affecting its biological activity or function.

In certain embodiments, a heterologous moiety increases the in vivo and/or in vitro half-life of the FVIII protein of the invention. In other embodiments, a heterologous moiety facilitates visualization or localization of the FVIII protein of the invention or a fragment thereof (e.g., a fragment comprising a heterologous moiety after proteolytic cleavage of the FVIII protein). Visualization and/or location of the FVIII protein of the invention or a fragment thereof can be in vivo, in vitro, ex vivo, or combinations thereof.

In other embodiments, a heterologous moiety increases stability of the FVIII protein of the invention or a fragment thereof (e.g., a fragment comprising a heterologous moiety after proteolytic cleavage of the FVIII protein). As used herein, the term "stability" refers to an art-recognized measure of the maintenance of one or more physical properties of the FVIII protein in response to an environmental condition (e.g., an elevated or lowered temperature). In certain aspects, the physical property can be the maintenance of the covalent structure of the FVIII protein (e.g., the absence of proteolytic cleavage, unwanted oxidation or deamidation). In other aspects, the physical property can also be the presence of the FVIII protein in a properly folded state (e.g., the absence of soluble or insoluble aggregates or precipitates). In one aspect, the stability of the FVIII protein is measured by assaying a biophysical property of the FVIII protein, for example thermal stability, pH unfolding profile, stable removal of glycosylation, solubility, biochemical function (e.g., ability to bind to a protein, receptor or ligand), etc., and/or combinations thereof. In another aspect, biochemical function is demonstrated by the binding affinity of the interaction. In one aspect, a measure of protein stability is thermal stability, i.e., resistance to thermal challenge. Stability can be measured using methods known in the art, such as, HPLC (high performance liquid chromatography), SEC (size exclusion chromatography), DLS (dynamic light scattering), etc. Methods to measure thermal stability include, but are not limited to differential scanning calorimetry (DSC), differential scanning fluorometry (DSF), circular dichroism (CD), and thermal challenge assay.

In certain aspects, a FVIII protein of the invention comprises at least one half-life extender, i.e., a heterologous moiety which increases the in vivo half-life of the FVIII protein with respect to the in vivo half-life of the corresponding FVIII protein lacking such heterologous moiety. In vivo half-life of a FVIII protein can be determined by any methods known to those of skill in the art, e.g., activity assays (chromogenic assay or one stage clotting aPTT assay), ELISA, ROTEM™, etc.

In some embodiments, the presence of one or more half-life extenders results in the half-life of the FVIII protein to be increased compared to the half-life of the corresponding protein lacking such one or more half-life extenders. The half-life of the FVIII protein comprising a half-life extender is at least about 1.5 times, at least about 2 times, at least about 2.5 times, at least about 3 times, at least about 4 times, at least about 5 times, at least about 6 times, at least about 7 times, at least about 8 times, at least about 9 times, at least about 10 times, at least about 11 times, or at least about 12 times longer than the in vivo half-life of the corresponding FVIII protein lacking such half-life extender.

In one embodiment, the half-life of the FVIII protein comprising a half-life extender is about 1.5-fold to about 20-fold, about 1.5 fold to about 15 fold, or about 1.5 fold to about 10 fold longer than the in vivo half-life of the corresponding protein lacking such half-life extender. In another embodiment, the half-life of FVIII protein comprising a half-life extender is extended about 2-fold to about 10-told, about 2-fold to about 9-fold, about 2-fold to about 8-fold, about 2-fold to about 7-fold, about 2-fold to about 6-fold, about 2-fold to about 5-fold, about 2-fold to about 4-fold, about 2-fold to about 3-fold, about 2.5-fold to about 10-fold, about 2.5-fold to about 9-fold, about 2.5-fold to about 8-fold, about 2.5-fold to about 7-fold, about 2.5-fold to about 6-fold, about 2.5-fold to about 5-fold, about 2.5-fold to about 4-fold, about 2.5-fold to about 3-fold, about 3-fold to about 10-fold, about 3-fold to about 9-fold, about 3-fold to about 8-fold, about 3-fold to about 7-fold, about 3-fold to about 6-fold, about 3-fold to about 5-fold, about 3-fold to about 4-fold, about 4-told to about 6 fold, about 5-fold to about 7-fold, or about 6-fold to about 8 fold as compared to the in vivo half-life of the corresponding protein lacking such half-life extender.

In other embodiments, the half-life of the FVIII protein comprising a half-life extender is at least about 17 hours, at least about 18 hours, at least about 19 hours, at least about 20 hours, at least about 21 hours, at least about 22 hours, at least about 23 hours, at least about 24 hours, at least about 25 hours, at least about 26 hours, at least about 27 hours, at least about 28 hours, at least about 29 hours, at least about 30 hours, at least about 31 hours, at least about 32 hours, at least about 33 hours, at least about 34 hours, at least about 35 hours, at least about 36 hours, at least about 48 hours, at least about 60 hours, at least about 72 hours, at least about 84 hours, at least about 96 hours, or at least about 108 hours.

In still other embodiments, the half-life of the FVIII protein comprising a half-life extender is about 15 hours to about two weeks, about 16 hours to about one week, about 17 hours to about one week, about 18 hours to about one week, about 19 hours to about one week, about 20 hours to about one week, about 21 hours to about one week, about 22 hours to about one week, about 23 hours to about one week, about 24 hours to about one week, about 36 hours to about one week, about 48 hours to about one week, about 60 hours to about one week, about 24 hours to about six days, about 24 hours to about five days, about 24 hours to about four days, about 24 hours to about three days, or about 24 hours to about two days.

In some embodiments, the average half-life per subject of the FVIII protein comprising a half-life extender is about 15 hours, about 16 hours, about 17 hours, about 18 hours, about 19 hours, about 20 hours, about 21 hours, about 22 hours, about 23 hours, about 24 hours (1 day), about 25 hours, about 26 hours, about 27 hours, about 28 hours, about 29 hours, about 30 hours, about 31 hours, about 32 hours, about 33 hours, about 34 hours, about 35 hours, about 36 hours, about 40 hours, about 44 hours, about 48 hours (2 days), about 54 hours, about 60 hours, about 72 hours (3 days), about 84 hours, about 96 hours (4 days), about 108 hours, about 120 hours (5 days), about six days, about seven days (one week), about eight days, about nine days, about 10 days, about 11 days, about 12 days, about 13 days, or about 14 days.

1. An Immunoglobulin Constant Region or a Portion Thereof

In another aspect, a heterologous moiety comprises one or more immunoglobulin constant regions or portions thereof (e.g., an Fc region). In one embodiment, an isolated nucleic acid molecule of the invention further comprises a heterologous nucleic acid sequence that encodes an immunoglobulin constant region or a portion thereof. In some embodiments, the immunoglobulin constant region or portion thereof is an Fc region.

An immunoglobulin constant region is comprised of domains denoted CH (constant heavy) domains (CH1, CH2, etc.). Depending on the isotype, (i.e. IgG, IgM, IgA IgD, or IgE), the constant region can be comprised of three or four CH domains. Some isotypes (e.g. IgG) constant regions also contain a hinge region. See Janeway et al. 2001, *Immunobiology*, Garland Publishing, N.Y., N.Y.

An immunoglobulin constant region or a portion thereof for producing the FVIII protein of the present invention can be obtained from a number of different sources. In one embodiment, an immunoglobulin constant region or a portion thereof is derived from a human immunoglobulin. It is understood, however, that the immunoglobulin constant region or a portion thereof can be derived from an immunoglobulin of another mammalian species, including for example, a rodent (e.g. a mouse, rat, rabbit, guinea pig) or non-human primate (e.g. chimpanzee, macaque) species. Moreover, the immunoglobulin constant region or a portion thereof can be derived from any immunoglobulin class, including IgM, IgG, IgD, IgA and IgE, and any immunoglobulin isotype, including IgG1, IgG2, IgG3 and IgG4. In one embodiment, the human isotype IgG1 is used.

A variety of the immunoglobulin constant region gene sequences (e.g. human constant region gene sequences) are available in the form of publicly accessible deposits. Constant region domains sequence can be selected having a particular effector function (or lacking a particular effector function) or with a particular modification to reduce immunogenicity. Many sequences of antibodies and antibody-encoding genes have been published and suitable Ig constant region sequences (e.g. hinge, CH2, and/or CH3 sequences, or portions thereof) can be derived from these sequences using art recognized techniques. The genetic material obtained using any of the foregoing methods can then be altered or synthesized to obtain polypeptides of the present invention. It will further be appreciated that the scope of this invention encompasses alleles, variants and mutations of constant region DNA sequences.

The sequences of the immunoglobulin constant region or a portion thereof can be cloned, e.g., using the polymerase chain reaction and primers which are selected to amplify the domain of interest. To clone a sequence of the immunoglobulin constant region or a portion thereof from an antibody, mRNA can be isolated from hybridoma, spleen, or lymph cells, reverse transcribed into DNA, and antibody genes amplified by PCR. PCR amplification methods are described in detail in U.S. Pat. Nos. 4,683,195; 4,683,202; 4,800,159; 4,965,188; and in, e.g., "PCR Protocols: A Guide to Methods and Applications" Innis et al. eds., Academic Press, San Diego, Calif. (1990); Ho et al. 1989. Gene 77:51; Horton et al. 1993. *Methods Enzymol.* 217:270). PCR can be initiated by consensus constant region primers or by more specific primers based on the published heavy and light chain DNA and amino acid sequences. PCR also can be used to isolate DNA clones encoding the antibody light and heavy chains. In this case the libraries can be screened by consensus primers or larger homologous probes, such as mouse constant region probes. Numerous primer sets suitable for amplification of antibody genes are known in the art (e.g., 5' primers based on the N-terminal sequence of purified antibodies (Benhar and Pastan. 1994. *Protein Engineering* 7:1509); rapid amplification of cDNA ends (Ruberti, F. et al. 1994. *J. Immunol. Methods* 173:33); antibody leader sequences (Larrick et al, 1989 *Biochem. Biophys. Res. Commun.* 160:1250). The cloning of antibody sequences is further described in Newman et al., U.S. Pat. No. 5,658,570, filed Jan. 25, 1995, which is incorporated by reference herein.

An immunoglobulin constant region used herein can include all domains and the hinge region or portions thereof. In one embodiment, the immunoglobulin constant region or a portion thereof comprises CH2 domain, CH3 domain, and a hinge region, i.e., an Fc region or an FcRn binding partner.

As used herein, the term "Fc region" is defined as the portion of a polypeptide which corresponds to the Fc region of native Ig, i.e., as formed by the dimeric association of the respective Fc domains of its two heavy chains. A native Fc region forms a homodimer with another Fc region. In contrast, the term "genetically-fused Fc region" or "single-chain Fc region" (scFc region), as used herein, refers to a synthetic dimeric Fc region comprised of Fc domains genetically linked within a single polypeptide chair (i.e., encoded in a single contiguous genetic sequence). See International Publication No. WO 2012/006635, incorporated herein by reference in its entirety.

In one embodiment, the "Fc region" refers to the portion of a single Ig heavy chain beginning in the hinge region just upstream of the papain cleavage site (i.e. residue 216 in IgG, taking the first residue of heavy chain constant region to be 114) and ending at the C-terminus of the antibody. Accordingly, a complete Fc region comprises at least a hinge domain, a CH2 domain, and a CH3 domain.

An immunoglobulin constant region or a portion thereof can be an FcRn binding partner. FcRn is active in adult epithelial tissues and expressed in the lumen of the intestines, pulmonary airways, nasal surfaces, vaginal surfaces, colon and rectal surfaces (U.S. Pat. No. 6,485,726). An FcRn binding partner is a portion of an immunoglobulin that binds to FcRn.

The FcRn receptor has been isolated from several mammalian species including humans. The sequences of the human FcRn, monkey FcRn, rat FcRn, and mouse FcRn are known (Story et al. 1994, J. Exp. Med. 180:2377). The FcRn receptor binds IgG (but not other immunoglobulin classes such as IgA, IgM, IgD, and IgE) at relatively low pH, actively transports the IgG transcellularly in a luminal to serosal direction, and then releases the IgG at relatively higher pH found in the interstitial fluids. It is expressed in adult epithelial tissue (U.S. Pat. Nos. 6,485,726, 6,030,613, 6,086,875; WO 03/077834; US2003-0235536A1) including lung and intestinal epithelium (Israel et al. 1997 Immunology 92:69) renal proximal tubular epithelium (Kobayashi et al. 2002, Am. J. Physiol. Renal Physiol. 282:F358) as well as nasal epithelium, vaginal surfaces, and biliary tree surfaces.

FcRn binding partners useful in the present invention encompass molecules that can be specifically bound by the FcRn receptor including whole IgG, the Fc fragment of IgG, and other fragments that include the complete binding region of the FcRn receptor. The region of the Fc portion of IgG that binds to, the FcRn receptor has been described based on X-ray crystallography (Burmeister et al. 1994, Nature 372:379). The major contact area of the Fc with the FcRn is near the junction of the CH2 and CH3 domains. Fc-FcRn contacts are all within a single Ig heavy chain. The FcRn binding partners include whole IgG, the Fc fragment of IgG, and other fragments of IgG that include the complete binding region of FcRn. The major contact sites include amino acid residues 248, 250-257, 272, 285, 288, 290-291, 308-311, and 314 of the CH2 domain and amino acid residues 385-387, 428, and 433-436 of the CH3 domain. References made to amino acid numbering of immunoglobulins or immunoglobulin fragments, or regions, are all based on Kabat et al. 1991, Sequences of Proteins of Immunological Interest, U.S. Department of Public Health, Bethesda, Md.

Fc regions or FcRn binding partners bound to FcRn can be effectively shuttled across epithelial barriers by FcRn, thus providing a non-invasive means to systemically administer a desired therapeutic molecule. Additionally, fusion proteins comprising an Fc region or an FcRn binding partner are endocytosed by cells expressing the FcRn. But instead of being marked for degradation, these fusion proteins are recycled out into circulation again, thus increasing the in vivo half-life of these proteins. In certain embodiments, the portions of immunoglobulin constant regions are an Fc region or an FcRn binding partner that typically associates, via disulfide bonds and other non-specific interactions, with another Fc region or another FcRn binding partner to form dimers and higher order multimers.

Two FcRn receptors can bind a single Fc molecule. Crystallographic data suggest that each FcRn molecule binds a single polypeptide of the Fc homodimer. In one embodiment, linking the FcRn binding partner, e.g., an Fc fragment of an IgG, to a biologically active molecule provides a means of delivering, the biologically active molecule orally, buccally, sublingually, rectally, vaginally, as an aerosol administered nasally or via a pulmonary route, or via an ocular route. In another embodiment, the FVIII protein can be administered invasively, e.g., subcutaneously, intravenously.

An FcRn binding partner region is a molecule or portion thereof that can be specifically bound by the FcRn receptor with consequent active transport by the FcRn receptor of the Fc region. Specifically bound refers to two molecules forming a complex that is relatively stable under physiologic conditions. Specific binding is characterized by a high affinity and a low to moderate capacity as distinguished from nonspecific binding which usually has a low affinity with a moderate to high capacity. Typically, binding is considered specific when the affinity constant $K_A$ is higher than $10^6$ $M^{-1}$, or higher than $10^8$ $M^{-1}$. If necessary, non-specific binding can be reduced without substantially affecting specific binding by varying the binding conditions. The appropriate binding conditions such as concentration of the molecules, ionic strength of the solution, temperature, time allowed for binding, concentration of a blocking agent (e.g., serum albumin, milk casein), etc., can be optimized by a skilled artisan using routine techniques.

In certain embodiments, a FVIII protein of the invention comprises one or more truncated Fc regions that are nonetheless sufficient to confer Fc receptor (FcR) binding properties to the Fc region. For example, the portion of an Fc region that binds to FcRn (i.e., the FcRn binding portion) comprises from about amino acids 282-438 of IgG1, EU numbering (with the primary contact sites being amino acids 248, 250-257, 272, 285, 288, 290-291, 308-311, and 314 of the CH2 domain and amino acid residues 385-387, 428, and 433-436 of the CH3 domain. Thus, an Fc region of the invention can comprise or consist of an FcRn binding portion. FcRn binding portions can be derived from heavy chains of any isotype, including IgG1, IgG2, IgG3 and IgG4. In one embodiment, an FcRn binding portion from an antibody of the human isotype IgG1 is used. In another embodiment, an FcRn binding portion from an antibody of the human isotype IgG4 is used.

The Fc region can be obtained from a number of different sources. In one embodiment, an Fc region of the polypeptide is derived from a human immunoglobulin. It is understood, however, that an Fc moiety can be derived from an immunoglobulin of another mammalian species, including for example, a rodent (e.g. a mouse, rat, rabbit, guinea pig) or non-human primate (e.g. chimpanzee, macaque) species. Moreover, the polypeptide of the Fc domains or portions thereof can be derived from any immunoglobulin class, including IgM, IgG, IgD, IgA and IgE, and any immunoglobulin isotype, including IgG1 IgG2, IgG3 and IgG4. In another embodiment, the human isotype IgG1 is used.

In certain embodiments, the Fc variant confers a change in at least one effector function imparted by an Fc moiety comprising said wild-type Fc domain (e.g. an improvement or reduction in the ability of the Fc region to bind to Fc receptors (e.g. FcγRI, FcγRII or FcγRIII) or complement proteins (e.g. C1q), or to trigger antibody dependent cytotoxicity (ADCC), phagocytosis, or complement-dependent cytotoxicity (CDCC)). In other embodiments, the Fc variant provides an engineered cysteine residue.

The Fc region of the invention can employ art-recognized Fc variants which are known to impart a change (e.g., an enhancement or reduction) in effector function and/or FcR or FcRn binding. Specifically, an Fc region of the invention can include, for example, a change (e.g., a substitution) at one or more of the amino acid positions disclosed in International PCT Publications WO88/07089A1, WO96/14339A1, WO98/05787A1, WO98/23289A1, WO99/51642A1, WO99/58572A1, WO00/09560A2, WO00/32767A1, WO00/42072A2, WO02/44215A2, WO02/060919A2, WO03/074569A2, WO04/016750A2, WO04/029207A2, WO04/035752A2, WO04/063351A2, WO04/074455A2, WO04/099249A2, WO05/040217A2, WO04/044859, WO05/070963A1, WO05/077981A2, WO05/092925A2, WO05/123780A2, WO06/019447A1, WO06/047350A2, and WO06/085967A2; US Patent Publication Nos. US2007/0231329, US2007/0231329, US2007/0237765, US2007/0237766, US2007/0237767, US2007/0243188, US20070248603, US20070286859, US20080057056; or U.S. Pat. Nos. 5,648,260; 5,739,277; 5,834,250; 5,869,046; 6,096,871; 6,121,022; 6,194,551; 6,242,195; 6,277,375; 6,528,624; 6,538,124; 6,737,056; 6,821,505; 6,998,253; 7,083,784; 7,404,956, and 7,317,091, each of which is incorporated by reference herein. In one embodiment, the specific change (e.g., the specific substitution of one or more amino acids disclosed in the art) can be made at one or more of the disclosed amino acid positions. In another embodiment, a different change at one or more of the disclosed amino acid positions (e.g., the different substitution of one or more amino acid position disclosed in the art) can be made.

The Fc region or FcRn binding partner of IgG can be modified according to well recognized procedures such as site directed mutagenesis and the like to yield modified IgG or Fc fragments or portions thereof that will be bound by FcRn. Such modifications include modifications remote from the FcRn contact sites as well as modifications within the contact sites that preserve or even enhance binding to the FcRn. For example, the following single amino acid residues in human IgG1 Fc (Fc γ1) can be substituted without significant loss of Fc binding affinity for FcRn: P238A, S239A, K246A, K248A, D249A, M252A, T256A, E258A, T260A, D265A, S267A, H268A, E269A, D270A, E272A, L274A, N276A, Y278A, D280A, V282A, E283A, H285A, N286A, T289A, K290A, R292A, E293A, E294A, Q295A, Y296F, N297A, S298A, Y300F, R301A, V303A, V305A, T307A, L309A, Q311A, D312A, N315A, K317A, E318A, K320A, K322A, S324A, K326A, A327Q, P329A, A330Q, P331A, E333A, K334A, T335A, S337A, K338A, K340A, Q342A, R344A, E345A, Q347A, R355A, E356A, M358A, T359A, K360A, N361A, Q362A, Y373A, S375A, D376A, A378Q, E380A, E382A, S383A, N384A, Q386A, E388A, N389A, N390A, Y391F, K392A, L398A, S400A, D401A, D413A, K414A, R416A, Q418A, Q419A, N421A, V422A, S424A, E430A, N434A, T437A, Q438A, K439A, S440A, S444A, and K447A, where for example P238A represents wild type proline substituted by alanine at position number 238. As an example, a specific embodiment incorporates the N297A mutation, removing a highly conserved N-glycosylation site. In addition to alanine other amino acids can be substituted for the wild type amino acids at the positions specified above. Mutations can be introduced singly into Fc giving rise to more than one hundred Fc regions distinct from the native Fc. Additionally, combinations of two, three, or more of these individual mutations can be introduced together, giving rise to hundreds more Fc regions.

Certain of the above mutations can confer new functionality upon the Fc region or FcRn binding partner. For example, one embodiment incorporates N297A, removing a highly conserved N-glycosylation site. The effect of this mutation is to reduce immunogenicity, thereby enhancing circulating half-life of the Fc region, and to render the Fc region incapable of binding to FcγRI, FcγRIIA, FcγRIIB, and FcγRIIIA, without compromising affinity for FcRn (Routledge et al. 1995, Transplantation 60:847; Friend et al. 1999, Transplantation 68:1632; Shields et al. 1995, J. Biol. Chem. 276:6591). As a further example of new functionality arising from mutations described above affinity for FcRn can be increased beyond that of wild type in some instances. This increased affinity can reflect an increased "on" rate, a decreased "off" rate or both an increased "on" rate and a decreased "off" rate. Examples of mutations believed to impart an increased affinity for FcRn include, but not limited to, T256A, T307A, E380A, and N434A (Shields et al. 2001, J. Biol. Chem. 276:6591).

Additionally, at least three human Fc gamma receptors appear to recognize a binding site on IgG within the lower hinge region, generally amino acids 234-237. Therefore, another example of new functionality and potential decreased immunogenicity can arise from mutations of this region, as for example by replacing amino acids 233-236 of human IgG1 "ELLG" (SEQ ID NO:29) to the corresponding sequence from IgG2 "PVA" (with one amino acid deletion). It has been shown that FcγRI, FcγRII, and FcγRIII, which mediate various effector functions will not bind to IgG1 when such mutations have been introduced. Ward and Ghetie 1995, Therapeutic Immunology 2:77 and Armour et al. 1999, Eur. J. Immunol. 29:2613.

In another embodiment, the immunoglobulin constant region or a portion thereof comprises an amino acid sequence in the hinge region or a portion thereof that forms one or more disulfide bonds with a second immunoglobulin constant region or a portion thereof. The second immunoglobulin constant region or a portion thereof an be linked to a second polypeptide, bringing the FVIII protein and the second polypeptide together. In some embodiments, the second polypeptide is an enhancer moiety. As used herein, the term "enhancer moiety" refers to a molecule, fragment thereof or a component of a polypeptide which is capable of enhancing the procoagulant activity of FVIII. The enhancer moiety can be a cofactor, such as soluble tissue factor (sTF), or a procoagulant peptide. Thus, upon activation of FVIII, the enhancer moiety is available to enhance FVIII activity.

In certain embodiments, a FVIII protein of the invention comprises an amino acid substitution to an immunoglobulin constant region or a portion thereof (e.g., Fc variants), which alters the antigen-independent effector functions of the Ig constant region, in particular the circulating half-life of the protein.

2. scFc Regions

In another aspect, a heterologous moiety comprises a scFc (single chain Fc) region. In one embodiment, an isolated nucleic acid molecule of the invention further comprises a heterologous nucleic acid sequence that encodes a scFc region. The scFc region comprises at least two immunoglobulin constant regions or portions thereof (e.g., Fc moieties or domains (e.g., 2, 3, 4, 5, 6, or more Fc moieties or domains)) within the same linear polypeptide chain that are capable of folding (e.g., intramolecularly or intermolecularly folding) to form one functional scFc region which is linked by an Fc peptide linker. For example, in one embodiment, a polypeptide of the invention is capable of binding, via its scFc region, to at least one Fc receptor (e.g. an FcRn, an FcγR receptor (e.g., FcγRIII), or a complement protein (e.g. C1q)) in order to improve half-life or trigger an immune effector function (e.g., antibody-dependent cytotoxicity (ADCC), phagocytosis, or complement-dependent cytotoxicity (CDCC) and/or to improve manufacturability).

3. CTP

In another aspect, a heterologous moiety comprises one C-terminal peptide (CTP) of the β subunit of human chorionic gonadotropin or fragment, variant, or derivative thereof. One or more CTP peptides inserted into a recombinant protein is known to increase the in vivo half-life of that protein. See, e.g., U.S. Pat. No. 5,712,122, incorporated by reference herein in its entirety.

Exemplary CTP peptides include DPRFQDSSSSKAP-PPSLPSPSRLPGPSDTPIL (SEQ ID NO:17) or SSSSKAP-PPSLPSPSRLPGPSDTPILPQ. (SEQ ID NO:18). See, e.g., U.S. Patent Application Publication No. US 2009/0087411 A1 incorporated by reference.

4. XTEN Sequence

In some embodiments, a heterologous moiety comprises one or more XTEN sequences, fragments, variants, or derivatives thereof. As used here "XTEN sequence" refers to extended length polypeptides with non-naturally occurring, substantially non-repetitive sequences that are composed mainly of small hydrophilic amino acids, with the sequence having a low degree or no secondary or tertiary structure under physiologic conditions. As a heterologous moiety, XTENs can serve as a half-life extension moiety. In addition, XTEN can provide desirable properties including but are not limited to enhanced pharmacokinetic parameters and solubility characteristics.

The incorporation of a heterologous moiety comprising an XTEN sequence into a protein of the invention can confer to the protein one or more of the following advantageous properties: conformational flexibility, enhanced aqueous solubility, high degree of protease resistance, low immunogenicity, low binding to mammalian receptors, or increased hydrodynamic (or Stokes) radii.

In certain aspects, an XTEN sequence can increase pharmacokinetic properties such as longer in vivo half-life or increased area under the curve (AUC), so that a protein of the invention stays in vivo and has procoagulant activity for an increased period of time compared to a protein with the same but without the XTEN heterologous moiety.

Examples of XTEN sequences that can be used as heterologous moieties in chimeric proteins of the invention are disclosed, e.g., in U.S. Patent Publication Nos. 2010/0239554 A1, 2010/0323956 A1, 2011/0046060 A1, 2011/0046061 A1, 2011/0077199 A1, or 2011/0172146 A1, or International Patent Publication Nos. WO 2010091122 A1, WO 2010144502 A2, WO 2010144508 A1, WO 2011028228 A1, WO 2011028229 A1, or WO 2011028344 A2, each of which is incorporated by reference herein in its entirety.

Exemplary XTEN sequences that can be used as heterologous moieties in chimeric protein of the invention include XTEN AE42-4 (SEQ ID NO:30, encoded by SEQ ID NO:31), XTEN 144-2A (SEQ ID NO:32, encoded by SEQ ID NO:33), XTEN A144-3B (SEQ ID NO:34, encoded by SEQ ID NO:35), XTEN AE144-4A (SEQ ID NO:36, encoded by SEQ ID NO:37), XTEN AE144-5A (SEQ ID NO:38, encoded by SEQ ID NO:39), XTEN AE144-6B (SEQ ID NO:40, encoded by SEQ ID NO:41), XTEN AG144-1 (SEQ ID NO:42, encoded by SEQ ID NO:43), XTEN AG144-A (SEQ ID NO:44, encoded by SEQ ID NO:45), XTEN AG144-B (SEQ ID NO:46, encoded by SEQ ID NO:47), XTEN AG144-C(SEQ ID NO:48, encoded by SEQ ID NO:49), and XTEN AG144-F (SEQ ID NO:50, encoded by SEQ ID NO:51).

5. Albumin or Fragment, Derivative, or Variant Thereof

In some embodiments, a heterologous moiety comprises albumin or a functional fragment thereof. Human serum albumin (HSA, or HA), a protein of 609 amino acids in its full-length form, is responsible for a significant proportion of the osmotic pressure of serum and also functions as a carrier of endogenous and exogenous ligands. The term "albumin" as used herein includes full-length albumin or a functional fragment, variant, derivative, or analog thereof. Examples of albumin or the fragments or variants thereof are disclosed in US Pat. Publ. Nos. 2008/0194481A1, 2008/0004206 A1, 2008/0161243 A1, 2008/0261877 A1, or 2008/0153751 A1 or PCT Appl. Publ. Nos. 2008/033413 A2, 2009/058322 A1, or 2007/021494 A2, which are incorporated herein by reference in their entireties.

In one embodiment, the FVIII protein of the invention comprises albumin, a fragment, or a variant thereof which is further linked to a second heterologous moiety selected from the group consisting of an immunoglobulin constant region or portion thereof (e.g., an Fc region), a PAS sequence, HES, and PEG.

6. Albumin-Binding Moiety

In certain embodiments, the heterologous moiety is an albumin-binding moiety, which comprises an albumin-binding peptide, a bacterial albumin-binding domain, an albumin-binding antibody fragment or any combinations thereof.

For example, the albumin-binding protein can be a bacterial albumin-binding protein, an antibody or an antibody fragment including domain antibodies (see U.S. Pat. No. 6,696,245). An albumin-binding protein, for example, can be a bacterial albumin-binding domain, such as the one of streptococcal protein G (Konig. T. and Skerra, A. (1998) *J. Immunol. Methods* 218, 73-83). Other examples of albumin-binding peptides that can be used as conjugation partner are, for instance, those having a Cys-$Xaa_1$-$Xaa_2$-$Xaa_3$-$Xaa_4$-Cys consensus sequence, wherein $Xaa_1$ is Asp, Asn, Ser, Thr, or Trp; $Xaa_2$ is Asn, Gln, H is, Ile, Leu, or Lys; $Xaa_3$ is Ala, Asp, Phe, Trp, or Tyr; and $Xaa_4$ is Asp, Gly, Leu, Phe, Ser, or Thr as described in US patent application 203/0069395 or Dennis et al. (Dennis et al. (2002) *J. Biol. Chem.* 277, 35035-35043).

Domain 3 from streptococcal protein G, as disclosed by Kraulis et al., FEBS Lett. 378:190-194 (1996) and Linhult et al., Protein Sci. 11:206-213 (2002) is an example of a bacterial albumin-binding domain. Examples of albumin-binding peptides include a series of peptides having the core sequence DICLPRWGCLW (SEQ ID NO:19). See, e,g., Dennis et al., J. Biol. Chem. 2002, 277: 35035-35043 (2002). Examples of albumin-binding antibody fragments are disclosed in Muller and Kontermann, Curr. Opin. Mol. Ther. 9:319-326 (2007); Roovers et al., Cancer Immunol. Immunother. 56:303-317 (2007), and Holt et al., Prot. Eng. Design Sci., 21:283-288 (2008), which are incorporated herein by reference in their entireties. An example of such albumin-binding moiety is 2-(3-maleimidopropanamido)-6-(4-(4-iodophenyl)butanamido) hexanoate ("Albu" tag) as disclosed by Trussel et al., Bioconjugate Chem 20:2286-2292 (2009).

Fatty acids, in particular long chain fatty acids (LCFA) and long chain fatty acid-like albumin-binding compounds can be used to extend the in vivo half-life of FVIII proteins of the invention. An example of a LCFA-like albumin-binding compound is 16-(1-(3-(9-(((2,5-dioxopyrrolidin-1-yloxy) carbonyloxy)-methyl)-7-sulfo-9H-fluoren-2-ylamino)-3-oxopropyl)-2,5-dioxopyrrolidin-3-ylthio) hexadecanoic acid (see, e.g., WO 2010/140148).

7. PAS Sequence

In other embodiments, the heterologous moiety is a PAS sequence. A PAS sequence, as used herein, means an amino acid sequence comprising mainly alanine and serine residues or comprising mainly alanine, serine, and proline residues, the amino acid sequence forming random coil conformation under physiological conditions. Accordingly, the PAS sequence is a building block, an amino acid polymer, or a sequence cassette comprising, consisting essentially of, or consisting of alanine, serine, and proline which can be used as a part of the heterologous moiety in the chimeric protein. Yet, the skilled person is aware that an amino acid polymer also can form random coil conformation when residues other than alanine, serine, and proline are added as a minor constituent in the PAS sequence. The term "minor constituent" as used herein means that amino acids other than alanine, serine, and proline can be added in the PAS sequence to a certain degree, e.g., up to about 12%, i.e., about 12 of 100 amino acids of the PAS sequence, up to about 10%, i.e. about 10 of 100 amino acids of the PAS sequence, up to about 9%, i.e., about 9 of 100 amino acids, up to about 8%, i.e., about 8 of 100 amino acids, about 6%, i.e., about 6 of 100 amino acids, about 5%, i.e., about 5 of 100 amino acids, about 4%, i.e., about 4 of 100 amino acids, about 3%, i.e., about 3 of 100 amino acids, about 2%, i.e., about 2 of 100 amino acids, about 1%, i.e., about 1 of 100 of the amino acids. The amino acids different from alanine, serine and proline can be selected from the group consisting of Arg, Asn, Asp, Cys, Gln, Glu, Gly, His, Ile, Leu, Lys, Met, Phe, Thr, Trp, Tyr, and Val.

Under physiological conditions, the PAS sequence stretch forms a random coil conformation and thereby can mediate an increased in vivo and/or in vitro stability to the FVIII protein. Since the random coil domain does not adopt a stable structure or function by itself, the biological activity mediated by the FVIII protein is essentially preserved. In other embodiments, the PAS sequences that form random coil domain are biologically inert, especially with respect to proteolysis in blood plasma, immunogenicity, isoelectric point/electrostatic behaviour, binding to cell surface receptors or internalisation, but are still biodegradable, which provides clear advantages over synthetic polymers such as PEG.

Non-limiting examples of the PAS sequences forming random coil conformation comprise an amino acid sequence selected from the group consisting of ASPAAPAPASPAAPAPSAPA (SEQ ID NO: 20), AAPASPAPAAPSAPAPAAPS (SEQ ID NO: 21), APSSPSPSAPSSPSPASPSS (SEQ ID NO: 22), APSSPSPSAPSSPSPASPS (SEQ ID NO: 23), SSPSAPSPSSPASPSPSSPA (SEQ ID NO: 24), AASPAAPSAPPAAASPAAPSAPPA (SEQ ID NO: 25) and ASAAAPAAASAAASAPSAAA (SEQ ID NO: 26) or any combinations thereof. Additional examples of PAS sequences are known from, e.g., US Pat. Publ. No. 2010/0292130 A1 and PCT Appl. Publ. No. WO 2008/155134 A1.

8. HAP Sequence

In certain embodiments, the heterologous moiety is a glycine-rich homo-amino-acid polymer (HAP). The HAP sequence can comprise a repetitive sequence of glycine, which has at least 50 amino acids, at least 100 amino acids, 120 amino acids, 140 amino acids, 160 amino acids, 180 amino acids, 200 amino acids, 250 amino, acids, 300 amino acids, 350 amino acids, 400 amino acids, 450 amino acids, or 500 amino acids in length. In one embodiment, the HAP sequence is capable of extending half-life of a moiety fused to or linked to the HAP sequence. Non-limiting examples of the HAP sequence includes, but are not limited to $(Gly)_n$, $(Gly_4Ser)_n$, or $S(Gly_4Ser)_n$, wherein n is 1, 2, 3, 4, 5, 6, 7, 8, 9, 10, 11, 12, 13, 14, 15, 16, 17, 18, 19, or 20. In one embodiment, n is 20, 21, 22, 23, 24, 25, 26, 26, 28, 29, 30, 31, 32, 33, 34, 35, 36, 37, 38, 39, or 40. In another embodiment, n is 50, 60, 70, 80, 90, 100, 110, 120, 130, 140, 150, 160, 170, 180, 190, or 200.

9. Transferrin or Fragment Thereof

In certain embodiments, the heterologous moiety is transferrin or a fragment thereof. Any transferrin can be used to make the FVIII proteins of the invention. As an example, wild-type human TF (TF) is a 679 amino acid protein, of approximately 75 KDa (not accounting for glycosylation), with two main domains, N (about 330 amino acids) and C (about 340 amino acids), which, appear to originate from a gene duplication. See GenBank accession numbers NM001063, XM002793, M12530, XM039845, XM 039847 and S95936 (www.ncbi.nlm.nih.gov/), all of which are herein incorporated by reference in their entirety. Transferrin comprises two domains, N domain and C domain. N domain comprises two subdomains, N1 domain and N2 domain, and C domain comprises two subdomains, C1 domain and C2 domain.

In one embodiment, the transferrin heterologous moiety includes a transferrin splice variant. In one example, a transferrin splice variant can be a splice variant of human transferrin, e.g., Genbank Accession AAA61140. In another embodiment, the transferrin portion of the chimeric protein includes one or more domains of the transferrin sequence, e.g., N domain, C domain, N1 domain, N2 domain, C1 domain, C2 domain or any combinations thereof.

10. Clearance Receptors

In certain embodiments, the heterologous moiety is a clearance receptor, fragment, variant, or derivative thereof. LRP1 is a 600 kDa integral membrane protein that is implicated in the receptor-mediate clearance of a variety of proteins, such as Factor X. See, e.g., Narita et al., Blood 91:555-560 (1998).

11. von Willebrand Factor or Fragments Thereof

In certain embodiments, the heterologous moiety is von Willebrand Factor (VWF) or fragments thereof.

VWF (also known as F8VWF) is a large multimeric glycoprotein present in blood plasma and produced constitutively in endothelium (in the Weibel-Palade bodies), megakaryocytes (α-granules of platelets), and subendothelian connective tissue. The basic VWF monomer is a 2813 amino acid protein. Every monomer contains a number of specific domains with a specific function, the D' and D3 domains (which together bind to Factor VIII), the A1 domain (which binds to platelet GPIb-receptor, heparin, and/or possibly collagen), the A3 domain' (which binds to collagen), the C1 domain (in which the RGD domain binds to platelet integrin αIIbβ3 when this is activated), and the "cysteine knot" domain at the C-terminal end of the protein (which VWF shares with platelet-derived growth factor (PDGF), transforming growth factor-β (TGFβ) and β-human chorionic gonadotropin (βHCG)).

The 2813 monomer amino acid sequence for human VWF is reported as Accession Number NP000543.2 in Genbank. The nucleotide sequence encoding the human VWF is reported as Accession Number NM000552.3 in Genbank. The nucleotide sequence of human VWF is designated as SEQ ID NO 27. SEQ ID NO 28 is the amino acid sequence encoded by SEQ ID NO: 27. The D' domain includes amino acids 764 to 866 of SEQ ID NO:28. The D3 domain includes amino acids 867 to 1240 of SEQ ID NO:28.

In plasma, 95-98% of FVIII circulates in a tight non-covalent complex with full-length VWF. The formation of this complex is important for the maintenance of appropriate plasma levels of FVIIII in vivo. Lenting et al., *Blood* 92(11): 3983-96 (1998); Lenting et al., *J. Thromb. Haemost.* 5(7): 1353-60 (2007). When FVIII is activated due to proteolysis at positions 372 and 740 in the heavy chain and at position 1689 in the light chain, the VWF bound to FVIII is removed from the activated FVIII In certain embodiments, the heterologous moiety is full length von Willebrand Factor. In other embodiments, the heterologous moiety is a von Willebrand Factor fragment. As used herein, the term "VWF fragment" or "VWF fragments" used herein means any VWF fragments that interact with FVIII and retain at least one or more properties that are normally provided to FVIII by full-length VWF, e.g., preventing premature activation to FVIIIa, preventing premature proteolysis, preventing association with phospholipid membranes that could lead to premature clearance, preventing binding to FVIII clearance receptors that, can bind naked FVIII but not VWF-bound FVIII, and/or stabilizing the FVIII heavy chain and light chain interactions. In a specific embodiment, the heterologous moiety is a (VWF) fragment comprising a D' domain and a D3 domain of VWF. The VWF fragment comprising the D' domain and the D3 domain can further comprise a VWF domain selected from the group consisting of an A1 domain, an A2 domain, an A3 domain, a D1 domain, a D2 domain, a D4 domain, a B1 domain, a B2 domain, a B3 domain, a C1 domain, a C2 domain, a CK domain, one or more fragments thereof, and any combinations thereof. Additional examples of the polypeptide having FVIII activity fused to the VWF fragment are disclosed in U.S. provisional patent application No. 61/667, 901, filed Jul. 3, 2012, incorporated herein by reference in its entirety.

12. Linker Moieties

In certain embodiments, the heterologous moiety is a peptide linker.

As used herein, the terms "peptide linkers" or "linker moieties" refer to a peptide or polypeptide sequence (e.g., a synthetic peptide or polypeptide sequence) which connects two domains in a linear amino acid sequence of a polypeptide chain.

In some embodiments, heterologous nucleotide sequences encoding peptide linkers can be inserted between the optimized FVIII polynucleotide sequences of the invention and a heterologous nucleotide sequence encoding, for example, one of the heterologous moieties described above, such as albumin. Peptide linkers can provide flexibility to the chimeric polypeptide molecule. Linkers are not typically cleaved, however such cleavage can be desirable. In one embodiment, these linkers are not removed during processing.

A type of linker which can be present in a chimeric protein of the invention is a protease cleavable linker which comprises a cleavage site (i.e., a protease cleavage site substrate, e.g., a factor XIa, Xa, or thrombin cleavage site) and which can include additional linkers on either the N-terminal of C-terminal or both sides of the cleavage site. These cleavable linkers when incorporated into a construct of the invention result in a chimeric molecule having a heterologous cleavage site.

In one embodiment, an FVIII polypeptide of the instant invention comprises two or more Fc domains or moieties linked via a cscFc linker to form an Fc region comprised in a single polypeptide chain. The cscFc linker is flanked by at least one intracellular processing site, i.e., a site cleaved by an intracellular enzyme. Cleavage of the polypeptide at the at least one intracellular processing site results in a polypeptide which comprises at least two polypeptide chains.

Other peptide linkers can optionally be used ID a construct of the invention, e.g., to connect an FVIII protein to an Fc region. Some exemplary linkers that can be used in connection with the invention include, e.g., polypeptides comprising Gly Ser amino acids described in more detail below.

In one embodiment the peptide linker is synthetic, i.e., non-naturally occurring. In one embodiment, a peptide linker includes peptides (or polypeptides) (which can or can not be naturally occurring) which comprise an amino acid sequence that links or genetically fuses a first linear sequence of amino acids to a second linear sequence of amino acids to which it is not naturally linked or genetically fused in nature. For example, in one embodiment the peptide linker can comprise non-naturally occurring polypeptides which are modified forms of naturally occurring polypeptides (e.g., comprising a mutation such as an addition, substitution or deletion). In another embodiment, the peptide linker can comprise non-naturally occurring amino acids. In another embodiment, the peptide linker can comprise naturally occurring amino acids occurring in a linear sequence that does not occur in nature. In still another embodiment, the peptide linker can comprise a naturally occurring polypeptide sequence.

For example, in certain embodiments, a peptide linker can be used to fuse identical Fc moieties, thereby forming a homodimeric scFc region. In other embodiments, a peptide linker can be used to fuse different Fc moieties (e.g. a wild-type Fc moiety and an Fc moiety variant), thereby forming a heterodimeric scFc region.

In another embodiment, a peptide linker comprises or consists of a gly-ser linker. In one embodiment, a scFc or cscFc linker comprises at least a portion of an immunoglobulin hinge and a gly-ser linker. As used herein, the term "gly-ser linker" refers to a peptide that consists of glycine and serine residues. In certain embodiments, said gly-ser linker can be inserted between two other sequences of the peptide linker. In other embodiments, a gly-ser linker is attached at one or both ends of another sequence of the peptide linker. In yet other embodiments, two or more gly-ser linker are incorporated in series in a peptide linker. In one embodiment, a peptide linker of the invention comprises at least a portion of an upper hinge region (e.g., derived from an IgG1, IgG2, IgG3, or IgG4 molecule), at least a portion of a middle hinge region (e.g., derived from an IgG1, IgG2, IgG3, or IgG4 molecule) and a series of gly/ser amino acid residues.

Peptide linkers of the invention are at least one amino acid in length and can be of varying lengths. In one embodiment, a peptide linker of the invention is from about 1 to about 50 amino acids in length. As used in this context, the term "about" indicates +/−two amino acid residues. Since linker length must be a positive integer, the length of from about 1 to about 50 amino acids in length, means a length of from 1-3 to 48-52 amino acids in length. In another embodiment, a peptide linker of the invention is from about 10 to about 20 amino acids in length. In another embodiment, a peptide linker of the invention, is from about 15 to about 50 amino acids in length. In another embodiment, a peptide linker of the invention is from about 20 to about 45 amino acids in length. In another embodiment, a peptide linker of the invention is from about 15 to about 35 or about 20 to about 30 amino acids in length. In another embodiment, a peptide linker of the invention is from about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 50, 60, 70, 80, 90, 100, 500, 1000, or 2000 amino acids in length. In one embodiment, a peptide linker of the invention is 20 or 30 amino acids in length.

In some embodiments, the peptide linker can comprise at least two, at least three, at least four, at least five, at least 10, at least 20, at least 30, at least 40, at least 50, at least 60, at least 70, at least 80, at least 90, or at least 100 amino acids. In other embodiments, the peptide linker can comprise at least 200, at least 300, at least 400, at least 500, at least 600, at least 700, at least 800, at least 900, or at least 1,000 amino acids. In some embodiments, the peptide linker can comprise at least about 10, 20, 30, 40, 50, 60, 70, 80, 90, 100, 150, 200, 300, 400, 500, 600, 700, 800, 900, 1000, 1100, 1200, 1300, 1400, 1500, 1600, 1700, 1800, 1900, or 2000 amino acids. The peptide linker can comprise 1-5 amino acids, 1-10 amino acids, 1-20 amino acids, 10-50 amino acids, 50-100 amino acids, 100-200 amino acids, 200-300 amino acids, 300-400 amino acids, 400-500 amino acids, 500-600 amino acids, 600-700 amino acids, 700-800 amino acids, 800-900 amino acids, or 900-1000 amino acids.

Peptide linkers can be introduced into polypeptide sequences using techniques known in the art. Modifications can be confirmed by DNA sequence analysis. Plasmid DNA can be used to transform host cells for stable production of the polypeptides produced.

Monomer-Dimer Hybrids

In some embodiments, the isolated nucleic acid molecules of the invention which farther comprise a heterologous nucleotide sequence encode a monomer-dimer hybrid molecule comprising FVIII.

The term "monomer-dimer hybrid" used herein refers to a chimeric protein comprising a first polypeptide chain and a second polypeptide chain, which are associated with each other by a disulfide bond, wherein the first chain comprises Factor VIII and a first Fc region and the second chain comprises, consists essentially of, or consists of a second Fc region without the FVIII. The monomer-dimer hybrid construct thus is a hybrid comprising a monomer aspect having only one clotting factor and a dimer aspect having two Fc regions.

Transcription Control Sequences

In some embodiments, the isolated nucleic acid molecules of the invention are operatively linked to at least one transcription control sequences. A transcription control sequences as used herein is any regulatory nucleotide sequence, such as a promoter sequence or promoter-enhancer combination, which facilitates the efficient transcription and translation of the coding nucleic acid to which it is operably linked. The gene expression control sequence can, for example, be a mammalian or viral promoter, such as a constitutive or inducible promoter. Constitutive mammalian promoters include, but are not limited to, the promoters for the following genes: hypoxanthine phosphoribosyl transferase (HPRT), adenosine deaminase, pyruvate kinase, beta-actin promoter, and other constitutive promoters. Exemplary viral promoters which function constitutively in eukaryotic cells include, for example, promoters from the cytomegalovirus (CMV), simian virus (e.g., SV40), papilloma virus, adenovirus, human immunodeficiency virus (HIV), Rous sarcoma virus, cytomegalovirus, the long terminal repeats (LTR) of Moloney leukemia virus, and other retroviruses, and the thymidine kinase promoter of herpes simplex virus. Other constitutive promoters are known to those of ordinary skill in the art. The promoters useful as gene expression sequences of the invention also include inducible promoters. Inducible promoters are expressed in the presence of an inducing agent. For example, the metallothionein promoter is induced to promote transcription and translation in the presence of certain metal ions. Other inducible promoters are known to those of ordinary skill in the art.

In general, the transcription control sequences shall include, as necessary, 5' non-transcribing and 5' non-translating sequences involved with the initiation of transcription and translation, respectively, such as a TATA box, capping sequence, CAAT sequence, and the like. Especially, such 5' non-transcribing sequences will include a promoter region which includes a promoter sequence for transcriptional control of the operably joined coding nucleic acid. The gene expression sequences optionally include enhancer sequences or upstream activator sequences as desired.

Vectors

The invention also provides vectors comprising the isolated nucleic acid molecules of the invention. Suitable vectors include expression vectors, viral vectors, and plasmid vectors.

As used herein, an expression vector refers to any nucleic acid construct which contains the necessary elements for the transcription and translation of an inserted coding sequence, or in the case of an RNA viral vector, the necessary elements for replication and translation, when introduced into an appropriate host cell. Expression vectors can include plasmids, phagemids, viruses, and derivatives thereof.

Expression vectors of the invention will include optimized polynucleotides encoding the BDD FVIII protein described herein. In one embodiment, the optimized coding sequences for the BDD FVIII protein is operably linked to an expression control sequence. As used herein, two nucleic acid sequences are operably linked when they are covalently linked in such a way as to permit each component nucleic acid sequence to retain its functionality. A coding sequence and a gene expression control sequence are said to be operably linked when they are covalently linked in such a way as to place the expression or transcription and/or translation of the coding sequence under the influence or control of the gene expression control sequence. Two DNA sequences are said to be operably linked if induction of a promoter in the 5' gene expression sequence results in the transcription of the coding sequence and if the nature of the linkage between the two DNA sequences does not (1) result in the introduction of a frame-shift mutation, (2) interfere with the ability of the promoter region to direct the transcription of the coding sequence, or (3) interfere with the ability of the corresponding RNA transcript to be translated into a protein. Thus, a gene expression sequence would be operably linked to a coding nucleic acid sequence if the gene expression sequence were capable of effecting transcription of that coding nucleic acid sequence such that the resulting transcript is translated into the desired protein or polypeptide.

Viral vectors include, but are not limited to, nucleic acid sequences from the following viruses: retrovirus, such as Moloney murine leukemia virus, Harvey murine sarcoma virus, murine mammary tumor virus, and Rous sarcoma virus; adenovirus, adeno-associated virus; SV40-type viruses; polyomaviruses; Epstein-Barr viruses; papilloma viruses; herpes virus; vaccinia virus; polio virus; and RNA virus such as a retrovirus. One can readily employ other vectors well-known in the art. Certain viral vectors are based on non-cytopathic eukaryotic viruses in which non-essential genes have been replaced with the gene of interest. Non-cytopathic viruses include retroviruses, the life cycle of which involves reverse transcription of genomic viral RNA into DNA with subsequent proviral integration into host cellular DNA. Retroviruses have been approved for human gene therapy trials. Most useful are those retroviruses that are replication-deficient (i.e., capable of directing synthesis of the desired proteins, but incapable of manufacturing an infectious particle). Such genetically altered retroviral expression vectors have general utility for the high efficiency transduction of genes in vivo. Standard protocols for producing replication-deficient retroviruses (including the steps of incorporation of exogenous, genetic material into a plasmid, transfection of a packaging cell line with plasmid, production of recombinant retroviruses by the packaging cell line, collection of viral particles from tissue culture media, and infection of the target cells with viral particles) are provided in Kriegler, M., Gene Transfer and Expression, A Laboratory Manual, W.H. Freeman Co., New York (1990) and Murry, E. J., Methods in Molecular Biology, Vol. 7, Humana Press, Inc., Cliffton, N.J. (1991).

In one embodiment, the virus is an adeno-associated virus, a double-stranded DNA virus. The adeno-associated virus can be engineered to be replication-deficient and is capable of infecting a wide range of cell types and species. It further has advantages such as heat and lipid solvent stability; high transduction frequencies in cells of diverse lineages, including hematopoietic cells; and lack of superinfection inhibition thus allowing multiple series of transductions. Reportedly, the adeno-associated virus can integrate into human cellular DNA in a site-specific manner, thereby minimizing the possibility of insertional mutagenesis and variability of inserted gene expression characteristic of retroviral infection. In addition, wild-type adeno-associated virus infections have been followed in tissue culture for greater than 100 passages in the absence of selective pressure, implying that the adeno-associated virus genomic integration is a relatively stable event. The adeno-associated virus can also function in an extrachromosomal fashion.

Other vectors include plasmid vectors. Plasmid vectors have been extensively described in the art and are well-known to those of skill in the art. See, e.g., Sambrook et al., Molecular Cloning: A Laboratory Manual, Second Edition, Cold Spring Harbor Laboratory Press, 1989. In the last few years, plasmid vectors have been found to be particularly advantageous for delivering genes to cells in vivo because of their inability to replicate within and integrate into a host genome. These plasmids, however, having a promoter compatible with the host cell, can express a peptide from a gene operably encoded within the plasmid. Some commonly used plasmids available from commercial suppliers include pBR322, pUC18, pUC19, various pcDNA plasmids, pRC/CMV, various pCMV plasmids, pSV40, and pBlueScript. Additional examples of specific plasmids include pcDNA3.1, catalog number V79020; pcDNA3.1/hygro, catalog number V87020; pcDNA4/myc-His, catalog number V86320; and pBudCE4.1, catalog number V53220, all from Invitrogen (Carlsbad, Calif.). Other plasmids are well-known to those of ordinary skill in the art. Additionally, plasmids can be custom designed using standard molecular biology techniques to remove and/or add specific fragments of DNA.

Host Cells

The invention also provides host cells comprising the isolated nucleic acid molecules of the invention. As used herein, the term "transformation" shall be used in a broad sense to refer to the introduction of DNA into a recipient host cell that changes the genotype and consequently results in a change in the recipient cell.

"Host cells" refers to cells that have been transformed with vectors constructed using recombinant DNA techniques and encoding at least one heterologous gene. The host cells of the present invention are preferably of mammalian origin; most preferably of human or mouse origin. Those skilled in the art are credited with ability to preferentially determine particular host cell lines which are best suited for their purpose. Exemplary host cell lines include, but are not limited to, CHO, DG44 and DUXB11 (Chinese Hamster Ovary lines, DHFR minus), HELA (human cervical carcinoma), CVI (monkey kidney line), COS (a derivative of CVI with SV40 T antigen), R1610 (Chinese hamster fibroblast) BALBC/3T3 (mouse fibroblast), HAK (hamster kidney line), SP2/O (mouse myeloma), P3.times.63-Ag3.653 (mouse myeloma), BFA-1c1BPT (bovine endothelial cells), RAJI (human lymphocyte), PER.C6®, NS0, CAP, BHK21, and HEK 293 (human kidney). Host cell lines are typically available from commercial services, the American Tissue Culture Collection, or from published literature.

Introduction of the isolated nucleic acid molecules of the invention into the host cell can be accomplished by various techniques well known to those of skill in the art, These include, but are not limited to, transfection (including electrophoresis and electroporation), protoplast fusion, calcium phosphate precipitation, cell fusion with enveloped DNA, microinjection, and infection with intact virus. See, Ridgway, A. A. G. "*Mammalian Expression Vectors*" Chapter 24.2, pp. 470-472 Vectors, Rodriguez and Denhardt, Eds. (Butterworths, Boston, Mass. 1988). Most preferably, plasmid introduction into the host is via electroporation. The transformed cells are grown under conditions appropriate to the production of the light chains and heavy chains, and assayed for heavy and/or light chain protein synthesis. Exemplary assay techniques include enzyme-linked immunosorbent assay (ELISA), radioimmunoassay (RIA), or flourescence-activated cell sorter analysis (FACS), immunohistochemistry and the like.

Host cells comprising the isolated nucleic acid molecules of the invention are grown in an appropriate growth medium. As used herein, the term "appropriate growth medium" means a medium containing nutrients required for the growth of cells. Nutrients required for cell growth can include a carbon source, a nitrogen source, essential amino acids, vitamins, minerals, and growth factors. Optionally, the media can contain one or more selection factors. Optionally the media can contain bovine calf serum or fetal calf serum (FCS). In one embodiment, the media contains substantially no IgG. The growth medium will generally select for cells containing the DNA construct by, for example, drug selection or deficiency in an essential nutrient which is complemented by the selectable marker on the DNA construct or co-transfected with the DNA construct. Cultured mammalian cells are generally grown in commercially available serum-containing or serum-free media (e.g., MEM, DMEM, DMEM/F12). In one embodiment, the medium is CDoptiCHO (Invitrogen, Carlsbad, Calif.). In another embodiment, the medium is CD17 (Invitrogen, Carlsbad, Calif.). Selection of a medium appropriate for the particular cell line used is within the level of those ordinary skilled in the art.

Preparation of Polypeptides

The invention also provides a polypeptide encoded by the isolated nucleic acid molecules of the invention. In other embodiments, the polypeptide of the invention is encoded by a vector comprising the isolated nucleic acids of the invention. In yet other embodiments, the polypeptide of the invention is produced by a host cell comprising the isolated nucleic molecules of the invention.

In other embodiments, the invention also provides a method of producing a polypeptide with FVIII activity, comprising culturing a host cell of the invention under conditions whereby a polypeptide with FVIII activity is produced, and recovering the polypeptide with FVIII activity. In some embodiments, the expression of the polypeptide with FVIII activity is increased relative to a host cell cultured under the same conditions but containing a reference nucleotide sequence comprising SEQ ID NO:3, the parental FVIII gene sequence.

In other embodiments, the invention provides a method of increasing the expression of a polyepetide with FVIII activity comprising culturing a host cell of the invention under conditions, whereby a polypeptide with FVIII activity is expressed by the nucleic acid molecule, wherein the expression of the polypeptide with FVIII activity is increased relative to a host cell cultured under the same conditions comprising a reference nucleic acid molecule comprising SEQ ID NO:3.

In other embodiments, the invention provides a method of improving yield of a polypeptide with Factor VIII activity comprising culturing a host cell under conditions whereby a polypeptide with Factor VIII activity is produced by the nucleic acid molecule, wherein the yield of polypeptide with Factor VIII activity is increased relative to a host cell cultured under the same conditions comprising a reference nucleic acid sequence comprising SEQ ID NO: 3.

A variety of methods are available for recombinantly producing a FVIII protein from the optimized nucleic acid molecule of the invention. A polynucleotide of the desired sequence can be produced by de novo solid-phase DNA synthesis or by PCR mutagenesis of an earlier prepared polynucleotide. Oligonucleotide-mediated mutagenesis is one method for preparing a substitution, insertion, deletion, or alteration (e.g., altered codon) in a nucleotide sequence. For example, the starting DNA is altered by hybridizing an oligonucleotide encoding the desired mutation to a single-stranded DNA template. After hybridization, a DNA polymerase is used to synthesize an entire second complementary strand of the template that incorporates the oligonucleotide primer. In one embodiment, genetic engineering, e.g., primer-based PCR mutagenesis, is sufficient to incorporate an alteration, as defined herein, for producing a polynucleotide of the invention.

For recombinant protein production, an optimized polynucleotide sequence of the invention encoding the FVIII protein is inserted into an appropriate expression vehicle, i.e., a vector which contains the necessary elements for the transcription and translation of the inserted coding sequence, or in the case of an RNA viral vector, the necessary elements for replication and translation.

The polynucleotide sequence of the invention is inserted into the vector in proper reading frame. The expression vector is then transfected into a suitable target cell which will express the polypeptide. Transfection techniques known in the art include, but are not limited to, calcium phosphate precipitation (Wigler et al. 1978, *Cell* 14: 725) and electroporation (Neumann et al. 1982, *EMBO, J.* 1: 841). A variety of host-expression vector systems can be utilized to express the FVIII proteins described herein in eukaryotic cells. In one embodiment, the eukaryotic cell is an animal cell, including mammalian cells (e.g. HEK293 cells, PER.C6®, CHO, BHK, Cos, HeLa cells). A polynucleotide sequence of the invention can also code for a signal sequence that will permit the FVIII protein to be secreted. One skilled in the art will understand that while the FVIII protein is translated the signal sequence is cleaved by the cell to form the mature protein. Various signal sequences are known in the art, e.g., native factor Vll signal sequence, native factor IX signal sequence and the mouse IgK light chain signal sequence. Alternatively, where a signal sequence is not included the FVIII protein can be recovered by lysing the cells.

The FVIII protein of the invention can be synthesized in a transgenic animal, such as a rodent, goat, sheep, pig, or cow. The term "transgenic animals" refers to non-human animals that have incorporated a foreign gene into their genome. Because this gene is present in germline tissues, it is passed from parent to offspring. Exogenous genes are introduced into single-celled embryos (Brinster et al. 1985, Proc. Natl. Acad. Sci. USA 82:4438). Methods of producing transgenic animals are known in the art including transgenics that produce immunoglobulin molecules (Wagner et al. 1981, Proc. Natl. Acad. Sci. USA 78: 6376; McKnight et al. 1983, Cell 34: 335; Brinster et al. 1983, Nature 306: 332; Ritchie et al. 1984, Nature 312: 517; Baldassarre et al. 2003, Theriogenology 59: 831; Robl et al. 2003, Theriogenology 59: 107; Malassagne et al. 2003, Xenotransplantation 10 (3): 267).

The expression vectors can encode for tags that permit for easy purification or identification of the recombinantly produced protein. Examples include, but are not limited to, vector pUR278 (Ruther et al. 1983, EMBO J. 2: 1791) in which the FVIII protein described herein coding sequence can be ligated into the vector in frame with the lac Z coding region so that a hybrid protein is produced; pGEX vectors can be used to express proteins with a glutathione S-transferase (GST) tag. These proteins are usually soluble and can easily be purified from cells by adsorption to glutathione-agarose beads followed by elution in the presence of free glutathione. The vectors include cleavage sites (e.g., Pre-Cission Protease (Pharmacia, Peapack, N. J.)) for easy removal of the tag after purification.

For the purposes of this invention, numerous expression vector systems can be employed. These expression vectors are typically replicable in the host organisms either as episomes or as an integral part of the host chromosomal DNA. Expression vectors can include expression control sequences including, but not limited to, promoters (e.g., naturally-associated or heterologous promoters), enhancers, signal sequences, splice signals, enhancer elements, and transcription termination sequences. Preferably, the expression control sequences are eukaryotic promoter systems in vectors capable of transforming or transfecting eukaryotic host cells. Expression vectors can also utilize DNA elements which are derived from animal viruses such as bovine papilloma virus, polyoma virus, adenovirus, vaccinia virus, baculovirus, retroviruses (RSV, MMTV or MOMLV), cytomegalovirus (CMV), or SV40 virus. Others involve the use of polycistronic systems with internal ribosome binding sites.

Commonly, expression vectors contain selection markers (e.g., ampicillin-resistance, hygromycin-resistance, tetracycline resistance or neomycin resistance) to permit detection of those cells transformed with the desired DNA sequences (see, e.g., Itakura et al., U.S. Pat. No. 4,704,362). Cells which have integrated the DNA into their chromosomes can be selected by introducing one or more markers which allow selection of transfected host cells. The marker can provide for prototrophy to an auxotrophic host, biocide resistance (e.g., antibiotics) or resistance to heavy metals such as copper. The selectable marker gene can either be directly linked to the DNA sequences to be expressed, or introduced into the same cell by cotransformation.

An example of a vector useful for expressing an optimized FVIII sequence is NEOSPLA (U.S. Pat. No. 6,159, 730). This vector contains the cytomegalovirus promoter/enhancer, the mouse beta globin major promoter, the SV40 origin of, replication, the bovine growth hormone polyadenylation sequence, neomycin phosphotransferase exon 1 and exon 2, the dihydrofolate reductase gene and leader sequence. This vector has been found to result in very high level expression of antibodies upon incorporation of variable and constant region genes, transfection in cells, followed by selection in G418 containing medium and methotrexate amplification. Vector systems are also taught in U.S. Pat. Nos. 5,736,137 and 5,658,570, each of which is incorporated by reference in its entirety herein. This system provides for high expression levels, e.g., >30 pg/cell/day. Other exemplary vector systems are disclosed e.g., in U.S. Pat. No. 6,413,777.

In other embodiments the polypeptides of the invention of the instant invention can be expressed using polycistronic constructs. In these expression systems, multiple gene products of interest such as multiple polypeptides of multimer binding protein can be produced from a single polycistronic construct. These systems advantageously use an internal ribosome entry site (IRES) to provide relatively high levels of polypeptides in eukaryotic host cells. Compatible IRES sequences are disclosed in U.S. Pat. No. 6,193,980 which is also incorporated herein.

More generally, once the vector or DNA sequence encoding a polypeptide has been prepared, the expression vector can be introduced into an appropriate host cell. That is, the host cells can be transformed. Introduction of the plasmid into the host cell can be accomplished by various techniques well known to those of skill in the art, as discussed above. The transformed cells are grown under conditions appropriate to the production of the FVIII polypeptide, and assayed for FVIII polypeptide synthesis. Exemplary assay techniques include enzyme-linked immunosorbent assay (ELISA), radioimmunoassay (RIA), or flourescence-activated cell sorter analysis (FACS), immunohistochemistry and the like.

In descriptions of processes for isolation of polypeptides from recombinant hosts, the terms "cell" and "cell culture" are used interchangeably to denote the source of polypeptide unless it is clearly specified otherwise. In other words, recovery of polypeptide from the "cells" can mean either from spun down whole cells, or from the cell culture containing both the medium and the suspended cells.

The host cell line used for protein expression is preferably of mammalian origin; most preferably of human or mouse origin, as the isolated nucleic acids of the invention have been optimized for expression in human cells, Exemplary host cell lines have been described above. In one embodiment of the method to produce a polypeptide with FVIII activity, the host cell is a HEK293 cell. In another embodiment of the method to produce a polypeptide with FVIII activity, the host cell is a CHO cell.

Genes encoding the polypeptides of the invention can also be expressed in non-mammalian cells such as bacteria or yeast or plant cells. In this regard it will be appreciated that various unicellular non-mammalian microorganisms such as bacteria can also be transformed; i.e., those capable of being grown in cultures or fermentation. Bacteria, which are susceptible to transformation, include members of the enterobacteriaceae, such as strains of *Escherichia coli* or *Salmonella*; Bacillaceae, such as *Bacillus subtilis*; *Pneumococcus*; *Streptococcus*, and *Haemophilus influenzae*. It will further be appreciated that, when expressed in bacteria, the polypeptides typically become part of inclusion bodies. The polypeptides must be isolated, purified and then assembled into functional molecules.

Alternatively, optimized nucleotide sequences of the invention can be incorporated in transgenes for introduction into the genome of a transgenic animal and subsequent expression in the milk of the transgenic animal (see, e.g., Deboer et al., U.S. Pat. No. 5,741,957, Rosen, U.S. Pat. No. 5,304,489, and Meade et al., U.S. Pat. No. 5,849,992). Suitable transgenes include coding sequences for polypeptides in operable linkage with a promoter and enhancer from a mammary gland specific gene, such as casein or beta lactoglobulin.

In vitro production allows scale-up to give large amounts of the desired polypeptides. Techniques for mammalian cell cultivation under tissue culture conditions are known in the art and include homogeneous suspension culture, e.g. in an airlift reactor or in a continuous stirrer reactor, or immobilized or entrapped cell culture, e.g. in hollow fibers, microcapsules, on agarose microbeads or ceramic cartridges. If necessary and/or desired, the solutions of polypeptides can be purified by the customary chromatography methods, for example gel filtration, ion-exchange chromatography, chromatography over DEAE-cellulose or (immuno-)affinity chromatography, e.g., after preferential biosynthesis of a synthetic hinge region polypeptide or prior to or subsequent to the HIC chromatography step described herein. An affinity tag sequence (e.g. a His(6) tag) can optionally be attached or included within the polypeptide sequence to facilitate downstream purification.

Once expressed, the FVIII protein can be purified according to standard procedures of the art, including ammonium sulfate precipitation, affinity column chromatography, HPLC purification, gel electrophoresis and the like (see generally Scopes, Protein Purification (Springer-Verlag, N.Y., (1982)). Substantially pure proteins of at least about 90 to 95% homogeneity are preferred, and 98 to 99% or more homogeneity most preferred, for pharmaceutical uses.

Pharmaceutical Composition

Compositions containing the FVIII protein of the present invention or the isolated nucleic acids of the present invention can contain a suitable pharmaceutically acceptable carrier. For example, they can contain excipients and/or auxiliaries that facilitate processing of the active compounds into preparations designed for delivery to the site of action.

The pharmaceutical composition can be formulated for parenteral administration (i.e. intravenous, subcutaneous, or intramuscular) by bolus injection. Formulations for injection can be presented in unit dosage form, e.g., in ampoules or in multidose containers with an added preservative. The compositions can take such forms as suspensions, solutions, or emulsions in oily or aqueous vehicles, and contain formulatory agents such as suspending, stabilizing and/or dispersing agents. Alternatively, the active ingredient can be in powder form for constitution with a suitable vehicle, e.g., pyrogen free water.

Suitable formulations for parenteral administration also include aqueous solutions of the active compounds in water-soluble form, for example, water-soluble salts. In addition, suspensions of the active compounds as appropriate oily injection suspensions can be administered. Suitable lipophilic solvents or vehicles include fatty oils, for example, sesame oil, or synthetic fatty acid esters, for example, ethyl oleate or triglycerides. Aqueous injection suspensions can contain substances, which increase the viscosity of the suspension, including, for example, sodium carboxymethyl cellulose, sorbitol and dextran. Optionally, the suspension can also contain stabilizers. Liposomes also can be used to encapsulate the molecules of the invention for delivery into cells or interstitial spaces. Exemplary pharmaceutically acceptable carriers are physiologically compatible solvents, dispersion media, coatings, antibacterial and antifungal agents, isotonic and absorption delaying agents, water, saline, phosphate buffered saline, dextrose, glycerol, ethanol and the like. In some embodiments, the composition comprises isotonic agents, for example, sugars, polyalcohols such as mannitol, sorbitol, or sodium chloride. In other embodiments, the compositions comprise pharmaceutically acceptable substances such as wetting agents or minor amounts of auxiliary substances such as wetting or emulsifying agents, preservatives or buffers, which enhance the shelf life or effectiveness of the active ingredients.

Compositions of the invention can be in a variety of forms, including, for example, liquid (e.g., injectable and infusible solutions), dispersions, suspensions, semi-solid and solid dosage forms. The preferred form depends on the mode of administration and therapeutic application.

The composition can be formulated as a solution, micro emulsion, dispersion, liposome, or other ordered structure suitable to high drug concentration. Sterile injectable solutions can be prepared by incorporating the active ingredient in the required amount in an appropriate solvent with one or a combination of ingredients enumerated above, as required, followed by filtered sterilization. Generally, dispersions are prepared by incorporating the active ingredient into a sterile vehicle that contains a basic dispersion medium and the required other ingredients from those enumerated above. In the case of sterile powders for the preparation of sterile injectable solutions, the preferred methods of preparation are vacuum drying and freeze-drying that yields a powder of the active ingredient plus any additional desired ingredient from a previously sterile-filtered solution. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin.

The active ingredient can be formulated with a controlled-release formulation or device. Examples of such formulations and devices include implants, transdermal patches, and microencapsulated delivery systems. Biodegradable, biocompatible polymers can be used, for example, ethylene vinyl acetate, polyanhydrides, polyglycolic acid, collagen, polyorthoesters, and polylactic acid. Methods for the preparation of such formulations and devices are known in the art. See e.g., Sustained and Controlled Release Drug Delivery Systems, J. R. Robinson, ed., Marcel Dekker, Inc., New York, 1978.

Injectable depot formulations can be made by forming microencapsulated matrices of the drug in biodegradable polymers such as polylactide-polyglycolide. Depending on the ratio of drug to polymer, and the nature of the polymer employed, the rate of drug release can be controlled. Other exemplary biodegradable polymers are polyorthoesters and polyanhydrides. Depot injectable formulations also can be prepared by entrapping the drug in liposomes or microemulsions.

Supplementary active compounds can be incorporated into the compositions. In one embodiment, the chimeric protein of the invention is formulated with another clotting factor, or a variant, fragment, analogue, or derivative thereof. For example, the clotting factor includes, but is not limited to, factor V, factor VII, factor VIII, factor IX, factor X, factor XI, factor XII, factor XIII, prothrombin, fibrinogen, von Willebrand factor or recombinant soluble tissue factor (rsTF) or activated forms of any of the preceding. The clotting factor of hemostatic agent can also include antifibrinolytic drugs, e.g., epsilon-amino-caproic acid, tranexamic acid.

Dosage regimens can be adjusted to provide the optimum desired response. For example, a single bolus can be administered, several divided doses can be administered over time, or the dose can be proportionally reduced or increased as indicated by the exigencies of the therapeutic situation. It is advantageous to formulate parenteral compositions in dosage unit form for ease of administration and uniformity of dosage. See, e.g., Remington's Pharmaceutical Sciences (Mack Pub. Co., Easton, Pa. 1980).

In addition to the active compound, the liquid dosage form can contain inert ingredients such as water, ethyl alcohol, ethyl carbonate, ethyl acetate, benzyl alcohol, benzyl benzoate, propylene glycol, 1,3-butylene glycol, dimethylformamide, oils, glycerol, tetrahydrofurfuryl alcohol, polyethylene glycols, and fatty acid esters of sorbitan.

Non-limiting examples of suitable pharmaceutical carriers are also described in Remington's Pharmaceutical Sciences by E. W. Martin. Some examples of excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol, and the like. The composition can also contain pH buffering reagents, and wetting or emulsifying agents.

For oral administration, the pharmaceutical composition can take the form of tablets or capsules prepared by conventional means. The composition can also be prepared as a liquid for example a syrup or a suspension. The liquid can include suspending agents (e.g., sorbitol syrup, cellulose derivatives or hydrogenated edible fats), emulsifying agents (lecithin or acacia), non-aqueous vehicles (e.g., almond oil, oily esters, ethyl alcohol, or fractionated vegetable oils), and preservatives (e.g., methyl or propyl-p-hydroxybenzoates or sorbic acid). The preparations can also include flavoring, coloring and sweetening agents. Alternatively, the composition can be presented as a dry product for constitution with water or another suitable vehicle.

For buccal administration, the composition can take the form of tablets or lozenges according to conventional protocols.

For administration by inhalation, the compounds for use according to the present invention are conveniently delivered in the form of a nebulized aerosol with or without excipients or in the form of an aerosol spray from a pressurized pack or nebulizer, with optionally a propellant, e.g., dichlorodifluoromethane, trichlorofluoromethane, dichlorotetrafluoromethane, carbon dioxide or other suitable gas. In the case of a pressurized aerosol the dosage unit can be determined by providing a valve to deliver a metered amount. Capsules and cartridges of, e.g., gelatin for use in an inhaler or insufflator can be formulated containing a powder mix of the compound and a suitable powder base such as lactose or starch.

The pharmaceutical composition can also be formulated for rectal administration as a suppository or retention enema, e.g., containing conventional suppository bases such as cocoa butter or other glycerides.

In one embodiment, a pharmaceutical composition comprises a FVIII protein, the optimized polynucleotide encoding the FVIII protein, the vector comprising the polynucleotide, or the host cell comprising the vector, and a pharmaceutically acceptable carrier. In some embodiments, the composition is administered by a route selected from the group consisting of topical administration, intraocular administration, parenteral administration, intrathecal administration, subdural administration and oral administration. The parenteral administration can be intravenous or subcutaneous administration.

In other embodiments, the composition is used to treat a bleeding disease or condition in a subject in need thereof. The bleeding disease or condition is selected from the group consisting of a bleeding coagulation disorder, hemarthrosis, muscle bleed, oral bleed, hemorrhage, hemorrhage into muscles, oral hemorrhage, trauma, trauma capitis, gastrointestinal bleeding, intracranial hemorrhage, intra-abdominal hemorrhage, intrathoracic hemorrhage, bone fracture, central nervous system bleeding, bleeding in the retropharyngeal space, bleeding in the retroperitoneal space, bleeding in the illiopsoas sheath and any combinations thereof. In still other embodiments, the subject is scheduled to undergo a surgery. In yet other embodiments, the treatment is prophylactic or on-demand.

Methods of Treatment

The invention provides a method of treating a bleeding disorder comprising administering to a subject in need thereof a nucleic acid molecule, vector, or polypeptide of the invention. In some embodiments, the bleeding disorder is characterized by a deficiency in Factor VIII. In some embodiments, the bleeding disorder is hemophilia. In some embodiments, the bleeding disorder is hemophilia A. In some embodiments of the method of treating a bleeding disorder, plasma Factor VIII activity at 24 hours post administration is increased relative to a subject administered a reference nucleic acid molecule comprising SEQ ID NO 3, a vector comprising the reference nucleic acid molecule, or a polypeptide encoded by the reference nucleic acid molecule.

The invention also relates to a method of treating, ameliorating, or preventing a hemostatic disorder in a subject comprising administering a therapeutically effective amount of a FVIII protein of the invention or an isolated nucleic acid molecule of the invention. The treatment, amelioration, and prevention by the FVIII protein or isolated nucleic acid molecule can be a bypass therapy. The subject receiving bypass therapy can have already developed an inhibitor to a clotting factor, e.g., Factor VIII, or is subject to developing a clotting factor inhibitor.

The nucleic acid molecules, vectors, or FVIII polypeptides of the invention treat or prevent a hemostatic disorder by promoting the formation of a fibrin clot. The FVIII protein of the invention can activate a member of a coagulation cascade. The clotting factor can be a participant in the extrinsic pathway, the intrinsic pathway or both.

The nucleic acid molecules, vectors, or FVIII polypeptides of the invention can be used to treat hemostatic disorders known to be treatable with FVIII. The hemostatic disorders that can be treated using methods of the invention include, but are not limited to, hemophilia A, hemophilia B, von Willebrand's disease, Factor XI deficiency (PTA deficiency), Factor XII deficiency, as well as deficiencies or structural abnormalities in fibrinogen, prothrombin, Factor V, Factor VII, Factor X, or Factor XIII, hemarthrosis, muscle bleed, oral bleed, hemorrhage, hemorrhage into muscles, oral hemorrhage, trauma, trauma capitis, gastrointestinal bleeding, intracranial hemorrhage, infra-abdominal hemorrhage, intrathoracic hemorrhage, bone fracture, central nervous system bleeding, bleeding in the retropharyngeal space, bleeding in the retroperitoneal space, and bleeding in the illiopsoas sheath. Compositions for administration to a subject include nucleic acid molecules which comprise an optimized nucleotide sequence of the invention encoding a FVIII clotting factor (for gene therapy applications) as well as FVIII polypeptide molecules.

In some embodiments, the hemostatic disorder is an inherited disorder. In one embodiment, the subject has hemophilia A. In other embodiments, the hemostatic disorder is the result of a deficiency in Factor VIII. In other embodiments, the hemostatic disorder can be the result of a defective FVIII clotting factor.

In another embodiment, the hemostatic disorder can be an acquired disorder. The acquired disorder can result from an underlying secondary disease or condition. The unrelated condition can be, as an example, but not as a limitation, cancer, an autoimmune disease, or pregnancy. The acquired disorder can result from old age or from medication to treat an underlying secondary disorder (e.g. cancer chemotherapy).

The invention also relates to methods of treating a subject that does not have a hemostatic disorder or a secondary disease or condition resulting in acquisition of a hemostatic disorder. The invention thus relates to a method of treating a subject in need of a general hemostatic agent comprising administering a therapeutically effective amount of the FVIII polypeptide of the invention or an isolated nucleic acid molecule of the invention. For example, in one embodiment, the subject in need of a general hemostatic agent is undergoing, or is about to undergo, surgery. The FVIII polypeptide of the invention or an isolated nucleic acid molecule of the invention can be administered prior to or after surgery as a prophylactic. The FVIII polypeptide of the invention or an isolated nucleic acid molecule of the invention can be administered during or after surgery to control an acute bleeding episode. The surgery can include, but is not limited to, liver transplantation, liver resection, or stem cell transplantation.

In another embodiment, the FVIII polypeptide of the invention or an isolated nucleic acid molecule of the invention can be used to treat a subject having an acute bleeding episode who does not have a hemostatic disorder. The acute bleeding episode can result from severe trauma, e.g., surgery, an automobile accident, wound, laceration gun shot, or any other traumatic event resulting in uncontrolled bleeding.

The FVIII protein or the isolated nucleic acid molecules of the invention can be used to prophylactically treat a subject with a hemostatic disorder. The FVIII protein or the isolated nucleic acid molecules of the invention can be used to treat an acute bleeding episode in a subject with a hemostatic disorder.

In some embodiments, a FVIII protein composition of the invention is administered in combination with at least one other agent that promotes hemostasis. Said other agent that promotes hemostasis in a therapeutic with demonstrated clotting activity. As an example, but not as a limitation, the hemostatic agent can include Factor V, Factor VII, Factor IX, Factor X, Factor XI, Factor XII, Factor XIII, prothrombin, or fibrinogen or activated forms of any of the preceding. The clotting factor or hemostatic agent can also include anti-fibrinolytic drugs, e.g., epsilon-amino-caproic acid, tranexamic acid.

In one embodiment of the invention, the composition (e.g., the FVIII polypeptide or the optimized nucleic acid molecule encoding the FVIII polypeptide) is one in which the FVIII is present in activatable form when administered to a subject. Such an activatable molecule can be activated in vivo at the site of clotting after administration to a subject.

The FVIII polypeptide or the optimized nucleic acid molecule encoding the FVIII polypeptide can be administered intravenously, subcutaneously, intramuscularly, or via any mucosal surface, e.g., orally, sublingually, buccally, sublingually, nasally, rectally, vaginally or via pulmonary route. The FVIII protein can be implanted within or linked to a biopolymer solid support that allows for the slow release of the chimeric protein to the desired site.

For oral administration, the pharmaceutical composition can take the form of tablets or capsules prepared by conventional means. The composition can also be prepared as a liquid for example a syrup or a suspension. The liquid can include suspending agents (e.g. sorbitol syrup, cellulose derivatives or hydrogenated edible fats), emulsifying agents (lecithin or acacia), non-aqueous vehicles (e.g. almond oil, oily esters, ethyl alcohol, or fractionated vegetable oils), and preservatives (e.g. methyl or propyl-p-hydroxybenzoates or sorbic acid). The preparations can also include flavoring, coloring and sweetening agents. Alternatively, the composition can be presented as a dry product for constitution with water or another suitable vehicle.

For buccal and sublingual administration the composition can take the form of tablets, lozenges or, fast dissolving films according to conventional protocols.

For administration by inhalation, the polypeptide having FVIII activity for use according to the present invention are conveniently delivered in the form of an aerosol spray from a pressurized pack or nebulizer (e.g. in PBS), with a suitable propellant, e.g., dichlorodifluoromethane, trichlorofluoromethane, dichlorotetrafluoromethane, carbon dioxide or other suitable gas. In the case of a pressurized aerosol the dosage unit can be determined by providing a valve to deliver a metered amount. Capsules and cartridges of, e.g., gelatin for use in an inhaler or insufflator can be formulated containing a powder mix of the compound and a suitable powder base such as lactose or starch.

In one embodiment, the route of administration of the FVIII polypeptide or the optimized nucleic acid molecule encoding the FVIII polypeptide is parenteral. The term parenteral as used herein includes intravenous, intraarterial, intraperitoneal, intramuscular, subcutaneous, rectal or vaginal, administration. The intravenous form of parenteral administration is preferred. While all these forms of administration are clearly contemplated as being within the scope of the invention, a form for administration would be a solution for injection, in particular for intravenous or intraarterial injection or dep. Usually, a suitable pharmaceutical composition for injection can comprise a buffer (e.g. acetate, phosphate or citrate buffer), a surfactant (e.g. polysorbate), optionally a stabilizer agent (e.g. human, albumin), etc. However, in other methods compatible with the teachings herein, the FVIII polypeptides or the optimized nucleic acid molecules encoding the FVIII polypeptides can be delivered directly to the site of the adverse cellular population thereby increasing the exposure of the diseased tissue to the therapeutic agent.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. In the subject invention, pharmaceutically acceptable carriers include, but are not limited to, 0.01-0.1M and preferably 0.05M phosphate buffer or 0.8% saline. Other common parenteral vehicles include sodium phosphate solutions, Ringer's dextrose, dextrose and sodium chloride, lactated Ringer's, or fixed oils. Intravenous vehicles include fluid and nutrient replenishers, electrolyte replenishers, such as those based on Ringer's dextrose, and the like. Preservatives and other additives can also be present such as for example, antimicrobials, antioxidants, chelating agents, and inert gases and the like.

More particularly, pharmaceutical compositions suitable for injectable use include sterile aqueous solutions (where water soluble) or dispersions and sterile powders for the extemporaneous preparation of sterile injectable solutions or dispersions. In such cases, the composition must be sterile and should be fluid to the extent that easy syringability exists. It should be stable under the conditions of manufacture and storage and will preferably be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants.

Prevention of the action of microorganisms can be achieved by various antibacterial and antifungal agents, for example, parabens, chlorobutanol, phenol, ascorbic acid, thimerosal and the like. In many cases, it will be preferable to include isotonic agents, for example, sugars, polyalcohols, such as mannitol, sorbitol, or sodium chloride in the composition. Prolonged absorption of the injectable compositions can be brought about by including in the composition an agent which delays absorption, for example, aluminum monostearate and gelatin.

In any case, sterile injectable solutions can be prepared by incorporating an active compound (e.g., a polypeptide by itself or in combination with other active agents) in the required amount in an appropriate solvent with one or a combination of ingredients enumerated herein, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, the preferred methods of preparation are vacuum drying and freeze-drying, which yields a powder of an active ingredient plus any additional desired ingredient from a previously sterile-filtered solution thereof. The preparations for injections are processed, filled into containers such as ampoules, bags, bottles, syringes or vials, and sealed under aseptic conditions according to methods known in the art. Further, the preparations can be packaged and sold in the form of a kit. Such articles of manufacture will preferably have labels or package inserts indicating that the associated compositions are useful for treating a subject suffering from, or predisposed to clotting disorders.

The pharmaceutical composition can also be formulated for rectal administration as a suppository or retention enema, e.g., containing conventional suppository bases such as cocoa butter or other glycerides.

Effective doses of the compositions of the present invention, for the treatment of conditions vary depending upon many different factors, including means of administration, target site, physiological state of the patient, whether the patient is human or an animal, other medications administered, and whether treatment is prophylactic or therapeutic. Usually, the patient is a human but non-human mammals including transgenic mammals can also be treated. Treatment dosages can be titrated using routine methods known to those of skill in the art to optimize safety and efficacy.

Dosages can range from 1000 ug/kg to 0.1 ng/kg body weight. In one embodiment, the dosing range is 1 ug/kg to 100 ug/kg. The FVIII polypeptide or the optimized nucleic acid molecule encoding the FVIII polypeptide can be administered continuously or at specific timed intervals. In vitro assays can be employed to determine optimal dose ranges and/or schedules for administration. In vitro assays that measure clotting factor activity are known in the art. Additionally, effective doses can be extrapolated from dose-response curves obtained from animal models, e.g., a hemophiliac dog (Mount et al. 2002, Blood 99 (8): 2670).

Doses intermediate in the above ranges are also intended to be within the scope of the invention. Subjects can be administered such doses daily, on alternative days, weekly or according to any other schedule determined by empirical analysis. An exemplary treatment entails administration in multiple dosages over a prolonged period, for example, of at least six months. In some methods, two or more polypeptides can be administered simultaneously, in which case the dosage of each polypeptide administered falls within the ranges indicated.

FVIII polypeptides or the optimized nucleic acid molecules encoding the FVIII polypeptides of the invention can be administered on multiple occasions. Intervals between single dosages can be daily, weekly, monthly or yearly. Intervals can also be irregular as indicated by measuring blood levels of modified polypeptide or antigen in the patient. Alternatively, polypeptides can be administered as a sustained release formulation, in which case less frequent administration is required. Dosage and frequency vary depending on the half-life of the polypeptide or polynucleotide in the patient.

The dosage and frequency of administration can vary depending on whether the treatment is prophylactic or therapeutic. In prophylactic applications, compositions containing the FVIII polypeptide or the optimized nucleic acid molecule encoding the FVIII polypeptide or a cocktail thereof are administered to a patient not already in the disease state to enhance the patient's resistance or minimize effects of disease. Such an amount is defined to be a "prophylactic effective dose." A relatively low dosage is administered at relatively infrequent intervals over a long period of time. Some patients continue to receive treatment for the rest of their lives.

FVIII polypeptides or the optimized nucleic acid molecules encoding the FVIII polypeptides of the invention can optionally be administered in combination with other agents that are effective in treating the disorder or condition in need of treatment (e.g., prophylactic or therapeutic).

As used herein, the administration of FVIII polypeptides or the optimized nucleic acid molecules encoding the FVIII polypeptides of the invention in conjunction or combination with an adjunct therapy means the sequential, simultaneous, coextensive, concurrent, concomitant or contemporaneous administration or application of the therapy and the disclosed polypeptides. Those skilled in the art will appreciate that the administration or application of the various components of the combined therapeutic regimen can be timed to enhance the overall effectiveness of the treatment. A skilled artisan (e.g. a physician) would be readily be able to discern effective combined therapeutic regimens without undue experimentation based on the selected adjunct therapy and the teachings of the instant specification.

It will further be appreciated that the FVIII polypeptide or the optimized nucleic acid molecule encoding the FVIII polypeptide of the instant invention can be used in conjunction or combination with an agent or agents (e.g. to provide a combined therapeutic regimen). Exemplary agents with which a polypeptide or polynucleotide of the invention can be combined include agents that represent the current standard of care for a particular disorder being treated. Such agents can be chemical or biologic in nature. The term "biologic" or "biologic agent" refers to any pharmaceutically active agent made from living organisms and/or their products which is intended for use as a therapeutic.

The amount of agent to be used in combination with the polynucleotides or polypeptides of the instant invention can vary by subject or can be administered according to what is known in the art. See for example, Bruce A Chabner et al., *Antineoplastic Agents*, in GOODMAN & GILMAN'S THE PHARMACOLOGICAL BASIS OF THERAPEUTICS 1233-1287 ((Joel G. Hardman et al., eds., 9<sup>th</sup> ed. 1996). In another embodiment, an amount of such an agent consistent with the standard of care is administered.

As previously discussed, the polynucleotides and polypeptides of the present invention, can be administered in a pharmaceutically effective amount for the in vivo treatment of clotting disorders. In this regard, it will be appreciated that the polypeptides or polynucleotides of the invention can be formulated to facilitate administration and promote stability of the active agent. Preferably, pharmaceutical compositions in accordance with the present invention comprise a pharmaceutically acceptable, non-toxic, sterile carrier such as physiological saline, non-toxic buffers, preservatives and the like. Of course, the pharmaceutical compositions of the present invention can be administered in single or multiple doses to provide for a pharmaceutically effective amount of the polypeptide.

A number of tests are available to assess the function of the coagulation system: activated partial thromboplastin time (aPTT) test, chromogenic assay, ROTEM® assay, prothrombin time (PT) test (also used to determine INR), fibrinogen testing (often by the Clauss method), platelet count, platelet function testing (often by PFA-100), TCT, bleeding time, mixing test (whether an abnormality corrects if the patient's plasma is mixed with normal plasma), coagulation factor assays, antiphosholipid antibodies, D-dimer, genetic tests (e.g., factor V Leiden, prothrombin mutation G20210A), dilute Russell's viper venom time (dRVVT), miscellaneous platelet function tests, thromboelastography (TEG or Sonoclot), thromboelastometry (TEM®, e.g., ROTEM®), or euglobulin lysis time (ELT).

The aPTT test is a performance indicator measuring the efficacy of both the "intrinsic" (also referred to the contact activation pathway) and the common coagulation pathways. This test is commonly used to measure clotting activity of commercially available recombinant clotting factors, e.g., FVIII or FIX. It is used in conjunction with prothrombin time (PT), which measures the extrinsic pathway.

ROTEM® analysis provides information on the whole kinetics of haemostasis: clotting time, clot formation, clot stability and lysis. The different parameters in thromboelastometry are dependent on the activity of the plasmatic coagulation system, platelet function, fibrinolysis, or many factors which influence these interactions. This assay can provide a complete view of secondary haemostasis.

Gene Therapy

The invention, provides a method of increasing expression of a polypeptide with Factor VIII activity in a subject comprising administering the isolated nucleic acid molecule of the invention to a subject in need thereof, wherein the expression of the polypeptide is increased relative to a reference nucleic acid molecule comprising SEQ ID NO 3. The invention also provides a method of increasing expression of a polypeptide with Factor VIII activity in a subject comprising administering, a vector of the invention to a subject in need thereof, wherein the expression of the polypeptide is increased relative to a vector comprising a reference nucleic acid molecule.

Somatic gene therapy has been explored as a possible treatment for hemophilia A. Gene therapy is a particularly appealing treatment for hemophilia because of its potential to cure the disease through continuous endogenous production of FVIII following a single administration of vector. Haemophilia A is well suited for, gene replacement approach because its clinical manifestations are entirely attributable to the lack of a single gene product (FVIII) that circulates in minute amounts (200 ng/ml) in the plasma.

A FVIII protein of the invention can be produced in vivo in a mammal, e.g., a human patient, using a gene therapy approach to treatment of a bleeding disease or disorder selected from the group consisting of a bleeding coagulation disorder, hemarthrosis, muscle bleed, oral bleed, hemorrhage, hemorrhage into muscles, oral hemorrhage, trauma, trauma capitis, gastrointestinal bleeding, intracranial hemorrhage, intra-abdominal hemorrhage, intrathoracic hemorrhage, bone fracture, central nervous system bleeding, bleeding in the retropharyngeal space, bleeding in the retroperitoneal space, and bleeding in the illiopsoas sheath would be therapeutically beneficial. In one embodiment, the bleeding disease or disorder is hemophilia. In another embodiment, the bleeding disease or disorder is hemophilia A. This involves administration of an optimized FVIII encoding nucleic acid operably linked to suitable expression control sequences. In certain embodiment, these sequences are incorporated into a viral vector. Suitable viral vectors for such gene therapy include adenoviral vectors, lentiviral vectors, baculoviral vectors, Epstein Barr viral vectors, papovaviral vectors, vaccinia viral vectors, herpes simplex viral vectors, and adeno associated virus (AAV) vectors. The viral vector can be a replication-defective viral vector. In other embodiments, an adenoviral vector has a deletion in its E1 gene or E3 gene. When an adenoviral vector is used, the mammal can not be exposed to a nucleic acid encoding a selectable marker gene. In other embodiments, the sequences are incorporated into a non-viral vector known to those skilled in the art.

All of the various aspects, embodiments, and options described herein can be combined in any and all variations.

All publications, patents, and patent applications mentioned in this specification are herein incorporated by reference to the same extent as if each individual publication, patent, or patent application was specifically and individually indicated to be incorporated by reference.

Having generally described this invention, a further understanding can be obtained by reference to the examples provided herein. These examples are for purposes of illustration only and are not intended to be limiting.

EXAMPLES

Two codon-optimized BDD FVIII sequences were designed with the following goals:
1. Remove all matrix attachment-like region (MAR) sequences (ATATTT and AAATAT; SEQ ID NOs:5 and 6, respectively);
2. Remove all destabilizing sequences (ATTTA, SEQ ID NO:8 and TAAAT, SEQ ID NO:9);
3. Remove promoter binding sequences (TATAA, SEQ ID NO:12 and TTATA, SEQ ID NO:13);
4. Remove AU-rich sequence elements (AREs): ATTTTATT (nucleotide 2468) and ATTTTTAA (nucleotide 3790) (SEQ ID NOs: 14 and 15, respectively);
5. Add kozak sequence (GCCGCCACC<u>ATG</u>C, underlined indicate the translation start codon; SEQ ID NO:16) to increase translational initiation;
6. Adjust restriction sites to facilitate cloning;
7. Adapt codon usage to the codon bias of *homo sapiens* genes;

8. Adjust to avoid regions of very high (>70%) or low (<30%) GC content, which can increase RNA stability or prolong RNA half-life.

Example 1: Codon Optimization by GENSCRIPT OPTIMUMGENE™

The BDD FVIII nucleotide sequence was codon optimized using GENSCRIPT OPTIMUMGENE™ codon optimization technology. (GenScript Corp., New Jersey, USA). The GENSCRIPT OPTIMUMGENE™ codon optimization technology is described in Burgess-Brown et al., Protein Expr Purif. 59(1):94-102 (2008).

The following human codon usage data was used for optimization:

| CODON | AMINO ACID | FRACTION | FREQUENCY/THOUSAND |
|---|---|---|---|
| TTT | F | 0.45 | 16.9 |
| TCT | S | 0.18 | 14.6 |
| TAT | Y | 0.43 | 12.0 |
| TGT | C | 0.45 | 9.9 |
| TTC | F | 0.55 | 20.4 |
| TCC | S | 0.22 | 17.4 |
| TAC | Y | 0.57 | 15.6 |
| TGC | C | 0.55 | 12.2 |
| TTA | L | 0.07 | 7.2 |
| TCA | S | 0.15 | 11.7 |
| TAA | * | 0.28 | 0.7 |
| TGA | * | 0.52 | 1.3 |
| TTG | L | 0.13 | 12.6 |
| TCG | S | 0.06 | 4.5 |
| TAG | * | 0.20 | 0.5 |
| TGG | W | 1.00 | 12.8 |
| CTT | L | 0.13 | 12.8 |
| CCT | P | 0.28 | 17.3 |
| CAT | H | 0.41 | 10.4 |
| CGT | R | 0.08 | 4.7 |
| CTC | L | 0.20 | 19.4 |
| CCC | P | 0.33 | 20.0 |
| CAC | H | 0.59 | 14.9 |
| CGC | R | 0.19 | 10.9 |
| CTA | L | 0.07 | 6.9 |
| CCA | P | 0.27 | 16.7 |
| CAA | Q | 0.25 | 11.8 |
| CGA | R | 0.11 | 6.3 |
| CTG | L | 0.41 | 40.3 |
| CCG | P | 0.11 | 7.0 |
| CAG | Q | 0.75 | 34.6 |
| CGG | R | 0.21 | 11.9 |
| ATT | I | 0.36 | 15.7 |
| ACT | T | 0.24 | 12.8 |
| AAT | N | 0.46 | 16.7 |
| AGT | S | 0.15 | 11.9 |
| ATC | I | 0.48 | 21.4 |
| ACC | T | 0.36 | 19.2 |
| AAC | N | 0.54 | 19.5 |
| AGC | S | 0.24 | 19.4 |
| ATA | I | 0.16 | 7.1 |
| ACA | T | 0.28 | 14.8 |
| AAA | K | 0.42 | 24.0 |
| AGA | R | 0.20 | 11.5 |
| ATG | M | 1.00 | 22.3 |
| ACG | T | 0.12 | 6.2 |
| AAG | K | 0.58 | 32.9 |
| AGG | R | 0.20 | 11.4 |
| GTT | V | 0.18 | 10.9 |
| GCT | A | 0.26 | 18.6 |
| GAT | D | 0.46 | 22.3 |
| GGT | G | 0.16 | 10.8 |
| GTC | V | 0.24 | 14.6 |
| GCC | A | 0.40 | 28.5 |
| GAC | D | 0.54 | 26.0 |
| GGC | G | 0.34 | 22.8 |
| GTA | V | 0.11 | 7.0 |
| GCA | A | 0.23 | 16.0 |
| GAA | E | 0.42 | 29.0 |
| GGA | G | 0.25 | 16.3 |
| GTG | V | 0.47 | 28.9 |
| GCG | A | 0.11 | 7.6 |
| GAG | E | 0.58 | 40.8 |
| GGG | G | 0.25 | 16.4 |

Codon usage was adjusted to human bias with the human codon adaption index (CAI) changing from 0.75 (wild type BDD FVIII) to 0.88 (GenScript optimized BDD FVIII). G/C content was increased from 46.16% to 51.56%. Peaks of G/C content in a 60 bp window were removed. The resulting sequence of GenScript optimized BDD FVIII is disclosed herein as SEQ ID NO:1 and is shown in FIG. 2.

Example 2: Codon Optimization by GENEART® GENEOPTIMIZER®

The BDD FVIII nucleotide sequence was codon optimized using GENEART® GENEOPTIMIZER® software. (Invitrogen LIFE TECHNOLOGIES™ Corp., Grand Island, N.Y.). The GENEART® GENEOPTIMIZER® codon optimization technology is described in Graf et al., J. Virol. 74(22):10822-10826 (2000).

Codon usage was adjusted to human bias with the human codon adaption index (CAI) changing from 0.75 (wild type BDD FVIII) to 0.96 (GeneArt optimized BDD FVIII). G/C content was increased from 46.16% to 59%. The resulting sequence of GeneArt optimized BDD FVIII is disclosed herein as SEQ ID NO:2 and is shown in FIG. 3.

Example 3: Expression Constructs

All constructs were made in the Invitrogen pcDNA™4 vector backbone, which contains a human cytomegalovirus immediate-early (CMV) promoter, a QBI SP163 translation enhancer, and a ZEOCIN™ resistance gene for selection.

pSYN-FVIII-066 drives expression of wild-type BDD FVIII SEQ ID NO:3) in pcDNA4 backbone (Invitrogen).

pSYN-FVIII-116 drives expression of codon-optimized BDD FVIII (SEQ ID NO:1) in pcDNA4 backbone. The construct is derived from pSYN-FVIII-066 by replacing wild-type BDD FVIII with codon-optimized BDD FVIII (SEQ ID NO:1) using BsiWI and XhoI sites.

pSYN-FVIII-115 drives expression of codon-optimized BDD FVIII (SEQ ID NO:2) in pcDNA4 backbone. The construct is derived from pSYN-FVIII-066 by replacing wild-type BDD FVIII with codon-optimized BDD FVIII (SEQ ID NO:2) using BsiWI and XhoI sites.

All constructs were confirmed by DNA sequencing.

Example 4: Codon Optimization Improves FVIII Expression in a HemA Mouse

To ask whether either codon optimized BDD FVIII constructs result in increased FVIII protein expression, expression plasmids pSYN-FVIII116, pSYN-FVIII115, and wild type control pSYN-FVIII-066 were introduced into HemA mice via hydrodynamic injection. Subsequently, FVIII expression levels were monitored in each injected mouse by plasma FVIII chromogenic assays.

Hydrodynamic injection is an efficient and safe non-viral method to deliver genes to the liver in small, animals, such as mice and rats. The protein of interest is produced in the liver and can be detected within 24 hours post-injection.

HemA mice weighing 20-35 grams were injected via intravenous tail vein injection with either pSYN-FVIII116, pSYN-FVIII115, or wild type control pSYN-FVIII-066. Injections were made up with 10 ug naked plasmid DNA free of endotoxin in 0.9% sterile saline solution, to a total volume of 2 ml. Injections were performed rapidly, taking no more than 4-7 seconds to inject the full 2 ml DNA solution. Mice were closely monitored for two hours after injection, or until normal activity resumed. At 24 hours post-injection, samples were collected via retro orbital blood collection, plasma was prepared and stored at −80° C. for further analysis.

Figure 7:
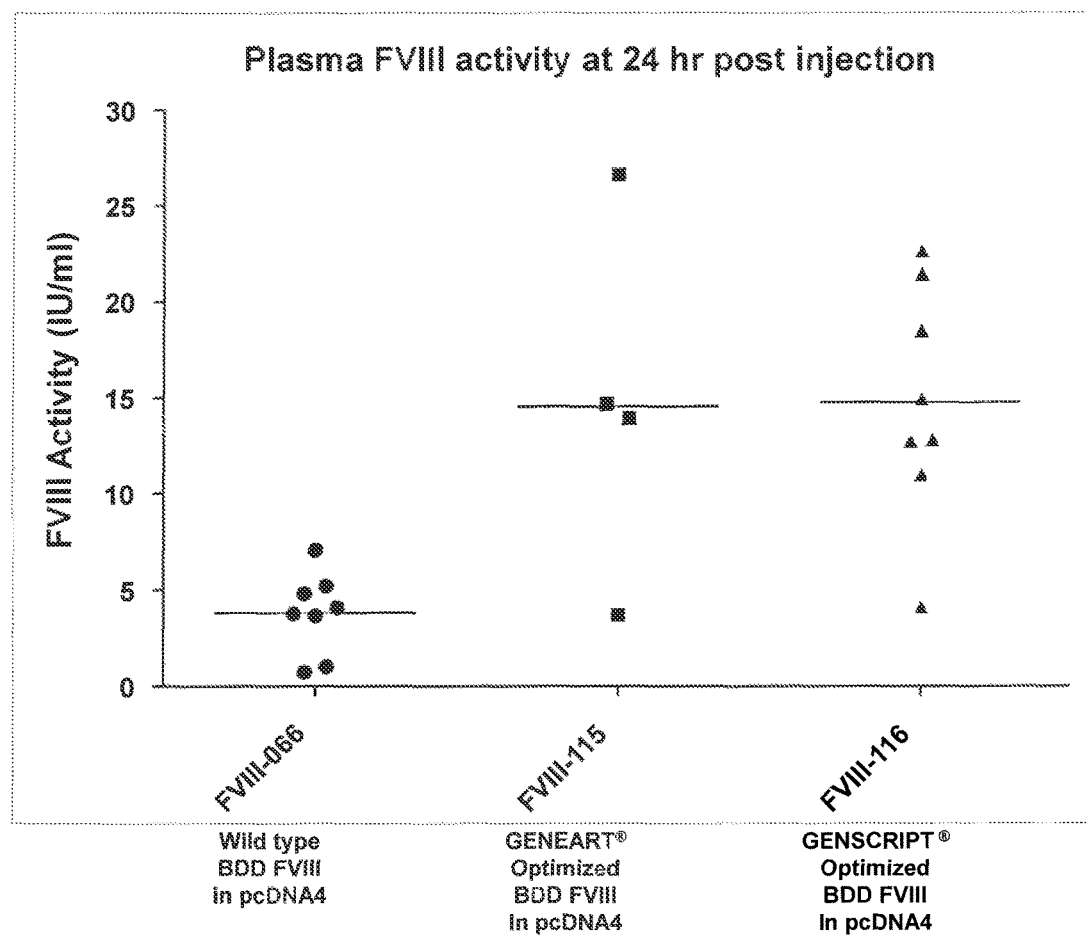
FIG. 7 is a histogram showing plasma FVIII activity in HemA mice 24 hours post hydrodynamic injection with plasmids containing either the starting BDD FVIII sequence (circles), optimized BDD FVIII sequence (SEQ ID NO:1) (squares), or optimized BDD FVIII sequence (SEQ ID NO:2) (triangles).

The FVIII activity was measured using the COATEST SP FVIII kit from DiaPharma (lot# N089019) and all incubations were performed on a 37° C. plate heater with shaking. rFVIII standards ranged from 100 mIU/mL to 0.78 mIU/mL. A pooled normal human plasma assay control and plasma samples (diluted with 1× Coatest buffer) were added into Immulon 2HB 96-well plates in duplicate (25 μL/well). Freshly prepared IXa/FX/Phospholipid mix (50 μL), 25 μL of 25 mM CaCl$_2$, and 50 μL of FXa substrate were added sequentially into each well with a 5 minutes incubation between each addition. After incubating with the substrate, 25 μL of 20% Acetic Acid was added to terminate the color reaction, and the absorbance at OD405 was measured with a SpectraMAX plus (Molecular Devices) instrument. Data were analyzed with SoftMax Pro software (version 5.2). The Lowest Level of Quantification (LLOQ) is 7.8 mIU/mL. Results are shown in FIG. 7.

Low levels of BDD FVIII activity is detected upon administration of FVIII expression plasmid pSYN-FVIII-066 (wild type BDD FVIII control). Average BDD FVIII activity in control mice is about 4-5 IU/mL (FIG. 7, circles). In contrast, on average about a three-fold increase in BDD FVIII activity is seen in the plasma of mice administered codon optimized pSYN-FVIII115 or pSYN-FVIII116 (FIG. 7, squares and triangles). Therefore, codon optimization of BDD FVIII by the approaches described above improve FVIII expression in a HemA mouse model.

SEQUENCES

```
optimized BDD FVIII
                                                                    SEQ ID NO: 1
CGTACGGCCGCCACCATGCAGATTGAGCTGTCTACTTGCTTTTTCCTGTGCCTGCTGAGGTTTTGCTTTTCCGCTACACG

AAGGTATTATCTGGGGGCTGTGGAACTGTCTTGGGATTACATGCAGAGTGACCTGGGAGAGCTGCCAGTGGACGCAAGGT

TTCCCCCTAGAGTCCCTAAGTCATTCCCCTTCAACACTAGCGTGGTCTACAAGAAAACACTGTTCGTGGAGTTTACTGAT

CACCTGTTCAACATCGCAAAGCCTAGGCCACCCTGGATGGGACTGCTGGGGCCAACAATCCAGGCCGAGGTGTACGACAC

CGTGGTCATTACACTTAAGAACATGCCTCACACCCCGTGAGCCTGCATGCTGTGGGCGTCAGCTACTGGAAGGCTTCCG

AAGGAGCAGAGTATGACGATCAGACTTCCCAGAGAGAAAAAGAGGACGATAAGGTGTTTCCTGGCGGATCTCATACCTAC

GTGTGGCAGGTCCTGAAAGAGAATGGCCCTATGGCCTCCGACCCTCTGTGCCTGACCTACTCTTATCTGAGTCACGTGGA

CCTGGTCAAGGATCTGAACAGCGGCCTGATCGGAGCCCTGCTGGTGTGCAGGGAAGGAAGCCTGGCTAAGGAGAAACCC

AGACACTGCATAAGTTCATTCTGCTGTTCGCCGTGTTTGACGAAGGGAAATCATGGCACAGCGAGACAAAGAATAGTCTG

ATGCAGGACAGGGATGCCGCTTCAGCCAGAGCTTGGCCCAAAATGCACACTGTGAACGGCTACGTCAATCGCTCACTGCC

TGGGCTGATCGGCTGCCACCGAAAGAGCGTGTATTGGCATGTCATCGGGATGGGCACCACACCTGAAGTGCACTCCATTT

TCCTGGAGGGACATACCTTTCTGGTCCGCAACCACCGACAGGCTTCCCTGGAGATCTCTCCAATTACCTTCCTGACAGCA

CAGACTCTGCTGATGGACCTGGGGCAGTTCCTGCTGTTTTGCCACATCAGCTCCCACCAGCATGATGGCATGGAGGCTTA

CGTGAAAGTGGACTCTTGTCCCGAGGAACCTCAGCTGCGGATGAAGAACAATGAGGAAGCAGAAGACTATGACGATGACC

TGACCGACTCCGAGATGGATGTGGTCCGATTCGATGACGATAACAGCCCCTCCTTTATCCAGATTAGATCTGTGGCCAAG

AAACACCCTAAGACATGGGTCCATTACATCGCAGCCGAGGAAGAGGACTGGGATTATGCACCACTGGTGCTGGCACCAGA

CGATCGCTCCTACAAATCTCAGTATCTGAACAATGGGCCACAGAGGATTGGCAGAAAGTACAAGAAAGTGCGGTTCATGG

CATATACCGATGAGACCTTCAAGACTCGCGAAGCCATCCAGCACGAGAGCGGCATCCTGGGACCACTGCTGTACGGAGAA

GTGGGAGACACCCTGCTGATCATTTTCAAGAACCAGGCCAGCCGGCCTTACAATATCTATCCACATGGGATTACAGATGT

GCGCCCTCTGTACAGCAGGAGACTGCCAAAGGGCGTCAAACACCTGAAGGACTTCCCAATCCTGCCCGGAGAAATCTTCA

AGTACAAGTGGACTGTCACCGTCGAGGATGGCCCCACTAAGAGCGACCCTCGGTGCCTGACCCGCTACTATTCTAGTTTC

GTGAATATGGAAAGAGATCTGGCAAGCGGACTGATCGGACCACTGCTGATTTGTTACAAAGAGAGCGTGGATCAGAGAGG

CAACCAGATCATGTCCGACAAGCGGAATGTGATTCTGTTCAGTGTCTTTGACGAAAACAGGTCATGGTACCTGACCGAGA

ACATCCAGAGATTCCTGCCTAATCCAGCTGGGGTGCAGCTGGAAGATCCTGAGTTTCAGGCATCTAACATCATGCATAGT

ATTAATGGCTACGTGTTCGACAGTTTGCAGCTGAGCGTGTGCCTGCACGAGGTCGCTTACTGGTATATCCTGAGCATTGG

GGCACAGACAGATTTCCTGAGCGTGTTCTTTTCCGGCTACACTTTTAAGCATAAAATGGTCTATGAGGACACACTGACTC
```

-continued

```
TGTTCCCCTTCAGCGGCGAAACCGTGTTTATGAGCATGGAGAATCCCGGACTGTGGATTCTGGGGTGCCACAACAGCGAT
TTCAGAAATCGCGGAATGACTGCCCTGCTGAAAGTGTCAAGCTGTGACAAGAACACCGGGGACTACTATGAAGATTCATA
CGAGGACATCAGCGCATATCTGCTGTCCAAAAACAATGCCATTGAACCCCGGTCTTTTAGTCAGAATCCTCCAGTGCTGA
AGCGGCACCAGCGCGAGATCACCCGCACTACCCTGCAGAGTGATCAGGAAGAGATCGACTACGACGATACAATTTCTGTG
GAAATGAAGAAAGAGGACTTCGATATCTATGACGAAGATGAGAACCAGAGTCCTCGATCATTCCAGAAGAAAACCAGGCA
TTACTTTATTGCCGCAGTGGAGCGGCTGTGGGATTATGGCATGTCCTCTAGTCCTCACGTGCTGCGAAATAGGGCCCAGT
CAGGAAGCGTCCCACAGTTCAAGAAAGTGGTCTTCCAGGAGTTTACAGACGGGTCCTTTACTCAGCCACTGTACAGGGGC
GAACTGAACGAGCACCTGGGACTGCTGGGGCCCTATATCAGAGCAGAAGTGGAGGATAACATTATGGTCACCTTCAGAAA
TCAGGCCTCTCGGCCTTACAGTTTTTATTCAAGCCTGATCTCTTACGAAGAGGACCAGCGACAGGGAGCTGAACCACGAA
AAAACTTCGTGAAGCCTAATGAGACCAAAACATACTTTTGGAAGGTGCAGCACCATATGGCCCCAACAAAAGACGAGTTC
GATTGCAAGGCATGGGCCTATTTTTCTGACGTGGATCTGGAGAAGGACGTGCACAGTGGCCTGATTGGCCCACTGCTGGT
GTGCCATACTAACACCCTGAATCCAGCCCACGGCCGGCAGGTCACTGTCCAGGAGTTCGCTCTGTTCTTTACCATCTTTG
ATGAGACAAAGAGCTGGTACTTCACCGAAAACATGGAGCGAAATTGCAGGGCTCCATGTAACATTCAGATGGAAGACCCC
ACATTCAAGGAGAACTACCGCTTTCATGCTATCAATGGATACATCATGGATACTCTGCCCGGGCTGGTCATGGCACAGGA
CCAGAGAATCCGGTGGTATCTGCTGAGCATGGGCAGCAACGAGAATATCCACTCAATTCATTTCAGCGGGCACGTGTTTA
CTGTCAGGAAGAAAGAAGAGTACAAGATGGCCCTGTACAACCTGTATCCCGGCGTGTTCGAAACCGTCGAGATGCTGCCT
AGCAAGGCCGGAATCTGGAGAGTGGAATGCCTGATTGGAGAGCACCTGCATGCTGGGATGTCTACCCTGTTTCTGGTGTA
CAGTAATAAGTGTCAGACACCCCTGGGAATGGCATCCGGCATATCAGGGATTTCCAGATTACCGCATCTGGACAGTACG
GACAGTGGGCACCTAAGCTGGCTAGACTGCACTATTCCGGATCTATCAACGCTTGGTCCACAAAAGAGCCTTTCTCTTGG
ATTAAGGTGGACCTGCTGGCCCCAATGATCATTCATGGCATCAAAACTCAGGGAGCTCGGCAGAAGTTCTCCTCTCTGTA
CATCTCACAGTTTATCATCATGTACAGCCTGGATGGGAAGAAATGGCAGACATACCGCGGCAATAGCACAGGAACTCTGA
TGGTGTTCTTTGGCAACGTGGACAGCAGCGGAATCAAGCACAACATTTTCAATCCCCCTATCATTGCTAGATACATCCGG
CTGCACCCAACCCATTATTCTATTCGAAGTACACTGAGGATGGAACTGATGGGATGCGATCTGAACAGTTGTTCAATGCC
CCTGGGGATGGAGTCCAAGGCAATCTCTGACGCCCAGATTACCGCTAGCTCCTACTTCACTAATATGTTTGCTACCTGGA
GCCCTTCCAAAGCAAGACTGCACCTGCAAGGCCGCAGCAACGCATGGCGACCACAGGTGAACAATCCCAAGGAGTGGTTG
CAGGTCGATTTTCAGAAAACTATGAAGGTGACCGGGGTCACAACTCAGGGCGTGAAAAGTCTGCTGACCTCAATGTACGT
CAAGGAGTTCCTGATCTCTAGTTCACAGGACGGACATCAGTGGACACTGTTCTTTCAGAACGGGAAGGTGAAAGTCTTCC
AGGGCAATCAGGATTCCTTTACACCTGTGGTCAACAGTCTAGACCCTCCACTGCTGACCAGATACCTGAGAATCCACCCT
CAGTCCTGGGTGCACCAGATTGCCCTGAGAATGGAAGTGCTGGGATGCGAGGCCCAGGATCTGTACTGATAACTCGAGTC
GACC
``` optimized BDD FVIII  
                                                              SEQ ID NO: 2

```
GGCGCGCCCGTACGGCCGCCACCATGCAGATCGAGCTGTCTACCTGCTTCTTCCTGTGCCTGCTGCGGTTCTGCTTCAGC
GCCACCCGGCGGTACTACCTGGGCGCCGTGGAACTGAGCTGGGACTACATGCAGAGCGACCTGGGGGAGCTGCCCGTGGA
CGCCAGATTCCCCCCAAGAGTGCCCAAGAGCTTCCCCTTCAACACCTCCGTGGTGTACAAGAAAACCCTGTTCGTCGAGT
TCACCGACCACCTGTTCAATATCGCCAAGCCCAGACCCCCCTGGATGGGCCTGCTGGGCCCTACAATCCAGGCCGAGGTG
TACGACACCGTGGTCATCACCCTTAAGAACATGGCCAGCCACCCCGTGTCCCTGCACGCCGTGGGCGTGTCCTACTGGAA
GGCCTCTGAGGGCGCTGAGTACGACGACCAGACCAGCCAGCGCGAGAAAGAGGACGACAAAGTCTTTCCTGGCGGCAGCC
ATACCTACGTGTGGCAGGTCCTGAAAGAAAACGGCCCTATGGCCTCCGACCCCCTGTGCCTGACCTACAGCTACCTGAGC
CACGTGGACCTGGTCAAGGACCTGAACAGCGGCCTGATTGGCGCCCTGCTCGTGTGTAGAGAGGGCAGCCTCGCCAAAGA
GAAAACCCAGACCCTGCACAAGTTCATCCTGCTGTTCGCCGTGTTCGACGAGGGCAAGAGCTGGCACAGCGAGACAAAGA
ACAGCCTGATGCAGGACCGGGACGCCGCCTCTGCCAGAGCCTGGCCTAAGATGCACACCGTGAACGGCTACGTGAACAGA
```

-continued

```
AGCCTGCCCGGACTGATCGGCTGCCACCGGAAGTCCGTGTACTGGCACGTGATCGGCATGGGCACCACCCCCGAGGTGCA
CAGCATCTTTCTGGAAGGCCACACCTTCCTCGTGCGGAACCACAGACAGGCCAGCCTGGAAATCAGCCCTATCACCTTCC
TGACCGCCCAGACACTGCTGATGGACCTGGGCCAGTTCCTGCTGTTTTGCCACATCAGCAGCCACCAGCACGACGGCATG
GAAGCCTACGTGAAGGTGGACAGCTGCCCCGAGGAACCCCAGCTGCGGATGAAGAACAACGAGGAAGCCGAGGACTACGA
CGACGACCTGACCGACAGCGAGATGGACGTCGTGCGCTTCGACGACGACAACAGCCCCAGCTTCATCCAGATCAGAAGCG
TGGCCAAGAAGCACCCCAAGACCTGGGTGCACTATATCGCCGCCGAGGAAGAGGACTGGGACTACGCCCCTCTGGTGCTG
GCCCCCGACGACAGAAGCTACAAGAGCCAGTACCTGAACAATGGCCCCCAGCGGATCGGCCGGAAGTACAAGAAAGTGCG
GTTCATGGCCTACACCGACGAGACATTCAAGACCAGAGAGGCCATCCAGCACGAGAGCGGCATCCTGGGCCCCCTGCTGT
ATGGCGAAGTGGGCGACACCCTGCTGATCATCTTCAAGAACCAGGCCAGCCGGCCCTACAACATCTACCCCCACGGCATC
ACCGACGTGCGGCCCCTGTACAGCAGACGGCTGCCCAAGGGCGTGAAGCACCTGAAGGACTTCCCCATCCTGCCCGGCGA
GATCTTCAAGTACAAGTGGACCGTGACCGTGGAAGATGGCCCCACCAAGAGCGACCCCAGATGCCTGACCCGGTACTACA
GCAGCTTCGTGAACATGGAACGGGACCTGGCCTCCGGGCTGATCGGCCCTCTGCTGATCTGCTACAAAGAAAGCGTGGAC
CAGCGGGGCAACCAGATCATGAGCGACAAGCGGAACGTGATCCTGTTCAGCGTGTTCGATGAGAATCGGTCCTGGTACCT
GACCGAGAATATCCAGCGGTTCCTGCCCAACCCTGCCGGCGTGCAGCTGGAAGATCCCGAGTTCCAGGCCAGCAACATCA
TGCACTCCATCAATGGCTACGTGTTCGACAGCCTCCAGCTGAGCGTGTGCCTGCACGAGGTGGCCTACTGGTACATCCTG
AGCATCGGCGCCCAGACCGACTTCCTGAGCGTGTTCTTCAGCGGCTACACCTTCAAGCACAAGATGGTGTACGAGGATAC
CCTGACCCTGTTCCCCTTCTCCGGCGAAACCGTGTTCATGAGCATGGAAAACCCCGGCCTGTGGATTCTGGGCTGCCACA
ACAGCGACTTCAGAAACCGGGGCATGACCGCCCTGCTGAAGGTGTCCAGCTGCGACAAGAACACCGGCGACTACTACGAG
GACAGCTATGAGGACATCAGCGCCTACCTGCTGAGCAAGAACAACGCCATCGAGCCCAGATCCTTCAGCCAGAACCCCCC
CGTGCTGAAGCGGCACCAGAGAGAGATCACCCGGACCACCCTGCAGTCCGACCAGGAAGAGATTGATTACGACGACACCA
TCAGCGTCGAGATGAAGAAAGAGGATTTCGACATCTACGACGAGGACGAGAACCAGAGCCCCCGGTCCTTCCAGAAGAAA
ACCCGGCACTACTTCATTGCCGCCGTGGAAAGACTGTGGGACTACGGCATGAGCAGCAGCCCCCACGTGCTGCGGAACAG
AGCCCAGAGCGGCAGCGTGCCCCAGTTCAAGAAAGTGGTGTTCCAGGAGTTCACCGACGGCAGCTTCACCCAGCCCCTGT
ATCGGGGCGAGCTGAACGAGCACCTGGGACTGCTGGGACCTTACATTAGAGCCGAGGTGGAAGATAACATCATGGTCACC
TTCAGAAACCAGGCCTCCAGACCCTACAGCTTCTACAGCAGCCTGATCAGCTACGAAGAGGACCAGCGGCAGGGCGCCGA
ACCCCGGAAGAACTTCGTGAAGCCCAACGAGACTAAGACCTACTTCTGGAAGGTGCAGCACCACATGGCCCCCACAAAGG
ACGAGTTCGACTGCAAGGCCTGGGCCTACTTCTCCGATGTGGACCTGGAAAAGGACGTGCACTCGGCCTGATTGGACCT
CTGCTCGTCTGCCACACCAACACCCTGAACCCCGCCCACGGCCGGCAGGTCACAGTGCAGGAATTTGCCCTGTTCTTCAC
CATCTTCGATGAGACAAAGAGCTGGTACTTCACCGAGAACATGGAAAGAAACTGTAGAGCCCCCTGCAACATCCAGATGG
AAGATCCTACCTTCAAAGAGAACTATCGGTTCCACGCCATCAACGGCTACATCATGGACACCCTGCCCGGCCTGGTCATG
GCCCAGGATCAGAGAATCCGGTGGTATCTGCTGAGCATGGGCAGCAACGAGAACATCCACAGCATCCACTTCAGCGGCCA
CGTGTTCACAGTGCGGAAGAAAGAAGAGTACAAGATGGCCCTGTACAACCTGTACCCGGCGTGTTCGAGACAGTGGAAA
TGCTGCCCAGCAAGGCCGGCATCTGGCGGGTGGAATGTCTGATCGGCGAGCATCTGCACGCCGGAATGAGCACCCTGTTT
CTGGTGTACAGCAACAAGTGCCAGACCCCTCTGGGCATGGCCAGCGGCCACATCCGGGACTTCCAGATCACCGCCTCCGG
CCAGTACGGCCAGTGGGCCCCTAAGCTGGCCCGGCTCCACTACTCCGGATCTATCAACGCCTGGTCCACCAAAGAGCCCT
TCAGCTGGATCAAGGTGGACCTGCTGGCCCCTATGATCATCCACGGAATCAAGACCCAGGGCGCCAGACAGAAGTTCAGC
AGCCTGTACATCAGCCAGTTCATCATCATGTACAGCCTGGACGGCAAGAAGTGGCAGACCTACCGGGGCAACAGCACCGG
CACCCTGATGGTGTTCTTCGGCAACGTGGACAGCAGCGGCATCAAGCACAACATCTTCAACCCCCCCATCATTGCCCGGT
ACATCCGGCTGCACCCCACCCACTACAGCATCCGGTCCACCCTGCGGATGGAACTGATGGGCTGCGACCTGAACTCTTGC
AGCATGCCCCTGGGGATGGAAAGCAAGGCCATCAGCGACGCCCAGATCACAGCCAGCAGCTACTTCACCAACATGTTCGC
CACCTGGTCCCCAAGCAAAGCCCGCCTGCATCTCCAAGGCAGAAGCAATGCCTGGCGGCCTCAGGTCAACAACCCCAAAG
```

-continued

```
AATGGCTCCAGGTGGACTTTCAGAAAACCATGAAGGTCACAGGCGTGACCACCCAGGGCGTGAAAAGCCTGCTGACCTCT
ATGTACGTGAAAGAGTTCCTGATCAGCAGCAGCCAGGACGGGCACCAGTGGACCCTGTTCTTTCAGAACGGCAAAGTGAA
AGTGTTCCAGGGCAACCAGGACTCCTTTACCCCCGTGGTCAACTCTCTAGACCCTCCACTGCTGACCAGATACCTGAGAA
TCCACCCTCAGTCCTGGGTGCACCAGATTGCCCTGAGAATGGAAGTGCTGGGATGCGAGGCCCAGGATCTGTACTGATAA
CTCGAGTCGACTTAATTAA
```

Nucleotide Sequence Encoding "Parental" BDD FVIII

SEQ ID NO: 3

```
ATGCAAATAGAGCTCTCCACCTGCTTCTTTCTGTGCCTTTTGCGATTCTGCTTTAGTGCCACCAGAAGATACTACCTGGG
TGCAGTGGAACTGTCATGGGACTATATGCAAAGTGATCTCGGTGAGCTGCCTGTGGACGCAAGATTTCCTCCTAGAGTGC
CAAAATCTTTTCCATTCAACACCTCAGTCGTGTACAAAAAGACTCTGTTTGTAGAATTCACGGATCACCTTTTCAACATC
GCTAAGCCAAGGCCACCCTGGATGGGTCTGCTAGGTCCTACCATCCAGGCTGAGGTTTATGATACAGTGGTCATTACACT
TAAGAACATGGCTTCCCATCCTGTCAGTCTTCATGCTGTTGGTGTATCCTACTGGAAAGCTTCTGAGGGAGCTGAATATG
ATGATCAGACCAGTCAAAGGGAGAAAGAAGATGATAAAGTCTTCCCTGGTGGAAGCCATACATATGTCTGGCAGGTCCTG
AAAGAGAATGGTCCAATGGCCTCTGACCCACTGTGCCTTACCTACTCATATCTTTCTCATGTGGACCTGGTAAAAGACTT
GAATTCAGGCCTCATTGGAGCCCTACTAGTATGTAGAGAAGGGAGTCTGGCCAAGGAAAAGACACAGACCTTGCACAAAT
TTATACTACTTTTTGCTGTATTTGATGAAGGGAAAAGTTGGCACTCAGAAACAAAGAACTCCTTGATGCAGGATAGGGAT
GCTGCATCTGCTCGGGCCTGGCCTAAAATGCACACAGTCAATGGTTATGTAAACAGGTCTCTGCCAGGTCTGATTGGATG
CCACAGGAAATCAGTCTATTGGCATGTGATTGGAATGGGCACCACTCCTGAAGTGCACTCAATATTCCTCGAAGGTCACA
CATTTCTTGTGAGGAACCATCGCCAGGCGTCCTTGGAAATCTCGCCAATAACTTTCCTTACTGCTCAAACACTCTTGATG
GACCTTGGACAGTTTCTACTGTTTTGTCATATCTCTTCCCACCAACATGATGGCATGGAAGCTTATGTCAAAGTAGACAG
CTGTCCAGAGGAACCCCAACTACGAATGAAAAATAATGAAGAAGCGGAAGACTATGATGATGATCTTACTGATTCTGAAA
TGGATGTGGTCAGGTTTGATGATGACAACTCTCCTTCCTTTATCCAAATTCGCTCAGTTGCCAAGAAGCATCCTAAAACT
TGGGTACATTACATTGCTGCTGAAGAGGAGGACTGGGACTATGCTCCCTTAGTCCTCGCCCCCGATGACAGAAGTTATAA
AAGTCAATATTTGAACAATGGCCCTCAGCGGATTGGTAGGAAGTACAAAAAAGTCCGATTTATGGCATACACAGATGAAA
CCTTTAAGACTCGTGAAGCTATTCAGCATGAATCAGGAATCTTGGGACCTTTACTTTATGGGGAAGTTGGAGACACACTG
TTGATTATATTTAAGAATCAAGCAAGCAGACCATATAACATCTACCCTCACGGAATCACTGATGTCCGTCCTTTGTATTC
AAGGAGATTACCAAAAGGTGTAAAACATTTGAAGGATTTTCCAATTCTGCCAGGAGAAATATTCAAATATAAATGGACAG
TGACTGTAGAAGATGGGCCAACTAAATCAGATCCTCGGTGCCTGACCCGCTATTACTCTAGTTTCGTTAATATGGAGAGA
GATCTAGCTTCAGGACTCATTGGCCCTCTCCTCATCTGCTACAAAGAATCTGTAGATCAAAGAGGGAAACCAGATAATGTC
AGACAAGAGGAATGTCATCCTGTTTTCTGTATTTGATGAGAACCGAAGCTGGTACCTCACAGAGAATATACAACGCTTTC
TCCCCAATCCAGCTGGAGTGCAGCTTGAGGATCCAGAGTTCCAAGCCTCCAACATCATGCACAGCATCAATGGCTATGTT
TTTGATAGTTTGCAGTTGTCAGTTTGTTTGCATGAGGTGGCATACTGGTACATTCTAAGCATTGGAGCACAGACTGACTT
CCTTTCTGTCTTCTTCTCTGGATATACCTTCAAACACAAAATGGTCTATGAAGACACACTCACCCTATTCCCATTCTCAG
GAGAAACTGTCTTCATGTCGATGGAAAACCCAGGTCTATGGATTCTGGGGTGCCACAACTCAGACTTTCGGAACAGAGGC
ATGACCGCCTTACTGAAGGTTTCTAGTTGTGACAAGAACACTGGTGATTATTACGAGGACAGTTATGAAGATATTTCAGC
ATACTTGCTGAGTAAAAACAATGCCATTGAACCAAGAAGCTTCTCTCAAAACCCACCAGTCTTGAAACGCCATCAACGGG
AAATAACTCGTACTACTCTTCAGTCAGATCAAGAGGAAATTGACTATGATGATACCATATCAGTTGAAATGAAGAAGGAA
GATTTTGACATTTATGATGAGGATGAAAATCAGAGCCCCCGCAGCTTTCAAAAGATAACACGACACTATTTTATTGCTGC
AGTGGAGAGGCTCTGGGATTATGGGATGAGTAGCTCCCCACATGTTCTAAGAAACAGGGCTCAGAGTGGCAGTGTCCCTC
AGTTCAAGAAAGTTGTTTTCCAGGAATTTACTGATGGCTCCTTTACTCAGCCCTTATACCGTGGAGAACTAAATGAACAT
TTGGGACTCCTGGGGCCATATATAAGAGCAGAAGTTGAAGATAATATCATGGTAACTTTCAGAAATCAGGCCTCTCGTCC
CTATTCCTTCTATTCTAGCCTTATTTCTTATGAGGAAGATCAGAGGCAAGGAGCAGAACCTAGAAAAAACTTTGTCAAGC
```

-continued

```
CTAATGAAACCAAAACTTACTTTTGGAAAGTGCAACATCATATGGCACCCACTAAAGATGAGTTTGACTGCAAAGCCTGG
GCTTATTTCTCTGATGTTGACCTGGAAAAAGATGTGCACTCAGGCCTGATTGGACCCCTTCTGGTCTGCCACACTAACAC
ACTGAACCCTGCTCATGGGAGACAAGTGACAGTACAGGAATTTGCTCTGTTTTTCACCATCTTTGATGAGACCAAAAGCT
GGTACTTCACTGAAAATATGGAAAGAAACTGCAGGGCTCCCTGCAATATCCAGATGGAAGATCCCACTTTTAAAGAGAAT
TATCGCTTCCATGCAATCAATGGCTACATAATGGATACACTACCTGGCTTAGTAATGGCTCAGGATCAAAGGATTCGATG
GTATCTGCTCAGCATGGGCAGCAATGAAAACATCCATTCTATTCATTTCAGTGGACATGTGTTCACTGTACGAAAAAAAG
AGGAGTATAAAATGGCACTGTACAATCTCTATCCAGGTGTTTTTGAGACAGTGGAAATGTTACCATCCAAAGCTGGAATT
TGGCGGGTGGAATGCCTTATTGGCGAGCATCTACATGGCTGGGATGAGCACACTTTTCTGGTGTACAGCAATAAGTGTCA
GACTCCCCTGGGAATGGCTTCTGGACACATTAGAGATTTTCAGATTACAGCTTCAGGACAATATGGACAGTGGGCCCCAA
AGCTGGCCAGACTTCATTATTCCGGATCAATCAATGCCTGGAGCACCAAGGAGCCCTTTTCTTGGATCAAGGTGGATCTG
TTGGCACCAATGATTATTCACGGCATCAAGACCCAGGGTGCCCGTCAGAAGTTCTCCAGCCTCTACATCTCTCAGTTTAT
CATCATGTATAGTCTTGATGGGAAGAAGTGGCAGACTTATCGAGGAAATTCCACTGGAACCTTAATGGTCTTCTTTGGCA
ATGTGGATTCATCTGGGATAAAACACAATATTTTTAACCCTCCAATTATTGCTCGATACATCCGTTTGCACCCAACTCAT
TATAGCATTCGCAGCACTCTTCGCATGGAGTTGATGGGCTGTGATTTAAATAGTTGCAGCATGCCATTGGGAATGGAGAG
TAAAGCAATATCAGATGCACAGATTACTGCTTCATCCTACTTTACCAATATGTTTGCCACCTGGTCTCCTTCAAAAGCTC
GACTTCACCTCCAAGGGAGGAGTAATGCCTGGAGACCTCAGGTGAATAATCCAAAAGAGTGGCTGCAAGTGGACTTCCAG
AAGACAATGAAAGTCACAGGAGTAACTACTCAGGGAGTAAAATCTCTGCTTACCAGCATGTATGTGAAGGAGTTCCTCAT
CTCCAGCAGTCAAGATGGCCATCAGTGGACTCTCTTTTTTCAGAATGGCAAAGTAAAGGTTTTTCAGGGAAATCAAGACT
CCTTCACACCTGTGGTGAACTCTCTAGACCCACCGTTACTGACTCGCTACCTTCGAATTCACCCCCAGAGTTGGGTGCAC
CAGATTGCCCTGAGGATGGAGGTTCTGGGCTGCGAGGCACAGGACCTCTAC
```

Amino Acid Sequence of BDD FVIII  
SEQ ID NO: 4

```
ATRRYYLGAVELSWDYMQSDLGELPVDARFPPRVPKSFPFNTSVVYKKTLFVEFTDHLFNIAKPRPPWMGLLGPTIQAEV
YDTVVITLKNMASHPVSLHAVGVSYWKASEGAEYDDQTSQREKEDDKVFPGGSHTYVWQVLKENGPMASDPLCLTYSYLS
HVDLVKDLNSGLIGALLVCREGSLAKEKTQTLHKFILLFAVFDEGKSWHSETKNSLMQDRDAASARAWPKMHTVNGYVNR
SLPGLIGCHRKSVYWHVIGMGTTPEVHSIFLEGHTFLVRNHRQASLEISPITFLTAQTLLMDLGQFLLFCHISSHQHDGM
EAYVKVDSCPEEPQLRMKNNEEAEDYDDDLTDSEMDVVRFDDDNSPSFIQIRSVAKKHPKTWVHYIAAEEEDWDYAPLVL
APDDRSYKSQYLNNGPQRIGRKYKKVREMAYTDETFKTREAIQHESGILGPLLYGEVGDTLLIIFKNQASRPYNIYPHGI
TDVRPLYSRRLPKGVKHLKDFPILPGEIFKYKWTVTVEDGPTKSDPRCLTRYYSSFVNMERDLASGLIGPLLICYKESVD
QRGNQIMSDKRNVILFSVFDENRSWYLTENIQRFLPNPAGVQLEDPEFQASNIMHSINGYVFDSLQLSVCLHEVAYWYIL
SIGAQTDFLSVFFSGYTFKHKMVYEDTLTLFPFSGETVFMSMENPGLWILGCHNSDFRNRGMTALLKVSSCDKNTGDYYE
DSYEDISAYLLSKNNAIEPRSFSQNPPVLKRHQREITRTTLQSDQEEIDYDDTISVEMKKEDFDIYDEDENQSPRSFQKK
TRHYFIAAVERLWDYGMSSSPHVLRNRAQSGSVPQFKKVVFQEFTDGSFTQPLYRGELNEHLGLLGPYIRAEVEDNIMVT
FRNQASRPYSFYSSLISYEEDQRQGAEPRKNFVKPNETKTYFWKVQHHMAPTKDEFDCKAWAYFSDVDLEKDVHSGLIGP
LLVCHTNTLNPAHGRQVTVQEFALFFTIFDETKSWYFTENMERNCRAPCNIQMEDPTFKENYRFHAINGYINDTLPGLVM
AQDQRIRWYLLSMGSNENIHSIHFSGHVFTVRKKEEYKMALYNLYPGVFETVEMLPSKAGIWRVECLIGEHLHAGMSTLF
LVYSNKCQTPLGMASGHIRDFQITASGQYGQWAPKLARLHYSGSINAWSTKEPFSWIKVDLLAPMIIHGIKTQGARQKFS
SLYISQFIIMYSLDGKKWQTYRGNSTGTLMVFFGNVDSSGIKHNIFNPPIIARYIRLHPTHYSIRSTLRMELMGCDLNSC
SMPLGMESKAISDAQTTASSYFTNMFATWSPSKARLHLQGRSNAWRPQVNNPKEWLQVDFQKTMKVTGVTTQGVKSLLTS
MYVKEFLISSSQDGHQWTLFFQNGKVKVFQGNQDSFTPVVNSLDPPLLTRYLRIHPQSWVHQIALRMEVLGCEAQDLY
```

MAR/ARS nucleotide sequence  
SEQ ID NO: 5

ATATTT

-continued

| | |
|---|---|
| MAR/ARS nucleotide sequence<br>AAATAT | SEQ ID NO: 6 |
| Potential Splice Site<br>GGTGAT | SEQ ID NO: 7 |
| Destabilizing Sequence<br>ATTTA | SEQ ID NO: 8 |
| Destabilizing Sequence<br>TAAAT | SEQ ID NO: 9 |
| poly-T Sequence<br>TTTTTT | SEQ ID NO: 10 |
| poly-A Sequence<br>AAAAAA | SEQ ID NO: 11 |
| Promoter Binding Site<br>TATAA | SEQ ID NO: 12 |
| Promoter Binding Site<br>TTATA | SEQ ID NO: 13 |
| AU Rich Sequence Elements (ARE)<br>ATTTTATT | SEQ ID NO: 14 |
| AU Rich Sequence Elements (ARE)<br>ATTTTTAA | SEQ ID NO: 15 |
| Kozak Consensus Sequence<br>GCCGCCACCATGC | SEQ ID NO: 16 |
| CTP peptide<br>DPRFQDSSSSKAPPPSLPSFSRLPGPSDTPIL | SEQ ID NO: 17 |
| CTP peptide<br>SSSSKAPPPSLPSPSRLPGPSDTPILPQ | SEQ ID NO: 18 |
| albumin-binding peptides core sequence<br>DICLPRWGCLW | SEQ ID NO: 19 |
| PAS Sequence<br>ASPAAPAPASPAAPAPSAPA | SEQ ID NO: 20 |
| PAS Sequence<br>AAPASPAPAAPSAPAPAAPS | SEQ ID NO: 21 |
| PAS Sequence<br>APSSPSPSAPSSPSPASPSS | SEQ ID NO: 22 |
| PAS Sequence<br>APSSPSPSAPSSPSPASPS | SEQ ID NO: 23 |
| PAS Sequence<br>SSPSAPSPSSPASPSPSSPA | SEQ ID NO: 24 |
| PAS Sequence<br>AASPAAPSAPPAAASPAAPSAPPA | SEQ ID NO: 25 |

PAS Sequence

SEQ ID NO: 26

ASAAAPAAASAAASAPSAAA

Full length von Willebrand Factor nucleotide sequence

SEQ ID NO: 27

ATGATTCCTGCCAGATTTGCCGGGGTGCTGCTTGCTCTGGCCCTCATTTTGCCAGGGACCCTTTGTGCAGAAGGAACTCGCGGCAG

GTCATCCACGGCCCTACTAAGGACGGTCTAAACGGCCCCACGACGAACGAGACCGGGAGTAAAACGGTCCCTGGGAAACACGTCTT

CCTTGAGCGCCGTCCAGTAGGTGCCGGGGATGCAGCCTTTTCGGAAGTGACTTCGTCAACACCTTTGATGGGAGCATGTACAGCTT

TGCGGGATACTGCAGTTACCTCCTGGCAGGGGGCTGCCAGAACTACGTCGGAAAAGCCTTCACTGAAGCAGTTGTGGAAACTACCC

TCGTACATGTCGAAACGCCCTATGACGTCAATGGAGGACCGTCCCCCGACGGTCTTACGCTCCTTCTCGATTATTGGGGACTTCCA

GAATGGCAAGAGAGTGAGCCTCTCCGTGTATCTTGGGGAATTTTTTGACATCCATTTGTTTGTCAATGGTTGCGAGGAAGAGCTAA

TAACCCCTGAAGGTCTTACCGTTCTCTCACTCGGAGAGGCACATAGAACCCCTTAAAAAACTGTAGGTAAACAAACAGTTACCAAC

CGTGACACAGGGGGACCAAAGAGTCTCCATGCCCTATGCCTCCAAAGGGCTGTATCTAGAAACTGAGGCTGGGTACTACAAGCTGT

CCGGTGAGGCCTTGGCACTGTGTCCCCCTGGTTTCTCAGAGGTACGGGATACGGAGGTTTCCCGACATAGATCTTTGACTCCGACC

CATGATGTTCGACAGGCCACTCCGGAATGGCTTTGTGGCCAGGATCGATGGCAGCGGCAACTTTCAAGTCCTGCTGTCAGACAGAT

ACTTCAACAAGACCTGCGGGCTGTGTGGCAACTTTAACATTACCGAAACACCGGTCCTAGCTACCGTCGCCGTTGAAAGTTCAGGA

CGACAGTCTGTCTATGAAGTTGTTCTGGACGCCCGACACACCGTTGAAATTGTACTTTGCTGAAGATGACTTTATGACCCAAGAAG

GGACCTTGACCTCGGACCCTTATGACTTTGCCAACTCATGGGCTCTGAGCAGTGGAGAACAGTGGTGTGAAACGACTTCTACTGAA

ATACTGGGTTCTTCCCTGGAACTGGAGCCTGGGAATACTGAAACGGTTGAGTACCCGAGACTCGTCACCTCTTGTCACCACAGAAC

GGGCATCTCCTCCCAGCAGCTCATGCAACATCTCCTCTGGGGAAATGCAGAAGGGCCTGTGGGAGCAGTGCCAGCTTCTGAAGAGC

ACCTCGGTGTCTTGCCCGTAGAGGAGGGTCGTCGAGTACGTTGTAGAGGAGACCCCTTTACGTCTTCCCGGACACCCTCGTCACGG

TCGAAGACTTCTCGTGGAGCCACATTGCCCGCTGCCACCCTCTGGTGGACCCCGAGCCTTTTGTGGCCCTGTGTGAGAAGACTTTG

TGTGAGTGTGCTGGGGGGCTGGAGTGCGCCTGCCCTGCAACGGGCGACGGTGGGAGACCACCTGGGGCTCGGAAAACACCGGGACA

CACTCTTCTGAAACACACTCACACGACCCCCCGACCTCACGCGGACGGGACGCCTCCTGGAGTACGCCCGGACCTGTGCCCAGGAG

GGAATGGTGCTGTACGGCTGGACCGACCACAGCGCGTGCAGCCCAGTGTGCCCTGCTGGTATGGAGGGAGGACCTCATGCGGGCCT

GGACACGGGTCCTCCCTTACCACGACATGCCGACCTGGCTGGTGTCGCGCACGTCGGGTCACACGGGACGACCATACCTCTATAGG

CAGTGTGTGTCCCCTTGCGCCAGGACCTGCCAGAGCCTGCACATCAATGAAATGTGTCAGGAGCGATGCGTGGATGGCTGCAGCTG

CCCTGAGGATATCCGTCACACACAGGGGAACGCGGTCCTGGACGGTCTCGGACGTGTAGTTACTTTACACAGTCCTCGCTACGCAC

CTACCGACGTCGACGGGACTCCGACAGCTCCTGGATGAAGGCCTCTGCGTGGAGAGCACCGAGTGTCCCTGCGTGCATTCCGGAAA

GCGCTACCCTCCCGGCACCTCCCTCTCTCGAGACTGCTGTCGAGGACCTACTTCCGGAGACGCACCTCTCGTGGCTCACAGGGACG

CACGTAAGGCCTTTCGCGATGGGAGGGCCGTGGAGGGAGAGAGCTCTGACCAACACCTGCATTTGCCGAAACAGCCAGTGGATCTG

CAGCAATGAAGAATGTCCAGGGGAGTGCCTTGTCACTGGTCAATCCCACTTCAAGAGCTTTGACGTTGTGGACGTAAACGGCTTTG

TCGGTCACCTAGACGTCGTTACTTCTTACAGGTCCCCTCACGGAACAGTGACCAGTTAGGGTGAAGTTCTCGAAACTGAACAGATA

CTTCACCTTCAGTGGGATCTGCCAGTACCTGCTGGCCCGGGATTGCCAGGACCACTCCTTCTCCATTGTCATTGAGACTGTCCAGT

GTGCTGTTGTCTATGAAGTGGAAGTCACCCTAGACGGTCATGGACGACCGGGCCCTAACGGTCCTGGTGAGGAAGAGGTAACAGTA

ACTCTGACAGGTCACACGACATGACCGCGACGCTGTGTGCACCCGCTCCGTCACCGTCCGGCTGCCTGGCCTGCACAACAGCCTTG

TGAAACTGAAGCATGGGGCAGGAGTTGCCATGGATACTGGCGCTGCGACACACGTGGGCGAGGCAGTGGCAGGCCGACGGACCGGA

CGTGTTGTCGGAACACTTTGACTTCGTACCCCGTCCTCAACGGTACCTTGGCCAGGACATCCAGCTCCCCCTCCTGAAAGGTGACC

TCCGCATCCAGCATACAGTGACGGCCTCCGTGCGCCTCAGCTACGGGGAGGACCTGCAGATGACCGGTCCTGTAGGTCGAGGGGGA

GGACTTTCCACTGGAGGCGTAGGTCGTATGTCACTGCCGGAGGCACGCGAGTCGATGCCCCTCCTGGACGTCTACGACTGGGATG

GCCGCGGGAGGCTGCTGGTGAAGCTGTCCCCCGTCTATGCCGGGAAGACCTGCGGCCTGTGTGGGAATTACAATGGCAACCAGGGC

GACGCTGACCCTACCGGCGCCCTCCGACGACCACTTCGACAGGGGGCAGATACGGCCTTCTGGACGCCGGACACACCCTTAATGT

TACCGTTGGTCCCGCTGCACTTCCTTACCCCCTCTGGGCTGGCRGAGCCCCGGGTGGAGGACTTCGGGAACGCCTGGAAGCTGCAC

-continued

```
GGGGACTGCCAGGACCTGCAGAAGCAGCACAGTGAAGGAATGGGGGAGACCCGACCGYCTCGGGGCCCACCTCCTGAAGCCCTTGC
GGACCTTCGACGTGCCCCTGACGGTCCTGGACGTCTTCGTCGTGTCCGATCCCTGCGCCCTCAACCCGCGCATGACCAGGTTCTCC
GAGGAGGCGTGCGCGGTCCTGACGTCCCCCACATTCGAGGCCTGCCATCGTGCCGTCAGCGCTAGGGACGCGGGAGTTGGGCGCGT
ACTGGTCCAAGAGGCTCCTCCGCACGCGCCAGGACTGCAGGGGGTGTAAGCTCCGGACGGTAGCACGGCAGTCGCCGCTGCCCTAC
CTGCGGAACTGCCGCTACGACGTGTGCTCCTGCTCGGACGGCCGCGAGTGCCTGTGCGGCGCCCTGGCCAGCTATGCCGCGGCCTG
CGGGCGACGGGATGGACGCCTTGACGGCGATGCTGCACACGAGGACGAGCCTGCCGGCGCTCACGGACACGCCGCGGGACCGGTCG
ATACGGCGCCGGACGCCGGGGAGAGGCGTGCGCGTCGCGTGGCGCGAGCCAGGCCGCTGTGAGCTGAACTGCCCGAAAGGCCAGGT
GTACCTGCAGTGCGGGACCCCCTGCAACCTGCCCCTCTCCGCACGCGCAGCGCACCGCGCTCGGTCCGGCGACACTCGACTTGACG
GGCTTTCCGGTCCACATGGACGTCACGCCCTGGGGGACGTTGGAGACCTGCCGCTCTCTCTCTTACCCGGATGAGGAATGCAATGA
GGCCTGCCTGGAGGGCTGCTTCTGCCCCCCAGGGCTCTACATGGATGAGAGGGGGGACCTGGACGGCGAGAGAGAGAATGGGCCTA
CTCCTTACGTTACTCCGGACGGACCTCCCGACGAAGACGGGGGGTCCCGAGATGTACCTACTCTCCCCCCTGTGCGTGCCCAAGGC
CCAGTGCCCCTGTTACTATGACGGTGAGATCTTCCAGCCAGAAGACATCTTCTCAGACCATCACACCATGTGCTACTGTGAGGATG
ACGCACGGGTTCCGGGTCACGGGACAATGATACTGCCACTCTAGAAGGTCGGTCTTCTGTAGAAGAGTCTGGTAGTGTGGTACAC
GATGACACTCCTACGCTTCATGCACTGTACCATGAGTGGAGTCCCCGGAAGCTTGCTGCCTGACGCTGTCCTCAGCAGTCCCCTGT
CTCATCGCAGCAAAAGGAGCCTATCCTGCGAAGTACGTGACATGGTACTCACCTCAGGGGCCTTCGAACGACGGACTGCGACAGGA
GTCGTCAGGGGACAGAGTAGCGTCGTTTTCCTCGGATAGGACTCGGCCCCCCATGGTCAAGCTGGTGTGTCCCGCTGACAACCTGC
GGGCTGAAGGGCTCGAGTGTACCAAAACGTGCCAGAACTATGACCTGGAGTGCATGAGCCGGGGGGTACCAGTTCGACCACACAGG
GCGACTGTTGGACGCCCGACTTCCCGAGCTCACATGGTTTTGCACGGTCTTGATACTGGACCTCACGTACAGCATGGGCTGTGTCT
CTGGCTGCCTCTGCCCCCCGGGCATGGTCCGGCATGAGAACAGATGTGTGGCCCTGGAAAGGTGTCCCTGCTTCCATCAGGGCATC
GTACCCGACACAGAGACCGACGGAGACGGGGGGCCCGTACCAGGCCGTACTCTTGTCTACACACCGGGACCTTTCCACAGGGACGA
AGGTAGTCCCGTAGGAGTATGCCCCTGGAGAAACAGTGAAGATTGGCTGCAACACTTGTGTCTGTCGGGACCGGAAGTGGAACTGC
ACAGACCATGTGTGTGATGCCACGTGTCCTCATACGGGGACCTCTTTGTCACTTCTAACCGACGTTGTGAACACAGACAGCCCTGG
CCTTCACCTTGACGTGTCTGGTACACACACTACGGTGCACCTCCACGATCGGCATGGCCCACTACCTCACCTTCGACGGGCTCAAA
TACCTGTTCCCCGGGGAGTGCCAGTACGTTCTGGTGCAGGATTACTGCGGCAGTGAGGTGCTAGCCGTACCGGGTGATGGAGTGGA
AGCTGCCCGAGTTTATGGACAAGGGGCCCCTCACGGTCATGCAAGACCACGTCCTAATGACGCCGTCAAACCCTGGGACCTTTCGG
ATCCTAGTGGGGAATAAGGGATGCAGCCACCCCTCAGTGAAATGCAAGAAACGGGTCACCATCCTGGTGGAGGGAGGAGAGATTGG
GACCCTGGAAAGCCTAGGATCACCCCTTATTCCCTACGTCGGTGGGGAGTCACTTTACGTTCTTTGCCCAGTGGTAGGACCACCTC
CCTCCTCTCTTTGAGCTGTTTGACGGGGAGGTGAATGTGAAGAGGCCCATGAAGGATGAGACTCACTTTGAGGTGGTGGAGTCTGG
CCGGTACATCATTCTGCTGCTGGGAACTCGACAAACTGCCCCTCCACTTACACTTCTCCGGGTACTTCCTACTCTGAGTGAAACTC
CACCACCTCAGACCGGCCATGTAGTAAGACGACGACCCCAAAGCCCTCTCCGTGGTCTGGGACCGCCACCTGAGCATCTCCGTGGT
CCTGAAGCAGACATACCAGGAGAAAGTGTGTGGCCTGTGTGGGAATTTTGATGTTTCGGGAGAGGCACCAGACCCTGGCGGTGGAC
TCGTAGAGGCACCAGGACTTCGTCTGTATGGTCCTCTTTCACACACCGGACACACCCTTAAAACTAGGCATCCAGAACAATGACCT
CACCAGCAGCAACCTCCAAGTGGAGGAAGACCCTGTGGACTTTGGGAACTCCTGGAAAGTGAGCTCGCAGTGTGCTGACACCGTAG
GTCTTGTTACTGGAGTGGTCGTCGTTGGAGGTTCACCTCCTTCTGGGACACCTGAAACCCTTGAGGACCTTTCACTCGAGCGTCAC
ACGACTGTCCAGAAAAGTGCCTCTGGACTCATCCCCTGCCACCTGCCATAACAACATCATGAAGCAGACGATGGTGGATTCCTCCT
GTAGAATCCTTACCAGTGACGTGGTCTTTTCACGGAGACCTGAGTAGGGGACGGTGGACGGTATTGTTGTAGTACTTCGTCTGCTA
CCACCTAAGGAGGACATCTTAGGAATGGTCACTGCACTTCCAGGACTGCAACAAGCTGGTGGACCCCGAGCCATATCTGGATGTCT
GCATTTACGACACCTGCTCCTGTGAGTCCATTGGGGACTGCGCCTGCTTCGAAGGTCCTGACGTTGTTGACCACCTGGGGCTCGG
TATAGACCTACAGACGTAAATGCTGTGGACGAGGACACTCAGGTAACCCCTGACGCGGACGAAGTGCGACACCATTGCTGCCTATG
CCCACGTGTGTGCCCAGCATGGCAAGGTGGTGACCTGGAGGACGGCCACATTGTGCCCCCAGAGCTGCGAGGAGAGGAACGCTGTG
GTAACGACGGATACGGGTGCACACACGGGTCGTACCGTTCCACCACTGGACCTCCTGCCGGTGTAACACGGGGGTCTCGACGCTCC
```

-continued

```
TCTCCTATCTCCGGGAGAACGGGTATGAGTGTGAGTGGCGCTATAACAGCTGTGCACCTGCCTGTCAAGTCACGTGTCAGCACCCT
GAGCCACTGGCCTGCCCTGTTAGAGGCCCTCTTGCCCATACTCACACTCACCGCGATATTGTCGACACGTGGACGGACAGTTCAGT
GCACAGTCGTGGGACTCGGTGACCGGACGGGACAGCAGTGTGTGGAGGGCTGCCATGCCCACTGCCCTCCAGGGAAAATCCTGGAT
GAGCTTTTGCAGACCTGCGTTGACCCTGAAGACTGTCCAGTGTGTGAGCGTCACACACCTCCCGACGGTACGGGTGACGGGAGGTC
CCTTTTAGGACCTACTCGAAAACGTCTGGACGCAACTGGGACTTCTGACAGGTCACACACTCGTGGCTGGCCGGCGTTTTGCCTCA
GGAAAGAAAGTCACCTTGAATCCCAGTGACCCTGAGCACTGCCAGATTTGCCACTGTGATGTTGTCAACCTCACCTCACCGACCGG
CCGCAAAACGGAGTCCTTTCTTTCAGTGGAACTTAGGGTCACTGGGACTCGTGACGGTCTAAACGGTGACACTACAACAGTTGGAG
TGGAGTGAAGCCTGCCAGGAGCCGGGAGGCCTGGTGGTGCCTCCCACAGATGCCCCGGTGAGCCCCACCACTCTGTATGTGGAGGA
CATCTCGGAACCGCCGTTCACTTCGGACGGTCCTCGGCCCTCCGGACCACCACGGAGGGTGTCTACGGGGCCACTCGGGGTGGTGA
GACATACACCTCCTGTAGAGCCTTGGCGGCAAGCACGATTTCTACTGCAGCAGGCTACTGGACCTGGTCTTCCTGCTGGATGGCTC
CTCCAGGCTGTCCGAGGCTGAGTTTGAAGTGCTGAAGGCCTTTGTGCGTGCTAAAGATGACGTCGTCCGATGACCTGGACCAGAAG
GACGACCTACCGAGGAGGTCCGACAGGCTCCGACTCAAACTTCACGACTTCCGGAAACACGTGGACATGATGGAGCGGCTGCGCAT
CTCCCAGAAGTGGGTCCGCGTGGCCGTGGTGGAGTACCACGACGGCTCCCACGCCTACATCGGGCTCAAGGACCCACCTGTACTAC
CTCGCCGACGCGTAGAGGGTCTTCACCCAGGCGCACCGGCACCACCTCATGGTGCTGCCGAGGGTGCGGATGTAGCCCGAGTTCCT
GGGGAAGCGACCGTCAGAGCTGCGGCGCATTGCCAGCCAGGTGAAGTATGCGGGCAGCCAGGTGGCCTCCACCAGCGAGGTCTTGA
AATACACACTGTTCCACCTTCGCTGGCAGTCTCGACGCCGCGTAACGGTCGGTCCACTTCATACGCCCGTCGGTCCACCGGAGGTG
GTCGCTCCAGAACTTTATGTGTGACAAGGTAATCTTCAGCAAGATCGACCGCCCTGAAGCCTCCCGCATCGCCCTGCTCCTGATGG
CCAGCCAGGAGCCCCAACGGATGTCCCGGAACTTTGTCCGCTACTTAGAAGTCGTTCTAGCTGGCGGGACTTCGGAGGGCGTAGCG
GGACGAGGACTACCGGTCGGTCCTCGGGGTTGCCTACAGGGCCTTGAAACAGGCGATGGTCCAGGGCCTGAAGAAGAAGAAGGTCA
TTGTGATCCCGGTGGGCATTGGGCCCCATGCCAACCTCAAGCAGATCCGCCTCATCGAGAAGCAGGCCCCTGCAGGTCCCGGACTT
CTTCTTCTTCCAGTAACACTAGGGCCACCCGTAACCCGGGGTACGGTTGGAGTTCGTCTAGGCGGAGTAGCTCTTCGTCCGGGGAC
AGAACAAGGCCTTCGTGCTGAGCAGTGTGGATGAGCTGGAGCAGCAAAGGGACGAGATCGTTAGCTACCTCTGTGACCTTGCCCCT
GAAGCCCCTCCTCCTCTTGTTCCGGAAGCACGACTCGTCACACCTACTCGACCTCGTCGTTTCCCTGCTCTAGCAATCGATGGAGA
CACTGGAACGGGACTTCGGGGAGGAGGTACTCTGCCCCCGACATGGCACAAGTCACTGTGGGCCCGGGGCTCTTGGGGGTTTCG
ACCCTGGGGCCCAAGAGGAACTCCATGGTTCTGGATGTGGCGATGAGACGGGGGGCTGTACCGTGTTCAGTGACACCCGGGCCCCG
AGAACCCCCAAAGCTGGGACCCCGGGTTCTCCTTGAGGTACCAAGACCTACACCGCTTCGTCCTGGAAGGATCGGACAAAATTGGT
GAAGCCGACTTCAACAGGAGCAAGGAGTTCATGGAGGAGGTGATTCAGCGGATGGATGTGGGCCAGGACAAAGCAGGACCTTCCTA
GCCTGTTTTAACCACTTCGGCTGAAGTTGTCCTCGTTCCTCAAGTACCTCCTCCACTAAGTCGCCTACCTACACCCGGTCCTGTGC
ATCCACGTCACGGTGCTGCAGTACTCCTACATGGTGACCGTGGAGTACCCCTTCAGCGAGGCACAGTCCAAAGGGGACATCCTGCA
GCGGGTGCGAGACGTAGGTGCAGTGCCACGACGTCATGAGGATGTACCACTGGCACCTCATGGGGAAGTCGCTCCGTGTCAGGTTT
CCCCTGTAGGACGTCGCCCACGCTCTGATCCGCTACCAGGGCGGCAACAGGACCAACACTGGGCTGGCCCTGCGGTACCTCTCTGA
CCACAGCTTCTTGGTCAGCCAGGGTGACCGGGAGCAGGCGCTAGGCGATGGTCCCGCCGTTGTCCTGGTTGTGACCCGACCGGGAC
GCCATGGAGAGACTGGTGTCGAAGAACCAGTCGGTCCCACTGGCCCTCGTCCGCCCCAACCTGGTCTACATGGTCACCGGAAATCC
TGCCTCTGATGAGATCAAGAGGCTGCCTGGAGACATCCAGGTGGTGCCCATTGGAGTGGGCCCTAATGGGGTTGGACCAGATGTAC
CAGTGGCCTTTAGGACGGAGACTACTCTAGTTCTCCGACGGACCTCTGTAGGTCCACCACGGGTAACCTCACCCGGGATTACCCAA
CGTGCAGGAGCTGGAGAGGATTGGCTGGCCCAATGCCCCTATCCTCATCCAGGACTTTGAGACGCTCCCCCGAGAGGCTCCTGACC
TGGTGCTGCAGGTTGCACGTCCTCGACCTCTCCTAACCGACCGGGTTACGGGGATAGGAGTAGGTCCTGAAACTCTGCGAGGGGGC
TCTCCGAGGACTGGACCACGACGTGAGGTGCTGCTCCGGAGAGGGGCTGCAGATCCCCACCCTCTCCCCTGCACCTGACTGCAGCC
AGCCCCTGGACGTGATCCTTCTCCTGGATGGCTCCTCCCTCCACGACGAGGCCTCTCCCCGACGTCTAGGGGTGGGAGAGGGGACG
TGGACTGACGTCGGTCGGGGACCTGCACTAGGAAGAGGACCTACCGAGGAGGAGTTTCCCAGCTTCTTATTTTGATGAAATGAAGA
GTTTCGCCAAGGCTTTCATTTCAAAAGCCAATATAGGGCCTCGTCTCACTCAGGTGTCAGTGCTGCTCAAAGGGTCGAAGAATAAA
```

-continued

```
ACTACTTTACTTCTCAAAGCGGTTCCGAAAGTAAAGTTTTCGGTTATATCCCGGAGCAGAGTGAGTCCACAGTCACGACGAGTATG
GAAGCATCACCACCATTGACGTGCCATGGAACGTGGTCCCGGAGAAAGCCCATTTGCTGAGCCTTGTGGACGTCATGCAGCGGGAG
GGAGGCCCTCATACCTTCGTAGTGGTGGTAACTGCACGGTACCTTGCACCAGGGCCTCTTTCGGGTAAACGACTCGGAACACCTGC
AGTACGTCGCCCTCCCTCCGGGCAGCCAAATCGGGGATGCCTTGGGCTTTGCTGTGCGATACTTGACTTCAGAAATGCATGGTGCC
AGGCCGGGAGCCTCAAAGGCGGTGGTCATCCTGGTCGTCGGTTTAGCCCCTACGGAACCCGAAACGACACGCTATGAACTGAAGTC
TTTACGTACCACGGTCCGGCCCTCGGAGTTTCCGCCACCAGTAGGACCAGACGGACGTCTCTGTGGATTCAGTGGATGCAGCAGCT
GATGCCGCCAGGTCCAACAGAGTGACAGTGTTCCCTATTGGAATTGGAGATCGCTACGATGCAGTGCCTGCAGAGACACCTAAGTC
ACCTACGTCGTCGACTACGGCGGTCCAGGTTGTCTCACTGTCACAAGGGATAACCTTAACCTCTAGCGATGCTACGTCCCCAGCTA
CGGATCTTGGCAGGCCCAGCAGGCGACTCCAACGTGGTGAAGCTCCAGCGAATCGAAGACCTCCCTACCATGGTCACCTTGGGCAA
TTCCTTGGGTCGATGCCTAGAACCGTCCGGGTCGTCCGCTGAGGTTGCACCACTTCGAGGTCGCTTAGCTTCTGGAGGGATGGTAC
CAGTGGAACCCGTTAAGGAACCTCCACAAACTGTGCTCTGGATTTGTTAGGATTTGCATGGATGAGGATGGGAATGAGAAGAGGCC
CGGGGACGTCTGGACCTTGCCAGACCAGTGCCACGGAGGTGTTTGACACGAGACCTAAACAATCCTAAACGTACCTACTCCTACCC
TTACTCTTCTCCGGGCCCCTGCAGACCTGGAACGGTCTGGTCACGGTGACCGTGACTTGCCAGCCAGATGGCCAGACCTTGCTGAA
GAGTCATCGGGTCAACTGTGACCGGGGGCTGAGGCCTTCGTGCCCTAACAGCCAGTCCCTGTGGCACTGAACGGTCGGTCTACCG
GTCTGGAACGACTTCTCAGTAGCCCAGTTGACACTGGCCCCCGACTCCGGAAGCACGGGATTGTCGGTCAGGGGACTTAAAGTGGA
AGAGACCTGTGGCTGCCGCTGGACCTGCCCCTGYGTGTGCACAGGCAGCTCCACTCGGCACATCGTGACCTTTGATGGGCAGAATT
TCAAAATTTCACCTTCTCTGGACACCGACGGCGACCTGGACGGGACRCACACGTGTCCGTCGAGGTGAGCCGTGTAGCACTGGAA
ACTACCCGTCTTAAAGTTGCTGACTGGCAGCTGTTCTTATGTCCTATTTCAAAACAAGGAGCAGGACCTGGAGGTGATTCTCCATA
ATGGTGCCTGCAGCCCTGGAGCAAGGCAGGGCCGACTGACCGTCGACAAGAATACAGGATAAAGTTTTGTTCCTCGTCCTGGACCT
CCACTAAGAGGTATTACCACGGACGTCGGGACCTCGTTCCGTCCCGTGCATGAAATCCATCGAGGTGAAGCACAGTGCCCTCTCCG
TCGAGSTGCACAGTGACATGGAGGTGACGGTGAATGGGAGACTGGTCTCTGTTCCTTACGACGTACTTTAGGTAGCTCCACTTCGT
GTCACGGGAGAGGCAGCTCSACGTGTCACTGTACCTCCACTGCCACTTACCCTCTGACCAGAGACAAGGAATGCTGGGTGGGAACA
TGGAAGTCAACGTTTATGGTGCCATCATGCATGAGGTCAGATTCAATCACCTTGGTCACATCTTCACATTCACTCCACAAAACAAT
GAACCCACCCTTGTACCTTCAGTTGCAAATACCACGGTAGTACGTACTCCAGTCTAAGTTAGTGGAACCAGTGTAGAAGTGTAAGT
GAGGTGTTTTGTTACTGTTCCAACTGCAGCTCAGCCCCAAGACTTTTGCTTCAAAGACGTATGGTCTGTGTGGGATCTGTGATGAG
AACGGAGCCAATGACTTCATGCTGAGGGATCAAGGTTGACGTCGAGTCGGGGTTCTGAAAACGAAGTTTCTGCATACCAGACACAC
CCTAGACACTACTCTTGCCTCGGTTACTGAAGTACGACTCCCTAGGCACAGTCACCACAGACTGGAAAACACTTGTTCAGGAATGG
ACTGTGCAGCGGCCAGGGCAGACGTGCCAGCCCATCCTGGAGGAGCAGTGTCTTGTCCCCGTGTCAGTGGTGTCTGACCTTTTGTG
AACAAGTCCTTACCTGACACGTCGCCGGTCCCGTCTGCACGGTCGGGTAGGACCTCCTCGTCACAGAACAGGCCGACAGCTCCCAC
TGCCAGGTCCTCCTCTTACCACTGTTTGCTGAATGCCACAAGGTCCTGGCTCCAGCCACATTCTATGCCATCTGCCAGCAGGACAG
GGCTGTCGAGGGTGACGGTCCAGGAGGAGAATGGTGACAAACGACTTACGGTGTTCCAGGACCGAGGTCGGTGTAAGATACGGTAG
ACGGTCGTCCTGTCTTGCCACCAGGAGCAAGTGTGTGAGGTGATCGCCTCTTATGCCCACCTCTGTCGGACCAACGGGGTCTGCGT
TGACTGGAGGACACCTGATTTCTGTGCTAACGGTGGTCCTCGTTCACACACTCCACTAGCGGAGAATACGGGTGGAGACAGCCTGG
TTGCCCCAGACGCAACTGACCTCCTGTGGACTAAAGACACGAATGTCATGCCCACCATCTCTGGTCTACAACCACTGTGAGCATGG
CTGTCCCCGGCACTGTGATGGCAACGTGAGCTCCTGTGGGACCATCCCTCCGAAGTACAGTACGGGTGGTAGAGACCAGATGTTG
GTGACACTCGTACCGACAGGGGCCGTGACACTACCGTTGCACTCGAGGACACCCCTGGTAGGAGGCTTCGCTGTTTCTGCCCTCC
AGATAAAGTCATGTTGGAAGGCAGCTGTGTCCCTGAAGAGGCCTGCACTCAGTGCATTGGTGAGGATGGAGTCCAGCACCAGTTCG
ACAAAGACGGGAGGTCTATTTCAGTACAACCTTCCGTCGACACAGGGACTTCTCCGGACGTGAGTCACGTAACCACTCCTACCTCA
GGTCGTGGTCAACCTGGAAGCCTGGGTCCCGGACCACCAGCCCTGTCAGATCTGCACATGCCTCAGCGGGCGGAAGGTCAACTGCA
CAACGCAGCCCTGCCCCACGGCCAAAGGACCTTCGGACCCAGGGCCTGGTGGTCGGGACAGTCTAGACGTGTACGGAGTCGCCCGC
CTTCCAGTTGACGTGTTGCGTCGGGACGGGGTGCCGGTTTGCTCCCACGTGTGGCCTGTGTGAAGTAGCCCGCCTCCGCCAGAATG
```

-continued

```
CAGACCAGTGCTGCCCCGAGTATGAGTGTGTGTGTGACCCAGTGAGCTGTGACCCGAGGGTGCACACCGGACACACTTCATCGGGC
GGAGGCGGTCTTACGTCTGGTCACGACGGGGCTCATACTCACACACACACTGGGTCACTCGACACTGGTGCCCCAGTGCCTCACT
GTGAACGTGGCCTCCAGCCCACACTGACCAACCCTGGCGAGTGCAGACCCAACTTCACCTGCGCCTGCAGGAAGGAGGAGTGACGG
GGGTCACGGAGTGACACTTGCACCGGAGGTCGGGTGTGACTGGTTGGGACCGCTCACGTCTGGGTTGAAGTGGACGCGGACGTCCT
TCCTCCTCACCAAAAGAGTGTCCCCACCCTCCTGCCCCCCGCACCGTTTGCCCACCCTTCGGAAGACCCAGTGCTGTGATGAGTAT
GAGTGTGCCTGCAACTGTGTCAACGTTTTCTCACAGGGGTGGGAGGACGGGGGGCGTGGCAAACGGGTGGGAAGCCTTCTGGGTCA
CGACACTACTCATACTCACACGGACGTTGACACAGTTGTCCACAGTGAGCTGTCCCCTTGGGTACTTGGCCTCAACCGCCACCAAT
GACTGTGGCTGTACCACAACCACCTGCCTTCCCGACAAGGTGTGTGTCCACCAGGTGTCACTCGACAGGGGAACCCATGAACCGGA
GTTGGCGGTGGTTACTGACACCGACATGGTGTTGGTGGACGGAAGGGCTGTTCCACACACAGGTGGGAAGCACCATCTACCCTGTG
GGCCAGTTCTGGGAGGAGGGCTGCGATGTGTGCACCTGCACCGACATGGAGGATGCCGTGATGGGCCTCCGCGTGGCCCACTTCGT
GGTAGATGGGACACCCGGTCAAGACCCTCCTCCCGACGCTACACACGTGGACGTGGCTGTACCTCCTACGGCACTACCCGGAGGCG
CACCGGGTGTGCTCCCAGAAGCCCTGTGAGGACAGCTGTCGGTCGGGCTTCACTTACGTTCTGCATGAAGGCGAGTGCTGTGGAAG
GTGCCTGCCATCTGCCTGTGAGCACGAGGGTCTTCGGGACACTCCTGTCGACAGCCAGCCCGAAGTGAATGCAAGACGTACTTCCG
CTCACGACACCTTCCACGGACGGTAGACGGACACTCGTGGTGACTGGCTCACCGCGGGGGGACTCCCAGTCTTCCTGGAAGAGTGT
CGGCTCCCAGTGGGCCTCCCCGGAGAACCCCTGCCTCATCAATGAGTGTGCACCACTGACCGAGTGGCGCCCCCCTGAGGGTCAGA
AGGACCTTCTCACAGCCGAGGGTCACCCGGAGGGGCCTCTTGGGGACGGAGTAGTTACTCACACTCCGAGTGAAGGAGGAGGTCTT
TATACAACAAAGGAACGTCTCCTGCCCCCAGCTGGAGGTCCCTGTCTGCCCCTCGGGCTTTCAGCTGAGCTGTAAGACAGGCTCAC
TTCCTCCTCCAGAAATATGTTGTTTCCTTGCAGAGGACGGGGTCGACCTCCAGGGACAGACGGGGAGCCCGAAAGTCGACTCGAC
ATTCTGCTCAGCGTGCTGCCCAAGCTGTCGCTGTGAGCGCATGGAGGCCTGCATGCTCAATGGCACTGTCATTGGGCCCGGGAAGA
CTGTGATGATCGATGTGTGCGAGTCGCACGACGGGTTCGACAGCGACACTCGCGTACCTCCGGACGTACGAGTTACCGTGACAGTA
ACCCGGGCCCTTCTGACACTACTAGCTACACACGACGACCTGCCGCTGCATGGTGCAGGTGGGGTCATCTCTGGATTCAAGCTGG
AGTGCAGGAAGACCACCTGCAACCCCTGCCCCCTGGGTTACAAGGAAGTGCTGGACGGCGACGTACCACGTCCACCCCCAGTAGAG
ACCTAAGTTCGACCTCACGTCCTTCTGGTGGACGTTGGGGACGGGGACCCAATGTTCCTTCAAAATAACACAGGTGAATGTTGTG
GGAGATGTTTGCCTACGGCTTGCACCATTCAGCTAAGAGGAGGACAGATCATGACACTGAAGCGTGATGAGACGCTTTTTATTGTG
TCCACTTACAACACCCTCTACAAACGGATGCCGAACGTGGTAAGTCGATTCTCCTCCTGTCTAGTACTGTGACTTCGCACTACTCT
GCGACCAGGATGGCTGTGATACTCACTTCTGCAAGGTCAATGAGAGAGGAGAGTACTTCTGGGAGAAGAGGGTCACAGGCTGCCCA
CCCTTTGATGAACACAAGGGTCCTACCGACACTATGAGTGAAGACGTTCCAGTTACTCTCTCCTCTCATGAAGACCCTCTTCTCCC
AGTGTCCGACGGGTGGGAAACTACTTGTGTTCTGTCTTGCTGAGGGAGGTAAAATTATGAAAATTCCAGGCACCTGCTGTGACACA
TGTGAGGAGCCTGAGTGCAACGACATCACTGCCAGGCTGCAGTATGACAGAACGACTCCCTCCATTTTAATACTTTTAAGGTCCGT
GGACGACACTGTGTACACTCCTCGGACTCACGTTGCTGTAGTGACGGTCCGACGTCATACTCAAGGTGGGAAGCTGTAAGTCTGAA
GTAGAGGTGGATATCCACTACTGCCAGGGCAAATGTGCCAGCAAAGCCATGTACTCCATTGACATCAACGATGTAGTTCCACCCTT
CGACATTCAGACTTCATCTCCACCTATAGGTGATGACGGTCCCGTTTACACGGTCGTTTCGGTACATGAGGTAACTGTAGTTGCTA
CAGCAGGACCAGTGCTCCTGCTGCTCTCCGACACGGACGGAGCCCATGCAGGTGGCCCTGCACTGCACCAATGGCTCTGTTGTGTA
CCATGAGGTTCTCAATCGTCCTGGTCACGAGGACGACGAGAGGCTGTGCCTGCCTCGGGTACGTCCACCGGGACGTGACGTGGTTA
CCGAGACAACACATGGTACTCCAAGAGTTAGCCATGGAGTGCAAATGCTCCCCCAGGAAGTGCAGCAAGTGA
```

Full length von Willebrand Factor peptide sequence (X is any natural amino acid)
SEQ ID NO: 28

MIPARFAGVLLALALILPGT LCAEGTRGRSSTARCSLFGS DFVNTFDGSMYSFAGYCSYL

LAGGCQKRSFSIIGDFQNGK RVSLSVYLGEFFDIHLFVNG TVTQGDQRVSMPYASKGLYL

ETEAGYYKLSGEAYGFVARI DGSGNFQVLLSDRYFNKTCG LCGNFNIFAEDDFMTQEGTL

TSDPYDFANSWALSSGEQWC ERASPFSSSCNISSGEMQKG LWEQCQLLKSTSVFARCHPL

VDPEPFVALCEKTLCECAGG LECACPALLEYARTCAQEGM VLYGWTDHSACSPVCPAGME

-continued

YRQCVSPCARTCQSLHINEM CQERCVDGCSCPEGQLLDEG LCVESTECPCVHSGKRYPPG
TSLSRDCNTCICRNSQWICS NEECPGECLVTGQSHFKSFD NRYFTFSGICQYLLARDCQD
HSFSIVIETVQCADDRDAVC TRSVTVRLPGLHNSLVKLKH GAGVAMDGQDIQLPLLKGDL
RIQHTVTASVRLSYGEDLQM DWDGRGRLLVKLSPVYAGKT CGLCGNYNGNQGDDFLTPSG
LAEPRVEDFGNAWKLHGDCQ DLQKQHSDPCALNPRMTRFS EEACAVLTSPTFEACHRAVS
PLPYLRNCRYDVCSCSDGRE CLCGALASYAAACAGRGVRV AWREPGRCELNCPKGQVYLQ
CGTPCNLTCRSLSYPDEECN EACLEGCFCPPGLYMDERGD CVPKAQCPCYYDGEIFQPED
IFSDHHTMCYCEDGFMHCTM SGVPGSLLPDAVLSSPLSHR SKRSLSCRPPMVKLVCPADN
LRAEGLECTKTCQNYDLECM SMGCVSGCLCPPGMVRHENR CVALERCPCFHQGKEYAPGE
TVKIGCNTCVCRDRKWNCTD HVCDATCSTIGMAHYLTFDG LKYLFPGECQYVLVQDYCGS
NPGTFRILVGNKGCSHPSVK CKKRVTILVEGGEIELFDGE VNVKRPMKDETHFEVVESGR
YIILLLGKALSVVWDRHLSI SVVLKQTYQEKVCGLCGNFD GIQNNDLTSSNLQVEEDPVD

FGNSWKVSSQCADTRKVPLD SSPATCHNNIMKQTMVDSSC RILTSDVFQDCNKLVDPEPY

LDVCIYDTCSCESIGDCACF CDTIAAYAHVCAQHGKVVTW RTATLCPQSCEERNLRENGY

ECEWRYNSCAPACQVTCQHP EPLACPVQCVEGCHAHCPPG KILDELLQTCVDPEDCPVCE

VAGRRFASGKKVTLNPSDPE HCQICHCDVVNLTCEACQEP GGLVVPPTDAPVSPTTLYVE

DISEPPLHDFYCSRLLDLVF LLDGSSRLSEAEFEVLKAFV VDMMERLRISQKWVRVAVVE

YHDGSHAYIGLKDRKRPSEL RRIASQVKYAGSQVASTSEV LKYTLFQIFSKIDRPEASRI

ALLLMASQEPQRMSRNFVRY VQGLKKKKVIVIPVGIGPHA NIKQIRLIEKQAPENKAFVL

SSVDELEQQRDEIVSYLCDL APEAPPPTLPPDMAQVTVGP GLLGVSTLGRKRNSMVLDVA

FVLEGSDKIGEADFNRSKEF MEEVIQRMDVGQDSIHVTVL QYSYMVTVEYPFSEAQSKGD

ILQRVREIRYQGGNRTNTGL ALRYLSDHSFLVSQGDREQA PNLVYMVTGNPASDEIKRLP

GDIQVVPIGVGPNANVQELE RIGWPNAPILIQDFETLPRE APDLVLQRCCSGEGLQIPTL

SPAPDCSQPLDVILLLDGSS SFPASYFDEMKSFAKAFISK ANIGPRLTQVSVLQYGSITT

IDVPWNVVPEKAHLLSLVDV MQREGGPSQIGDALGFAVRY LTSEMHGARPGASKAVVILV

TDVSVDSVDAAADAARSNRV TVFPIGIGDRYDAAQLRILA GPAGDSNVVKLQRIEDLPTM

VTLGNSFLHKLCSGFVRICM DEDGNEKRPGDVWTLPDQGH TVTCQPDGQTLLKSHRVNCD

RGLRPSCPNSQSRVKVEETC GCRWTCPCVCTGSSTRHIVT FDGQNFKLTGSCSYVLFQNK

EQDLEVILHNGACSPGARQG CMKSIEVKHSALSVEXHSDM EVTVNGRLVSTPYVGGNMEV

NVYGAIMHEVRFNHLGHIFTFTPQNNEFQLQLSPKT FASKTYGLQGIGDENGANDF

MLRPGTVTTDWKTLVQEWTV QRPGQTCQPILEEQQLVPDS SHCQVLLLPLFAECHKVLAP

ATFYAICQQDSCHQEQVCEV IASYAHLCRTNGVCVDWRTP DFCAMSCPPSLVYNHCEHGC

PRHCDGNVSSCGDHPSEGCF CPPDKVMLEGSCVPEEACTQ CIGEDGVQHQFLEAWVPDHQ

PCQICTCLSGRKVNCTTQPC PTAKAPTCGLCEVARLRQNA DQCCPEYECVCDPVSCDLPP

VPHCERGLQPTLTNPGECRP NFTCACRKEECKRVSPPSCP PHRLPTLRKTQCCDEYECAC

NCVNSTVSCPLGYLASTATN DCGCTTTTCLPDKVCVHRST IYPVGQFWEEGCDVCTCTDM

EDAVMGLRVAQCSQKPCEDS CRSGFTYVLHEGECCGRCLP SACEVVTGCPRGDSASSWKS

VGSQWASPENPCLINECVRV KEEVFIQQRNVSCPQLEVPV CPSGFQLSCKTSACCPSCRC

ERMEACMLNGTVIGPGKTVM IDVCTTCRCMVQVGVISGFK LECRKTTCNPCRLGYKEENN

TGECCGRCLPTACTIQLRGG QIMTLKRDETLQDGCDTHFC KVNERGEYFWEKRVTGCPPF

```
DEHKCLAEGGKIMKIPGTCC DTCEEPECNDITARLQYVKV GSCKSEVEVDIHYCQGKCAS

KAMYSIDINDVQDQCSCCSP TRTEPMQVALHCTNGSVVYH EVLNAMECKCSPRKCSK
``` human IgG1 amino acids 233-236                                              SEQ ID NO: 29

ELLG

XTEN AE42-4, protein sequence                                               SEQ ID NO: 30

GAPGSPAGSPTSTEEGTSESATPESGPGSEPATSGSETPASS

XTEN AE42-4, DNA sequence                                                   SEQ ID NO: 31

```
GGCGCGCCAGGTTQTCCTGCTGGCTCCCCCACQTCAACAGAAGAGGGGACAAGCGAAAGC

GCTACGCCTGAGAGTGGCCCTGGCTCTGAGCCAGCCACCTQCGGCTCTGAAACCCCTGCC

TCGAGC
```

XTEN AE144-2A, protein sequence                                             SEQ ID NO: 32

```
TSTEPSEGSAPGSPAGSPTSTEEGTSTEPSEGSAPGTSESATPESGPG

TSTEPSEGSAPGTSESATPESGPGSEPATSGSETPGTSTEPSEGSAPGTSTEPSEGSAPG

TSESATPESGPGTSESATPESGPG
```

XTEN AE144-2A, DNA sequence                                                 SEQ ID NO: 33

```
GGCGCGCCAACCAGTACGGAGCCGTCCGAGGGGAGGGCACCAGGAAGCCCGGCTGGGAGC

CCGACTTCTACCGAAGAGGGTACATCTACCGAACCAAGTGAAGGTTCAGCACCAGGCACC

TCAACAGAACCCTCTGAGGGCTCGGCGCCTGGTACAAGTGAGTCCGCCACCCCAGAATCC

GGGCCTGGGACAAGCACAGAACCTTCGGAAGGGAGTGCCCCTGGAACATCCGAATCGGCA

ACCCCAGAATCAGGGCCAGGATCTGAGCCCGCGACTTCGGGCTCCGAGACGCCTGGGACA

TCCACCGAGCCCTCCGAAGGATCAGCCCCAGGCACCAGCACGGAGCCCTCTGAGGGAAGC

GCACCTGGTACCAGCGAAAGCGCAACTCCCGAATCAGGTCCCGGTACGAGCGAGTCGGCG

ACCCCGGAGAGCGGGCCAGGTGCCTCGAGC
```

XTEN AE144-3B, protein sequence                                             SEQ ID NO: 34

```
SPAGSPTSTEEGTSESATPESGPGSEPATSGSETPGTSESATPESGPGTSTEPSEGSAPG

TSTEPSEGSAPGTSTEPSEGSAPGTSTEPSEGSAPGTSTEPSEGSAPGTSTEPSEGSAPG

SPAGSPTSTEEGTSTEPSEGSAPG
```

XTEN AE144-3B, DNA sequence                                                 SEQ ID NO: 35

```
GGCGCGCCAAGTCCCGCTGGAAGCCCAACTAGCACCGAAGAGGGGACCTCAGAGTCCGCC

ACCCCCGAGTCCGGCCCTGGCTCTGAGCCTGCCACTAGCGGCTCCGAGACTCCTGGCACA

TCCGAAAGCGCTACACCCGAGAGTGGACCCGGCACCTCTACCGAGCCCAGTGAGGGCTCC

GCCCCTGGAACAAGCACCGAGCCCAGCGAAGGCAGCGCCCCAGGGACCTCCACAGAGCCC

AGTGAAGGCAGTGCTCCTGGCACCAGCACCGAACCAAGCGAGGGCTCTGCACCCGGGACC

TCCACCGAGCCAAGCGAAGGCTCTGCCCCTGGCACTTCCACCGAGCCCAGCGAAGGCAGC

GCCCCTGGGAGCCCCGCTGGCTCTCCCACCAGCACTGAGGAGGGCACATCTACCGAACCA

AGTGAAGGCTCTGCACCAGGTGCCTCGAGC
```

XTEN AE144-4A, protein sequence                                             SEQ ID NO: 36

```
TSESATPESGPGSEPATSGSETPGTSESATPESGPCSEPATSGSETPGTSESATPESGPG

TSTEPSEGSAPGTSESATPESGPGSPAGSPTSTEEGSPAGSPTSTEEGSPAGSPTSTEEG

TSESATPESGPGTSTEPSEGSAPG
```

XTEN AE144-4A, DNA sequence

SEQ ID NO: 37

GGCGCGCCAACGTCCGAAAGTGCTACCCCTGAGTCAGGCCCTGGTAGTGAGCCTGCCACA

AGCGGAAGCGAAACTCCGGGGACCTCAGAGTCTGCCACTCCCGAATCGGGGCCAGGCTCT

GAACCGGCCACTTCAGGGAGCGAAACACCAGGAACATCGGAGAGCGCTACCCCGGAGAGC

GGGCCAGGAACTAGTACTGAGCCTAGCGAGGGAAGTGCACCTGGTACAAGCGAGTCCGCC

ACACCCGAGTCTGGCCCTGGCTCTCCAGCGGGCTCACCCACGAGCACTGAAGAGGGCTCT

CCCGCTGGCAGCCCAACGTCGACAGAAGAAGGATCACCAGCAGGCTCCCCCACATCAACA

GAGGAGGGTACATCAGAATCTGCTACTCCCGAGAGTGGACCCGGTACCTCCACTGAGCCC

AGCGAGGGGAGTGCACCAGGTGCCTCGAGC

XTEN AE144-5A, protein sequence

SEQ ID NO: 38

TSESATPESGPGSEPATSGSETPGTSESATPESGPGSEPATSGSETPGTSESATPESGPG

TSTEPSEGSAPGSPAGSPTSTEEGTSESATPESGPGSEPATSGSETPGTSESATPESGPG

SPAGSPTSTEEGSPAGSPTSTEEG

XTEN AE144-5A, DNA sequence

SEQ ID NO: 39

GGCGCGCCAACATCAGAGAGCGCCACCCCTGAAAGTGGTCCCGGGAGCGAGCCAGCCACA

TCTGGGTCGGAAACGCCAGGCACAAGTGAGTCTGCAACTCCCGAGTCCGGACCTGGCTCC

GAGCCTGCCACTAGCGGCTCCGAGACTCCGGGAACTTCCGAGAGCGCTACACCAGAAAGC

GGACCCGGAACCAGTACCGAACCTAGCGAGGGCTCTGCTCCGGGCAGCCCAGCCGGCTCT

CCTACATCCACGGAGGAGGGCACTTCCGAATCCGCCACCCCGGAGTCAGGGCCAGGATCT

GAACCCGCTACCTCAGGCAGTGAGACGCCAGGAACGAGCGAGTCCGCTACACCGGAGAGT

GGGCCAGGGAGCCCTGCTGGATCTCCTACGTCCACTGAGGAAGGGTCACCAGCGGGCTCG

CCCACCAGCACTGAAGAAGGTGCCTCGAGC

XTEN AE144-6B, protein sequence

SEQ ID NO: 40

TSTEPSEGSAPGTSESATPESGPGTSESATPESGPGTSESATPESGPGSEPATSGSETPG

SEPATSGSETPGSPAGSPTSTEEGTSTEPSEGSAPGTSTEPSEGSAPGSEPATSGSETPG

TSESATPESGPGTSTEPSEGSAPG

XTEN AE144-6B, DNA sequence

SEQ ID NO: 41

GGCGCGCCAACATCTACCGAGCCTTCCGAAGGCTCTGCCCCTGGGACCTCAGAATCTGCA

ACCCCTGAAAGCGGCCCTGGAACCTCCGAAAGTGCCACTCCCGAGAGCGGCCCCAGGGACA

AGCGAGTCAGCAACCCCTGAGTCTGGACCCGGCAGCGAGCCTGCAACCTCTGGCTCAGAG

ACTCCCGGCTCAGAACCCGCTACCTCAGGCTCCGAGACACCCGGCTCTCCTGCTGGGAGT

CCCACTTCCACCGAGGAAGGAACATCCACTGAGCCTAGTGAGGGCTCTGCCCCTGGAACC

AGCACAGAGCCAAGTGAGGGCAGTGCACCAGGATCCGAGCCAGCAACCAGCGGGTCCGAG

ACTCCCGGGACCTCTGAGTCTGCCACCCCAGAGAGCGGACCCGGCACTTCAACCGAGCCC

TCCGAAGGATCAGCACCAGGTGCCTCGAGC

XTEN AG144-1, protein sequence

SEQ ID NO: 42

PGSSPSASTGTGPGSSPSASTGTGPGTPGSGTASSSPGSSTPSGATGSPGSSPSASTGTG

PGASPGTSSTGSPGTPGSGTASSSPGSSTPSGATGSPGTPGSGTASSSPGASPGTSSTGS

PGASPGTSSTGSPGTPGSGTASSS

-continued

XTEN AG144-1, DNA sequence
SEQ ID NO: 43
GGCGCGCCACCCGGGTCGTCCCCGTCGGCGTCCACCGGAACAGGGCCAGGGTCATCCCCG
TCAGCGTCGACTGGGACGGGACCCGGGACACCCGGTTCGGGGACTGCATCCTCCTCGCCT
GGTTCGTCCACCCCGTCAGGAGCCACGGGTTCGCCGGGAAGCAGCCCAAGCGCATCCACT
GGTACAGGGCCTGGGGCTTCACCGGGTACTTCATCCACGGGGTCACCGGGAACGCCCGGA
TCGGGGACGGCTTCCTCATCACCAGGATCGTCAACACCCTCGGGCGCAACGGGCAGCCCC
GGAACCCCTGGTTCGGGTACGGCGTCGTCGAGCCCCGGTGCGAGCCCGGGAACAAGCTCG
ACAGGATCGCCTGGGCGTCACCCGGCACGTCGAGCACAGGCAGCCCCGGAACCCCTGGA
TCGGGAACCGCGTCGTCAAGCGCCTCGAGC XTEN AG144-A, protein sequence
SEQ ID NO: 44
GASPGTSSTGSPGSSPSASTGTGPGSSPSASTGTGPGTPGSGTASSSPGSSTPSGATGSP
GSSPSASTGTGPGASPGTSSTGSPGTPGSGTASSSPGSSTPSGATGSPGTPGSGTASSSP
GASPGTSSTGSPGASPGTSSTGSP XTEN AG144-A, DNA sequence
SEQ ID NO: 45
GGCGCGCCAGGTGCCTCGCCGGGAACATCATCAACTGGTTCACCCGGGTCATCCCCCTCG
GCCTCAACCGGGACGGGTCCCGGCTCATCCCCCAGCGCCAGCACTGGAACAGGTCCTGGC
ACTCCTGGTTCCGGTACGGCATCGTCATCCCCGGGAAGCTCAACACCGTCCGGAGCGACA
GGATCACCTGGCTCGTCACCTTCGGCGTCAACTGGAACGGGGCCAGGGGCCTCACCCGGA
ACGTCCTCGACTGGGTCGCCTGGTACGCCGGGATCAGGAACGGCCTCATCCTCGCCTGGG
TCCTCAACGCCCTCGGGTGCGACTGGTTCGCCGGGAACTCCTGGCTCGGGGACGGCCTCG
TCGTCGCCTGGGGCATCACCGGGGACGAGCTCCACGGGGTCCCCTGGAGCGTCACCGGGG
ACCTCCTCGACAGGTAGCCCGGCCTCGAGC XTEN AG144-B, protein sequence
SEQ ID NO: 46
GTPGSGTASSSPGSSTPSGATGSPGASPGTSSTGSPGTPGSGTASSSPGSSTPSGATGSP
GSSPSASTGTGPGSSPSASTGTGPGSSTPSGATGSPGSSTPSGATGSPGASPGTSSTGSP
GASPGTSSTGSPGASPGTSSTGSP XTEN AG144-B, DNA sequence
SEQ ID NO: 47
GGCGCGCCAGGTACACCGGGCAGCGGCACGGCTTCGTCGTCACCCGGCTCGTCCACACCG
TCGGGAGCTACGGGAAGCCCAGGAGCGTCACCGGGAACGTCGTCAACGGGGTCACCGGGT
ACGCCAGGTAGCGGCACGGCCAGCAGCTCGCCAGGTTCATCGACCCCGTCGGGAGCGACT
GGGTCGCCCGGATCAAGCCCGTCAGCTTCCACTGGAACAGGACCCGGGTCGTCGCCGTCA
GCCTCAACGGGGACAGGACCTGGTTCATCGACGCCGTCAGGGGCGACAGGCTCGCCCGGA
TCGTCAACACCCTCGGGGGCAACGGGGAGCCCTGGTGCGTCGCCTGGAACCTCATCCACC
GGAAGCCCGGGGGCCTCGCCGGGTACGAGCTCCACGGGATCGCCCGGAGCGTCCCCCGGA
ACTTCAAGCACAGGGAGCCCTGCCTCGAGC XTEN AG144-C, protein sequence
SEQ ID NO: 48
GTPGSGTASSSPGASPGTSSTGSPGASPGTSSTGSPGASPGTSSTGSPGSSPSASTGTGP
GTPGSGTASSSPGASPGTSSTGSPGASPGTSSTGSPGASPGTSSTGSPGSSTPSGATGSP
GSSTPSGATGSPGASPGTSSTGSP XTEN AG144-C, DNA sequence

SEQ ID NO: 49

GGCGCGCCAGGTACACCCGGATCGGGTACAGCGTCATCGAGCCCCGGTGCGTCACCTGGT
ACGTCGAGCACGGGGTCGCCAGGGGCGTCCCCTGGGACGTCCTCAACAGGCTCGCCCGGT
GCGTCACCCGGCACGTCGTCCACGGGTTCACCTGGTAGCTCCCCTTCCGCGTCCACTGGC
ACCGGGCCTGGAACTCCGGGGAGCGGCACAGCGAGCTCGTCGCCGGGAGCATCGCCTGGG
ACATCGAGCACCGGGTCGCCAGGAGCATCGCCCGGAACATCCAGCACAGGAAGCCCCGGC
GCGTCGCCCGGGACATCAAGCACAGGTTCCCCGGGATCGAGCACGCCGTCCGGAGCCACT
GGATCACCAGGGAGCTCGACACCTTCCGGCGCAACGGGATCGCCCGGAGCCAGCCCGGGT
ACGTCAAGCACTGGCTCCCCTGCCTCGAGC

XTEN AG144-F, protein sequence

SEQ ID NO: 50

GSSPSASTGTGPGSSPSASTGTGPGASPGTSSTGSPGASPGTSSTGSPGSSTPSGATGSP
GSSPSASTGTGPGASPGTSSTGSPGSSPSASTGTGPGTPGSGTASSSPGSSTPSGATGSP
GSSTPSGATGSPGASPGTSSTGSP

XTEN AG144-F, DNA sequence

SEQ ID NO: 51

GGCGCGCCAGGCTCCAGCCCCTCCGCGAGCACGGGAACCGGACCAGGTTCGTCACCCTCA
GCATCAACGGGGACGGGACCGGGGGCGTCACCAGGAACGTCCTCCACCGGCTCGCCGGGT
GCATCACCCGGAACGTCATCGACCGGATCGCCAGGGAGCTCGACGCCATCAGGCGCAACA
GGATCACCTGGCTCAAGCCCTAGCGCGTCAACCGGCACGGGTCCGGGTGCCTCCCCTGGC
ACGTCCAGCACCGGATCACCCGGATCGAGCCCATCCGCCTCAACCGGAACCGGACCCGGT
ACACCAGGGTCGGGAACAGCCTCCTCGTCACCAGGCTCCTCAACCCCCTCGGGAGCCACG
GGTTCGCCCGGTTCGTCAACGCCTTCCGGAGCAACTGGTAGCCCCGGAGCATCGCCAGGA
ACTTCGAGCACGGGGTCGCCCGCCTCGAGC

---

What is claimed is:

1. An isolated nucleic acid molecule comprising a nucleotide sequence having at least 96% sequence identity to SEQ ID NO:2, wherein the nucleotide sequence encodes a polypeptide with Factor VIII activity.

2. The isolated nucleic acid molecule of claim 1, wherein the nucleotide sequence has one or more of the following characteristics:
 a. the nucleotide sequence contains fewer MARS/ARS sequences (SEQ ID NO:5 and SEQ ID NO:6) relative to SEQ ID NO:3;
 b. the nucleotide sequence does not contain the splice site GGTGAT (SEQ ID NO:7);
 c. the nucleotide sequence contains fewer destabilizing elements (SEQ ID NO:8 and SEQ ID NO:9) relative to SEQ ID NO:3;
 d. the nucleotide sequence does not contain a poly-T sequence (SEQ ID NO: 10); and
 e. the nucleotide sequence does not contain a poly-A sequence (SEQ ID NO:11).

3. The isolated nucleic acid molecule of claim 2, wherein the human codon adaptation index is about 0.88.

4. The isolated nucleic acid molecule of claim 2, wherein the percentage of G/C nucleotides is about 51%.

5. The isolated nucleic acid molecule of claim 2, wherein the nucleotide sequence contains at most one MARS/ARS sequence.

6. The isolated nucleic acid molecule of claim 2, wherein the nucleotide sequence contains at most 4 destabilizing elements.

7. The isolated nucleic acid molecule of claim 1, which further comprises a heterologous nucleotide sequence.

8. The isolated nucleic acid molecule of claim 7, wherein the heterologous nucleotide sequence encodes a heterologous amino acid sequence that is a half-life extender.

9. The isolated nucleic acid molecule of claim 8, wherein the heterologous amino acid sequence is an Fc region.

10. The isolated nucleic acid molecule of claim 8, wherein the heterologous amino acid sequence is linked to the N-terminus or the C-terminus of the amino acid sequence encoded by the nucleotide sequence or inserted between two amino acids in the amino acid sequence encoded by the nucleotide sequence.

11. The isolated nucleic acid molecule of claim 1, operably linked to at least one transcription control sequence.

12. A vector comprising the nucleic acid molecule of claim 1.

13. A host cell comprising the nucleic acid molecule of claim 1.

14. A method of producing a polypeptide with Factor VIII activity, comprising culturing the host cell of claim 13 under conditions whereby a polypeptide with Factor VIII activity is produced; and, recovering the polypeptide with Factor VIII activity.

15. The vector of claim 12, wherein the vector is suitable for gene therapy.

16. The vector of claim 15, wherein the vector is a lentiviral or adeno associated virus (AAV) vector.

* * * * *

SEQUENCE LISTING

<160> NUMBER OF SEQ ID NOS: 51

<210> SEQ ID NO 1
<211> LENGTH: 4404
<212> TYPE: DNA
<213> ORGANISM: Artificial Sequence
<220> FEATURE:
<223> OTHER INFORMATION: optimized BDD FVIII

<400> SEQUENCE: 1

```
cgtacggccg ccaccatgca gattgagctg tctacttgct ttttcctgtg cctgctgagg      60
ttttgctttt ccgctacacg aaggtattat ctgggggctg tggaactgtc ttgggattac    120
atgcagagtg acctgggaga gctgccagtg gacgcaaggt tccccctag agtccctaag      180
tcattcccct tcaacactag cgtggtctac aagaaaacac tgttcgtgga gtttactgat     240
cacctgttca acatcgcaaa gcctaggcca cctggatgg gactgctggg gccaacaatc       300
caggccgagg tgtacgacac cgtggtcatt acacttaaga acatggcctc acaccccgtg     360
agcctgcatg ctgtgggcgt cagctactgg aaggcttccg aaggagcaga gtatgacgat     420
cagacttccc agagagaaaa agaggacgat aaggtgtttc ctggcggatc tcatacctac     480
gtgtggcagg tcctgaaaga gaatggccct atggcctccg accctctgtg cctgacctac     540
tcttatctga gtcacgtgga cctggtcaag gatctgaaca gcggcctgat cggagcactg     600
```

```
ctggtgtgca gggaaggaag cctggctaag gagaaaaccc agacactgca taagttcatt      660
ctgctgttcg ccgtgtttga cgaagggaaa tcatggcaca gcgagacaaa gaatagtctg      720
atgcaggaca gggatgccgc ttcagccaga gcttggccca aaatgcacac tgtgaacggc      780
tacgtcaatc gctcactgcc tgggctgatc ggctgccacc gaaagagcgt gtattggcat      840
gtcatcggga tgggcaccac acctgaagtg cactccattt tcctggaggg acatacctttt      900
ctggtccgca accaccgaca ggcttccctg gagatctctc caattacctt cctgacagca      960
cagactctgc tgatggacct ggggcagttc ctgctgtttt gccacatcag ctcccaccag     1020
catgatggca tggaggctta cgtgaaagtg gactcttgtc ccgaggaacc tcagctgcgg     1080
atgaagaaca atgaggaagc agaagactat gacgatgacc tgaccgactc cgagatggat     1140
gtggtccgat tcgatgacga taacagcccc tcctttatcc agattagatc tgtggccaag     1200
aaacacccta agacatgggt ccattacatc gcagccgagg aagaggactg ggattatgca     1260
ccactggtgc tggcaccaga cgatcgctcc tacaaatctc agtatctgaa caatgggcca     1320
cagaggattg gcagaaagta caagaaagtg cggttcatgg catataccga tgagaccttc     1380
aagactcgcg aagccatcca gcacgagagc ggcatcctgg accactgct gtacggagaa      1440
gtgggagaca ccctgctgat cattttcaag aaccaggcca gccggcctta caatatctat     1500
ccacatggga ttacagatgt gcgccctctg tacagcagga gactgccaaa gggcgtcaaa     1560
cacctgaagg acttcccaat cctgcccgga gaaatcttca gtacaagtg gactgtcacc      1620
gtcgaggatg gccccactaa gagcgaccct cggtgcctga cccgctacta ttctagtttc     1680
gtgaatatgg aaagagatct ggcaagcgga ctgatcggac cactgctgat ttgttacaaa     1740
gagagcgtgg atcagagagg caaccagatc atgtccgaca gcggaatgt gattctgttc      1800
agtgtctttg acgaaaacag gtcatggtac ctgaccgaga catccagag attcctgcct      1860
aatccagctg gggtgcagct ggaagatcct gagtttcagg catctaacat catgcatagt     1920
attaatggct acgtgttcga cagttttcag ctgagcgtgt gcctgcacga ggtcgcttac     1980
tggtatatcc tgagcattgg ggcacagaca gatttcctga gcgtgttctt ttccggctac     2040
acttttaagc ataaaatggt ctatgaggac acactgactc tgttcccctt cagcggcgaa     2100
accgtgttta tgagcatgga gaatcccgga ctgtggattc tggggtgcca acagcgcat      2160
ttcagaaaatc gcggaatgac tgccctgctg aaagtgtcaa gctgtgacaa gaacaccggg     2220
gactactatg aagattcata cgaggacatc agcgcatatc tgctgtccaa aaacaatgcc     2280
attgaacccc ggtctttag tcagaatcct ccagtgctga gcggcacca gcgcgagatc       2340
acccgcacta cctgcagag tgatcaggaa gagatcgact acgacgatac aatttctgtg     2400
gaaatgaaga aagaggactt cgatatctat gacgaagatg agaaccagag tcctcgatca     2460
ttccagaaga aaaccaggca ttactttatt gccgcagtgg agcggctgtg ggattatggc     2520
atgtcctcta gtcctcacgt gctgcgaaat agggcccagt caggaagcgt cccacagttc     2580
aagaaagtgg tcttccagga gtttacagac gggtccttta ctcagccact gtacaggggc     2640
gaactgaacg agcacctggg actgctgggg ccctatatca gagcagaagt ggaggataac     2700
attatggtca ccttcagaaa tcaggcctct cggccttaca gttttattc aagcctgatc     2760
tcttacgaag aggaccagcg acagggagct gaaccacgaa aaaacttcgt gaagcctaat     2820
gagaccaaaa catacttttg gaaggtgcag caccatatgg ccccaacaaa agacgagttc     2880
gattgcaagg catgggccta ttttttctgac gtggatctgg agaaggacgt gcacagtggc     2940
ctgattggcc cactgctggt gtgccatact aacaccctga atccagccca cggccggcag     3000
```

```
gtcactgtcc aggagttcgc tctgttcttt accatctttg atgagacaaa gagctggtac    3060
ttcaccgaaa acatggagcg aaattgcagg gctccatgta acattcagat ggaagacccc    3120
acattcaagg agaactaccg cttccatgct atcaatggat acatcatgga tactctgccc    3180
gggctggtca tggcacagga ccagagaatc cggtggtatc tgctgagcat gggcagcaac    3240
gagaatatcc actcaattca tttcagcggg cacgtgttta ctgtcaggaa gaaagaagag    3300
tacaagatgg ccctgtacaa cctgtatccc ggcgtgttcg aaaccgtcga gatgctgcct    3360
agcaaggccg gaatctggag agtggaatgc ctgattggag agcacctgca tgctgggatg    3420
tctaccctgt ttctggtgta cagtaataag tgtcagacac ccctgggaat ggcatccggg    3480
catatcaggg atttccagat taccgcatct ggacagtacg acagtgggc acctaagctg    3540 gctagactgc actattccgg atctatcaac gcttggtcca caaagagcc tttctcttgg    3600 attaaggtgg acctgctggc cccaatgatc attcatggca tcaaaactca gggagctcgg    3660
cagaagttct cctctctgta catctcacag tttatcatca tgtacagcct ggatgggaag    3720 aaaatggcaga cataccgcgg caatagcaca ggaactctga tggtgttctt tggcaacgtg    3780
gacagcagcg gaatcaagca caacattttc aatccccta tcattgctag atacatccgg    3840
ctgcacccaa cccattattc tattcgaagt acactgagga tggaactgat gggatgcgat    3900
ctgaacagtt gttcaatgcc cctggggatg gagtccaagg caatctctga cgcccagatt    3960
accgctagct cctacttcac taatatgttt gctacctgga gcccttccaa agcaagactg    4020
cacctgcaag gccgcagcaa cgcatggcga ccacaggtga caatcccaa ggagtggttg    4080 caggtcgatt ttcagaaaac tatgaaggtg accggggtca caactcaggg cgtgaaaagt    4140
ctgctgacct caatgtacgt caaggagttc ctgatctcta gttcacagga cggacatcag    4200
tggacactgt tctttcagaa cgggaaggtg aaagtcttcc agggcaatca ggattccttt    4260
acacctgtgg tcaacagtct agaccctcca ctgctgacca gataccgtgag aatccaccct    4320 cagtcctggg tgcaccagat tgccctgaga atggaagtgc tgggatgcga ggcccaggat    4380
ctgtactgat aactcgagtc gacc    4404
```

<210> SEQ ID NO 2
<211> LENGTH: 4419
<212> TYPE: DNA
<213> ORGANISM: Artificial Sequence
<220> FEATURE:
<223> OTHER INFORMATION: optimized BDD FVIII

<400> SEQUENCE: 2

```
ggcgcgcccg tacggccgcc accatgcaga tcgagctgtc tacctgcttc ttcctgtgcc    60
tgctgcggtt ctgcttcagc gccacccggc ggtactacct gggcgccgtg gaactgagct    120
gggactacat gcagagcgac ctgggggagc tgcccgtgga cgccagattc cccccaagag    180
tgcccaagag cttccccttc aacacctccg tggtgtacaa gaaaaccctg ttcgtcgagt    240
tcaccgacca cctgttcaat atcgccagc ccagaccccc ctggatgggc ctgctgggcc    300
ctacaatcca ggccgaggtg tacgacaccg tggtcatcac ccttaagaac atggccagcc    360
accccgtgtc cctgcacgcc gtgggcgtgt cctactggaa ggcctctgag ggcgctgagt    420
acgacgacca gaccagccag cgcgagaaag aggacgacaa agtctttcct ggcggcagcc    480
atacctacgt gtggcaggtc ctgaaagaaa acggccctat ggcctccgac ccctgtgcc    540 tgacctacag ctacctgagc cacgtggacc tggtcaagga cctgaacagc ggcctgattg    600
gcgccctgct cgtgtgtaga gagggcagcc tcgccaaaga gaaacccag accctgcaca    660
```

```
agttcatcct gctgttcgcc gtgttcgacg agggcaagag ctggcacagc gagacaaaga    720
acagcctgat gcaggaccgg gacgccgcct ctgccagagc ctggcctaag atgcacaccg    780
tgaacggcta cgtgaacaga agcctgcccg gactgatcgg ctgccaccgg aagtccgtgt    840
actggcacgt gatcggcatg ggcaccaccc ccgaggtgca cagcatcttt ctggaaggcc    900
acaccttcct cgtgcggaac cacagacagg ccagcctgga aatcagccct atcaccttcc    960
tgaccgccca gacactgctg atggacctgg gccagttcct gctgttttgc cacatcagca   1020
gccaccagca cgacggcatg gaagcctacg tgaaggtgga cagctgcccc gaggaacccc   1080
agctgcggat gaagaacaac gaggaagccg aggactacga cgacgacctg accgacagcg   1140
agatggacgt cgtgcgcttc gacgacgaca acagccccag cttcatccag atcagaagcg   1200
tggccaagaa gcaccccaag acctgggtgc actatatcgc cgccgaggaa gaggactggg   1260
actacgcccc tctggtgctg gcccccgacg acagaagcta caagagccag tacctgaaca   1320
atggcccccg gcggatcggc cggaagtaca agaaagtgcg gttcatggcc tacaccgacg   1380
agacattcaa gaccagagag gccatccagc acgagagcgg catcctgggc ccctgctgt    1440 atggcgaagt gggcgacacc ctgctgatca tcttcaagaa ccaggccagc cggccctaca   1500
acatctaccc ccacgcatc accgacgtgc ggccctgta cagcagacgg ctgcccaagg     1560
gcgtgaagca cctgaaggac ttccccatcc tgcccggcga gatcttcaag tacaagtgga   1620
ccgtgaccgt ggaagatggc cccaccaaga gcgaccccag atgcctgacc cggtactaca   1680
gcagcttcgt gaacatggaa cgggacctgg cctccgggct gatcggccct ctgctgatct   1740
gctacaaaga aagcgtggac cagcggggca accagatcat gagcgacaag cggaacgtga   1800
tcctgttcag cgtgttcgat gagaatcggt cctggtacct gaccgagaat atccagcggt   1860
tcctgcccaa ccctgccggc gtgcagctgg aagatcccga gttccaggcc agcaacatca   1920
tgcactccat caatggctac gtgttcgaca gcctccagct gagcgtgtgc ctgcacgagg   1980
tggcctactg gtacatcctg agcatcgcg cccagaccga cttcctgagc gtgttcttca   2040
gcggctacac cttcaagcac aagatggtgt acgaggatac cctgacccg ttccccttct    2100 ccggcgaaac cgtgttcatg agcatggaaa accccggcct gtggattctg gctgccaca    2160 acagcgactt cagaaaccgg ggcatgaccg ccctgctgaa ggtgtccagc tgcgacaaga   2220
acaccggcga ctactacgag gacagctatg aggacatcag cgcctacctg ctgagcaaga   2280
acaacgccat cgagcccaga tccttcagcc agaaccccc cgtgctgaag cggcaccaga   2340
gagagatcac ccgaccacc ctgcagtccg accaggaaga gattgattac gacgacacca    2400
tcagcgtcga gatgaagaaa gaggatttcg acatctacga cgaggacgag aaccagagcc   2460
cccggtcctt ccagaagaaa acccggcact acttcattgc cgccgtggaa agactgtggg   2520
actacggcat gagcagcagc ccccacgtgc tgcggaacag agcccagagc ggcagcgtgc   2580
cccagttcaa gaaagtggtg ttccaggagt tcaccgacgg cagcttcacc cagcccctgt   2640
atcggggcga gctgaacgag cacctgggac tgctgggacc ttacattaga gccgaggtgg   2700
aagataacat catggtcacc ttcagaaacc aggcctccag accctacagc ttctacagca   2760
gcctgatcag ctacgaagag gaccagcggc agggcgccga accccggaag aacttcgtga   2820
agcccaacga gactaagacc tacttctgga aggtgcagca ccacatggcc cccacaaagg   2880
acgagttcga ctgcaaggcc tgggcctact ctccgatgt ggacctggaa aaggacgtgc    2940
actctggcct gattggacct ctgctcgtct gccacaccaa cacccctgaac cccgcccacg   3000 gccggcaggt cacagtgcag gaatttgccc tgttcttcac catcttcgat gagacaaaga   3060
```

```
gctggtactt caccgagaac atggaaagaa actgtagagc cccctgcaac atccagatgg   3120
aagatcctac cttcaaagag aactatcggt tccacgccat caacggctac atcatggaca   3180
ccctgcccgg cctggtcatg gcccaggatc agagaatccg gtggtatctg ctgagcatgg   3240
gcagcaacga gaacatccac agcatccact tcagcggcca cgtgttcaca gtgcggaaga   3300
aagaagagta caagatggcc ctgtacaacc tgtaccccgg cgtgttcgag acagtggaaa   3360
tgctgcccag caaggccggc atctggcggg tggaatgtct gatcggcgag catctgcacg   3420
ccggaatgag caccctgttt ctggtgtaca gcaacaagtg ccagacccct ctgggcatgg   3480
ccagcggcca catccgggac ttccagatca ccgcctccgg ccagtacggc cagtgggccc   3540
ctaagctggc ccggctccac tactccggat ctatcaacgc ctggtccacc aaagagccct   3600
tcagctggat caaggtggac ctgctggccc ctatgatcat ccacggaatc aagacccagg   3660
gcgccagaca gaagttcagc agcctgtaca tcagccagtt catcatcatg tacagcctgg   3720
acggcaagaa gtggcagacc taccggggca cagcaccgg cacccctgatg gtgttcttcg   3780
gcaacgtgga cagcagcggc atcaagcaca acatcttcaa ccccccccatc attgcccggt   3840
acatccggct gcaccccacc cactacagca tccggtccac cctgcggatg gaactgatgg   3900
gctgcgacct gaactcttgc agcatgcccc tggggatgga aagcaaggcc atcagcgacg   3960
cccagatcac agccagcagc tacttcacca acatgttcgc cacctggtcc ccaagcaaag   4020
cccgcctgca tctccaaggc agaagcaatg cctggcggcc tcaggtcaac aaccccaaag   4080
aatggctcca ggtggacttt cagaaaacca tgaaggtcac aggcgtgacc acccagggcg   4140
tgaaaagcct gctgacctct atgtacgtga aagagttcct gatcagcagc agccaggacg   4200
ggcaccagtg gaccctgttc tttcagaacg gcaaagtgaa agtgttccag ggcaaccagg   4260
actcctttac cccgtggtc aactctctag accctccact gctgaccaga tacctgagaa   4320
tccacccctca gtcctgggtg caccagattg ccctgagaat ggaagtgctg ggatgcgagg   4380
cccaggatct gtactgataa ctcgagtcga cttaattaa                          4419
```

<210> SEQ ID NO 3
<211> LENGTH: 4371
<212> TYPE: DNA
<213> ORGANISM: Artificial Sequence
<220> FEATURE:
<223> OTHER INFORMATION: Parental BDD FVIII

<400> SEQUENCE: 3

```
atgcaaatag agctctccac ctgcttcttt ctgtgccttt tgcgattctg ctttagtgcc     60
accagaagat actacctggg tgcagtggaa ctgtcatggg actatatgca aagtgatctc    120
ggtgagctgc ctgtggacgc aagatttcct cctagagtgc caaaatcttt tccattcaac    180
acctcagtcg tgtacaaaaa gactctgttt gtagaattca cggatcacct tttcaacatc    240
gctaagccaa ggccaccctg gatgggtctg ctaggtccta ccatccaggc tgaggtttat    300
gatacagtgg tcattacact taagaacatg gcttcccatc ctgtcagtct tcatgctgtt    360
ggtgtatcct actggaaagc ttctgaggga gctgaatatg atgatcagac cagtcaaagg    420
gagaaagaag atgataaagt cttccctggt ggaagccata catatgtctg caggtcctg    480
aaagagaatg gtccaatggc ctctgaccca ctgtgcctta cctactcata tctttctcat    540
gtggacctgg taaagacttt gaattcaggc ctcattggag ccctactagt atgtagagaa    600
gggagtctgg ccaggaaaaa gacacagacc ttgcacaaat ttatactact ttttgctgta    660
tttgatgaag ggaaaagttg gcactcagaa acaaagaact ccttgatgca ggatagggat    720
```

```
gctgcatctg ctcgggcctg gcctaaaatg cacacagtca atggttatgt aaacaggtct    780
ctgccaggtc tgattggatg ccacaggaaa tcagtctatt ggcatgtgat tggaatgggc    840
accactcctg aagtgcactc aatattcctc gaaggtcaca catttcttgt gaggaaccat    900
cgccaggcgt ccttggaaat ctcgccaata actttcctta ctgctcaaac actcttgatg    960
gaccttggac agtttctact gttttgtcat atctcttccc accaacatga tggcatggaa   1020
gcttatgtca aagtagacag ctgtccagag aaccccaac tacgaatgaa aaataatgaa    1080
gaagcggaag actatgatga tgatcttact gattctgaaa tggatgtggt caggtttgat   1140
gatgacaact ctccttcctt tatccaaatt cgctcagttg ccaagaagca tcctaaaact   1200
tgggtacatt acattgctgc tgaagaggag gactgggact atgctccctt agtcctcgcc   1260
cccgatgaca gaagttataa aagtcaatat ttgaacaatg ccctcagcg gattggtagg    1320
aagtacaaaa aagtccgatt tatggcatac acagatgaaa cctttaagac tcgtgaagct   1380
attcagcatg aatcaggaat cttgggacct ttactttatg gggaagttgg agacacactg   1440
ttgattatat ttaagaatca agcaagcaga ccatataaca tctaccctca cggaatcact   1500
gatgtccgtc ctttgtattc aaggagatta ccaaaaggtg taaaacattt gaaggatttt   1560
ccaattctgc caggagaaat attcaaatat aaatggacag tgactgtaga agatgggcca   1620
actaaatcag atcctcggtg cctgacccgc tattactcta gtttcgttaa tatggagaga   1680
gatctagctt caggactcat tggccctctc ctcatctgct acaaagaatc tgtagatcaa   1740
agaggaaacc agataatgtc agacaagagg aatgtcatcc tgttttctgt atttgatgag   1800
aaccgaagct ggtacctcac agagaatata caacgctttc tccccaatcc agctggagtg   1860
cagcttgagg atccagagtt ccaagcctcc aacatcatgc acagcatcaa tggctatgtt   1920
tttgatagtt tgcagttgtc agtttgtttg catgaggtgg catactggta cattctaagc   1980
attggagcac agactgactt cctttctgtc ttcttctctg gatataccttt caaacacaaa   2040
atggtctatg aagacacact caccctattc ccattctcag gagaaactgt cttcatgtcg   2100
atggaaaacc caggtctatg gattctgggg tgccacaact cagactttcg gaacagaggc   2160
atgaccgcct tactgaaggt ttctagttgt gacaagaaca ctggtgatta ttacgaggac   2220
agttatgaag atatttcagc atacttgctg agtaaaaaca atgccattga ccaagaagc    2280
ttctctcaaa acccaccagt cttgaaacgc catcaacggg aaataactcg tactactctt   2340
cagtcagatc aagaggaaat tgactatgat gataccatat cagttgaaat gaagaaggaa   2400
gattttgaca tttatgatga ggatgaaaat cagagccccc gcagctttca aaagaaaaca   2460
cgacactatt ttattgctgc agtggagagg ctctgggatt atgggatgag tagctcccca   2520
catgttctaa gaaacagggc tcagagtggc agtgtccctc agttcaagaa agttgttttc   2580
caggaattta ctgatggctc ctttactcag cccttatacc gtggagaact aaatgaacat   2640
ttgggactcc tggggccata tataagagca gaagttgaag ataatatcat ggtaactttc   2700
agaaatcagg cctctcgtcc ctattccttc tattctagcc ttatttctta tgaggaagat   2760
cagaggcaag gagcagaacc tagaaaaaac tttgtcaagc ctaatgaaac caaaacttac   2820
ttttggaaag tgcaacatca tatggcaccc actaaagatg agtttgactg caaagcctgg   2880
gcttatttct ctgatgttga cctggaaaaa gatgtgcact caggcctgat tggacccctt   2940
ctggtctgcc acactaacac actgaaccct gctcatggga gacaagtgac agtacaggaa   3000
tttgctctgt ttttcaccat ctttgatgag accaaaagct ggtacttcac tgaaaatatg   3060
gaaagaaact gcagggctcc ctgcaatatc cagatggaag atcccacttt taaagagaat   3120
```

```
tatcgcttcc atgcaatcaa tggctacata atggatacac tacctggctt agtaatggct   3180
caggatcaaa ggattcgatg gtatctgctc agcatgggca gcaatgaaaa catccattct   3240
attcatttca gtggacatgt gttcactgta cgaaaaaaag aggagtataa aatggcactg   3300
tacaatctct atccaggtgt ttttgagaca gtggaaatgt taccatccaa agctggaatt   3360
tggcgggtgg aatgccttat tggcgagcat ctacatgctg ggatgagcac actttttctg   3420
gtgtacagca ataagtgtca gactcccctg ggaatggctt ctggacacat tagagatttt   3480
cagattacag cttcaggaca atatggacag tgggccccaa agctggccag acttcattat   3540
tccggatcaa tcaatgcctg gagcaccaag gagccctttt cttggatcaa ggtggatctg   3600
ttggcaccaa tgattattca cggcatcaag acccagggtg cccgtcagaa gttctccagc   3660
ctctacatct ctcagtttat catcatgtat agtcttgatg ggaagaagtg gcagacttat   3720
cgaggaaatt ccactggaac cttaatggtc ttctttggca atgtggattc atctgggata   3780
aaacacaata tttttaaccc tccaattatt gctcgataca tccgtttgca cccaactcat   3840
tatagcattc gcagcactct tcgcatggag ttgatgggct gtgatttaaa tagttgcagc   3900
atgccattgg gaatggagag taaagcaata tcagatgcac agattactgc ttcatcctac   3960
tttaccaata tgtttgccac ctggtctcct tcaaaagctc gacttcacct ccaagggagg   4020
agtaatgcct ggagacctca ggtgaataat ccaaaagagt ggctgcaagt ggacttccag   4080
aagacaatga aagtcacagg agtaactact cagggagtaa aatctctgct taccagcatg   4140
tatgtgaagg agttcctcat ctccagcagt caagatggcc atcagtggac tctctttttt   4200
cagaatggca aagtaaaggt ttttcaggga aatcaagact ccttcacacc tgtggtgaac   4260
tctctagacc caccgttact gactcgctac cttcgaattc acccccagag ttgggtgcac   4320
cagattgccc tgaggatgga ggttctgggc tgcgaggcac aggacctcta c            4371
```

<210> SEQ ID NO 4
<211> LENGTH: 1438
<212> TYPE: PRT
<213> ORGANISM: Artificial Sequence
<220> FEATURE:
<223> OTHER INFORMATION: BDD FVIII

<400> SEQUENCE: 4

```
Ala Thr Arg Arg Tyr Tyr Leu Gly Ala Val Glu Leu Ser Trp Asp Tyr
1               5                   10                  15

Met Gln Ser Asp Leu Gly Glu Leu Pro Val Asp Ala Arg Phe Pro Pro
            20                  25                  30

Arg Val Pro Lys Ser Phe Pro Phe Asn Thr Ser Val Val Tyr Lys Lys
        35                  40                  45

Thr Leu Phe Val Glu Phe Thr Asp His Leu Phe Asn Ile Ala Lys Pro
    50                  55                  60

Arg Pro Pro Trp Met Gly Leu Leu Gly Pro Thr Ile Gln Ala Glu Val
65                  70                  75                  80

Tyr Asp Thr Val Val Ile Thr Leu Lys Asn Met Ala Ser His Pro Val
                85                  90                  95

Ser Leu His Ala Val Gly Val Ser Tyr Trp Lys Ala Ser Glu Gly Ala
            100                 105                 110

Glu Tyr Asp Asp Gln Thr Ser Gln Arg Glu Lys Glu Asp Asp Lys Val
        115                 120                 125

Phe Pro Gly Gly Ser His Thr Tyr Val Trp Gln Val Leu Lys Glu Asn
    130                 135                 140
```

-continued

```
Gly Pro Met Ala Ser Asp Pro Leu Cys Leu Thr Tyr Ser Tyr Leu Ser
145                 150                 155                 160

His Val Asp Leu Val Lys Asp Leu Asn Ser Gly Leu Ile Gly Ala Leu
                165                 170                 175

Leu Val Cys Arg Glu Gly Ser Leu Ala Lys Glu Lys Thr Gln Thr Leu
            180                 185                 190

His Lys Phe Ile Leu Leu Phe Ala Val Phe Asp Glu Gly Lys Ser Trp
        195                 200                 205

His Ser Glu Thr Lys Asn Ser Leu Met Gln Asp Arg Asp Ala Ala Ser
    210                 215                 220

Ala Arg Ala Trp Pro Lys Met His Thr Val Asn Gly Tyr Val Asn Arg
225                 230                 235                 240

Ser Leu Pro Gly Leu Ile Gly Cys His Arg Lys Ser Val Tyr Trp His
                245                 250                 255

Val Ile Gly Met Gly Thr Thr Pro Glu Val His Ser Ile Phe Leu Glu
            260                 265                 270

Gly His Thr Phe Leu Val Arg Asn His Arg Gln Ala Ser Leu Glu Ile
        275                 280                 285

Ser Pro Ile Thr Phe Leu Thr Ala Gln Thr Leu Leu Met Asp Leu Gly
    290                 295                 300

Gln Phe Leu Leu Phe Cys His Ile Ser Ser His Gln His Asp Gly Met
305                 310                 315                 320

Glu Ala Tyr Val Lys Val Asp Ser Cys Pro Glu Glu Pro Gln Leu Arg
                325                 330                 335

Met Lys Asn Asn Glu Glu Ala Glu Asp Tyr Asp Asp Asp Leu Thr Asp
            340                 345                 350

Ser Glu Met Asp Val Val Arg Phe Asp Asp Asp Asn Ser Pro Ser Phe
        355                 360                 365

Ile Gln Ile Arg Ser Val Ala Lys Lys His Pro Lys Thr Trp Val His
    370                 375                 380

Tyr Ile Ala Ala Glu Glu Glu Asp Trp Asp Tyr Ala Pro Leu Val Leu
385                 390                 395                 400

Ala Pro Asp Asp Arg Ser Tyr Lys Ser Gln Tyr Leu Asn Asn Gly Pro
                405                 410                 415

Gln Arg Ile Gly Arg Lys Tyr Lys Lys Val Arg Phe Met Ala Tyr Thr
            420                 425                 430

Asp Glu Thr Phe Lys Thr Arg Glu Ala Ile Gln His Glu Ser Gly Ile
        435                 440                 445

Leu Gly Pro Leu Leu Tyr Gly Glu Val Gly Asp Thr Leu Leu Ile Ile
    450                 455                 460

Phe Lys Asn Gln Ala Ser Arg Pro Tyr Asn Ile Tyr Pro His Gly Ile
465                 470                 475                 480

Thr Asp Val Arg Pro Leu Tyr Ser Arg Arg Leu Pro Lys Gly Val Lys
                485                 490                 495

His Leu Lys Asp Phe Pro Ile Leu Pro Gly Glu Ile Phe Lys Tyr Lys
            500                 505                 510

Trp Thr Val Thr Val Glu Asp Gly Pro Thr Lys Ser Asp Pro Arg Cys
        515                 520                 525

Leu Thr Arg Tyr Tyr Ser Ser Phe Val Asn Met Glu Arg Asp Leu Ala
    530                 535                 540

Ser Gly Leu Ile Gly Pro Leu Leu Ile Cys Tyr Lys Glu Ser Val Asp
545                 550                 555                 560
```

```
Gln Arg Gly Asn Gln Ile Met Ser Asp Lys Arg Asn Val Ile Leu Phe
                565                 570                 575
Ser Val Phe Asp Glu Asn Arg Ser Trp Tyr Leu Thr Glu Asn Ile Gln
            580                 585                 590
Arg Phe Leu Pro Asn Pro Ala Gly Val Gln Leu Glu Asp Pro Glu Phe
        595                 600                 605
Gln Ala Ser Asn Ile Met His Ser Ile Asn Gly Tyr Val Phe Asp Ser
610                 615                 620
Leu Gln Leu Ser Val Cys Leu His Glu Val Ala Tyr Trp Tyr Ile Leu
625                 630                 635                 640
Ser Ile Gly Ala Gln Thr Asp Phe Leu Ser Val Phe Phe Ser Gly Tyr
                645                 650                 655
Thr Phe Lys His Lys Met Val Tyr Glu Asp Thr Leu Thr Leu Phe Pro
            660                 665                 670
Phe Ser Gly Glu Thr Val Phe Met Ser Met Glu Asn Pro Gly Leu Trp
        675                 680                 685
Ile Leu Gly Cys His Asn Ser Asp Phe Arg Asn Arg Gly Met Thr Ala
690                 695                 700
Leu Leu Lys Val Ser Ser Cys Asp Lys Asn Thr Gly Asp Tyr Tyr Glu
705                 710                 715                 720
Asp Ser Tyr Glu Asp Ile Ser Ala Tyr Leu Leu Ser Lys Asn Asn Ala
                725                 730                 735
Ile Glu Pro Arg Ser Phe Ser Gln Asn Pro Pro Val Leu Lys Arg His
            740                 745                 750
Gln Arg Glu Ile Thr Arg Thr Thr Leu Gln Ser Asp Gln Glu Glu Ile
        755                 760                 765
Asp Tyr Asp Asp Thr Ile Ser Val Glu Met Lys Lys Glu Asp Phe Asp
770                 775                 780
Ile Tyr Asp Glu Asp Glu Asn Gln Ser Pro Arg Ser Phe Gln Lys Lys
785                 790                 795                 800
Thr Arg His Tyr Phe Ile Ala Ala Val Glu Arg Leu Trp Asp Tyr Gly
                805                 810                 815
Met Ser Ser Ser Pro His Val Leu Arg Asn Arg Ala Gln Ser Gly Ser
            820                 825                 830
Val Pro Gln Phe Lys Lys Val Val Phe Gln Glu Phe Thr Asp Gly Ser
        835                 840                 845
Phe Thr Gln Pro Leu Tyr Arg Gly Glu Leu Asn Glu His Leu Gly Leu
850                 855                 860
Leu Gly Pro Tyr Ile Arg Ala Glu Val Glu Asp Asn Ile Met Val Thr
865                 870                 875                 880
Phe Arg Asn Gln Ala Ser Arg Pro Tyr Ser Phe Tyr Ser Ser Leu Ile
                885                 890                 895
Ser Tyr Glu Glu Asp Gln Arg Gln Gly Ala Glu Pro Arg Lys Asn Phe
            900                 905                 910
Val Lys Pro Asn Glu Thr Lys Thr Tyr Phe Trp Lys Val Gln His His
        915                 920                 925
Met Ala Pro Thr Lys Asp Glu Phe Asp Cys Lys Ala Trp Ala Tyr Phe
930                 935                 940
Ser Asp Val Asp Leu Glu Lys Asp Val His Ser Gly Leu Ile Gly Pro
945                 950                 955                 960
Leu Leu Val Cys His Thr Asn Thr Leu Asn Pro Ala His Gly Arg Gln
                965                 970                 975
```

-continued

```
Val Thr Val Gln Glu Phe Ala Leu Phe Phe Thr Ile Phe Asp Glu Thr
            980             985             990

Lys Ser Trp Tyr Phe Thr Glu Asn Met Glu Arg Asn Cys Arg Ala Pro
        995             1000            1005

Cys Asn Ile Gln Met Glu Asp Pro Thr Phe Lys Glu Asn Tyr Arg
        1010            1015            1020

Phe His Ala Ile Asn Gly Tyr Ile Met Asp Thr Leu Pro Gly Leu
        1025            1030            1035

Val Met Ala Gln Asp Gln Arg Ile Arg Trp Tyr Leu Leu Ser Met
        1040            1045            1050

Gly Ser Asn Glu Asn Ile His Ser Ile His Phe Ser Gly His Val
        1055            1060            1065

Phe Thr Val Arg Lys Lys Glu Glu Tyr Lys Met Ala Leu Tyr Asn
        1070            1075            1080

Leu Tyr Pro Gly Val Phe Glu Thr Val Glu Met Leu Pro Ser Lys
        1085            1090            1095

Ala Gly Ile Trp Arg Val Glu Cys Leu Ile Gly Glu His Leu His
        1100            1105            1110

Ala Gly Met Ser Thr Leu Phe Leu Val Tyr Ser Asn Lys Cys Gln
        1115            1120            1125

Thr Pro Leu Gly Met Ala Ser Gly His Ile Arg Asp Phe Gln Ile
        1130            1135            1140

Thr Ala Ser Gly Gln Tyr Gly Gln Trp Ala Pro Lys Leu Ala Arg
        1145            1150            1155

Leu His Tyr Ser Gly Ser Ile Asn Ala Trp Ser Thr Lys Glu Pro
        1160            1165            1170

Phe Ser Trp Ile Lys Val Asp Leu Leu Ala Pro Met Ile Ile His
        1175            1180            1185

Gly Ile Lys Thr Gln Gly Ala Arg Gln Lys Phe Ser Ser Leu Tyr
        1190            1195            1200

Ile Ser Gln Phe Ile Ile Met Tyr Ser Leu Asp Gly Lys Lys Trp
        1205            1210            1215

Gln Thr Tyr Arg Gly Asn Ser Thr Gly Thr Leu Met Val Phe Phe
        1220            1225            1230

Gly Asn Val Asp Ser Ser Gly Ile Lys His Asn Ile Phe Asn Pro
        1235            1240            1245

Pro Ile Ile Ala Arg Tyr Ile Arg Leu His Pro Thr His Tyr Ser
        1250            1255            1260

Ile Arg Ser Thr Leu Arg Met Glu Leu Met Gly Cys Asp Leu Asn
        1265            1270            1275

Ser Cys Ser Met Pro Leu Gly Met Glu Ser Lys Ala Ile Ser Asp
        1280            1285            1290

Ala Gln Ile Thr Ala Ser Ser Tyr Phe Thr Asn Met Phe Ala Thr
        1295            1300            1305

Trp Ser Pro Ser Lys Ala Arg Leu His Leu Gln Gly Arg Ser Asn
        1310            1315            1320

Ala Trp Arg Pro Gln Val Asn Asn Pro Lys Glu Trp Leu Gln Val
        1325            1330            1335

Asp Phe Gln Lys Thr Met Lys Val Thr Gly Val Thr Thr Gln Gly
        1340            1345            1350

Val Lys Ser Leu Leu Thr Ser Met Tyr Val Lys Glu Phe Leu Ile
        1355            1360            1365
```

-continued

Ser Ser Ser Gln Asp Gly His Gln Trp Thr Leu Phe Phe Gln Asn
    1370              1375                 1380

Gly Lys Val Lys Val Phe Gln Gly Asn Gln Asp Ser Phe Thr Pro
    1385              1390                 1395

Val Val Asn Ser Leu Asp Pro Pro Leu Leu Thr Arg Tyr Leu Arg
    1400              1405                 1410

Ile His Pro Gln Ser Trp Val His Gln Ile Ala Leu Arg Met Glu
    1415              1420                 1425

Val Leu Gly Cys Glu Ala Gln Asp Leu Tyr
    1430              1435

<210> SEQ ID NO 5
<211> LENGTH: 6
<212> TYPE: DNA
<213> ORGANISM: Artificial Sequence
<220> FEATURE:
<223> OTHER INFORMATION: MAR/ARS

<400> SEQUENCE: 5 atattt                                                          6

<210> SEQ ID NO 6
<211> LENGTH: 6
<212> TYPE: DNA
<213> ORGANISM: Artificial Sequence
<220> FEATURE:
<223> OTHER INFORMATION: MAR/ARS

<400> SEQUENCE: 6 aaatat                                                          6

<210> SEQ ID NO 7
<211> LENGTH: 6
<212> TYPE: DNA
<213> ORGANISM: Artificial Sequence
<220> FEATURE:
<223> OTHER INFORMATION: Potential Splice Site

<400> SEQUENCE: 7 ggtgat                                                          6

<210> SEQ ID NO 8
<211> LENGTH: 5
<212> TYPE: DNA
<213> ORGANISM: Artificial Sequence
<220> FEATURE:
<223> OTHER INFORMATION: Destabilizing Sequence

<400> SEQUENCE: 8 attta                                                           5

<210> SEQ ID NO 9
<211> LENGTH: 5
<212> TYPE: DNA
<213> ORGANISM: Artificial Sequence
<220> FEATURE:
<223> OTHER INFORMATION: Destabilizing Sequence

<400> SEQUENCE: 9 taaat                                                           5

```
<210> SEQ ID NO 10
<211> LENGTH: 6
<212> TYPE: DNA
<213> ORGANISM: Artificial Sequence
<220> FEATURE:
<223> OTHER INFORMATION: poly-T Sequence

<400> SEQUENCE: 10 tttttt                                                                    6

<210> SEQ ID NO 11
<211> LENGTH: 7
<212> TYPE: DNA
<213> ORGANISM: Artificial Sequence
<220> FEATURE:
<223> OTHER INFORMATION: poly-A Sequence

<400> SEQUENCE: 11 aaaaaaa                                                                   7

<210> SEQ ID NO 12
<211> LENGTH: 5
<212> TYPE: DNA
<213> ORGANISM: Artificial Sequence
<220> FEATURE:
<223> OTHER INFORMATION: Promoter Binding Site

<400> SEQUENCE: 12 tataa                                                                     5

<210> SEQ ID NO 13
<211> LENGTH: 5
<212> TYPE: DNA
<213> ORGANISM: Artificial Sequence
<220> FEATURE:
<223> OTHER INFORMATION: Promoter Binding Sequence

<400> SEQUENCE: 13 ttata                                                                     5

<210> SEQ ID NO 14
<211> LENGTH: 8
<212> TYPE: DNA
<213> ORGANISM: Artificial Sequence
<220> FEATURE:
<223> OTHER INFORMATION: AU Rich Sequence Elements (ARE)

<400> SEQUENCE: 14 attttatt                                                                  8

<210> SEQ ID NO 15
<211> LENGTH: 8
<212> TYPE: DNA
<213> ORGANISM: Artificial Sequence
<220> FEATURE:
<223> OTHER INFORMATION: AU Rich Sequence Elements (ARE)

<400> SEQUENCE: 15 atttttaa                                                                  8

<210> SEQ ID NO 16
<211> LENGTH: 13
<212> TYPE: DNA
<213> ORGANISM: Artificial Sequence
<220> FEATURE:
<223> OTHER INFORMATION: Kozak Consensus Sequence
```

-continued

```
<400> SEQUENCE: 16
gccgccacca tgc                                                        13

<210> SEQ ID NO 17
<211> LENGTH: 32
<212> TYPE: PRT
<213> ORGANISM: Artificial Sequence
<220> FEATURE:
<223> OTHER INFORMATION: CTP peptide

<400> SEQUENCE: 17

Asp Pro Arg Phe Gln Asp Ser Ser Ser Ser Lys Ala Pro Pro Pro Ser
1               5                  10                  15

Leu Pro Ser Pro Ser Arg Leu Pro Gly Pro Ser Asp Thr Pro Ile Leu
            20                  25                  30

<210> SEQ ID NO 18
<211> LENGTH: 28
<212> TYPE: PRT
<213> ORGANISM: Artificial Sequence
<220> FEATURE:
<223> OTHER INFORMATION: CTP peptide

<400> SEQUENCE: 18

Ser Ser Ser Ser Lys Ala Pro Pro Pro Ser Leu Pro Ser Pro Ser Arg
1               5                  10                  15

Leu Pro Gly Pro Ser Asp Thr Pro Ile Leu Pro Gln
            20                  25

<210> SEQ ID NO 19
<211> LENGTH: 11
<212> TYPE: PRT
<213> ORGANISM: Artificial Sequence
<220> FEATURE:
<223> OTHER INFORMATION: albumin-binding peptides core sequence

<400> SEQUENCE: 19

Asp Ile Cys Leu Pro Arg Trp Gly Cys Leu Trp
1               5                  10

<210> SEQ ID NO 20
<211> LENGTH: 20
<212> TYPE: PRT
<213> ORGANISM: Artificial Sequence
<220> FEATURE:
<223> OTHER INFORMATION: PAS Sequence

<400> SEQUENCE: 20

Ala Ser Pro Ala Ala Pro Ala Pro Ala Ser Pro Ala Ala Pro Ala Pro
1               5                  10                  15

Ser Ala Pro Ala
            20

<210> SEQ ID NO 21
<211> LENGTH: 20
<212> TYPE: PRT
<213> ORGANISM: Artificial Sequence
<220> FEATURE:
<223> OTHER INFORMATION: PAS Sequence
```

```
<400> SEQUENCE: 21

Ala Ala Pro Ala Ser Pro Ala Pro Ala Ala Pro Ser Ala Pro Ala Pro
1               5                   10                  15

Ala Ala Pro Ser
            20

<210> SEQ ID NO 22
<211> LENGTH: 20
<212> TYPE: PRT
<213> ORGANISM: Artificial Sequence
<220> FEATURE:
<223> OTHER INFORMATION: PAS Sequence

<400> SEQUENCE: 22

Ala Pro Ser Ser Pro Ser Pro Ser Ala Pro Ser Ser Pro Ser Pro Ala
1               5                   10                  15

Ser Pro Ser Ser
            20

<210> SEQ ID NO 23
<211> LENGTH: 19
<212> TYPE: PRT
<213> ORGANISM: Artificial Sequence
<220> FEATURE:
<223> OTHER INFORMATION: PAS Sequence

<400> SEQUENCE: 23

Ala Pro Ser Ser Pro Ser Pro Ser Ala Pro Ser Ser Pro Ser Pro Ala
1               5                   10                  15

Ser Pro Ser

<210> SEQ ID NO 24
<211> LENGTH: 20
<212> TYPE: PRT
<213> ORGANISM: Artificial Sequence
<220> FEATURE:
<223> OTHER INFORMATION: PAS Sequence

<400> SEQUENCE: 24

Ser Ser Pro Ser Ala Pro Ser Pro Ser Ser Pro Ala Ser Pro Ser Pro
1               5                   10                  15

Ser Ser Pro Ala
            20

<210> SEQ ID NO 25
<211> LENGTH: 24
<212> TYPE: PRT
<213> ORGANISM: Artificial Sequence
<220> FEATURE:
<223> OTHER INFORMATION: PAS Sequence

<400> SEQUENCE: 25

Ala Ala Ser Pro Ala Ala Pro Ser Ala Pro Pro Ala Ala Ala Ser Pro
1               5                   10                  15

Ala Ala Pro Ser Ala Pro Pro Ala
            20

<210> SEQ ID NO 26
<211> LENGTH: 20
<212> TYPE: PRT
<213> ORGANISM: Artificial Sequence
<220> FEATURE:
<223> OTHER INFORMATION: PAS Sequence
```

<400> SEQUENCE: 26

Ala Ser Ala Ala Ala Pro Ala Ala Ala Ser Ala Ala Ser Ala Pro
1               5                   10                  15

Ser Ala Ala Ala
            20

<210> SEQ ID NO 27
<211> LENGTH: 16842
<212> TYPE: DNA
<213> ORGANISM: Homo sapiens

<400> SEQUENCE: 27

```
atgattcctg ccagatttgc cggggtgctg cttgctctgg ccctcatttt gccagggacc      60
ctttgtgcag aaggaactcg cggcaggtca tccacggccc tactaaggac ggtctaaacg     120
gccccacgac gaacgagacc gggagtaaaa cggtccctgg gaaacacgtc ttccttgagc     180
gccgtccagt aggtgccggg gatgcagcct tttcggaagt gacttcgtca acacctttga     240
tgggagcatg tacagctttg cgggatactg cagttacctc ctggcagggg gctgccagaa     300
ctacgtcgga aaagccttca ctgaagcagt tgtggaaact accctcgtac atgtcgaaac     360
gccctatgac gtcaatggag gaccgtcccc cgacggtctt acgctccttc tcgattattg     420
gggacttcca gaatggcaag agagtgagcc tctccgtgta tcttgggaa ttttttgaca     480 tccatttgtt tgtcaatggt tgcgaggaag agctaataac ccctgaaggt cttaccgttc     540
tctcactcgg agaggcacat agaaccccct taaaaactgt aggtaaacaa acagttacca     600
accgtgacac aggggaccca aagagtctcc atgccctatg cctccaaagg gctgtatcta     660
gaaactgagg ctgggtacta caagctgtcc ggtgaggcct tggcactgtg tccccctggt     720
ttctcagagg tacgggatac ggaggtttcc cgacatagat ctttgactcc gacccatgat     780
gttcgacagg ccactccgga atggctttgt ggccaggatc gatggcagcg gcaactttca     840
agtcctgctg tcagacagat acttcaacaa gacctgcggg ctgtgtggca actttaacat     900
taccgaaaca ccggtcctag ctaccgtcgc cgttgaaagt tcaggacgac agtctgtcta    960
tgaagttgtt ctggacgccc gacacaccgt tgaaattgta cttgtgctgaa gatgacttta    1020 tgacccaaga agggaccttg acctcggacc cttatgactt tgccaactca tgggctctga    1080
gcagtggaga acagtggtgt gaaacgactt ctactgaaat actgggttct tccctggaac    1140
tggagcctgg gaatactgaa acggttgagt acccgagact cgtcacctct tgtcaccaca    1200
gaacgggcat ctcctcccag cagctcatgc aacatctcct ctggggaaat gcagaagggc    1260
ctgtgggagc agtgccagct tctgaagagc acctcggtgt cttgcccgta gaggagggtc    1320
gtcgagtacg ttgtagagga ccccttta cgtcttcccg acacccctcg tcacggtcga    1380
agacttctcg tggagccaca ttgcccgctg ccaccctctg gtggaccccg agccttttgt    1440
ggccctgtgt gagaagactt tgtgtgagtg tgctgggggg ctggagtgcg cctgccctgc    1500
aacgggcgac ggtgggagac cacctggggc tcggaaaaca ccgggacaca ctcttctgaa    1560
acacactcac acgacccccc gacctcacgc ggacgggacg cctcctggag tacgcccgga    1620
cctgtgccca ggaggaatg tgctgtacg gctggaccga ccacagcgcg tgcagcccag    1680
tgtgccctgc tggtatggag ggaggacctc atgcgggcct ggacacgggt cctcccttac    1740
cacgacatgc cgacctggct ggtgtcgcgc acgtcgggtc acacgggacg accatacctc    1800
tataggcagt gtgtgtcccc ttgcgccagg acctgccaga gcctgcacat caatgaaatg    1860
tgtcaggagc gatgcgtgga tggctgcagc tgccctgagg atatccgtca cacacagggg    1920
```

```
aacgcggtcc tggacggtct cggacgtgta gttactttac acagtcctcg ctacgcacct    1980
accgacgtcg acgggactcc gacagctcct ggatgaaggc ctctgcgtgg agagcaccga    2040
gtgtccctgc gtgcattccg gaaagcgcta ccctcccggc acctccctct ctcgagactg    2100
ctgtcgagga cctacttccg gagacgcacc tctcgtggct cacagggacg cacgtaaggc    2160
ctttcgcgat gggagggccg tggagggaga gagctctgac caacacctgc atttgccgaa    2220
acagccagtg gatctgcagc aatgaagaat gtccaggga gtgccttgtc actggtcaat    2280
cccacttcaa gagctttgac gttgtggacg taaacggctt tgtcggtcac ctagacgtcg    2340
ttacttctta caggtcccct cacggaacag tgaccagtta gggtgaagtt ctcgaaactg    2400
aacagatact tcaccttcag tgggatctgc cagtacctgc tggcccggga ttgccaggac    2460
cactccttct ccattgtcat tgagactgtc cagtgtgctg ttgtctatga agtggaagtc    2520
accctagacg gtcatggacg accgggccct aacggtcctg gtgaggaaga ggtaacagta    2580
actctgacag gtcacacgac atgaccgcga cgctgtgtgc acccgctccg tcaccgtccg    2640
gctgcctggc ctgcacaaca gccttgtgaa actgaagcat ggggcaggag ttgccatgga    2700
tactggcgct gcgacacacg tgggcgaggc agtggcaggc cgacggaccg gacgtgttgt    2760
cggaacactt tgacttcgta ccccgtcctc aacggtacct tggccaggac atccagctcc    2820
ccctcctgaa aggtgacctc cgcatccagc atacagtgac ggcctccgtg cgcctcagct    2880
acggggagga cctgcagatg accggtcctg taggtcgagg gggaggactt tccactggag    2940
gcgtaggtcg tatgtcactg ccggaggcac gcggagtcga tgcccctcct ggacgtctac    3000
gactgggatg gccgcgggag gctgctggtg aagctgtccc ccgtctatgc cgggaagacc    3060
tgcggcctgt gtgggaatta caatggcaac cagggcgacg ctgaccctac cggcgccctc    3120
cgacgaccac ttcgacaggg ggcagatacg gcccttctgg acgccggaca cacccttaat    3180
gttaccgttg gtcccgctgc acttccttac cccctctggg ctggcrgagc cccgggtgga    3240
ggacttcggg aacgcctgga agctgcacg ggactgccag gacctgcaga agcagcacag    3300
tgaaggaatg ggggagaccc gaccgyctcg gggcccacct cctgaagccc ttgcggacct    3360
tcgacgtgcc cctgacggtc ctggacgtct tcgtcgtgtc cgatccctgc gccctcaacc    3420
cgcgcatgac caggttctcc gaggaggcgt gcgcggtcct gacgtccccc acattcgagg    3480
cctgccatcg tgccgtcagc gctagggacg cgggagttgg gcgcgtactg gtccaagagg    3540
ctcctccgca cgcgccagga ctgcagggg tgtaagctcc ggacggtagc acggcagtcg    3600
ccgctgccct acctgcggaa ctgccgctac gacgtgtgct cctgctcgga cggccgcgag    3660
tgcctgtgcg gcgccctggc cagctatgcc gcggcctgcg ggcgacggga tggacgcctt    3720
gacggcgatg ctgcacacga ggacgagcct gccggcgctc acggacacgc cgcgggaccg    3780
gtcgatacgg cgccggacgc cggggagagg cgtgcgcgtc gcgtggcgcg agccaggccg    3840
ctgtgagctg aactgcccga aaggccaggt gtacctgcag tgcggaccc cctgcaacct    3900
gcccctctcc gcacgcgcag cgcaccgcgc tcggtccggc gacactcgac ttgacgggct    3960
ttccggtcca catggacgtc acgccctggg ggacgttgga gacctgccgc tctctctctt    4020
acccggatga ggaatgcaat gaggcctgcc tggaggctg cttctgcccc ccagggctct    4080
acatggatga gaggggggac ctggacggcg agagagagaa tgggcctact ccttacgtta    4140
ctccggacgg acctcccgac gaagacgggg ggtcccgaga tgtacctact ctcccccctg    4200
tgcgtgccca aggcccagtg cccctgttac tatgacggtg agatcttcca gccagaagac    4260
atcttctcag accatcacac catgtgctac tgtgaggatg acgcacgggt tccgggtcac    4320
```

```
ggggacaatg atactgccac tctagaaggt cggtcttctg tagaagagtc tggtagtgtg    4380
gtacacgatg acactcctac gcttcatgca ctgtaccatg agtggagtcc ccggaagctt    4440
gctgcctgac gctgtcctca gcagtcccct gtctcatcgc agcaaaagga gcctatcctg    4500
cgaagtacgt gacatggtac tcacctcagg ggccttcgaa cgacggactg cgacaggagt    4560
cgtcagggga cagagtagcg tcgttttcct cggataggac tcggcccccc atggtcaagc    4620
tggtgtgtcc cgctgacaac ctgcgggctg aagggctcga gtgtaccaaa acgtgccaga    4680
actatgacct ggagtgcatg agccgggggg taccagttcg accacacagg gcgactgttg    4740
gacgcccgac ttcccgagct cacatggttt gcacggtct tgatactgga cctcacgtac    4800
agcatgggct gtgtctctgg ctgcctctgc cccccgggca tggtccggca tgagaacaga    4860
tgtgtggccc tggaaaggtg tccctgcttc catcagggca tcgtacccga cacagagacc    4920
gacggagacg gggggcccgt accaggccgt actcttgtct acacaccggg accttccac    4980
agggacgaag gtagtcccgt aggagtatgc ccctggagaa acagtgaaga ttggctgcaa    5040
cacttgtgtc tgtcgggacc ggaagtggaa ctgcacagac catgtgtgtg atgccacgtg    5100
tcctcatacg gggacctctt tgtcacttct aaccgacgtt gtgaacacag acagccctgg    5160
ccttcacctt gacgtgtctg gtacacacac tacggtgcac ctccacgatc ggcatggccc    5220
actacctcac cttcgacggg ctcaaatacc tgttccccgg ggagtgccag tacgttctgg    5280
tgcaggatta ctgcggcagt gaggtgctag ccgtaccggg tgatggagtg gaagctgccc    5340
gagtttatgg acaaggggcc cctcacggtc atgcaagacc acgtcctaat gacgccgtca    5400
aaccctggga cctttcggat cctagtgggg aataagggat gcagccaccc ctcagtgaaa    5460
tgcaagaaac gggtcaccat cctggtggag ggaggagaga ttgggaccct ggaaagccta    5520
ggatcacccc ttattcccta cgtcggtggg gagtcacttt acgttctttg cccagtggta    5580
ggaccacctc cctcctctct ttgagctgtt tgacgcggag gtgaatgtga agaggcccat    5640
gaaggatgag actcactttg aggtggtgga gtctggccgg tacatcattc tgctgctggg    5700
aactcgacaa actgcccctc cacttacact tctccgggta cttcctactc tgagtgaaac    5760
tccaccacct cagaccggcc atgtagtaag acgacgaccc caaagccctc tccgtggtct    5820
gggaccgcca cctgagcatc tccgtggtcc tgaagcagac ataccaggag aaagtgtgtg    5880
gcctgtgtgg gaattttgat gtttcgggag aggcaccaga ccctggcggt ggactcgtag    5940
aggcaccagg acttcgtctg tatggtcctc tttcacacac cggacacacc cttaaaacta    6000
ggcatccaga acaatgacct caccagcagc aacctccaag tggaggaaga ccctgtggac    6060
tttgggaact cctggaaagt gagctcgcag tgtgctgaca ccgtaggtct tgttactgga    6120
gtggtcgtcg ttggaggttc acctccttct gggacacctg aaaccccttga ggacctttca    6180
ctcgagcgtc acacgactgt ccagaaaagt gcctctggac tcatcccctg ccacctgcca    6240
taacaacatc atgaagcaga cgatggtgga ttcctcctgt agaatcctta ccagtgacgt    6300
ggtcttttca cggagacctg agtaggggac ggtggacggt attgttgtag tacttcgtct    6360
gctaccacct aaggaggaca tcttaggaat ggtcactgca cttccaggac tgcaacaagc    6420
tggtggaccc cgagccatat ctggatgtct gcatttacga cacctgctcc tgtgagtcca    6480
ttggggactg cgcctgcttc gaaggtcctg acgttgttcg accacctggg gctcggtata    6540
gacctacaga cgtaaatgct gtggacgagg acactcaggt aaccctgac gcggacgaag    6600
tgcgacacca ttgctgccta tgcccacgtg tgtcccagc atggcaaggt ggtgacctgg    6660
aggacggcca cattgtgccc ccagagctgc gaggagagga acgctgtggt aacgacggat    6720
```

```
acgggtgcac acacgggtcg taccgttcca ccactggacc tcctgccggt gtaacacggg    6780
ggtctcgacg ctcctctcct atctccggga aacgggtat gagtgtgagt ggcgctataa    6840
cagctgtgca cctgcctgtc aagtcacgtg tcagcaccct gagccactgg cctgccctgt    6900
tagaggccct cttgcccata ctcacactca ccgcgatatt gtcgacacgt ggacggacag    6960
ttcagtgcac agtcgtggga ctcggtgacc ggacgggaca gcagtgtgtg gagggctgcc    7020
atgcccactg ccctccaggg aaaatcctgg atgagctttt gcagacctgc gttgaccctg    7080
aagactgtcc agtgtgtgag cgtcacacac ctcccgacgg tacgggtgac gggaggtccc    7140
ttttaggacc tactcgaaaa cgtctggacg caactgggac ttctgacagg tcacacactc    7200
gtggctggcc ggcgttttgc ctcaggaaag aaagtcacct tgaatcccag tgaccctgag    7260
cactgccaga tttgccactg tgatgttgtc aacctcacct caccgaccgg ccgcaaaacg    7320
gagtcctttc tttcagtgga acttagggtc actgggactc gtgacggtct aaacggtgac    7380
actacaacag ttggagtgga gtgaagcctg ccaggagccg ggaggcctgg tggtgcctcc    7440
cacagatgcc ccggtgagcc ccaccactct gtatgtggag gacatctcgg aaccgccgtt    7500
cacttcggac ggtcctcggc cctccggacc accacggagg gtgtctacgg ggccactcgg    7560
ggtggtgaga catacacctc ctgtagagcc ttggcggcaa gcacgatttc tactgcagca    7620
ggctactgga cctggtcttc ctgctggatg gctcctccag gctgtccgag gctgagtttg    7680
aagtgctgaa ggcctttgtg cgtgctaaag atgacgtcgt ccgatgacct ggaccagaag    7740
gacgacctac cgaggaggtc cgacaggctc cgactcaaac ttcacgactt ccggaaacac    7800
gtggacatga tggagcggct gcgcatctcc cagaagtggg tccgcgtggc cgtggtggag    7860
taccacgacg gctcccacgc ctacatcggg ctcaaggacc cacctgtact acctcgccga    7920
cgcgtagagg gtcttcaccc aggcgcaccg gcaccacctc atggtgctgc cgagggtgcg    7980
gatgtagccc gagttcctgg ggaagcgacc gtcagagctg cggcgcattg ccagccaggt    8040
gaagtatgcg ggcagccagg tggcctccac cagcgaggtc ttgaaataca cactgttcca    8100
ccttcgctgg cagtctcgac gccgcgtaac ggtcggtcca cttcatacgc ccgtcggtcc    8160
accggaggtg gtcgctccag aactttatgt gtgacaaggt aatcttcagc aagatcgacc    8220
gccctgaagc ctcccgcatc gccctgctcc tgatggccag ccaggagccc aacggatgt    8280
cccgaacttt tgtccgctac ttagaagtcg ttctagctgg cgggacttcg gagggcgtag    8340
cgggacgagg actaccggtc ggtcctcggg gttgcctaca gggccttgaa acaggcgatg    8400
gtccagggcc tgaagaagaa gaaggtcatt gtgatcccgg tgggcattgg gccccatgcc    8460
aacctcaagc agatccgcct catcgagaag caggcccctg caggtcccgg acttcttctt    8520
cttccagtaa cactagggcc acccgtaacc cggggtacgg ttggagttcg tctaggcgga    8580
gtagctcttc gtccggggac agaacaaggc cttcgtgctg agcagtgtgg atgagctgga    8640
gcagcaaagg gacgagatcg ttagctacct ctgtgacctt gccctgaag ccctcctcc    8700
tcttgttccg gaagcacgac tcgtcacacc tactcgacct cgtcgtttcc ctgctctagc    8760
aatcgatgga gacactggaa cggggacttc ggggaggagg tactctgccc ccgacatgg    8820
cacaagtcac tgtgggcccg gggctcttgg ggtttcgac cctggggccc aagaggaact    8880
ccatggttct ggatgtggcg atgagacggg gggctgtacc gtgttcagtg acacccgggc    8940
cccgagaacc cccaaagctg ggaccccggg ttctccttga ggtaccaaga cctacaccgc    9000
ttcgtcctgg aaggatcgga caaaattggt gaagccgact tcaacaggag caaggagttc    9060
atggaggagg tgattcagcg gatggatgtg ggccaggaca aagcaggacc ttcctagcct    9120
```

```
gttttaacca cttcggctga agttgtcctc gttcctcaag tacctcctcc actaagtcgc   9180
ctacctacac ccggtcctgt gcatccacgt cacggtgctg cagtactcct acatggtgac   9240
cgtggagtac cccttcagcg aggcacagtc caaaggggac atcctgcagc gggtgcgaga   9300
cgtaggtgca gtgccacgac gtcatgagga tgtaccactg gcacctcatg gggaagtcgc   9360
tccgtgtcag gtttcccctg taggacgtcg cccacgctct gatccgctac cagggcggca   9420
acaggaccaa cactgggctg gccctgcggt acctctctga ccacagcttc ttggtcagcc   9480
agggtgaccg ggagcaggcg ctaggcgatg gtcccgccgt tgtcctggtt gtgacccgac   9540
cgggacgcca tggagagact ggtgtcgaag aaccagtcgg tcccactggc cctcgtccgc   9600
cccaacctgg tctacatggt caccggaaat cctgcctctg atgagatcaa gaggctgcct   9660
ggagacatcc aggtggtgcc cattggagtg ggccctaatg gggttggacc agatgtacca   9720
gtggccttta ggacggagac tactctagtt ctccgacgga cctctgtagg tccaccacgg   9780
gtaacctcac ccgggattac ccaacgtgca ggagctggag aggattggct ggcccaatgc   9840
ccctatcctc atccaggact ttgagacgct ccccgagag gctcctgacc tggtgctgca   9900
ggttgcacgt cctcgacctc tcctaaccga ccgggttacg gggataggag taggtcctga   9960
aactctgcga gggggctctc cgaggactgg accacgacgt gaggtgctgc tccggagagg  10020
ggctgcagat ccccacccctc tcccctgcac ctgactgcag ccagcccctg acgtgatcc  10080
ttctcctgga tggctcctcc ctccacgacg aggcctctcc ccgacgtcta ggggtgggag  10140
aggggacgtg gactgacgtc ggtcggggac ctgcactagg aagaggacct accgaggagg  10200
agtttcccag cttcttattt tgatgaaatg aagagtttcg ccaaggcttt catttcaaaa  10260
gccaatatag ggcctcgtct cactcaggtg tcagtgctgc tcaaagggtc gaagaataaa  10320
actactttac ttctcaaagc ggttccgaaa gtaaagtttt cggttatatc ccggagcaga  10380
gtgagtccac agtcacgacg agtatggaag catcaccacc attgacgtgc catggaacgt  10440
ggtcccggag aaagcccatt tgctgagcct tgtggacgtc atgcagcggg agggaggccc  10500
tcataccttc gtagtggtgg taactgcacg gtaccttgca ccagggcctc tttcgggtaa  10560
acgactcgga acacctgcag tacgtcgccc tccctccggg cagccaaatc ggggatgcct  10620
tgggctttgc tgtgcgatac ttgacttcag aaatgcatgg tgccaggccg ggagcctcaa  10680
aggcggtggt catcctggtc gtcggtttag cccctacgga acccgaaacg acacgctatg  10740
aactgaagtc tttacgtacc acggtccggc cctcggagtt tccgccacca gtaggaccag  10800
acggacgtct ctgtggattc agtggatgca gcagctgatg ccgccaggtc caacagagtg  10860
acagtgttcc ctattggaat tggagatcgc tacgatgcag tgcctgcaga gacacctaag  10920
tcacctacgt cgtcgactac ggcggtccag gttgtctcac tgtcacaagg gataacctta  10980
acctctagcg atgctacgtc cccagctacg gatcttggca ggcccagcag gcgactccaa  11040
cgtggtgaag ctccagcgaa tcgaagacct ccctaccatg gtcaccttgg gcaattcctt  11100
gggtcgatgc ctagaaccgt ccgggtcgtc cgctgaggtt gcaccacttc gaggtcgctt  11160
agcttctgga gggatggtac cagtggaacc cgttaaggaa cctccacaaa ctgtgctctg  11220
gatttgttag gatttgcatg gatgaggatg ggaatgagaa gaggcccggg gacgtctgga  11280
ccttgccaga ccagtgccac ggaggtgttt gacacgagac ctaaacaatc ctaaacgtac  11340
ctactcctac ccttactctt ctccgggccc ctgcagacct ggaacggtct ggtcacggtg  11400
accgtgactt gccagccaga tggccagacc ttgctgaaga gtcatcgggt caactgtgac  11460
cgggggctga ggccttcgtg ccctaacagc cagtcccctg tggcactgaa cggtcggtct  11520
```

```
accggtctgg aacgacttct cagtagccca gttgacactg gcccccgact ccggaagcac    11580
gggattgtcg gtcaggggac ttaaagtgga agagacctgt ggctgccgct ggacctgccc    11640
ctgygtgtgc acaggcagct ccactcggca catcgtgacc tttgatgggc agaatttcaa    11700
aatttcacct tctctggaca ccgacggcga cctggacggg gacrcacacg tgtccgtcga    11760
ggtgagccgt gtagcactgg aaactacccg tcttaaagtt gctgactggc agctgttctt    11820
atgtcctatt tcaaaacaag gagcaggacc tggaggtgat tctccataat ggtgcctgca    11880
gccctggagc aaggcagggc cgactgaccg tcgacaagaa tacaggataa agttttgttc    11940
ctcgtcctgg acctccacta agaggtatta ccacggacgt cgggacctcg ttccgtcccg    12000
tgcatgaaat ccatcgaggt gaagcacagt gccctctccg tcgagstgca cagtgacatg    12060
gaggtgacgg tgaatgggag actggtctct gttccttacg acgtacttta ggtagctcca    12120
cttcgtgtca cgggagaggc agctcsacgt gtcactgtac ctccactgcc acttaccctc    12180
tgaccagaga caaggaatgc tgggtgggaa catggaagtc aacgtttatg gtgccatcat    12240
gcatgaggtc agattcaatc accttggtca catcttcaca ttcactccac aaaacaatga    12300
acccacccct gtaccttcag ttgcaaatac cacggtagta cgtactccag tctaagttag    12360
tggaaccagt gtagaagtgt aagtgaggtg ttttgttact gttccaactg cagctcagcc    12420
ccaagacttt tgcttcaaag acgtatggtc tgtgtgggat ctgtgatgag aacggagcca    12480
atgacttcat gctgagggat caaggttgac gtcgagtcgg ggttctgaaa acgaagtttc    12540
tgcataccag acacacccta gacactactc ttgcctcggt tactgaagta cgactcccta    12600
ggcacagtca ccacagactg gaaaacactt gttcaggaat ggactgtgca gcggccaggg    12660
cagacgtgcc agcccatcct ggaggagcag tgtcttgtcc ccgtgtcagt ggtgtctgac    12720
cttttgtgaa caagtcctta cctgacacgt cgccggtccc gtctgcacgg tcgggtagga    12780
cctcctcgtc acagaacagg ccgacagctc ccactgccag gtcctcctct taccactgtt    12840
tgctgaatgc cacaaggtcc tggctccagc cacattctat gccatctgcc agcaggacag    12900
ggctgtcgag ggtgacggtc caggaggaga atggtgacaa acgacttacg tgttccagg    12960
accgaggtcg gtgtaagata cggtagacgg tcgtcctgtc ttgccaccag gagcaagtgt    13020
gtgaggtgat cgcctcttat gcccacctct gtcggaccaa cggggtctgc gttgactgga    13080
ggacacctga tttctgtgct aacggtggtc ctcgttcaca cactccacta gcggagaata    13140
cgggtggaga cagcctggtt gccccagacg caactgacct cctgtggact aaagacacga    13200
atgtcatgcc caccatctct ggtctacaac cactgtgagc atggctgtcc ccggcactgt    13260
gatggcaacg tgagctcctg tggggaccat ccctccgaag tacagtacgg gtggtagaga    13320
ccagatgttg gtgacactcg taccgacagg ggccgtgaca ctaccgttgc actcgaggac    13380
accccctggta gggaggcttc gctgtttctg ccctccagat aaagtcatgt tggaaggcag    13440
ctgtgtccct gaagaggcct gcactcagtg cattggtgag gatggagtcc agcaccagtt    13500
cgacaaagac gggaggtcta tttcagtaca accttccgtc gacacaggga cttctccgga    13560
cgtgagtcac gtaaccactc ctacctcagg tcgtggtcaa cctggaagcc tgggtcccgg    13620
accaccagcc ctgtcagatc tgcacatgcc tcagcgggcg gaaggtcaac tgcacaacgc    13680
agccctgccc cacggccaaa ggaccttcgg acccagggcc tggtggtcgg gacagtctag    13740
acgtgtacgg agtcgcccgc cttcagttg acgtgttgcg tcgggacggg gtgccggttt    13800
gctcccacgt gtggcctgtg tgaagtagcc cgcctccgcc agaatgcaga ccagtgctgc    13860
cccgagtatg agtgtgtgtg tgacccagtg agctgtgacc cgagggtgca caccggacac    13920
```

```
acttcatcgg gcggaggcgg tcttacgtct ggtcacgacg gggctcatac tcacacacac   13980
actgggtcac tcgacactgg tgccccagt gcctcactgt gaacgtggcc tccagcccac    14040
actgaccaac cctggcgagt gcagacccaa cttcacctgc gcctgcagga aggaggagtg   14100
acggggtca cggagtgaca cttgcaccgg aggtcgggtg tgactggttg ggaccgctca    14160
cgtctgggtt gaagtggacg cggacgtcct tcctcctcac caaaagagtg tccccaccct   14220
cctgccccc gcaccgtttg cccacccttc ggaagaccca gtgctgtgat gagtatgagt    14280
gtgcctgcaa ctgtgtcaac gttttctcac aggggtggga ggacgggggg cgtggcaaac   14340
gggtgggaag ccttctgggt cacgacacta ctcatactca cacggacgtt gacacagttg   14400
tccacagtga gctgtcccct tgggtacttg gcctcaaccg ccaccaatga ctgtggctgt   14460
accacaacca cctgccttcc cgacaaggtg tgtgtccacc aggtgtcact cgacagggga   14520
acccatgaac cggagttggc ggtggttact gacaccgaca tggtgttggt ggacggaagg   14580
gctgttccac acacaggtgg gaagcaccat ctaccctgtg ggccagttct gggaggaggg   14640
ctgcgatgtg tgcacctgca ccgacatgga ggatgccgtg atgggcctcc gcgtggccca   14700
cttcgtggta gatgggacac ccggtcaaga ccctcctccc gacgctacac acgtggacgt   14760
ggctgtacct cctacggcac tacccggagg cgcaccgggt gtgctcccag aagccctgtg   14820
aggacagctg tcgtcgggc ttcacttacg ttctgcatga aggcgagtgc tgtggaaggt   14880
gcctgccatc tgcctgtgag cacgagggtc ttcgggacac tcctgtcgac agccagcccg   14940
aagtgaatgc aagacgtact tccgctcacg acaccttcca cggacggtag acggacactc   15000
gtggtgactg gctcaccgcg gggggactcc cagtcttcct ggaagagtgt cggctcccag   15060
tgggcctccc cggagaaccc ctgcctcatc aatgagtgtg caccactgac cgagtggcgc   15120
ccccctgagg gtcagaagga ccttctcaca gccgagggtc acccggaggg gcctcttggg   15180
gacggagtag ttactcacac tccgagtgaa ggaggaggtc tttatacaac aaaggaacgt   15240
ctcctgcccc cagctggagg tccctgtctg cccctcgggc tttcagctga gctgtaagac   15300
aggctcactt cctcctccag aaatatgttg tttccttgca gaggacgggg gtcgacctcc   15360
agggacagac ggggagcccg aaagtcgact cgacattctg ctcagcgtgc tgcccaagct   15420
gtcgctgtga gcgcatggag gcctgcatgc tcaatggcac tgtcattggg cccgggaaga   15480
ctgtgatgat cgatgtgtgc gagtcgcacg acggggttcga cagcgacact cgcgtacctc   15540
cggacgtacg agttaccgtg acagtaaccc gggcccttct gacactacta gctacacacg   15600
acgacctgcc gctgcatggt gcaggtgggg gtcatctctg gattcaagct ggagtgcagg   15660
aagaccacct gcaaccctg ccccctgggt tacaaggaag tgctggacgg cgacgtacca    15720
cgtccacccc cagtagagac ctaagttcga cctcacgtcc ttctggtgga cgttgggac    15780
gggggaccca atgttccttc aaaataacac aggtgaatgt tgtgggagat gtttgcctac   15840
ggcttgcacc attcagctaa gaggaggaca gatcatgaca ctgaagcgtg atgagacgct   15900
ttttattgtg tccacttaca acaccctcta caaacggatg ccgaacgtgg taagtcgatt   15960
ctcctcctgt ctagtactgt gacttcgcac tactctgcga ccaggatggc tgtgatactc   16020
acttctgcaa ggtcaatgag agaggagagt acttctggga gaagagggtc acaggctgcc   16080
caccctttga tgaacacaag ggtcctaccg acactatgag tgaagacgtt ccagttactc   16140
tctcctctca tgaagaccct cttctcccag tgtccgacgg gtgggaaact acttgtgttc   16200
tgtcttgctg agggaggtaa aattatgaaa attccaggca cctgctgtga cacatgtgag   16260
gagcctgagt gcaacgacat cactgccagg ctgcagtatg acagaacgac tccctccatt   16320
```

```
ttaatactttt taaggtccgt ggacgacact gtgtacactc ctcggactca cgttgctgta    16380
gtgacggtcc gacgtcatac tcaaggtggg aagctgtaag tctgaagtag aggtggatat    16440
ccactactgc cagggcaaat gtgccagcaa agccatgtac tccattgaca tcaacgatgt    16500
agttccaccc ttcgacattc agacttcatc tccacctata ggtgatgacg gtcccgttta    16560
cacggtcgtt tcggtacatg aggtaactgt agttgctaca gcaggaccag tgctcctgct    16620
gctctccgac acggacggag cccatgcagg tggccctgca ctgcaccaat ggctctgttg    16680
tgtaccatga ggttctcaat cgtcctggtc acgaggacga cgagaggctg tgcctgcctc    16740
gggtacgtcc accgggacgt gacgtggtta ccgagacaac acatggtact ccaagagtta    16800
gccatggagt gcaaatgctc ccccaggaag tgcagcaagt ga                        16842
```

<210> SEQ ID NO 28
<211> LENGTH: 2813
<212> TYPE: PRT
<213> ORGANISM: Homo sapiens
<220> FEATURE:
<221> NAME/KEY: misc_feature
<222> LOCATION: (2016)..(2016)
<223> OTHER INFORMATION: Xaa can be any naturally occurring amino acid

<400> SEQUENCE: 28

```
Met Ile Pro Ala Arg Phe Ala Gly Val Leu Leu Ala Leu Ala Leu Ile
1               5                   10                  15

Leu Pro Gly Thr Leu Cys Ala Glu Gly Thr Arg Gly Arg Ser Ser Thr
            20                  25                  30

Ala Arg Cys Ser Leu Phe Gly Ser Asp Phe Val Asn Thr Phe Asp Gly
        35                  40                  45

Ser Met Tyr Ser Phe Ala Gly Tyr Cys Ser Tyr Leu Leu Ala Gly Gly
    50                  55                  60

Cys Gln Lys Arg Ser Phe Ser Ile Ile Gly Asp Phe Gln Asn Gly Lys
65                  70                  75                  80

Arg Val Ser Leu Ser Val Tyr Leu Gly Glu Phe Phe Asp Ile His Leu
                85                  90                  95

Phe Val Asn Gly Thr Val Thr Gln Gly Asp Gln Arg Val Ser Met Pro
            100                 105                 110

Tyr Ala Ser Lys Gly Leu Tyr Leu Glu Thr Glu Ala Gly Tyr Tyr Lys
        115                 120                 125

Leu Ser Gly Glu Ala Tyr Gly Phe Val Ala Arg Ile Asp Gly Ser Gly
    130                 135                 140

Asn Phe Gln Val Leu Leu Ser Asp Arg Tyr Phe Asn Lys Thr Cys Gly
145                 150                 155                 160

Leu Cys Gly Asn Phe Asn Ile Phe Ala Glu Asp Asp Phe Met Thr Gln
                165                 170                 175

Glu Gly Thr Leu Thr Ser Asp Pro Tyr Asp Phe Ala Asn Ser Trp Ala
            180                 185                 190

Leu Ser Ser Gly Glu Gln Trp Cys Glu Arg Ala Ser Pro Pro Ser Ser
        195                 200                 205

Ser Cys Asn Ile Ser Ser Gly Glu Met Gln Lys Gly Leu Trp Glu Gln
    210                 215                 220

Cys Gln Leu Leu Lys Ser Thr Ser Val Phe Ala Arg Cys His Pro Leu
225                 230                 235                 240

Val Asp Pro Glu Pro Phe Val Ala Leu Cys Glu Lys Thr Leu Cys Glu
                245                 250                 255
```

```
Cys Ala Gly Gly Leu Glu Cys Ala Cys Pro Ala Leu Leu Glu Tyr Ala
                260                 265                 270

Arg Thr Cys Ala Gln Glu Gly Met Val Leu Tyr Gly Trp Thr Asp His
            275                 280                 285

Ser Ala Cys Ser Pro Val Cys Pro Ala Gly Met Glu Tyr Arg Gln Cys
        290                 295                 300

Val Ser Pro Cys Ala Arg Thr Cys Gln Ser Leu His Ile Asn Glu Met
305                 310                 315                 320

Cys Gln Glu Arg Cys Val Asp Gly Cys Ser Cys Pro Glu Gly Gln Leu
                325                 330                 335

Leu Asp Glu Gly Leu Cys Val Glu Ser Thr Glu Cys Pro Cys Val His
            340                 345                 350

Ser Gly Lys Arg Tyr Pro Pro Gly Thr Ser Leu Ser Arg Asp Cys Asn
        355                 360                 365

Thr Cys Ile Cys Arg Asn Ser Gln Trp Ile Cys Ser Asn Glu Glu Cys
    370                 375                 380

Pro Gly Glu Cys Leu Val Thr Gly Gln Ser His Phe Lys Ser Phe Asp
385                 390                 395                 400

Asn Arg Tyr Phe Thr Phe Ser Gly Ile Cys Gln Tyr Leu Leu Ala Arg
                405                 410                 415

Asp Cys Gln Asp His Ser Phe Ser Ile Val Ile Glu Thr Val Gln Cys
            420                 425                 430

Ala Asp Asp Arg Asp Ala Val Cys Thr Arg Ser Val Thr Val Arg Leu
        435                 440                 445

Pro Gly Leu His Asn Ser Leu Val Lys Leu Lys His Gly Ala Gly Val
450                 455                 460

Ala Met Asp Gly Gln Asp Ile Gln Leu Pro Leu Leu Lys Gly Asp Leu
465                 470                 475                 480

Arg Ile Gln His Thr Val Thr Ala Ser Val Arg Leu Ser Tyr Gly Glu
                485                 490                 495

Asp Leu Gln Met Asp Trp Asp Gly Arg Gly Arg Leu Leu Val Lys Leu
            500                 505                 510

Ser Pro Val Tyr Ala Gly Lys Thr Cys Gly Leu Cys Gly Asn Tyr Asn
        515                 520                 525

Gly Asn Gln Gly Asp Asp Phe Leu Thr Pro Ser Gly Leu Ala Glu Pro
    530                 535                 540

Arg Val Glu Asp Phe Gly Asn Ala Trp Lys Leu His Gly Asp Cys Gln
545                 550                 555                 560

Asp Leu Gln Lys Gln His Ser Asp Pro Cys Ala Leu Asn Pro Arg Met
                565                 570                 575

Thr Arg Phe Ser Glu Glu Ala Cys Ala Val Leu Thr Ser Pro Thr Phe
            580                 585                 590

Glu Ala Cys His Arg Ala Val Ser Pro Leu Pro Tyr Leu Arg Asn Cys
        595                 600                 605

Arg Tyr Asp Val Cys Ser Cys Ser Asp Gly Arg Glu Cys Leu Cys Gly
    610                 615                 620

Ala Leu Ala Ser Tyr Ala Ala Ala Cys Ala Gly Arg Gly Val Arg Val
625                 630                 635                 640

Ala Trp Arg Glu Pro Gly Arg Cys Glu Leu Asn Cys Pro Lys Gly Gln
                645                 650                 655

Val Tyr Leu Gln Cys Gly Thr Pro Cys Asn Leu Thr Cys Arg Ser Leu
            660                 665                 670
```

```
Ser Tyr Pro Asp Glu Glu Cys Asn Glu Ala Cys Leu Glu Gly Cys Phe
            675                 680                 685

Cys Pro Pro Gly Leu Tyr Met Asp Glu Arg Gly Asp Cys Val Pro Lys
690                     695                 700

Ala Gln Cys Pro Cys Tyr Tyr Asp Gly Glu Ile Phe Gln Pro Glu Asp
705                 710                 715                 720

Ile Phe Ser Asp His His Thr Met Cys Tyr Cys Glu Asp Gly Phe Met
                725                 730                 735

His Cys Thr Met Ser Gly Val Pro Gly Ser Leu Leu Pro Asp Ala Val
            740                 745                 750

Leu Ser Ser Pro Leu Ser His Arg Ser Lys Arg Ser Leu Ser Cys Arg
755                 760                 765

Pro Pro Met Val Lys Leu Val Cys Pro Ala Asp Asn Leu Arg Ala Glu
770                 775                 780

Gly Leu Glu Cys Thr Lys Thr Cys Gln Asn Tyr Asp Leu Glu Cys Met
785                 790                 795                 800

Ser Met Gly Cys Val Ser Gly Cys Leu Cys Pro Pro Gly Met Val Arg
            805                 810                 815

His Glu Asn Arg Cys Val Ala Leu Glu Arg Cys Pro Cys Phe His Gln
            820                 825                 830

Gly Lys Glu Tyr Ala Pro Gly Glu Thr Val Lys Ile Gly Cys Asn Thr
            835                 840                 845

Cys Val Cys Arg Asp Arg Lys Trp Asn Cys Thr Asp His Val Cys Asp
            850                 855                 860

Ala Thr Cys Ser Thr Ile Gly Met Ala His Tyr Leu Thr Phe Asp Gly
865                 870                 875                 880

Leu Lys Tyr Leu Phe Pro Gly Glu Cys Gln Tyr Val Leu Val Gln Asp
                885                 890                 895

Tyr Cys Gly Ser Asn Pro Gly Thr Phe Arg Ile Leu Val Gly Asn Lys
            900                 905                 910

Gly Cys Ser His Pro Ser Val Lys Cys Lys Lys Arg Val Thr Ile Leu
            915                 920                 925

Val Glu Gly Gly Glu Ile Glu Leu Phe Asp Gly Glu Val Asn Val Lys
            930                 935                 940

Arg Pro Met Lys Asp Glu Thr His Phe Glu Val Val Glu Ser Gly Arg
945                 950                 955                 960

Tyr Ile Ile Leu Leu Leu Gly Lys Ala Leu Ser Val Val Trp Asp Arg
                965                 970                 975

His Leu Ser Ile Ser Val Val Leu Lys Gln Thr Tyr Gln Glu Lys Val
            980                 985                 990

Cys Gly Leu Cys Gly Asn Phe Asp  Gly Ile Gln Asn Asn  Asp Leu Thr
            995                 1000                1005

Ser Ser Asn Leu Gln Val Glu  Glu Asp Pro Val Asp  Phe Gly Asn
    1010                1015                1020

Ser Trp Lys Val Ser Ser Gln  Cys Ala Asp Thr Arg  Lys Val Pro
    1025                1030                1035

Leu Asp  Ser Ser Pro Ala Thr  Cys His Asn Asn Ile  Met Lys Gln
    1040                1045                1050

Thr Met  Val Asp Ser Ser Cys  Arg Ile Leu Thr Ser  Asp Val Phe
    1055                1060                1065

Gln Asp  Cys Asn Lys Leu Val  Asp Pro Glu Pro Tyr  Leu Asp Val
    1070                1075                1080
```

-continued

Cys Ile Tyr Asp Thr Cys Ser Cys Glu Ser Ile Gly Asp Cys Ala
1085                1090                1095

Cys Phe Cys Asp Thr Ile Ala Ala Tyr Ala His Val Cys Ala Gln
1100                1105                1110

His Gly Lys Val Val Thr Trp Arg Thr Ala Thr Leu Cys Pro Gln
1115                1120                1125

Ser Cys Glu Glu Arg Asn Leu Arg Glu Asn Gly Tyr Glu Cys Glu
1130                1135                1140

Trp Arg Tyr Asn Ser Cys Ala Pro Ala Cys Gln Val Thr Cys Gln
1145                1150                1155

His Pro Glu Pro Leu Ala Cys Pro Val Gln Cys Val Glu Gly Cys
1160                1165                1170

His Ala His Cys Pro Pro Gly Lys Ile Leu Asp Glu Leu Leu Gln
1175                1180                1185

Thr Cys Val Asp Pro Glu Asp Cys Pro Val Cys Glu Val Ala Gly
1190                1195                1200

Arg Arg Phe Ala Ser Gly Lys Lys Val Thr Leu Asn Pro Ser Asp
1205                1210                1215

Pro Glu His Cys Gln Ile Cys His Cys Asp Val Val Asn Leu Thr
1220                1225                1230

Cys Glu Ala Cys Gln Glu Pro Gly Gly Leu Val Val Pro Pro Thr
1235                1240                1245

Asp Ala Pro Val Ser Pro Thr Thr Leu Tyr Val Glu Asp Ile Ser
1250                1255                1260

Glu Pro Pro Leu His Asp Phe Tyr Cys Ser Arg Leu Leu Asp Leu
1265                1270                1275

Val Phe Leu Leu Asp Gly Ser Ser Arg Leu Ser Glu Ala Glu Phe
1280                1285                1290

Glu Val Leu Lys Ala Phe Val Val Asp Met Met Glu Arg Leu Arg
1295                1300                1305

Ile Ser Gln Lys Trp Val Arg Val Ala Val Val Glu Tyr His Asp
1310                1315                1320

Gly Ser His Ala Tyr Ile Gly Leu Lys Asp Arg Lys Arg Pro Ser
1325                1330                1335

Glu Leu Arg Arg Ile Ala Ser Gln Val Lys Tyr Ala Gly Ser Gln
1340                1345                1350

Val Ala Ser Thr Ser Glu Val Leu Lys Tyr Thr Leu Phe Gln Ile
1355                1360                1365

Phe Ser Lys Ile Asp Arg Pro Glu Ala Ser Arg Ile Ala Leu Leu
1370                1375                1380

Leu Met Ala Ser Gln Glu Pro Gln Arg Met Ser Arg Asn Phe Val
1385                1390                1395

Arg Tyr Val Gln Gly Leu Lys Lys Lys Lys Val Ile Val Ile Pro
1400                1405                1410

Val Gly Ile Gly Pro His Ala Asn Leu Lys Gln Ile Arg Leu Ile
1415                1420                1425

Glu Lys Gln Ala Pro Glu Asn Lys Ala Phe Val Leu Ser Ser Val
1430                1435                1440

Asp Glu Leu Glu Gln Gln Arg Asp Glu Ile Val Ser Tyr Leu Cys
1445                1450                1455

Asp Leu Ala Pro Glu Ala Pro Pro Pro Thr Leu Pro Pro Asp Met
1460                1465                1470

```
Ala Gln Val Thr Val Gly Pro Gly Leu Leu Gly Val Ser Thr Leu
1475                1480                1485

Gly Pro Lys Arg Asn Ser Met Val Leu Asp Val Ala Phe Val Leu
1490                1495                1500

Glu Gly Ser Asp Lys Ile Gly Glu Ala Asp Phe Asn Arg Ser Lys
1505                1510                1515

Glu Phe Met Glu Glu Val Ile Gln Arg Met Asp Val Gly Gln Asp
1520                1525                1530

Ser Ile His Val Thr Val Leu Gln Tyr Ser Tyr Met Val Thr Val
1535                1540                1545

Glu Tyr Pro Phe Ser Glu Ala Gln Ser Lys Gly Asp Ile Leu Gln
1550                1555                1560

Arg Val Arg Glu Ile Arg Tyr Gln Gly Gly Asn Arg Thr Asn Thr
1565                1570                1575

Gly Leu Ala Leu Arg Tyr Leu Ser Asp His Ser Phe Leu Val Ser
1580                1585                1590

Gln Gly Asp Arg Glu Gln Ala Pro Asn Leu Val Tyr Met Val Thr
1595                1600                1605

Gly Asn Pro Ala Ser Asp Glu Ile Lys Arg Leu Pro Gly Asp Ile
1610                1615                1620

Gln Val Val Pro Ile Gly Val Gly Pro Asn Ala Asn Val Gln Glu
1625                1630                1635

Leu Glu Arg Ile Gly Trp Pro Asn Ala Pro Ile Leu Ile Gln Asp
1640                1645                1650

Phe Glu Thr Leu Pro Arg Glu Ala Pro Asp Leu Val Leu Gln Arg
1655                1660                1665

Cys Cys Ser Gly Glu Gly Leu Gln Ile Pro Thr Leu Ser Pro Ala
1670                1675                1680

Pro Asp Cys Ser Gln Pro Leu Asp Val Ile Leu Leu Leu Asp Gly
1685                1690                1695

Ser Ser Ser Phe Pro Ala Ser Tyr Phe Asp Glu Met Lys Ser Phe
1700                1705                1710

Ala Lys Ala Phe Ile Ser Lys Ala Asn Ile Gly Pro Arg Leu Thr
1715                1720                1725

Gln Val Ser Val Leu Gln Tyr Gly Ser Ile Thr Thr Ile Asp Val
1730                1735                1740

Pro Trp Asn Val Val Pro Glu Lys Ala His Leu Leu Ser Leu Val
1745                1750                1755

Asp Val Met Gln Arg Glu Gly Gly Pro Ser Gln Ile Gly Asp Ala
1760                1765                1770

Leu Gly Phe Ala Val Arg Tyr Leu Thr Ser Glu Met His Gly Ala
1775                1780                1785

Arg Pro Gly Ala Ser Lys Ala Val Val Ile Leu Val Thr Asp Val
1790                1795                1800

Ser Val Asp Ser Val Asp Ala Ala Ala Asp Ala Ala Arg Ser Asn
1805                1810                1815

Arg Val Thr Val Phe Pro Ile Gly Ile Gly Asp Arg Tyr Asp Ala
1820                1825                1830

Ala Gln Leu Arg Ile Leu Ala Gly Pro Ala Gly Asp Ser Asn Val
1835                1840                1845

Val Lys Leu Gln Arg Ile Glu Asp Leu Pro Thr Met Val Thr Leu
1850                1855                1860
```

```
Gly Asn Ser Phe Leu His Lys Leu Cys Ser Gly Phe Val Arg Ile
1865                 1870                1875

Cys Met Asp Glu Asp Gly Asn Glu Lys Arg Pro Gly Asp Val Trp
1880                 1885                1890

Thr Leu Pro Asp Gln Cys His Thr Val Thr Cys Gln Pro Asp Gly
1895                 1900                1905

Gln Thr Leu Leu Lys Ser His Arg Val Asn Cys Asp Arg Gly Leu
1910                 1915                1920

Arg Pro Ser Cys Pro Asn Ser Gln Ser Pro Val Lys Val Glu Glu
1925                 1930                1935

Thr Cys Gly Cys Arg Trp Thr Cys Pro Cys Val Cys Thr Gly Ser
1940                 1945                1950

Ser Thr Arg His Ile Val Thr Phe Asp Gly Gln Asn Phe Lys Leu
1955                 1960                1965

Thr Gly Ser Cys Ser Tyr Val Leu Phe Gln Asn Lys Glu Gln Asp
1970                 1975                1980

Leu Glu Val Ile Leu His Asn Gly Ala Cys Ser Pro Gly Ala Arg
1985                 1990                1995

Gln Gly Cys Met Lys Ser Ile Glu Val Lys His Ser Ala Leu Ser
2000                 2005                2010

Val Glu Xaa His Ser Asp Met Glu Val Thr Val Asn Gly Arg Leu
2015                 2020                2025

Val Ser Val Pro Tyr Val Gly Gly Asn Met Glu Val Asn Val Tyr
2030                 2035                2040

Gly Ala Ile Met His Glu Val Arg Phe Asn His Leu Gly His Ile
2045                 2050                2055

Phe Thr Phe Thr Pro Gln Asn Asn Glu Phe Gln Leu Gln Leu Ser
2060                 2065                2070

Pro Lys Thr Phe Ala Ser Lys Thr Tyr Gly Leu Cys Gly Ile Cys
2075                 2080                2085

Asp Glu Asn Gly Ala Asn Asp Phe Met Leu Arg Asp Gly Thr Val
2090                 2095                2100

Thr Thr Asp Trp Lys Thr Leu Val Gln Glu Trp Thr Val Gln Arg
2105                 2110                2115

Pro Gly Gln Thr Cys Gln Pro Ile Leu Glu Glu Gln Cys Leu Val
2120                 2125                2130

Pro Asp Ser Ser His Cys Gln Val Leu Leu Leu Pro Leu Phe Ala
2135                 2140                2145

Glu Cys His Lys Val Leu Ala Pro Ala Thr Phe Tyr Ala Ile Cys
2150                 2155                2160

Gln Gln Asp Ser Cys His Gln Glu Gln Val Cys Glu Val Ile Ala
2165                 2170                2175

Ser Tyr Ala His Leu Cys Arg Thr Asn Gly Val Cys Val Asp Trp
2180                 2185                2190

Arg Thr Pro Asp Phe Cys Ala Met Ser Cys Pro Pro Ser Leu Val
2195                 2200                2205

Tyr Asn His Cys Glu His Gly Cys Pro Arg His Cys Asp Gly Asn
2210                 2215                2220

Val Ser Ser Cys Gly Asp His Pro Ser Glu Gly Cys Phe Cys Pro
2225                 2230                2235

Pro Asp Lys Val Met Leu Glu Gly Ser Cys Val Pro Glu Glu Ala
2240                 2245                2250
```

```
Cys Thr Gln Cys Ile Gly Glu Asp Gly Val Gln His Gln Phe Leu
    2255                2260                2265

Glu Ala Trp Val Pro Asp His Gln Pro Cys Gln Ile Cys Thr Cys
    2270                2275                2280

Leu Ser Gly Arg Lys Val Asn Cys Thr Thr Gln Pro Cys Pro Thr
    2285                2290                2295

Ala Lys Ala Pro Thr Cys Gly Leu Cys Glu Val Ala Arg Leu Arg
    2300                2305                2310

Gln Asn Ala Asp Gln Cys Cys Pro Glu Tyr Glu Cys Val Cys Asp
    2315                2320                2325

Pro Val Ser Cys Asp Leu Pro Pro Val Pro His Cys Glu Arg Gly
    2330                2335                2340

Leu Gln Pro Thr Leu Thr Asn Pro Gly Glu Cys Arg Pro Asn Phe
    2345                2350                2355

Thr Cys Ala Cys Arg Lys Glu Glu Cys Lys Arg Val Ser Pro Pro
    2360                2365                2370

Ser Cys Pro Pro His Arg Leu Pro Thr Leu Arg Lys Thr Gln Cys
    2375                2380                2385

Cys Asp Glu Tyr Glu Cys Ala Cys Asn Cys Val Asn Ser Thr Val
    2390                2395                2400

Ser Cys Pro Leu Gly Tyr Leu Ala Ser Thr Ala Thr Asn Asp Cys
    2405                2410                2415

Gly Cys Thr Thr Thr Thr Cys Leu Pro Asp Lys Val Cys Val His
    2420                2425                2430

Arg Ser Thr Ile Tyr Pro Val Gly Gln Phe Trp Glu Glu Gly Cys
    2435                2440                2445

Asp Val Cys Thr Cys Thr Asp Met Glu Asp Ala Val Met Gly Leu
    2450                2455                2460

Arg Val Ala Gln Cys Ser Gln Lys Pro Cys Glu Asp Ser Cys Arg
    2465                2470                2475

Ser Gly Phe Thr Tyr Val Leu His Glu Gly Glu Cys Cys Gly Arg
    2480                2485                2490

Cys Leu Pro Ser Ala Cys Glu Val Val Thr Gly Ser Pro Arg Gly
    2495                2500                2505

Asp Ser Gln Ser Ser Trp Lys Ser Val Gly Ser Gln Trp Ala Ser
    2510                2515                2520

Pro Glu Asn Pro Cys Leu Ile Asn Glu Cys Val Arg Val Lys Glu
    2525                2530                2535

Glu Val Phe Ile Gln Gln Arg Asn Val Ser Cys Pro Gln Leu Glu
    2540                2545                2550

Val Pro Val Cys Pro Ser Gly Phe Gln Leu Ser Cys Lys Thr Ser
    2555                2560                2565

Ala Cys Cys Pro Ser Cys Arg Cys Glu Arg Met Glu Ala Cys Met
    2570                2575                2580

Leu Asn Gly Thr Val Ile Gly Pro Gly Lys Thr Val Met Ile Asp
    2585                2590                2595

Val Cys Thr Thr Cys Arg Cys Met Val Gln Val Gly Val Ile Ser
    2600                2605                2610

Gly Phe Lys Leu Glu Cys Arg Lys Thr Thr Cys Asn Pro Cys Pro
    2615                2620                2625

Leu Gly Tyr Lys Glu Glu Asn Asn Thr Gly Glu Cys Cys Gly Arg
    2630                2635                2640
```

```
Cys Leu Pro Thr Ala Cys Thr Ile Gln Leu Arg Gly Gly Gln Ile
    2645                2650                2655

Met Thr Leu Lys Arg Asp Glu Thr Leu Gln Asp Gly Cys Asp Thr
    2660                2665                2670

His Phe Cys Lys Val Asn Glu Arg Gly Glu Tyr Phe Trp Glu Lys
    2675                2680                2685

Arg Val Thr Gly Cys Pro Pro Phe Asp Glu His Lys Cys Leu Ala
    2690                2695                2700

Glu Gly Gly Lys Ile Met Lys Ile Pro Gly Thr Cys Cys Asp Thr
    2705                2710                2715

Cys Glu Glu Pro Glu Cys Asn Asp Ile Thr Ala Arg Leu Gln Tyr
    2720                2725                2730

Val Lys Val Gly Ser Cys Lys Ser Glu Val Glu Val Asp Ile His
    2735                2740                2745

Tyr Cys Gln Gly Lys Cys Ala Ser Lys Ala Met Tyr Ser Ile Asp
    2750                2755                2760

Ile Asn Asp Val Gln Asp Gln Cys Ser Cys Cys Ser Pro Thr Arg
    2765                2770                2775

Thr Glu Pro Met Gln Val Ala Leu His Cys Thr Asn Gly Ser Val
    2780                2785                2790

Val Tyr His Glu Val Leu Asn Ala Met Glu Cys Lys Cys Ser Pro
    2795                2800                2805

Arg Lys Cys Ser Lys
    2810

<210> SEQ ID NO 29
<211> LENGTH: 4
<212> TYPE: PRT
<213> ORGANISM: Artificial Sequence
<220> FEATURE:
<223> OTHER INFORMATION: human IgG1

<400> SEQUENCE: 29

Glu Leu Leu Gly
1

<210> SEQ ID NO 30
<211> LENGTH: 42
<212> TYPE: PRT
<213> ORGANISM: Artificial Sequence
<220> FEATURE:
<223> OTHER INFORMATION: XTEN AE42-4

<400> SEQUENCE: 30

Gly Ala Pro Gly Ser Pro Ala Gly Ser Pro Thr Ser Thr Glu Glu Gly
1               5                   10                  15

Thr Ser Glu Ser Ala Thr Pro Glu Ser Gly Pro Gly Ser Glu Pro Ala
                20                  25                  30

Thr Ser Gly Ser Glu Thr Pro Ala Ser Ser
        35                  40

<210> SEQ ID NO 31
<211> LENGTH: 126
<212> TYPE: DNA
<213> ORGANISM: Artificial Sequence
<220> FEATURE:
<223> OTHER INFORMATION: XTEN AE42-4
```

-continued

<400> SEQUENCE: 31

```
ggcgcgccag gttctcctgc tggctccccc acctcaacag aagagggggac aagcgaaagc    60
gctacgcctg agagtggccc tggctctgag ccagccacct ccggctctga aaccccctgcc   120
tcgagc                                                               126
```

<210> SEQ ID NO 32
<211> LENGTH: 144
<212> TYPE: PRT
<213> ORGANISM: Artificial Sequence
<220> FEATURE:
<223> OTHER INFORMATION: XTEN AE144-2A

<400> SEQUENCE: 32

```
Thr Ser Thr Glu Pro Ser Glu Gly Ser Ala Pro Gly Ser Pro Ala Gly
1               5                   10                  15

Ser Pro Thr Ser Thr Glu Glu Gly Thr Ser Thr Glu Pro Ser Glu Gly
            20                  25                  30

Ser Ala Pro Gly Thr Ser Thr Glu Pro Ser Glu Gly Ser Ala Pro Gly
        35                  40                  45

Thr Ser Glu Ser Ala Thr Pro Glu Ser Gly Pro Gly Thr Ser Thr Glu
    50                  55                  60

Pro Ser Glu Gly Ser Ala Pro Gly Thr Ser Glu Ser Ala Thr Pro Glu
65                  70                  75                  80

Ser Gly Pro Gly Ser Glu Pro Ala Thr Ser Gly Ser Glu Thr Pro Gly
                85                  90                  95

Thr Ser Thr Glu Pro Ser Glu Gly Ser Ala Pro Gly Thr Ser Thr Glu
            100                 105                 110

Pro Ser Glu Gly Ser Ala Pro Gly Thr Ser Glu Ser Ala Thr Pro Glu
        115                 120                 125

Ser Gly Pro Gly Thr Ser Glu Ser Ala Thr Pro Glu Ser Gly Pro Gly
    130                 135                 140
```

<210> SEQ ID NO 33
<211> LENGTH: 450
<212> TYPE: DNA
<213> ORGANISM: Artificial Sequence
<220> FEATURE:
<223> OTHER INFORMATION: XTEN AE144-2A

<400> SEQUENCE: 33

```
ggcgcgccaa ccagtacgga gccgtccgag gggagcgcac caggaagccc ggctgggagc    60
ccgacttcta ccgaagaggg tacatctacc gaaccaagtg aaggttcagc accaggcacc   120
tcaacagaac cctctgaggg ctcggcgcct ggtacaagtg agtccgccac ccagaatcc    180
gggcctggga caagcacaga accttcggaa gggagtgccc ctggaacatc gaatcggca    240
accccagaat cagggccagg atctgagccc gcgacttcgg gctccgagac gcctgggaca   300
tccaccgagc cctccgaagg atcagcccca ggcaccagca cggagccctc tgagggaagc   360
gcacctggta ccagcgaaag cgcaactccc gaatcaggtc ccgtacgag cgagtcggcg    420
accccggaga gcgggccagg tgcctcgagc                                    450
```

<210> SEQ ID NO 34
<211> LENGTH: 144
<212> TYPE: PRT
<213> ORGANISM: Artificial Sequence
<220> FEATURE:
<223> OTHER INFORMATION: XTEN AE144-3B -continued

<400> SEQUENCE: 34

Ser Pro Ala Gly Ser Pro Thr Ser Glu Glu Gly Thr Ser Glu Ser
1               5                   10                  15

Ala Thr Pro Glu Ser Gly Pro Gly Ser Glu Pro Ala Thr Ser Gly Ser
                20                  25                  30

Glu Thr Pro Gly Thr Ser Glu Ser Ala Thr Pro Glu Ser Gly Pro Gly
            35                  40                  45

Thr Ser Thr Glu Pro Ser Glu Gly Ser Ala Pro Gly Thr Ser Thr Glu
        50                  55                  60

Pro Ser Glu Gly Ser Ala Pro Gly Thr Ser Thr Glu Pro Ser Glu Gly
65                  70                  75                  80

Ser Ala Pro Gly Thr Ser Thr Glu Pro Ser Glu Gly Ser Ala Pro Gly
                85                  90                  95

Thr Ser Thr Glu Pro Ser Glu Gly Ser Ala Pro Gly Thr Ser Thr Glu
            100                 105                 110

Pro Ser Glu Gly Ser Ala Pro Gly Ser Pro Ala Gly Ser Pro Thr Ser
        115                 120                 125

Thr Glu Glu Gly Thr Ser Thr Glu Pro Ser Glu Gly Ser Ala Pro Gly
    130                 135                 140

<210> SEQ ID NO 35
<211> LENGTH: 450
<212> TYPE: DNA
<213> ORGANISM: Artificial Sequence
<220> FEATURE:
<223> OTHER INFORMATION: XTEN AE144-3B

<400> SEQUENCE: 35
ggcgcgccaa gtcccgctgg aagcccaact agcaccgaag aggggacctc agagtccgcc      60
accccccgagt ccggccctgg ctctgagcct gccactagcg gctccgagac tcctggcaca    120
tccgaaagcg ctacacccga gagtggaccc ggcacctcta ccgagcccag tgagggctcc    180
gccccctggaa caagcaccga gcccagcgaa ggcagcgccc cagggacctc cacagagccc    240
agtgaaggca gtgctcctgg caccagcacc gaaccaagcg agggctctgc acccgggacc    300
tccaccgagc caagcgaagg ctctgcccct ggcacttcca ccgagcccag cgaaggcagc    360
gcccctggga gccccgctgg ctctcccacc agcactgagg agggcacatc taccgaacca    420
agtgaaggct ctgcaccagg tgcctcgagc                                     450

<210> SEQ ID NO 36
<211> LENGTH: 144
<212> TYPE: PRT
<213> ORGANISM: Artificial Sequence
<220> FEATURE:
<223> OTHER INFORMATION: XTEN AE144-4A

<400> SEQUENCE: 36

Thr Ser Glu Ser Ala Thr Pro Glu Ser Gly Pro Gly Ser Glu Pro Ala
1               5                   10                  15

Thr Ser Gly Ser Glu Thr Pro Gly Thr Ser Glu Ser Ala Thr Pro Glu
                20                  25                  30

Ser Gly Pro Gly Ser Glu Pro Ala Thr Ser Gly Ser Glu Thr Pro Gly
            35                  40                  45

Thr Ser Glu Ser Ala Thr Pro Glu Ser Gly Pro Gly Thr Ser Thr Glu
        50                  55                  60

Pro Ser Glu Gly Ser Ala Pro Gly Thr Ser Glu Ser Ala Thr Pro Glu
65                  70                  75                  80

Ser Gly Pro Gly Ser Pro Ala Gly Ser Pro Thr Ser Thr Glu Glu Gly
                85                  90                  95

Ser Pro Ala Gly Ser Pro Thr Ser Thr Glu Glu Gly Ser Pro Ala Gly
            100                 105                 110

Ser Pro Thr Ser Thr Glu Glu Gly Thr Ser Glu Ser Ala Thr Pro Glu
            115                 120                 125

Ser Gly Pro Gly Thr Ser Thr Glu Pro Ser Glu Gly Ser Ala Pro Gly
            130                 135                 140

<210> SEQ ID NO 37
<211> LENGTH: 450
<212> TYPE: DNA
<213> ORGANISM: Artificial Sequence
<220> FEATURE:
<223> OTHER INFORMATION: XTEN AE144-4A

<400> SEQUENCE: 37

```
ggcgcgccaa cgtccgaaag tgctacccct gagtcaggcc ctggtagtga gcctgccaca      60
agcggaagcg aaactccggg gacctcagag tctgccactc ccgaatcggg gccaggctct     120
gaaccggcca cttcagggag cgaaacacca ggaacatcgg agagcgctac cccggagagc     180
gggccaggaa ctagtactga gcctagcgag ggaagtgcac ctggtacaag cgagtccgcc     240
acacccgagt ctggccctgg ctctccagcg ggctcaccca cgagcactga gagggctct     300
cccgctggca gcccaacgtc gacagaagaa ggatcaccag caggctcccc cacatcaaca     360
gaggagggta catcagaatc tgctactccc gagagtggac ccggtacctc cactgagccc     420
agcgagggga gtgcaccagg tgcctcgagc                                      450
```

<210> SEQ ID NO 38
<211> LENGTH: 144
<212> TYPE: PRT
<213> ORGANISM: Artificial Sequence
<220> FEATURE:
<223> OTHER INFORMATION: XTEN AE144-5A

<400> SEQUENCE: 38

Thr Ser Glu Ser Ala Thr Pro Glu Ser Gly Pro Gly Ser Glu Pro Ala
1               5                   10                  15

Thr Ser Gly Ser Glu Thr Pro Gly Thr Ser Glu Ser Ala Thr Pro Glu
                20                  25                  30

Ser Gly Pro Gly Ser Glu Pro Ala Thr Ser Gly Ser Glu Thr Pro Gly
            35                  40                  45

Thr Ser Glu Ser Ala Thr Pro Glu Ser Gly Pro Gly Thr Ser Thr Glu
        50                  55                  60

Pro Ser Glu Gly Ser Ala Pro Gly Ser Pro Ala Gly Ser Pro Thr Ser
65                  70                  75                  80

Thr Glu Glu Gly Thr Ser Glu Ser Ala Thr Pro Glu Ser Gly Pro Gly
                85                  90                  95

Ser Glu Pro Ala Thr Ser Gly Ser Glu Thr Pro Gly Thr Ser Glu Ser
            100                 105                 110

Ala Thr Pro Glu Ser Gly Pro Gly Ser Pro Ala Gly Ser Pro Thr Ser
            115                 120                 125

Thr Glu Glu Gly Ser Pro Ala Gly Ser Pro Thr Ser Thr Glu Glu Gly
            130                 135                 140

<210> SEQ ID NO 39
<211> LENGTH: 450
<212> TYPE: DNA
<213> ORGANISM: Artificial Sequence
<220> FEATURE:
<223> OTHER INFORMATION: XTEN AE144-5A

<400> SEQUENCE: 39

```
ggcgcgccaa catcagagag cgccaccect gaaagtggtc ccgggagcga gccagccaca      60
tctgggtcgg aaacgccagg cacaagtgag tctgcaactc ccgagtccgg acctggctcc     120
gagcctgcca ctagcggctc cgagactccg gaacttccg agagcgctac accagaaagc     180
ggacccggaa ccagtaccga acctagcgag ggctctgctc cgggcagccc agccggctct     240
cctacatcca cggaggaggg cacttccgaa tccgccaccc cggagtcagg gccaggatct     300
gaacccgcta cctcaggcag tgagacgcca ggaacgagcg agtccgctac accggagagt     360
gggccaggga gccctgctgg atctcctacg tccactgagg aagggtcacc agcgggctcg     420
cccaccagca ctgaagaagg tgcctcgagc                                       450
```

<210> SEQ ID NO 40
<211> LENGTH: 144
<212> TYPE: PRT
<213> ORGANISM: Artificial Sequence
<220> FEATURE:
<223> OTHER INFORMATION: XTEN AE144-6B

<400> SEQUENCE: 40

```
Thr Ser Thr Glu Pro Ser Glu Gly Ser Ala Pro Gly Thr Ser Glu Ser
1               5                   10                  15

Ala Thr Pro Glu Ser Gly Pro Gly Thr Ser Glu Ser Ala Thr Pro Glu
            20                  25                  30

Ser Gly Pro Gly Thr Ser Glu Ser Ala Thr Pro Glu Ser Gly Pro Gly
        35                  40                  45

Ser Glu Pro Ala Thr Ser Gly Ser Glu Thr Pro Gly Ser Glu Pro Ala
    50                  55                  60

Thr Ser Gly Ser Glu Thr Pro Gly Ser Pro Ala Gly Ser Pro Thr Ser
65                  70                  75                  80

Thr Glu Glu Gly Thr Ser Thr Glu Pro Ser Glu Gly Ser Ala Pro Gly
                85                  90                  95

Thr Ser Thr Glu Pro Ser Glu Gly Ser Ala Pro Gly Ser Glu Pro Ala
            100                 105                 110

Thr Ser Gly Ser Glu Thr Pro Gly Thr Ser Glu Ser Ala Thr Pro Glu
        115                 120                 125

Ser Gly Pro Gly Thr Ser Thr Glu Pro Ser Glu Gly Ser Ala Pro Gly
    130                 135                 140
```

<210> SEQ ID NO 41
<211> LENGTH: 450
<212> TYPE: DNA
<213> ORGANISM: Artificial Sequence
<220> FEATURE:
<223> OTHER INFORMATION: XTEN AE144-6B

<400> SEQUENCE: 41

```
ggcgcgccaa catctaccga gccttccgaa ggctctgccc ctgggacctc agaatctgca      60
accectgaaa gcggccctgg aacctccgaa agtgccactc ccgagagcgg cccagggaca     120
agcgagtcag caacccctga gtctggaccc ggcagcgagc ctgcaacctc tggctcagag     180
actcccggct cagaacccgc tacctcaggc tccgagacac ccggctctcc tgctgggagt     240
```

```
cccacttcca ccgaggaagg aacatccact gagcctagtg agggctctgc ccctggaacc    300
agcacagagc caagtgaggg cagtgcacca ggatccgagc cagcaaccag cgggtccgag    360
actcccggga cctctgagtc tgccacccca gagagcggac ccggcacttc aaccgagccc    420
tccgaaggat cagcaccagg tgcctcgagc                                     450
```

<210> SEQ ID NO 42
<211> LENGTH: 144
<212> TYPE: PRT
<213> ORGANISM: Artificial Sequence
<220> FEATURE:
<223> OTHER INFORMATION: XTEN AG144-1

<400> SEQUENCE: 42

```
Pro Gly Ser Ser Pro Ser Ala Ser Thr Gly Thr Gly Pro Gly Ser Ser
1               5                   10                  15

Pro Ser Ala Ser Thr Gly Thr Gly Pro Gly Thr Pro Gly Ser Gly Thr
            20                  25                  30

Ala Ser Ser Ser Pro Gly Ser Ser Thr Pro Ser Gly Ala Thr Gly Ser
        35                  40                  45

Pro Gly Ser Ser Pro Ser Ala Ser Thr Gly Thr Gly Pro Gly Ala Ser
    50                  55                  60

Pro Gly Thr Ser Ser Thr Gly Ser Pro Gly Thr Pro Gly Ser Gly Thr
65                  70                  75                  80

Ala Ser Ser Ser Pro Gly Ser Ser Thr Pro Ser Gly Ala Thr Gly Ser
                85                  90                  95

Pro Gly Thr Pro Gly Ser Gly Thr Ala Ser Ser Ser Pro Gly Ala Ser
            100                 105                 110

Pro Gly Thr Ser Ser Thr Gly Ser Pro Gly Ala Ser Pro Gly Thr Ser
        115                 120                 125

Ser Thr Gly Ser Pro Gly Thr Pro Gly Ser Gly Thr Ala Ser Ser Ser
    130                 135                 140
```

<210> SEQ ID NO 43
<211> LENGTH: 450
<212> TYPE: DNA
<213> ORGANISM: Artificial Sequence
<220> FEATURE:
<223> OTHER INFORMATION: XTEN AG144-1

<400> SEQUENCE: 43

```
ggcgcgccac ccgggtcgtc cccgtcggcg tccaccggaa cagggccagg tcatccccg     60 tcagcgtcga ctgggacggg acccgggaca cccggttcgg ggactgcatc ctcctcgcct   120
ggttcgtcca ccccgtcagg agccacgggt tcgccgggaa gcagcccaag cgcatccact   180
ggtacagggc ctggggcttc accgggtact tcatccacgg ggtcaccggg aacgcccgga   240
tcggggacgg cttcctcatc accaggatcg tcaacaccct cgggcgcaac gggcagcccc   300
ggaacccctg gttcgggtac ggcgtcgtcg agccccggtg cgagcccggg aacaagctcg   360
acaggatcgc ctggggcgtc accggcacg tcgagcacag gcagcccggg aacccctgga   420
tcgggaaccg cgtcgtcaag cgcctcgagc                                    450
```

<210> SEQ ID NO 44
<211> LENGTH: 144
<212> TYPE: PRT
<213> ORGANISM: Artificial Sequence
<220> FEATURE:
<223> OTHER INFORMATION: XTEN AG144-A

<400> SEQUENCE: 44

Gly Ala Ser Pro Gly Thr Ser Ser Thr Gly Ser Pro Gly Ser Ser Pro
1               5                   10                  15

Ser Ala Ser Thr Gly Thr Gly Pro Gly Ser Ser Pro Ser Ala Ser Thr
                20                  25                  30

Gly Thr Gly Pro Gly Thr Pro Gly Ser Gly Thr Ala Ser Ser Ser Pro
            35                  40                  45

Gly Ser Ser Thr Pro Ser Gly Ala Thr Gly Ser Pro Gly Ser Ser Pro
        50                  55                  60

Ser Ala Ser Thr Gly Thr Gly Pro Gly Ala Ser Pro Gly Thr Ser Ser
65                  70                  75                  80

Thr Gly Ser Pro Gly Thr Pro Gly Ser Gly Thr Ala Ser Ser Ser Pro
                85                  90                  95

Gly Ser Ser Thr Pro Ser Gly Ala Thr Gly Ser Pro Gly Thr Pro Gly
            100                 105                 110

Ser Gly Thr Ala Ser Ser Ser Pro Gly Ala Ser Pro Gly Thr Ser Ser
        115                 120                 125

Thr Gly Ser Pro Gly Ala Ser Pro Gly Thr Ser Ser Thr Gly Ser Pro
    130                 135                 140

<210> SEQ ID NO 45
<211> LENGTH: 450
<212> TYPE: DNA
<213> ORGANISM: Artificial Sequence
<220> FEATURE:
<223> OTHER INFORMATION: XTEN AG144-A

<400> SEQUENCE: 45
ggcgcgccag gtgcctcgcc gggaacatca tcaactggtt cacccgggtc atcccctcg      60
gcctcaaccg ggacgggtcc cggctcatcc cccagcgcca gcactggaac aggtcctggc    120
actcctggtt ccggtacggc atcgtcatcc ccgggaagct caacaccgtc cggagcgaca    180
ggatcacctg gctcgtcacc ttcggcgtca actggaacgg ggccaggggc ctcacccgga    240
acgtcctcga ctgggtcgcc tggtacgccg ggatcaggaa cggcctcatc ctcgcctggg    300
tcctcaacgc cctcgggtgc gactggttcg ccgggaactc ctggctcggg acggcctcg     360
tcgtcgcctg gggcatcacc ggggacgagc tccacggggt ccctggagc gtcaccgggg    420
acctcctcga caggtagccc ggcctcgagc                                     450

<210> SEQ ID NO 46
<211> LENGTH: 144
<212> TYPE: PRT
<213> ORGANISM: Artificial Sequence
<220> FEATURE:
<223> OTHER INFORMATION: XTEN AG144-B

<400> SEQUENCE: 46

Gly Thr Pro Gly Ser Gly Thr Ala Ser Ser Ser Pro Gly Ser Ser Thr
1               5                   10                  15

Pro Ser Gly Ala Thr Gly Ser Pro Gly Ala Ser Pro Gly Thr Ser Ser
                20                  25                  30

Thr Gly Ser Pro Gly Thr Pro Gly Ser Gly Thr Ala Ser Ser Ser Pro
            35                  40                  45

Gly Ser Ser Thr Pro Ser Gly Ala Thr Gly Ser Pro Gly Ser Ser Pro
        50                  55                  60

Ser Ala Ser Thr Gly Thr Gly Pro Gly Ser Ser Pro Ser Ala Ser Thr
65                  70                  75                  80

Gly Thr Gly Pro Gly Ser Ser Thr Pro Ser Gly Ala Thr Gly Ser Pro
                85                  90                  95

Gly Ser Ser Thr Pro Ser Gly Ala Thr Gly Ser Pro Gly Ala Ser Pro
            100                 105                 110

Gly Thr Ser Ser Thr Gly Ser Pro Gly Ala Ser Pro Gly Thr Ser Ser
        115                 120                 125

Thr Gly Ser Pro Gly Ala Ser Pro Gly Thr Ser Ser Thr Gly Ser Pro
    130                 135                 140

<210> SEQ ID NO 47
<211> LENGTH: 450
<212> TYPE: DNA
<213> ORGANISM: Artificial Sequence
<220> FEATURE:
<223> OTHER INFORMATION: XTEN AG144-B

<400> SEQUENCE: 47
ggcgcgccag gtacaccggg cagcggcacg gcttcgtcgt cacccggctc gtccacaccg    60
tcgggagcta cgggaagccc aggagcgtca ccgggaacgt cgtcaacggg gtcaccgggt   120
acgccaggta gcggcacggc cagcagctcg ccaggttcat cgaccccgtc gggagcgact   180
gggtcgcccg gatcaagccc gtcagcttcc actggaacag acccgggtc gtcgccgtca    240 gcctcaacgg ggacaggacc tggttcatcg acgccgtcag gggcgacagg ctcgcccgga   300
tcgtcaacac cctcggggc aacggggagc cctggtgcgt cgcctggaac ctcatccacc    360
ggaagcccgg gggcctcgcc gggtacgagc tccacgggat cgcccggagc gtcccccgga   420
acttcaagca cagggagccc tgcctcgagc                                   450

<210> SEQ ID NO 48
<211> LENGTH: 144
<212> TYPE: PRT
<213> ORGANISM: Artificial Sequence
<220> FEATURE:
<223> OTHER INFORMATION: XTEN AG144-C

<400> SEQUENCE: 48

Gly Thr Pro Gly Ser Gly Thr Ala Ser Ser Pro Gly Ala Ser Pro
1               5                   10                  15

Gly Thr Ser Ser Thr Gly Ser Pro Gly Ala Ser Pro Gly Thr Ser Ser
            20                  25                  30

Thr Gly Ser Pro Gly Ala Ser Pro Gly Thr Ser Ser Thr Gly Ser Pro
        35                  40                  45

Gly Ser Ser Pro Ser Ala Ser Thr Gly Thr Gly Pro Gly Thr Pro Gly
    50                  55                  60

Ser Gly Thr Ala Ser Ser Pro Gly Ala Ser Pro Gly Thr Ser Ser
65                  70                  75                  80

Thr Gly Ser Pro Gly Ala Ser Pro Gly Thr Ser Ser Thr Gly Ser Pro
            85                  90                  95

Gly Ala Ser Pro Gly Thr Ser Ser Thr Gly Ser Pro Gly Ser Ser Thr
            100                 105                 110

Pro Ser Gly Ala Thr Gly Ser Pro Gly Ser Ser Thr Pro Ser Gly Ala
        115                 120                 125

Thr Gly Ser Pro Gly Ala Ser Pro Gly Thr Ser Ser Thr Gly Ser Pro
    130                 135                 140

<210> SEQ ID NO 49
<211> LENGTH: 450
<212> TYPE: DNA
<213> ORGANISM: Artificial Sequence
<220> FEATURE:
<223> OTHER INFORMATION: XTEN AG144-C

<400> SEQUENCE: 49

```
ggcgcgccag gtacacccgg atcgggtaca gcgtcatcga gccccggtgc gtcacctggt      60
acgtcgagca cggggtcgcc aggggcgtcc cctgggacgt cctcaacagg ctcgcccggt     120
gcgtcacccg gcacgtcgtc cacgggttca cctggtagct ccccttccgc gtccactggc     180
accgggcctg gaactccggg gagcggcaca gcgagctcgt cgccgggagc atcgcctggg     240
acatcgagca ccgggtcgcc aggagcatcg cccggaacat ccagcacagg aagccccggc     300
gcgtcgcccg gacatcaag cacaggttcc cgggatcga gcacgccgtc cggagccact      360
ggatcaccag ggagctcgac accttccggc gcaacgggat cgcccggagc cagcccgggt     420
acgtcaagca ctggctcccc tgcctcgagc                                     450
```

<210> SEQ ID NO 50
<211> LENGTH: 144
<212> TYPE: PRT
<213> ORGANISM: Artificial Sequence
<220> FEATURE:
<223> OTHER INFORMATION: XTEN AG144-F

<400> SEQUENCE: 50

```
Gly Ser Ser Pro Ser Ala Ser Thr Gly Thr Gly Pro Gly Ser Ser Pro
1               5                   10                  15
Ser Ala Ser Thr Gly Thr Gly Pro Gly Ala Ser Pro Gly Thr Ser Ser
            20                  25                  30
Thr Gly Ser Pro Gly Ala Ser Pro Gly Thr Ser Ser Thr Gly Ser Pro
        35                  40                  45
Gly Ser Ser Thr Pro Ser Gly Ala Thr Gly Ser Pro Gly Ser Ser Pro
    50                  55                  60
Ser Ala Ser Thr Gly Thr Gly Pro Gly Ala Ser Pro Gly Thr Ser Ser
65                  70                  75                  80
Thr Gly Ser Pro Gly Ser Ser Pro Ser Ala Ser Thr Gly Thr Gly Pro
                85                  90                  95
Gly Thr Pro Gly Ser Gly Thr Ala Ser Ser Ser Pro Gly Ser Ser Thr
                100                 105                 110
Pro Ser Gly Ala Thr Gly Ser Pro Gly Ser Ser Thr Pro Ser Gly Ala
            115                 120                 125
Thr Gly Ser Pro Gly Ala Ser Pro Gly Thr Ser Ser Thr Gly Ser Pro
        130                 135                 140
```

<210> SEQ ID NO 51
<211> LENGTH: 450
<212> TYPE: DNA
<213> ORGANISM: Artificial Sequence
<220> FEATURE:
<223> OTHER INFORMATION: XTEN AG144-F

<400> SEQUENCE: 51

```
ggcgcgccag gctccagccc ctccgcgagc acgggaaccg gaccaggttc gtcaccctca      60
gcatcaacgg ggacgggacc ggggcgtca ccaggaacgt cctccaccgg ctcgcccggt     120
gcatcacccg gaacgtcatc gaccggatcg ccagggagct cgacgccatc aggcgcaaca     180
ggatcacctg gctcaagccc tagcgcgtca accggcacgg gtccgggtgc ctcccctggc     240
```

-continued

| | | | | | |
|---|---|---|---|---|---|
| acgtccagca | ccggatcacc | cggatcgagc | ccatccgcct | caaccggaac | cggaccggt 300 |
| acaccagggt | cgggaacagc | ctcctcgtca | ccaggctcct | caaccccctc | gggagccacg 360 |
| ggttcgcccg | gttcgtcaac | gccttccgga | gcaactggta | gccccggagc | atcgccagga 420 |
| acttcgagca | cggggtcgcc | cgcctcgagc | | | 450 |